United States Patent
Liu et al.

(10) Patent No.: US 10,166,215 B2
(45) Date of Patent: Jan. 1, 2019

(54) SUBSTITUTED BICYCLIC COMPOUNDS AS BROMODOMAIN INHIBITORS

(71) Applicant: ZENITH EPIGENETICS LTD., Calgary (CA)

(72) Inventors: Shuang Liu, Schenectady, NY (US); John Frederick Quinn, Albany, NY (US); Bryan Cordell Duffy, Glenmont, NY (US); Ruifang Wang, Schenectady, NY (US); May Xiaowu Jiang, Guilderland, NY (US); Gregory Scott Martin, Colonie, NY (US); He Zhao, Madison, CT (US); Michael Ellis, Clifton Park, NY (US); Gregory Steven Wagner, Foster City, CA (US); Peter Ronald Young, San Francisco, CA (US)

(73) Assignee: Zenith Epigenetics Ltd., Calgary, AB (CA)

( * ) Notice: Subject to any disclaimer, the term of this patent is extended or adjusted under 35 U.S.C. 154(b) by 0 days.

(21) Appl. No.: 15/492,838

(22) Filed: Apr. 20, 2017

(65) Prior Publication Data
US 2017/0216257 A1    Aug. 3, 2017

Related U.S. Application Data

(63) Continuation of application No. 14/900,139, filed as application No. PCT/IB2014/002238 on Jun. 20, 2014, now Pat. No. 9,662,311.

(60) Provisional application No. 61/911,668, filed on Dec. 4, 2013, provisional application No. 61/837,830, filed on Jun. 21, 2013.

(51) Int. Cl.
| | |
|---|---|
| A61K 31/4184 | (2006.01) |
| A61K 31/422 | (2006.01) |
| A61K 31/423 | (2006.01) |
| A61K 31/427 | (2006.01) |
| A61K 31/428 | (2006.01) |
| A61K 31/4439 | (2006.01) |
| A61K 45/06 | (2006.01) |
| A61K 31/4709 | (2006.01) |
| A61K 31/496 | (2006.01) |
| A61K 31/497 | (2006.01) |
| A61K 31/506 | (2006.01) |
| A61K 31/5377 | (2006.01) |
| A61K 31/454 | (2006.01) |

(52) U.S. Cl.
CPC ........ *A61K 31/4184* (2013.01); *A61K 31/422* (2013.01); *A61K 31/423* (2013.01); *A61K 31/427* (2013.01); *A61K 31/428* (2013.01); *A61K 31/4439* (2013.01); *A61K 31/454* (2013.01); *A61K 31/4709* (2013.01); *A61K 31/496* (2013.01); *A61K 31/497* (2013.01); *A61K 31/506* (2013.01); *A61K 31/5377* (2013.01); *A61K 45/06* (2013.01)

(58) Field of Classification Search
CPC .................................................. A61K 31/4184
USPC .......................................................... 424/581
See application file for complete search history.

(56) References Cited

U.S. PATENT DOCUMENTS

| | | | |
|---|---|---|---|
| 4,748,163 A | 5/1988 | Schmidt et al. | |
| 5,385,925 A | 1/1995 | Narr et al. | |
| 5,565,469 A | 10/1996 | Mihm et al. | |
| 5,591,762 A | 1/1997 | Hauel et al. | |
| 6,380,235 B1 | 4/2002 | Zhang et al. | |
| 8,053,440 B2 | 11/2011 | Hansen | |
| 8,093,273 B2 | 1/2012 | Wong et al. | |
| 8,691,747 B2 | 4/2014 | Kruidenier et al. | |
| 8,697,725 B2 | 4/2014 | Demont et al. | |
| 8,735,586 B2 | 5/2014 | Alonso et al. | |
| 8,993,554 B2 | 3/2015 | Amans et al. | |
| 9,029,395 B2 | 5/2015 | Amans et al. | |
| 9,067,936 B2 | 6/2015 | Demont et al. | |
| 9,073,878 B2 | 7/2015 | Fairfax et al. | |
| 9,102,677 B2 | 8/2015 | Bailey et al. | |
| 9,125,915 B2 | 9/2015 | Miyoshi et al. | |

(Continued)

FOREIGN PATENT DOCUMENTS

| | | |
|---|---|---|
| CA | 2087800 A1 | 7/1993 |
| CA | 2093785 A1 | 10/1993 |

(Continued)

OTHER PUBLICATIONS

Aiello. R.J., et al., "Monocyte chemoattractant protein-1 accelerates atherosclerosis in apolipoprotein E-deficient mice" *Arterioscler Thromb. Vasc. Biol.* 19(6): 1518-25 (1999).

(Continued)

*Primary Examiner* — Kahsay Habte
(74) *Attorney, Agent, or Firm* — Finnegan, Henderson, Farabow, Garrett & Dunner, LLP

(57) ABSTRACT

The invention relates to substituted bicyclic compounds, which are useful for inhibition of BET protein function by binding to bromodomains, pharmaceutical compositions comprising these compounds, and use of the compounds and compositions in therapy.

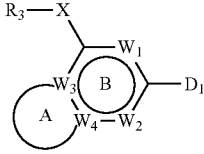

Formula I

14 Claims, No Drawings

(56) References Cited

U.S. PATENT DOCUMENTS

| | | |
|---|---|---|
| 9,271,978 B2 | 3/2016 | Liu et al. |
| 9,278,940 B2 | 3/2016 | Fairfax et al. |
| 9,315,487 B2 | 4/2016 | Amans et al. |
| 9,321,765 B2 | 4/2016 | Gong |
| 9,388,161 B2 | 7/2016 | Bair et al. |
| 9,393,232 B2 | 7/2016 | Ren et al. |
| 9,422,281 B2 | 8/2016 | Bair et al. |
| 9,458,156 B2 | 10/2016 | Norris et al. |
| 9,598,367 B2 | 3/2017 | Liu et al. |
| 9,636,328 B2 | 5/2017 | Liu et al. |
| 9,662,311 B2 * | 5/2017 | Liu .................. A61K 31/4184 |
| 9,663,520 B2 | 5/2017 | Quinn et al. |
| 9,765,039 B2 | 9/2017 | Fairfax et al. |
| 9,855,271 B2 | 1/2018 | Quinn et al. |
| 9,861,637 B2 | 1/2018 | Liu et al. |
| 2002/0019395 A1 | 2/2002 | Zhu et al. |
| 2003/0036545 A1 | 2/2003 | Castelhano et al. |
| 2004/0044203 A1 | 3/2004 | Wittman et al. |
| 2004/0166137 A1 | 8/2004 | Lackey |
| 2005/0014812 A1 | 1/2005 | Hayashida et al. |
| 2005/0176858 A1 | 8/2005 | Nohara et al. |
| 2007/0134161 A1 | 6/2007 | Brown |
| 2007/0275984 A1 | 11/2007 | Imogai et al. |
| 2008/0015196 A1 | 1/2008 | Doller et al. |
| 2008/0262207 A1 | 10/2008 | Duffin et al. |
| 2010/0267714 A1 | 10/2010 | Jorgensen et al. |
| 2011/0070297 A1 | 3/2011 | Cao et al. |
| 2011/0136834 A1 | 6/2011 | Critchley et al. |
| 2012/0004261 A1 | 1/2012 | Jorgensen et al. |
| 2012/0028912 A1 | 2/2012 | Zhou et al. |
| 2012/0157428 A1 | 6/2012 | Albrecht et al. |
| 2012/0208798 A1 | 8/2012 | Demont et al. |
| 2012/0208800 A1 | 8/2012 | Chung et al. |
| 2012/0208814 A1 | 8/2012 | Demont et al. |
| 2012/0220573 A1 | 8/2012 | Gosmini et al. |
| 2013/0085133 A1 | 4/2013 | Severson et al. |
| 2013/0143880 A1 | 6/2013 | Dudkin et al. |
| 2013/0261109 A1 | 10/2013 | Miyoshi et al. |
| 2013/0281396 A1 | 10/2013 | McLure et al. |
| 2013/0281397 A1 | 10/2013 | McLure et al. |
| 2013/0281398 A1 | 10/2013 | McLure et al. |
| 2013/0281399 A1 | 10/2013 | McLure et al. |
| 2014/0031336 A1 | 1/2014 | Amans et al. |
| 2014/0045834 A1 | 2/2014 | Demont et al. |
| 2014/0162971 A1 | 6/2014 | Wang et al. |
| 2014/0171462 A1 | 6/2014 | Demont et al. |
| 2014/0256700 A1 | 9/2014 | Poss et al. |
| 2014/0256705 A1 | 9/2014 | Hasvold et al. |
| 2014/0256706 A1 | 9/2014 | Wang et al. |
| 2014/0256710 A1 | 9/2014 | Liu et al. |
| 2014/0275030 A1 | 9/2014 | Combs et al. |
| 2014/0275079 A1 | 9/2014 | Hasvold et al. |
| 2014/0296246 A1 | 10/2014 | Aktoudianakis et al. |
| 2014/0303121 A1 | 10/2014 | Zhang et al. |
| 2014/0336190 A1 | 11/2014 | Aktoudianakis et al. |
| 2014/0349990 A1 | 11/2014 | Blank et al. |
| 2015/0011540 A1 | 1/2015 | Combs et al. |
| 2015/0246919 A1 | 9/2015 | Engelhardt et al. |
| 2016/0137613 A1 | 5/2016 | Hansen |
| 2016/0193218 A1 | 7/2016 | Quinn et al. |
| 2017/0143731 A1 | 5/2017 | Liu et al. |
| 2017/0182029 A1 | 6/2017 | Liu et al. |
| 2017/0216301 A1 | 8/2017 | Quinn et al. |
| 2017/0320866 A1 | 11/2017 | Jiang et al. |
| 2017/0360756 A1 | 12/2017 | Brown et al. |
| 2017/0360760 A1 | 12/2017 | Kharenko et al. |
| 2017/0360765 A1 | 12/2017 | Jiang et al. |

FOREIGN PATENT DOCUMENTS

| | | |
|---|---|---|
| CA | 2195107 A1 | 2/1996 |
| CA | 2440211 A1 | 9/2002 |
| CA | 2911408 A1 | 11/2014 |
| CN | 1113235 A | 12/1995 |
| CN | 1636977 A | 7/2005 |
| CN | 1263757 C | 7/2006 |
| CN | 1934092 A | 3/2007 |
| CN | 101061098 A | 10/2007 |
| CN | 101220077 A | 7/2008 |
| CN | 101384593 A | 3/2009 |
| CN | 101636386 A | 1/2010 |
| CN | 101983198 A | 3/2011 |
| CN | 102186833 A | 9/2011 |
| CN | 105102453 A | 11/2015 |
| EP | 0 385 850 A2 | 9/1990 |
| EP | 0 556 789 A2 | 8/1993 |
| EP | 0 566 020 A1 | 10/1993 |
| EP | 0 195 947 B1 | 4/1996 |
| EP | 1375486 A1 | 1/2004 |
| EP | 1 944 311 A1 | 7/2008 |
| EP | 2 792 355 A1 | 10/2014 |
| JP | S61-207388 A | 9/1986 |
| JP | H04-253966 A | 9/1992 |
| JP | H04-346978 A | 12/1992 |
| JP | H05-279341 A | 10/1993 |
| JP | 2000-072675 A | 3/2000 |
| JP | 2003-523353 A | 8/2003 |
| JP | 2004-519512 A | 7/2004 |
| JP | 2004-526727 A | 9/2004 |
| JP | 2004-534010 A | 11/2004 |
| JP | 2006-511600 A | 4/2006 |
| JP | 2006-528677 A | 12/2006 |
| JP | 2007-530477 A | 11/2007 |
| JP | 2008-513414 A | 5/2008 |
| JP | 2008-169212 A | 7/2008 |
| JP | 2008-533151 A | 8/2008 |
| JP | 2009-517438 A | 4/2009 |
| JP | 2009-528989 A | 8/2009 |
| JP | 2009-532424 A | 9/2009 |
| JP | 2010-513224 A | 4/2010 |
| JP | 2010-532768 A | 10/2010 |
| JP | 2010-540590 A | 12/2010 |
| JP | 2012-500260 A | 1/2012 |
| JP | 2012-513418 A | 6/2012 |
| JP | 2012-520884 A | 9/2012 |
| JP | 2015-532650 A | 11/2015 |
| JP | 2016-515584 A | 5/2016 |
| JP | 2016-520062 A | 7/2016 |
| KR | 10-1165996 B1 | 10/2011 |
| KR | 10-1242572 B1 | 4/2012 |
| WO | WO 96/33194 A1 | 10/1996 |
| WO | WO 00/34248 A1 | 6/2000 |
| WO | WO 00/66564 A1 | 11/2000 |
| WO | WO 01/55132 A1 | 8/2001 |
| WO | WO 02/057267 A1 | 7/2002 |
| WO | WO 02/070486 A1 | 9/2002 |
| WO | WO 02/072576 A1 | 9/2002 |
| WO | WO 02/076976 A2 | 10/2002 |
| WO | WO 02/079192 A1 | 10/2002 |
| WO | WO 2004/024897 A2 | 3/2004 |
| WO | WO 2004/054984 A1 | 7/2004 |
| WO | WO 2004/078733 A1 | 9/2004 |
| WO | WO 2004/098494 A2 | 11/2004 |
| WO | WO 2004/108686 A2 | 12/2004 |
| WO | WO 2005/012292 A1 | 2/2005 |
| WO | WO 2005/013950 A2 | 2/2005 |
| WO | WO 2005/080383 A1 | 9/2005 |
| WO | WO 2005/090317 A1 | 9/2005 |
| WO | WO 2005/121132 A1 | 12/2005 |
| WO | WO 2006/030032 A1 | 3/2006 |
| WO | WO 2006/099379 A2 | 9/2006 |
| WO | WO 2007/016525 A2 | 2/2007 |
| WO | WO 2007/040208 A1 | 4/2007 |
| WO | WO 2007/063012 A1 | 6/2007 |
| WO | WO 2007/093901 A1 | 8/2007 |
| WO | WO 2007/113232 A1 | 10/2007 |
| WO | WO 2008/072784 A1 | 6/2008 |
| WO | WO 2008/153701 A1 | 12/2008 |
| WO | WO 2009/043883 A1 | 4/2009 |
| WO | WO 2009/079001 A1 | 6/2009 |
| WO | WO 2009/099801 A1 | 8/2009 |
| WO | WO 2010/021693 A2 | 2/2010 |
| WO | WO 2010/068483 A2 | 6/2010 |
| WO | WO 2010/106436 A2 | 9/2010 |

(56) References Cited

FOREIGN PATENT DOCUMENTS

| | | |
|---|---|---|
| WO | WO 2010/107739 A2 | 9/2010 |
| WO | WO 2010/123975 A1 | 10/2010 |
| WO | WO 2011/054843 A1 | 5/2011 |
| WO | WO 2011/054846 A1 | 5/2011 |
| WO | WO 2011/143669 A2 | 11/2011 |
| WO | WO 2012/003576 A1 | 1/2012 |
| WO | WO 2012/009258 A2 | 1/2012 |
| WO | WO 2012/021382 A1 | 2/2012 |
| WO | WO 2012/075456 A1 | 6/2012 |
| WO | WO 2012/143413 A1 | 10/2012 |
| WO | WO 2012/143416 A2 | 10/2012 |
| WO | WO 2012/174487 A2 | 12/2012 |
| WO | WO 2013/024104 A1 | 2/2013 |
| WO | WO 2013/027168 A1 | 2/2013 |
| WO | WO 2013/064900 A1 | 5/2013 |
| WO | WO 2013/082429 A1 | 6/2013 |
| WO | WO 2013/156869 A1 | 10/2013 |
| WO | WO 2013/158952 A1 | 10/2013 |
| WO | WO 2013/184878 A1 | 12/2013 |
| WO | WO 2013/186229 A1 | 12/2013 |
| WO | WO 2014/037340 A1 | 3/2014 |
| WO | WO 2014/043246 A1 | 3/2014 |
| WO | WO 2014/078257 A1 | 5/2014 |
| WO | WO 2014/095775 A1 | 6/2014 |
| WO | WO 2014/128070 A1 | 8/2014 |
| WO | WO 2014/128111 A1 | 8/2014 |
| WO | WO 2014/128655 A1 | 8/2014 |
| WO | WO 2014/134267 A1 | 9/2014 |
| WO | WO 2014/140076 A1 | 9/2014 |
| WO | WO 2014/140077 A1 | 9/2014 |
| WO | WO 2014/152029 A2 | 9/2014 |
| WO | WO 2014/154760 A1 | 10/2014 |
| WO | WO 2014/154762 A1 | 10/2014 |
| WO | WO 2014/159837 A1 | 10/2014 |
| WO | WO 2014/160873 A1 | 10/2014 |
| WO | WO 2014/165143 A1 | 10/2014 |
| WO | WO 2014/170350 A1 | 10/2014 |
| WO | WO 2014/173241 A1 | 10/2014 |
| WO | WO 2014/182929 A1 | 11/2014 |
| WO | WO 2014/202578 A1 | 12/2014 |
| WO | WO 2015/002754 A2 | 1/2015 |
| WO | WO 2015/011084 A1 | 1/2015 |
| WO | WO 2015/013635 A2 | 1/2015 |
| WO | WO 2015/015318 A2 | 2/2015 |
| WO | WO 2015/086507 A1 | 6/2015 |
| WO | WO 2016/087936 A1 | 6/2016 |
| WO | WO 2016/087942 A1 | 6/2016 |
| WO | WO 2016/092375 A1 | 6/2016 |
| WO | WO 2016/097863 A1 | 6/2016 |
| WO | WO 2016/097870 A1 | 6/2016 |

OTHER PUBLICATIONS

Alexandraki, K. et al., "Inflammatory process in type 2 diabetes: The role of cytokines" *Ann N Y Acad Sci*, 2006. 1084:89-117.
Antonelli, A. et al., "Serum levels of proinflammatory cytokines interleukin-1beta, interleukin-6, and tumor necrosis factor alpha in mixed cryoglobulinemia" *Arthritis Rheum*, 2009 60(12);3841-7.
Aricha, R. et al., "Blocking of IL-6 suppresses experimental autoimmune myasthenia gravis" *J Autoimmun*, 2011. 36(2):135-41.
Arif, M. et al., "Protein lysine acetylation in cellular function and its role in cancer manifestation" *Biochim Biophys Acta*, 2010. 1799(10-12):702-16.
Ash, Z. and P. Emery, "The role of tocilizumab in the management of rheumatoid arthritis" *Expert Opin Biol Ther*, 2012. 12(9): 1277-89.
Bandukwala, H.S. et al. "Selective inhibition of CD4+ T-cell cytokine production and autoimmunity by BET protein and c-Myc inhibitors" *Proc Natl Acad Sci USA*, 2012. 109(36);14532-7.
Bandyopadhyay, K. et al., "Spermidinyl-CoA-based HAT inhibitors block DNA repair and provide cancer-specific chemo- and radiosensitization" *Cell Cycle*, 2009. 8(17):2779-88. (Author's manuscript, 19 pages).

Banerjee, C. et al., "BET bromodomain inhibition as a novel strategy for reactivation of HIV-1" *J Leukoc Biol*, 2012. 92(6):1147-54.
Baron, P. et al., "Production of IL-6 by human myoblasts stimulated with Abeta: relevance in the pathogenesis of IBM" *Neurology*, 2001. 57(9):1561-5.
Bartholomeeusen, K. et al., "BET bromodomain inhibition activates transcription via a transient release of P-TEFb from 7SK snRNP" *JBC In Press*, 2012. M112.410746, 16 pages. Final publication in: *J Biol Chem*, 287:36609-16.
Bassiouny, D.A. and O. Shaker, "Role of Interleukin-17 in the pathogenesis of vitiligo" *Clin Exp Dermatol*, 2011. 36(3):292-7.
Bayraktaroglu, T. et al., "Serum levels of tumor necrosis factor-alpha, interleukin-6 and interleukin-8 are not increased in dyspeptic patients with Helicobacter pylori-associated gastritis" *Mediators Inflamm*, 2004. 13(1):25-8.
Belanger, D.B. et al., "Discovery of imidazo[1,2-a]pyrazine-based Aurora kinase inhibitors" *Bioorg. Med. Chem. Lett.*, 20:5170-5174 (2010).
Belkina, A.C. and G.V. Denis, "BET domains co-regulators in obesity, inflammation and cancer" *Nat Rev Cancer*, 2012. 12(7):465-77.
Bellan, C. et al., "CDK9/CYCLIN T1 expression during normal lymphoid differentiation and malignant transformation" *J. Pathol.*, 2004. 203(4):946-52.
Belli, F. et al., "Cytokines assay in peripheral blood and bronchoalveolar lavage in the diagnosis and staging of pulmonary granulomatous diseases" *Int J Immunopathol Pharmacol*, 2000. 13(2):61-67.
Berkovits, B.D. et al., "The testis-specific double bromodomain-containing protein BRDT forms a complex with multiple spliceosome components and is required for mRNA splicing and 3'-UTR truncation in round spermatids" *Nucleic Acids Res*, 2012. 40(15):7162-75.
Besnard, A.G. et al., "Inflammasome-IL-1-Th17 response in allergic lung inflammation" *J Mol Cell Biol*, 2012. 4(1):3-10.
Boring, L. et al., "Decreased lesion formation in CCR2-/- mice reveals a role for chemokines in the initiation of atherosclerosis" *Nature*, 1998. 394(6696):894-7.
Bradley, D.T. and S.E. Kountakis, "Role of interleukins and transforming growth factor-beta in chronic rhinosinusitis and nasal polyposis" *Laryngoscope*, 2005. 115(4):684-6.
Brennan, P., "Isoxazole Inhibitors of Bromodomains" presented at the *RSC Advances in Synthesis and Medicinal Chemistry Conference*, BioPark, Welwyn Garden City, UK, May 1, 2012 (46 pages).
Brodmerkel, C.M. et al., "Discovery and pharmacological characterization of a novel rodent-active CCR2 antagonist, INCB3344" *J Immunol*, 2005. 175(8):5370-8.
Brühl, H. et al., "Dual role of CCR2 during initiation and progression of collagen-induced arthritis: evidence for regulatory activity of CCR2+ T cells" *J Immunol*, 2004. 172(2):890-8.
Chaidos, A. et al., "Inhibition of bromodomain and extraterminal proteins (BET) as a potential therapeutic approach in haematological malignancies: emerging preclinical and clinical evidence" *Ther Adv Hematol*, 6(3):128-141 (2015).
Chemical Abstracts Service, 'Registry' File, RN 1209999-95-0; STN Database [online]. Entry Date: Mar. 15, 2010 (1 page).
Chemical Abstracts Service, 'Registry' File, RN 1348682-08-5; STN Database [online]. Entry Date: Dec. 4, 2011 (1 page).
Chemical Abstracts Service, 'Registry' File, RN 1349387-93-4; STN Database [online]. Entry Date: Dec. 6, 2011 (1 page).
Chen, L. et al., "IL-17RA aptamer-mediated repression of IL-6 inhibits synovium inflammation in a murine model of osteoarthritis" *Osteoarthritis Cartilage*, 2011. 19(6):711-8.
Chevrel, G. et al., "Interleukin-17 increases the effects of IL-1 beta on muscle cells: arguments for the role of T cells in the pathogenesis of myositis" *J Neuroimmunol*, 2003. 137(1-2):125-33.
Chung, C.W. et al., "Bromodomains: a new traget class for small molecule drug discovery" *Drug Discovery Today: Therapeutic Strategies* 9(2-3):e111-e120 (2012).
Chung, C.W. et al., "Discovery and characterization of small molecule inhibitors of the BET family bromodomains" *J Med Chem*, 2011. 54(11):3827-38.

(56) References Cited

OTHER PUBLICATIONS

Chung, C.W., "Small Molecule Bromodomain Inhibitors: Extending the Druggable Genome" *Progr. Med. Chem.* 51:1-55 (2012).
Clinical Trials.Gov, "A Study to Investigate the Safety, Pharmacokinetics, Pharmacodynamics, and Clinical Activity of GSK525762 in Subjects With NUT Midline Carcinoma (NMC) and Other Cancers" GlaxoSmithKline, Identifier NCT01587703, verified Dec. 2016, [online]. Retrieved from: https://clinicaltrials.gov/ct2/show/NCT01587703, on Dec. 28, 2016 (6 pages).
Costello, J.F. et al., "Cyclin-dependent kinase 6 (CDK5) amplification in human gliomas identified using two-dimensional separation of genomic DNA" *Cancer Res.* 1997. 57(7):1250-4.
D'Auria, L. et al., "Cytokines and bullous pemphigoid" *Eur Cytokine Netw,* 1999. 10(2):123-34.
Dawson, J. et al., "Targeting monocyte chemoattractant protein-1 signalling in disease" *Expert Opin Ther Targets,* 2003. 7(1):35-48.
Dawson, M.A. et al., "Inhibition of BET Recruitment to Chromatin as an Effective Treatment for MLL-fusion Leukaemia" *Nature,* 2011, 478:529-533.
De Falco, G. et al., "Cdk9 regulates neural differentiation and its expression correlates with the differentiation grade of neuroblastoma and PNET tumors" *Cancer Biol Ther,* 2005. 4(3):277-81.
De Lemos, J.A. et al., "Association between plasma levels of monocyte chemoattractant protein-1 and long-term clinical outcomes in patients with acute coronary syndromes" *Circulation,* 2003. 107(5):690-5.
De Paiva, C.S. et al., "IL-17 disrupts corneal barrier following desiccating stress" *Mucosal Immunol,* 2009. 2(3):243-53.
Degoma, E.M. and D.J. Rader, "Novel HDL-directed pharmacotherapeutic strategies" *Nat Rev Cardiol,* 2011. 8(5):266-77.
Delmore, J.E. et al., "BET bromodomain inhibition as a therapeutic strategy to target c-Myc" *Cell,* 2011 146(6):904-17.
Deng, J. et al., "Th17 and Th1 T-cell responses in giant cell arteritis" *Circulation,* 2010. 121(7):906-15.
Denis, G.V. et al., "An emerging role for bromodomain-containing proteins in chromatin regulation and transcriptional control of adipogenesis" *FEBS Lett,* 2010. 584(15):3260-8: (Author manuscript, 21 pages).
Denis. G.V., "Bromodomain coactivators in cancer, obesity, type 2 diabetes, and inflammation" *Discov Med,* 2010. 10(55):489-99.
Deo, R. et al., "Association among plasma levels of monocyte chemoattractant protein-1, traditional cardiovascular risk factors, and subclinical atherosclerosis" *J Am Coll Cardiol,* 2004. 44(9): p. 1812-8.
Dias, P.M. and G. Banerjee, "The Role of Th17/IL-17 on Eosinophilic Inflammation" *J Autoimmun,* 2012. Article in Press: http://dx.doi.org/10.1016/j.jaut.2012.07.004, 12 pages.
Elliott, D.A. et al., "Apolipoproteins in the brain: implications for neurological and psychiatric disorders" *Clin Lipidol,* 2010. 51(4):555-573. (Author manuscript, 28 pages.).
El-Osta, H.E. and R. Kurzrock, "Castleman's disease: from basic mechanisms to molecular therapeutics" *Oncologist* 2011. 16(4):497-511.
European Patent Application No. 14820520.6, by Zenith Epigenetics Corp.: Extended European Search Report, including Search Opinion, dated Feb. 8, 2017 (9 pages).
European Patent Application No, 14822480.1, by Zenith Epigenetics Corp.: Extended European Search Report, including Search Opinion, dated Jan. 4, 2017 (10 pages).
European Patent Application No. 14822511.3, by Zenith Epigenetics Corp.: Extended European Search Report, including Search Opinion, dated Jan. 2, 2017 (7 pages).
European Patent Application No. 14832298.5, by Zenith Epigenetics Corp.: Extended European Search Report, including Search Opinion, dated Nov. 11, 2016 (6 pages).
European Patent No. EP 0 385 850 A2: Machine English translation; retrieved from ProQuest Dialog, on Aug. 15, 2016; 68 pages.
European Patent No. EP 0 556 789 A2: Machine English translation; retrieved from ProQuest Dialog, on Aug. 15, 2015; 59 pages.

Feng, Q. et al., "An epigenomic approach to therapy for tamoxifen-resistant breast cancer" *Cell Research,* 24:809-819 (2014).
Fife, B.T. et al., "CC chemokine receptor 2 is critical for induction of experimental autoimmune encephalomyelitis" *J Exp Med,* 192(6):899-905 (2000).
Figueroa-Vega. N. et al., "Increased circulating pro-inflammatory cytokines and Th17 lymphocytes in Hashimoto's thyroiditis" *J Clin Endocrinol Metab,* 95(2):953-62 (2010).
Filippakopoulos, P. and S. Knapp, "Targeting bromodomains: epigenetic readers of lysine acetylation:" *Nature Reviews,* 13:337-356 (2014).
Filippakopoulos, P. et al., "Selective Inhibition of BET Bromodomains" *Nature,* 68:1067-1073 (2010).
Freireich, E.J. et al., "Quantitative comparison of toxicity of anti-cancer agents in mouse, rat, hamster, dog, monkey, and man" *Cancer Chemother Rep.* 50(4)219-244 (1966).
French, C.A., "NUT midline carcinoma" *Cancer Genet Cytogenet,* 2010. 203(1):16-20. (Author manuscript, 9 pages.).
Fujioka, A. et al., "The analysis of mRNA expression of cytokines from skin lesions in Churg-Strauss syndrome" *J Dermatol,* 1998. 25(3):171-7.
Fujishima, S. et al., "Involvement of IL-17F via the induction of IL-6 in psoriasis" *Arch Dermatol Res,* 2010. 302(7):499-505.
Gagnon, D. et al., "Proteasomal degradation of the papillomavirus E2 protein is inhibited by overexpression of bromodomain-containing protein 4" *J Virol,* 2009. 83(9):4127-39.
Gaucher, J. et al., "Bromodomain-dependent stage-specific male genome programming by Brdt" *EMBO J,* 2012. 31(19):3809-20.
Gloddek, B. et al., "Pharmacological influence on inner ear endothelial cells in relation to the pathogenesis of sensorineural hearing loss" *Adv Otorhinolaryngol,* 2002. 59:75-83.
Gong, J-H. et al., "An antagonist of monocyte chemoattractant protein 1 (MCP-1) inhibits arthritis in the MRL-lpr mouse mode," *J Exp Med,* 1997. 186(1):131-7.
Gong, J.-H. et al., "Post-onset inhibition of murine arthritis using combined chemokine antagonist therapy" *Rheumatology.* 2004. 43(1):39-42.
Gonzalez-Serrano. M.E. et al., "Increased Pro-inflammatory Cytokine Production After Lipopolysaccharide Stimulation in Patients with X-linked Agammaglobulinemia" *J Clin Immunol.* 2012. 32(5):967-74.
Gosling, J. et al, "MCP-1 deficiency reduces susceptibility to atherosclerosis in mice that overexpress human apolipoprotein B" *J Clin Invest,* 1999. 103(6):773-8.
Gottschalk, S. et al., "An Epstein-Barr virus deletion mutant associated with fatal lymphoproliferative disease unresponsive to therapy with virus-specific CTLs" *Blood,* 2001. 97:835-843.
Graber, J.J. et al., "Interleukin-17 in transverse myelitis and multiple sclerosis" *J Neuroimmunol,* 2008. 196(1-2):124-32.
Greenwald, R.J. et al., "E mµ-BRD2 transgenic mice develop B-cell lymphoma and leukemia" *Blood,* 2004. 103(4):1475-84.
Grunwald, C. et al., "Expression of multiple epigeneticaily regu-lated cancer/germline genes in nonsmall cell lung cancer" *Int J Cancer,* 2006. 118(10):2522-8.
Gu, L. et al., "Absence of monocyte chemoattractant protein-1 reduces atherosclerosis in low density lipoprotein receptor-deficient mice" *Mol Cell,* 1998, 2(2):275-81.
Gu, Y. et al., "Interleukin (IL)-17 promotes macrophages to produce IL-8, IL-6 and tumour necrosis factor-alpha in aplastic anaemia" *Br J Haematol,* 2008. 142(1)-109-14.
Hankovszky, H.O. et al, "Synthesis and reaction of ortho-flucronitroaryl nitroxides. Novel versatile synthons and reagents for spin-labelling studies" *Can J Chem,* 67:1392-1400 (1989).
Harada, K. et al., "Periductal interleukin-17 production in association with biliary innate immunity contributes to the pathogenesis of cholangiopathy in primary biliary cirrhosis" *Clin Exp Immonol,* 2009. 157(2):261-70.
Haruta, H. et al., "Blockade of interleukin-6 signaling suppresses not only TH17 but also interphotoreceptor retinoid binding protein-specific Th1 by promoting regulatory T cells in experimental autoimmune uveoretinitis" *Invest. Ophthalmol Vis Sci,* 2011. 52(6):3264-71.

(56) References Cited

OTHER PUBLICATIONS

Hay et al., "The design and synthesis of 5- and 6-isoxazolylbenzimidazoles as selective inhibitors of the BET bromodomains" *Med. Chem. Commun.* 4:140-144 (2013).
Hay, D.A. et al., "Discovery and Optimization of Small-Molecule Ligands for the CBP/p300 Bormodomains" *J. Am. Chem. Soc.* 136:9308-9319 (2014).
He, A. and J.J.L. Miranda, "JQ1 reduces Epstein-Barr virus-associated lymphoproliferative disease in mice without sustained oncogene repression" *Leukemia & Lymphoma*, 2017. DOI: 10.1080/10428194.2017.1372578 [online]. Retrieved Oct. 31, 2017 (5 pages).
Hewings et al., "3,5-Dimethylisoxazoles Act As Acetyl-lysine-mimetic Bromodomain Ligands" *J. Med. Chem.* 54:6761-6770 (2011).
Hewings et al., "3,5-Dimethylisoxazoles inhibit the bromodomain-histone protein-protein interaction" 243rd National Spring Meeting of the American-Chemical-Society (Symposium on Ionic Liquids—Science and Applications) San Diego, CA. General Poster Session, Mar. 28, 2012, Poster 326 Abstract [online].Retrieved from: http://acselb-529643017.us-west-2.elb.amazonaws.com/chem/chem/243nm/program/view.php?pub_num=326&car=MEDI.
Hewings et al., "Optimization of 3.5-Dimethylisoxazole Derivatives as Potent Bromodomain Ligands" *J. Med. Chem.* 56:3217-3227 (2013).
Hewings et al., "Progress in the development and application of small molecule inhibitors of bromodomain-acetyl-lysine interactions" *J. Med. Chem.* 55:9393-9413 (2012).
Hohki. S. et al., "Blockade of interleukin-6 signaling suppresses experimental autoimmune uveoretinitis by the inhibition of inflammatory Th17 responses" *Exp Eye Res,* 2010, 91(2):162-70.
Hölttä, V. et al., "IL-23/IL-17 immunity as a hallmark of Crohn's disease" *Inflamm Bowel Dis,* 2008. 14(9):1175-84.
Hoshino, I. and H. Matsubara, "Recent advances in histone deacetylase targeted cancer therapy" *Surg Today,* 2010. 40(9):809-15.
Huang, D. et al., "Absence of monocyte chemoattractant protein 1 in mice leads to decreased local macrophage recruitment and antigen-specific T helper cell type 1 immune response in experimental autoimmune encephalomyelitis" *J Exp Med,* 2001. 193(6):713-26.
Içöz, S. et al., " Enhanced IL-6 production in aquaporin-4 antibody positive neuromyelitis optica patients" *Int J Neurosci,* 2010. 120(1):71-5.
International Search Reprot and Written Opinion issued in International Application No. PCT/IB2014/002238; dated Apr. 23, 2015.
International Search Report and Written Opinion issued in International Application No. PCT/IB2014/002240; dated Mar. 10, 2015.
International Search Report and Written Opinion issued in International Application No. PCT/IB2015/002479; dated Apr. 21, 2016.
International Search Report and Written Opinion issued in International Application No. PCT/IB2015/002490: dated Apr. 1, 2016.
International Search Report and Written Opinion issued in International Application No. PCT/IB2015/002522; dated Apr. 13, 2016.
International Search Report and Written Opinion issued in International Application No. PCT/IB2016/001874; dated Apr. 25, 2016.
International Search Report and Written Opinion issued in International Application No. PCT/US2014/043423; dated Jan. 12, 2005.
Ishizu, T. et al., "CSF cytokine and chemokine profiles in acute disseminated encephalomyelitis" *J Neuroimmunol,* 2006. 175(1-2):52-58.
Ito, Y. et al., "Pathogenic significance of interleukin-6 in a patient with antiglomerular basement membrane antibody-induced glomerulonephritis with multinucleated giant cells" *Am J Kidney Dis,* 1995. 26(1):72-9.
Jadidi-Niaragh, F. and A. Mirshafley, "Th17 cell, the new player of neuroinflammatory process in multiple sclerosis" *Scand J Immunol,* 2011, 74(1):1-13.
Jahagirdar, R. et al., "An Orally Bioavailabie Small Molecule RVX-297 Significantly Decreases Disease in a Mouse Modelof Multiple Sclerosis" (Poster Presentation) World Congress of Inflammation, Paris, France, 2011, 1 page.
Jen, H.-Y. et al., "Increased serum interleukin-17 and peripheral Th17 cells in children with acute Henoch-Schonlein purpura" *Pediatr Allergy Immunol,* 2011. 22(8):862-8.
Jia, S., et al., "The T helper type 17/regulatory T cell imbalance in patients with acute Kawasaki disease" *Clin Exp Immunol,* 2010. 162(1):131-7.
Johnson, R.B. et al., "interleukin-11 and IL-17 and the pathogenesis of periodontal disease" *J Periodontol,* 2004. 75(1):37-43.
Kahawita, I.P. and D.N. Lockwood, "Towards understanding the pathology of erythema nodosum leprosum" *Trans R Soc Trop Med Hyg,* 2008. 102(4):329-37.
Kallen, K.J. et al., "New developments in IL-6 dependent biology and therapy: where do we stand and what are the options?" *Expert Opin Investig Drugs,* 1999. 8(9):1327-49.
Kaplanski, G. et al., "Jarisch-Herxheimer reaction complicating the treatment of chronic Q fever endocarditis: elevated TNFalpha and IL-6 serum levels" *J Infect,* 1998. 37(1):63-4.
Kappel, L.W. et al., "IL-17 contributes to CD4-mediated graft-versus-host disease" *Blood,* 2009. 113(4):945-52.
Katsifis, G.E. et al., "Systemic and local interleukin-17 and linked cytokines associated with Sjogren's syndrome immunopathogenesis" *Am J Pathol,* 2009, 175(3):1167-77.
Kawai, M. et al., "Sustained response to tocilizumab, anti-interleukin-6 receptor antibody, In two patients with refractory relapsing polychondritis" *Rheumatology,* 2009. 48(3):318-9.
Kawakami, T. et al., "Reduction of interleukin-6, interleukin-8, and anti-phosphatidylserine-prothrombin complex antibody by granulocyte and monocyte adsorption apheresis in a patient with pyoderma gangrenosum and ulcerative colitis" *Am J Gastroenterol,* 2009. 104(9):2363-4.
Kawakami T. et al., "Serum levels of interleukin-6 in patients with cutaneous polyarteritis nodosa" *Acta Derm Venereol,* 2012. 92(3):322-3.
Kelly, P.N. and A. Strasser, "The role of Bcl-2 and its pro-survival relatives in tumourigenesis and cancer therapy" *Cell Death Differ,* 2011. 18(9):1414-24.
Kim, S.E. et al., "Increased serum interleukin-17 in Graves' ophthalmopathy" *Graefes Arch Clin Exp Ophthalmol,* 2012. 250(10):1521-6.
Kimura, A. and T. Kishimoto, "IL-6: regulator of Treg/Th17 balance" *Eur J Immunol,* 2010. 40(7):1830-5.
Koch, A.E. et al., "Enhanced production of monocyte chemoattractant protein-1 in rheumatoid arthritis" *J Clin Invest,* 1992. 90(3):772-9.
Kyburz, D. and M. Corr, "Th17 cells generated in the absence of TGF-beta induce experimental allergic encephalitis upon adoptive transfer" *Expert Rev Clin Immunol,* 2011. 7(3):283-5.
Lahdenpera, A.I. et al., "Up-regulation of small intestinal interleukin-17 immunity in untreated coeliac disease but not in potential coeliac disease or in type 1 diabetes" *Clin Exp Immunol,* 2012. 167(2):226-34.
Lamale, L.M. et al., "Interleukin-6, histamine, and methylhistamine as diagnostic markers for interstitial cystitis" *Urology,* 2006. 68(4):702-6.
Lamotte, Y. et al., "Identification of a novel series of BET family Bromodomain inhibitors: binding mode and profile of I-BET151 (GSK1210151A)" Bioorganic & Medicinal Chemistry Letters, 2012. Accepted manuscript, doi: 10.1016/j.bmcl.2012.02.041. Final publication as: Seal, J. et al., "Identification of a novel series of BET family bromodomain inhibitors: binding mode and profile of I-BET151 (GSK1210151A)" *Bioorg Med Chem Lett,* 2012. 22(8):2968-72.
Latifi, S.Q. et al., "Persistent elevation of serum interleukin-6 in intraabdominal sepsis identifies those with prolonged length of stay" *J Pediatr Surg,* 2004. 39(10):1548-52.
Lee, D.K. et al., "Androgen receptor interacts with the positive elongation factor P-TEFb and enhances the efficiency of transcriptional elongation" *J Biol Chem,* 2001. 276(13):9978-84.
Li, Z. et al., "The BET bromodomain inhibitor JQ1 activates HIV latency through antagonizing Brd4 inhibition of Tat-transactivation" *Nucleic Acids Res Advance Access,* 2012. DOI:10.1093/nar/gks976. 11 pages.
Lin, F.J. et al., "Imbalance of regulatory T cells to Th17 cells in IgA nephropathy" *Scand J Clin Lab Invest,* 2012. 72(3):221-9.

(56) References Cited

OTHER PUBLICATIONS

Linhares, U.C. et al., "The Ex Vivo Production of IL-6 and IL-21 by CD4(+) T Cells is Directly Associated with Neurological Disability in Neuromyelitis Optica Patients" *J Clin Immunol,* 2012, DOI 10.1007/s10875-012-9780-2, 11 pages.
Lopez-Robles, E. et al., "TNFalpha and IL-6 are mediators in the blistering process of pemphigus" *Int J Dermatol,* 2001. 40(3):185-8.
Lu, M.O. and J. Zhu, "The role of cytokines in Guillain-Barre syndrome" *J Neurol,* 2011. 258(4):533-48.
Ma, D. et al., "Profile of Th17 cytokines (IL-17, TGF-beta, IL-6) and Th1 cytokine (IFN-gamma) in patients with immune thrombocytopenic purpura" *Ann Hematol,* 2008. 87(11):899-904.
Mahad, D.J. and R.M. Ransohoff, "The role of MCP-1 (CCL2) and CCR2 in multiple sclerosis and experimental autoimmune encephalomyelitis (EAE)" *Semin Immunol,* 2003. 15(1):23-32.
Matzuk, M.M. et al., "Small-Molecule inhibition of BRDT for Male Contraception" *Cell,* 2012. 150(4):673-684, with supplemental pp. S1-S8.
McLaughlin-Drubin, M.E. and K. Munger, "Viruses Associated with Human Cancer" *Biochim Biophys Acta,* 2008. 1782(3):127-150. NIH Public Access Author Manuscript; available in PMC Mar. 1, 2009 (50 pages).
McKinley, L. et al., "TH17 cells mediate steroid-resistant airway inflammation and airway hyperresponsiveness in mice" *J Immunol,* 2008. 181(6):4089-97.
McMahon, G. "VEGF Receptor Signaling in Tumor Angiogenesis" *The Oncologist,* 5(Suppl 1):3-10 (2000).
Mendrzyk, F. et al., "Genomic and protein expression profiling identifies CDK6 as novel independent prognostic marker in medulloblastoma" *J Clin Oncol,* 2005. 23(34):8853-62.
Mertz, J.A., "Targeting MYC Dependence in Cancer by Inhibiting BET Bromodomains", *PNAS,* 108(40):16669-16674 (2011).
Min, C.K. et al., "Cutaneous leucoclastic vasculitis (LV) following bortezomib therapy in a myeloma patient: association with pro-inflammatory cytokines" *Eur J Haematol,* 2006. 76(3):265-8.
Mirguet, O. et al., "From ApoA1 upregulation to BET family bromodomain inhibition: discovery of I-BET151" *Bioorg Med Chem Lett,* Article in Press, 2012. doi: 10.1016/j.bmcl.2012.01.125, 5 pages. Final publication in vol. 22, No. 8, pp. 2963-2967.
Mitsuyama, K. et al., "STAT3 activation via interleukin 6 trans-signalling contributes to ileitis in SAMP1/Yit mice" *Gut,* 2006. 55(9):1263-9.
Miyazaki, et al. "Intravenous Injection of Rabbit Apolipoprotein A-I inhibits the Progression of Atherosclerosis in Cholesterol-Fed Rabbits" *Arterioscler. Thromb. Vasc. Biol.* 15:1882-1888 (1995).
Mok, M.Y. et al., "The relation of interleukin 17 (IL-17) and IL-23 to Th1/Th2 cytokines and disease activity in systemic lupus erythematosus" *J Rheumatol,* 2010. 37(10):2046-52.
Morin, R.D. et al., "Frequent mutation of histone-modifying genes in non-Hodgkin lymphoma" *Nature,* 2011. 476(7360):298-303. (Author manuscript, 17 pages.).
Mudter, J. and M.F. Neurath, "IL-6 signaling in inflammatory bowel disease: pathophysiological role and clinical relevance" *Inflamm Bowel Dis,* 2007. 13(8):1016-23.
Muller Kobold, A.C. et al., "In vitro up-regulation of E-selectin and induction of interleukin-6 in endothelial cells by autoantibodies in Wegener's granulomatosis and microscopic polyangiitis" *Clin Exp Rheumatol,* 1999. 17(4):433-40.
Muller, S. et al., "Bromodomains as therapeutic targets" *Expert Rev Mol Med,* 2011. 13: e29, 21 pages.
Nakahama, H. et al., "Distinct responses of interleukin-6 and other laboratory parameters to treatment in a patient with Wegener's granulomatosis" *Intern Med,* 1993. 32(2):189-92.
Nelken, N.A. et al., "Monocyte chemoattractant protein-1 in human atheromatous plaques" *J Clin Invest,* 1991. 88(4):1121-7.
Ni, J. et al., "Involvement of interleukin-17A in Pancreatic Damage in Rat Experimental Acute Necrotizing Pancreatitis" *Inflammation,* 2012. [online] DOI: 10.1007/s10753-012-9519-5, published Sep. 19, 2012 (13 pages).
Niu, J. and P.E. Kolattukudy, "Role of MCP-1 in cardiovascular disease: molecular mechanisms and clinical implications" *Clin Sci,* 2009. 117(3):95-109.
Ooi, J.D. et al, "Review: T helper 17 cells: their role in glomerulonephritis" *Nephrology,* 2010. 15(5):513-21.
Ortiz-Lucas, M. et al., "Irritable bowel syndrome immune hypothesis. Part two: the role of cytokines" *Rev Esp Enferm Dig,* 2010. 102(12):711-7.
Ott, C.J. et al., "BET bromodomain inhibition targets both c-Myc and IL7R in high-risk acute lymphoblastic leukemia" *Blood,* 2012. 120(14):2843-52.
Pakrashi, S.C. "4-Quinazolinones. II, Self-condensation of anthranilamide" *J Org Chem,* 36(5):642-645 (1971).
Palermo, R.D. et al., "RNA polymerase II stalling promotes nucleosome occlusion and pTEFb recruitment to drive immortalization by Epstein-Barr virus." *PLoS Pathog,* 2011. 7(10): e1002334, 15 pages.
Paquet, P. and G.E. Pierard, "Interleukin-6 and the skin" *Int Arch Allergy Immunol,* 1996:109(4):308-17.
Patton, J.T. et al., "Silvestrol Modulates Direct Anti-Tumor Activity Against Epstein-Barr Virus (EBV) Associated Lymphomas While Sparing Innate and Antigen Specific Adaptive Immunity" *Blood,* 2011. 118:Abstract 104 (2 pages).
Peserico, A. and C. Simone, "Physical and functional HAT/HDAC interplay regulates protein acetylation balance" *J Biomed Biotechnol,* 2011. 371832, 10 pages.
Pinedo, H.M. and D.J. Slamon, "Translational Research: The Role of VEGF in Tumor Angiogenesis" *The Oncologist.* 5(Suppl. 1):1-2 (2000).
Poreba, E. et al., "Epigenetic mechanisms in virus-induced tumorigenesis" *Clin Epigenetics,* 2011. 2(2):233-47.
Prabakaran, K. et al., "Iridium bromide catalysed, ultrasound-assisted, region-selective synthesis of ethyl-5-(trifluoromethyl)-1-(3-substituted-isoquinolin-l-yl)-1H-pyrazole-4-carboxylates", *Res. Chem. Intermed.,* 38:429-441 (2012).
Prinjha, R.K. et al., "Place your BETs: the therapeutic potential of bromodomains" *Trends Pharmacol Sci,* 2012. 33(3):146-53.
Radstake, T.R. et al., "The pronounced Th17 profile in systemic sclerosis (SSc) together with intracellular expression of TGFbeta and IFNgamma distinguishes SSc phenotypes" *PLoS One,* 2009. 4(6):e5903. 9 pages.
Ramsay, R.G. and T.J. Gonda, "MYB function in normal and cancer cells" *Nat Rev Cancer,* 2008. 8(7):523-34.
Raychaudhuri, S.P. et al., "IL-17 receptor and its functional significance in psoriatic arthritis" *Mol Cell Biochem,* 2012. 359(1-2):419-29.
Rhodus, N.L. et al., "Proinflammatory cytokine levels in saliva before and after treatment of (erosive) oral lichen planus with dexamethasone" *Oral Dis,* 2006. 12(2):112-6.
Rodriguez, R.M. et al., "Aberrant epigenetic regulation of bromodomain BRD4 in human colon cancer" *J Mol Med,* 2012. 90(5):587-95.
Roger, V.L. et al., "Heart disease and stroke statistics—2012 update: a report from the American Heart Association" *Circulation,* 2012. 125(1):3-e220.
Ruden, M. and N. Puri, "Novel anticancer therapeutics targeting telomerase" *Cancer Treat Rev,* 2012. Article in Press: http://dx.doi.org/10.1016/j.ctrv.2012.06.007, 13 pages.
Rudloff, U. and Y. Samuels, "TYRO3-mediated regulation of MITF: a novel target in melanoma" *Pigment Cell Melanoma Res,* 2010, 23(1):9-11.
Sanchez, R. and M.M. Zhou, "The role of human bromodomains in chromatin biology and gene transcription" *Curr Opin Drug Discov Devel,* 2009, 12(5):659-65. (Author manuscript, 12 pages.).
Scanlan, M.J. et al., "Expression of cancer testis antigens in lung cancer: definition of bromodomain testis-specific gene (BRDT) as a new CT gene, CT9" *Cancer Lett,* 2000. 150(2):155-64.
Seal, J. et al., "Identification of a novel series of BET family bromodomain inhibitors Binding mode and profile of I-BET15l(GSK121051A)" *Bioorg. Med. Chem. Lett.,* 22:2968-2972 (2012).

(56) References Cited

OTHER PUBLICATIONS

Segura, M.F. et al., "BRD4 is a novel therapeutic target in melanoma" Poster Presentation, AACR 103rd Annual Meeting, Mar. 31-Apr. 4. 2012 in Chicago, IL. Cancer Research, 2012. 72(8), Supplement 1, Abstract 2185.
Shang, E. et al., "The first bromodomain of Brdt, a testis-specific member of the BET sub-family of double-bromodomain-containing proteins, is essential for male germ cell differentiation" Development, 2007. 134(19):3507-15.
Shibuya, M. et al., "Successful treatment with tocilizumab in a case of Cogan's syndrome complicated with aortitis" Mod Rheumatol, 2012. online: DOI 10.1007/s10165-012-0691-0, 5 pages.
Simmons, E.M. et al., "Plasma cytokine levels predict mortality in patients with acute renal failure" Kidney Int, 2004. 65(4):1357-65.
Simone, C. and A. Giordano, "Abrogation of signal-dependent activation of the cdk9/cyclin T2a complex in human RD rhabdomyosarcoma cells" Cell Death Differ, 2007. 14(1):192-5.
Soltesz, P. et al., "Immunological features of primary antiphospholipid syndrome in connection with endothelial dysfunction" Rheumatology, 2008. 47(11):1628-34.
Stenman, G. et al., "New tricks from an old oncogene: gene fusion and copy number alterations of MYB in human cancer" Cell Cycle, 2010. 9(15):2986-95.
Sun, Y. et al., "MMP-9 and IL-6 are potential biomarkers for disease activity in Takayasu's arteritis" Int J Cardiol, 2012. 156(2):236-8.
Tang, X. et al, "Assessment of Brd4 inhibition in idiopathic pulmonary fibrosis lung fibroblasts and in vivo models of lung fibrosis" Am. J. Pathol., 183(2):470-479 (2013).
Taylan, A. et al., "Evaluation of the T helper 17 axis in ankylosing spondylitis" Rheumatol Int, 2012. 32(8):2511-5.
Tong, W.G. et al., "Phase I and pharmacologic study of SNS-032, a potent and selective Cdk2, 7, and 9 inhibitor, in patients with advanced chronic lymphocytic leukemia and multiple myeloma" J Clin Oncol, 2010. 28(18):3015-22.
Traves, S.L. and L.E. Donnelly, "Th17 cells in airway diseases" Curr. Mol. Med., 2008. 8(5):416-26.
Uchida. T. et al., "Antitumor effect of bcl-2 antisense phosphorothioate oligodeoxynucleotides on human renal-cell carcinoma cells in vitro and in mice" Mol Urol, 2001. 5(2):71-8.
Urano, W. et al., "The inflammatory process in the mechanism of decreased serum uric acid concentrations during acute gouty arthritis" J Rheumatol, 2002. 29(9):1950-3.
Utsunomiya, I. et al., "Preparation of Alkyl-Substituted Indoles in the Benzene Portion. Part 13. Enantiospecific Synthesis of Mitosene Analogues Related to FFR 900482 and FR 66979" Chem Pharm Bull, 43(1):37-48.
Velisek, L. et al., "GABAergic neuron deficit as an idiopathic epilepsy mechanism: the role of BRD2 haploinsufficiency in juvenile myoclonic epilepsy" PLoS One, 2011 6(8): e23656, 8 pages.
Vernarecci, S. et al., "Tuning acetyiated chromatin with HAT inhibitors: a novel tool for therapy" Epigenetics, 2010. 5(2): p. 105-11.
Vippagunta, S.R. et al., "Crystalline solids" Adv Drug Del Rev, 2001. 46:3-26.
Vita, M. and M. Henriksson, "The Myc oncoprotein as a therapeutic target for human cancer" Semin Cancer Biol, 2006. 16(4):318-30.
Wang, F. et al., "Brd2 disruption in mice causes severe obesity without Type 2 diabetes" Biochem J, 2010. 425(1). p. 71-83, with supplemental online material, 2 pages.
Wang, G. et al., "Increased cyclin-dependent kinase 6 expression in bladder cancer" Oncol Lett, 2012. 4(1): p. 43-46.
Wang, S. and P.M. Fischer, "Cyclin-dependent kinase 9: a key transcriptional regulator and potential drug target in oncology, virology and cardiology" Trends Pharmacol Sci, 2008. 29(6):302-13.
Watson, J.D., "Curing "incurable" cancer" Cancer Discov, 2011. 1(6):477-80.
Whelligan, D.K. et al. "Aminopyrazine inhibitors binding to an unusual inactive conformation of the mitotic kinase Nek2: SAR and structural characterization" J Med Chem, 53(21):7682-7698 (2010).
Wu, S.Y. and C.M. Chiang, "The double bromodomain-containing chromatin adaptor Brd4 and transcriptional regulation" J Biol Chem, 2007 282(18):13141-5.
Xu, L. et al., "Critical role of Th17 cells in development of autoimmune hemolytic anemia" Exp Hematol, 2012. Article in Press: http://dx.doi.org/10.1016/j.exphem.2012.08.008, 15 pages.
Yamaguchi, M. et al., "Novel Antiasthmatic Agents with Dual Activities of Thromboxane $A_2$ Synthetase Inhibition and Bronchodilation. 1,2-[2-(1-imidazolyl)alkyl]-1(2H)-phthalazinones" J. Med. Chem., 36:4052-4060 (1993).
Yamashita, T. et al., "IL-6-mediated Th17 differentiation through RORγt is essential for the initiation of experimental autoimmune myocarditis" Cardiovasc Res, 2011. 91(4):640-8.
Yoshii, T. et al., "Local levels of interleukin-1beta, -4, -6 and tumor necrosis factor alpha in an experimental model of murine osteomyelitis due to Staphylococcus aureus" Cytokine, 2002. 19(2):59-65.
Yoshimura, T. et al., "Involvement of Th17 cells and the effect of anti-IL-6 therapy in autoimmune uveitis" Rheumatology, 48(4):347-354 (2009).
You, J. et al., "Kaposi's sarcoma-associated herpesvirus latency-associated nuclear antigen interacts with bromodomain protein Brd4 on host mitotic chromosomes" J Virol, 2006. 80(18):8909-19.
Yu et al., "Toll-Like Receptor 7 Agonists. Chemical Feature Based Pharmacophore Identification and Molecular Docking Studies" PLoS One 8(3):e56514, doi:10.1371/journal.pone.0056514 (2013).
Zhang, G. et al., "Down-regulation of NF-kappaB Transcriptional Activity in HIVassociated Kidney Disease by BRD4 Inhibition" JBC Papers in Press, 2012. M112.359505 with supplement, 38 pages. Final publication in: J Biol Chem, 287(34):28840-51.
Zhang, W.S. et al., "Bromodomain-Containing-Protein 4 (BRD4) Regulates RNA Polymerase II Serine 2 Phosphorylation in Human CD4+ T Cells" JBC Papers in Press, 2012. M112.413047, 30 pages. Final publication: J Biol Chem, 287:43137-55.
Zhao, L. et al., "Interleukin-17 contributes to the pathogenesis of autoimmune hepatitis through inducing hepatic interleukin-6 expression" PLoS One, 2011. 6(4):e18909, 8 pages.
Zhou, M. et al., "Bromodomain protein Brd4 regulates human immunodeficiency virus transcription through phosphorylation of CDK9 at threonine 29" J Virol, 2009. 83(2):1036-44.
Zhu, J. et al., "Reactivation of Latent HIV-1 by inhibition of BRD4" Cell Rep, 2012. 2:1-10, with supplemental pages S1-S7.
Zuber, J. et al., "RNAi screen identifies Brd4 as a therapeutic target in acute myeloid leukaemia" Nature, 2011. 478(7370):524-8.

\* cited by examiner

SUBSTITUTED BICYCLIC COMPOUNDS AS BROMODOMAIN INHIBITORS

CROSS-REFERENCE TO RELATED PATENT APPLICATIONS

This application is a continuation of U.S. application Ser. No. 14/900,139, filed Apr. 11, 2016, which is a national stage entry of International Patent Application No. PCT/IB2014/002238, filed Jun. 20, 2014, which claims the benefit of priority to U.S. Provisional Application No. 61/837,830, filed Jun. 21, 2013, and U.S. Provisional Application No. 61/911,668, filed Dec. 4, 2013, each of which is incorporated herein by reference in its entirety.

The invention provides novel compounds, pharmaceutical compositions containing such compounds, and their use in prevention and treatment of diseases and conditions associated with bromodomain and extra terminal domain (BET) proteins. Post-translational modifications (PTMs) of histones are involved in regulation of gene expression and chromatin organization in eukaryotic cells. Histone acetylation at specific lysine residues is a PTM that is regulated by histone acetylases (HATs) and deacetylases (HDACs). Peserico, A. and C. Simone, "Physical and functional HAT/HDAC interplay regulates protein acetylation balance," *J Biomed Biotechnol*, 2011:371832 (2011). Small molecule inhibitors of HDACs and HATs are being investigated as cancer therapy. Hoshino, I. and H. Matsubara, "Recent advances in histone deacetylase targeted cancer therapy" *Surg Today* 40(9):809-15 (2010); Vernarecci, S., F. Tosi, and P. Filetici, "Tuning acetylated chromatin with HAT inhibitors: a novel tool for therapy" *Epigenetics* 5(2):105-11 (2010); Bandyopadhyay, K., et al., "Spermidinyl-CoA-based HAT inhibitors block DNA repair and provide cancer-specific chemo- and radiosensitization," *Cell Cycle* 8(17):2779-88 (2009); Arif, M., et al., "Protein lysine acetylation in cellular function and its role in cancer manifestation," *Biochim Biophys Acta* 1799(10-12):702-16 (2010). Histone acetylation controls gene expression by recruiting protein complexes that bind directly to acetylated lysine via bromodomains. Sanchez, R. and M. M. Zhou, "The role of human bromodomains in chromatin biology and gene transcription," *Curr Opin Drug Discov Devel* 12(5):659-65 (2009). One such family, the bromodomain and extra terminal domain (BET) proteins, comprises Brd2, Brd3, Brd4, and BrdT, each of which contains two bromodomains in tandem that can independently bind to acetylated lysines, as reviewed in Wu, S. Y. and C. M. Chiang, "The double bromodomain-containing chromatin adaptor Brd4 and transcriptional regulation," *J Biol Chem* 282(18):13141-5 (2007).

Interfering with BET protein interactions via bromodomain inhibition results in modulation of transcriptional programs that are often associated with diseases characterized by dysregulation of cell cycle control, inflammatory cytokine expression, viral transcription, hematopoietic differentiation, insulin transcription, and adipogenesis. Belkina, A. C. and G. V. Denis, "BET domain co-regulators in obesity, inflammation and cancer," *Nat Rev Cancer* 12(7): 465-77 (2012). BET inhibitors are believed to be useful in the treatment of diseases or conditions related to systemic or tissue inflammation, inflammatory responses to infection or hypoxia, cellular activation and proliferation, lipid metabolism, fibrosis, and the prevention and treatment of viral infections. Belkina, A. C. and G. V. Denis, "BET domain co-regulators in obesity, inflammation and cancer," *Nat Rev Cancer* 12(7):465-77 (2012); Prinjha, R. K., J. Witherington, and K. Lee, "Place your BETs: the therapeutic potential of bromodomains," *Trends Pharmacol Sci* 33(3):146-53 (2012).

Autoimmune diseases, which are often chronic and debilitating, are a result of a dysregulated immune response, which leads the body to attack its own cells, tissues, and organs. Pro-inflammatory cytokines including IL-1β, TNF-α, IL-6, MCP-1, and IL-17 are overexpressed in autoimmune disease. IL-17 expression defines the T cell subset known as Th17 cells, which are differentiated, in part, by IL-6, and drive many of the pathogenic consequences of autoimmune disease. Thus, the IL-6/Th17 axis represents an important, potentially druggable target in autoimmune disease therapy. Kimura, A. and T. Kishimoto, "IL-6: regulator of Treg/Th17 balance," *Eur J Immunol* 40(7):1830-5 (2010). BET inhibitors are expected to have anti-inflammatory and immunomodulatory properties. Belkina, A. C. and G. V. Denis, "BET domain co-regulators in obesity, inflammation and cancer," *Nat Rev Cancer* 12(7):465-77 (2012); Prinjha, R. K., J. Witherington, and K. Lee, "Place your BETs: the therapeutic potential of bromodomains," *Trends Pharmacol Sci* 33(3):146-53 (2012). BET inhibitors have been shown to have a broad spectrum of anti-inflammatory effects in vitro including the ability to decrease expression of pro-inflammatory cytokines such as IL-1β, MCP-1, TNF-α, and IL-6 in activated immune cells. Mirguet, O., et al., "From ApoA1 upregulation to BET family bromodomain inhibition: discovery of I-BET151," *Bioorg Med Chem Lett* 22(8):2963-7 (2012); Nicodeme, E., et al., "Suppression of inflammation by a synthetic histone mimic," *Nature* 468(7327):1119-23 (2010); Seal, J., et al., "Identification of a novel series of BET family bromodomain inhibitors: binding mode and profile of I-BET151 (GSK1210151A)," *Bioorg Med Chem Lett* 22(8):2968-72 (2012). The mechanism for these anti-inflammatory effects may involve BET inhibitor disruption of Brd4 co-activation of NF-κB-regulated pro-inflammatory cytokines and/or displacement of BET proteins from cytokine promoters, including IL-6. Nicodeme, E., et al., "Suppression of inflammation by a synthetic histone mimic," *Nature* 468(7327):1119-23 (2010); Zhang, G., et al., "Down-regulation of NF-kappaB Transcriptional Activity in HIVassociated Kidney Disease by BRD4 Inhibition," *J Biol Chem*, 287(34):8840-51 (2012); Zhou, M., et al., "Bromodomain protein Brd4 regulates human immunodeficiency virus transcription through phosphorylation of CDK9 at threonine 29," *J Virol* 83(2):1036-44 (2009). In addition, because Brd4 is involved in T-cell lineage differentiation, BET inhibitors may be useful in inflammatory disorders characterized by specific programs of T cell differentiation. Zhang, W. S., et al., "Bromodomain-Containing-Protein 4 (BRD4) Regulates RNA Polymerase II Serine 2 Phosphorylation in Human CD4+ T Cells," *J Biol Chem* (2012).

The anti-inflammatory and immunomodulatory effects of BET inhibition have also been confirmed in vivo. A BET inhibitor prevented endotoxin- or bacterial sepsis-induced death and cecal ligation puncture-induced death in mice, suggesting utility for BET inhibitors in sepsis and acute inflammatory disorders. Nicodeme, E., et al., "Suppression of inflammation by a synthetic histone mimic," *Nature* 468(7327):1119-23 (2010). A BET inhibitor has been shown to ameliorate inflammation and kidney injury in HIV-1 transgenic mice, an animal model for HIV-associated nephropathy, in part through inhibition of Brd4 interaction with NF-MB. Zhang, G., et al., "Down-regulation of NF-kappaB Transcriptional Activity in HIV associated Kidney Disease by BRD4 Inhibition," *J Biol Chem*, 287(34):8840-51 (2012). The utility of BET inhibition in autoimmune disease was demonstrated in a mouse model of multiple sclerosis, where BET inhibition resulted in abrogation of clinical signs of disease, in part, through inhibition of 11-6 and IL-17. R. Jahagirdar, S. M. et al., "An Orally Bioavailable Small Molecule RVX-297 Significantly Decreases Disease in a Mouse Model of Multiple Sclerosis," *World Congress of Inflammation*, Paris, France (2011). These results were supported in a similar mouse model where it was shown that treatment with a BET inhibitor inhibited T cell differentiation into pro-autoimmune Th1 and Th17 subsets in vitro, and further abrogated disease induction by pro-inflammatory Th1 cells. Bandukwala, H. S., et al., "Selective inhibition of CD4+ T-cell cytokine production and autoimmunity by BET protein and c-Myc inhibitors," *Proc Natl Acad Sci USA*, 109(36):14532-7 (2012).

BET inhibitors may be useful in the treatment of a variety of chronic autoimmune inflammatory conditions. Thus, one aspect of the invention provides compounds, compositions, and methods for treating autoimmune and/or inflammatory diseases by administering one or more compounds of the invention or pharmaceutical compositions comprising one or more of those compounds. Examples of autoimmune and inflammatory diseases, disorders, and syndromes that may be treated using the compounds and methods of the invention include but are not limited to, inflammatory pelvic disease, urethritis, skin sunburn, sinusitis, pneumonitis, encephalitis, meningitis, myocarditis, nephritis (Zhang, G., et al., "Down-regulation of NF-kappaB Transcriptional Activity in HIVassociated Kidney Disease by BRD4 Inhibition," *J Biol Chem*, 287(34):8840-51 (2012)), osteomyelitis, myositis, hepatitis, gastritis, enteritis, dermatitis, gingivitis, appendicitis, pancreatitis, cholecystitis, agammaglobulinemia, psoriasis, allergy, Crohn's disease, irritable bowel syndrome, ulcerative colitis (Prinjha, R. K., J. Witherington, and K. Lee, "Place your BETs: the therapeutic potential of bromodomains," *Trends Pharmacol Sci* 33(3):146-53 (2012)), Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis (Bandukwala, H. S., et al., "Selective inhibition of CD4+ T-cell cytokine production and autoimmunity by BET protein and c-Myc inhibitors," *Proc Natl Acad Sci USA*, 109(36):14532-7 (2012)), scleroderma, vasculitis, autoimmune hemolytic and thrombocytopenic states, Goodpasture's syndrome, atherosclerosis, Addison's disease, Parkinson's disease, Alzheimer's disease, Type I diabetes (Belkina, A. C. and G. V. Denis, "BET domain co-regulators in obesity, inflammation and cancer," *Nat Rev Cancer* 12(7):465-77 (2012)), septic shock (Zhang, G., et al., "Down-regulation of NF-kappaB Transcriptional Activity in HIVassociated Kidney Disease by BRD4 Inhibition," *J Biol Chem*, 287(34):8840-51 (2012)), systemic lupus erythematosus (SLE) (Prinjha, R. K., J. Witherington, and K. Lee, "Place your BETs: the therapeutic potential of bromodomains," *Trends Pharmacol Sci* 33(3):146-53 (2012)), rheumatoid arthritis (Denis, G. V., "Bromodomain coactivators in cancer, obesity, type 2 diabetes, and inflammation," *Discov Med* 10(55):489-99 (2010)), psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, uveitis, dry eye disease, scleroderma, mycosis fungoides, and Graves' disease.

BET inhibitors may be useful in the treatment of a wide variety of acute inflammatory conditions. Thus, one aspect of the invention provides compounds, compositions, and methods for treating inflammatory conditions including but not limited to, acute gout, giant cell arteritis, nephritis including lupus nephritis, vasculitis with organ involvement, such as glomerulonephritis, vasculitis, including giant cell arteritis, Wegener's granulomatosis, polyarteritis nodosa, Behcet's disease, Kawasaki disease, and Takayasu's arteritis.

BET inhibitors may be useful in the prevention and treatment of diseases or conditions that involve inflammatory responses to infections with bacteria, viruses, fungi, parasites, and their toxins, such as, but not limited to sepsis, sepsis syndrome, septic shock (Nicodeme, E., et al., "Suppression of inflammation by a synthetic histone mimic," *Nature* 468(7327):1119-23 (2010)), systemic inflammatory response syndrome (SIRS), multi-organ dysfunction syndrome, toxic shock syndrome, acute lung injury, adult respiratory distress syndrome (ARDS), acute renal failure, fulminant hepatitis, burns, post-surgical syndromes, sarcoidosis, Herxheimer reactions, encephalitis, myelitis, meningitis, malaria, and SIRS associated with viral infections, such as influenza, herpes zoster, herpes simplex, and coronavirus. Belkina, A. C. and G. V. Denis, "BET domain co-regulators in obesity, inflammation and cancer," *Nat Rev Cancer* 12(7):465-77 (2012). Thus, one aspect of the invention provides compounds, compositions, and methods for treating these inflammatory responses to infections with bacteria, viruses, fungi, parasites, and their toxins described herein.

Cancer is a group of diseases caused by dysregulated cell proliferation. Therapeutic approaches aim to decrease the numbers of cancer cells by inhibiting cell replication or by inducing cancer cell differentiation or death, but there is still significant unmet medical need for more efficacious therapeutic agents. Cancer cells accumulate genetic and epigenetic changes that alter cell growth and metabolism, promoting cell proliferation and increasing resistance to programmed cell death, or apoptosis. Some of these changes include inactivation of tumor suppressor genes, activation of oncogenes, and modifications of the regulation of chromatin structure, including deregulation of histone PTMs. Watson, J. D., "Curing 'incurable' cancer," *Cancer Discov* 1(6):477-80 (2011); Morin, R. D., et al., "Frequent mutation of histone-modifying genes in non-Hodgkin lymphoma" *Nature* 476(7360):298-303 (2011).

One aspect of the invention provides compounds, compositions, and methods for treating human cancer, including, but not limited to, cancers that result from aberrant translocation or overexpression of BET proteins (e.g., NUT midline carcinoma (NMC) (French, C. A., "NUT midline carcinoma," *Cancer Genet Cytogenet* 203(1):16-20 (2010) and B-cell lymphoma (Greenwald, R. J., et al., "E mu-BRD2 transgenic mice develop B-cell lymphoma and leukemia," *Blood* 103(4):1475-84 (2004)). NMC tumor cell growth is driven by a translocation of the Brd4 or Brd3 gene to the nutlin 1 gene. Filippakopoulos, P., et al., "Selective inhibition of BET bromodomains," *Nature* 468(7327):1067-73 (2010). BET inhibition has demonstrated potent antitumor activity in murine xenograft models of NMC, a rare but lethal form of cancer. The present disclosure provides a method for treating human cancers, including, but not limited to, cancers dependent on a member of the myc family of oncoproteins including c-myc, MYCN, and L-myc. Vita, M. and M. Henriksson, "The Myc oncoprotein as a therapeutic target for human cancer," *Semin Cancer Biol* 16(4): 318-30 (2006). These cancers include Burkitt's lymphoma, acute myelogenous leukemia, multiple myeloma, and aggressive human medulloblastoma. Vita, M. and M. Henriksson, "The Myc oncoprotein as a therapeutic target for human cancer," *Semin Cancer Biol* 16(4):318-30 (2006). Cancers in which c-myc is overexpressed may be particularly susceptible to BET protein inhibition; it has been shown that treatment of tumors that have activation of c-myc with a BET inhibitor resulted in tumor regression through inactivation of c-myc transcription. Dawson, M. A., et al., Inhibition of BET recruitment to chromatin as an effective treatment for MLL-fusion leukaemia. Nature, 2011. 478 (7370): p. 529-33; Delmore, J. E., et al., "BET bromodomain inhibition as a therapeutic strategy to target c-Myc," *Cell* 146(6):904-17 (2010); Mertz, J. A., et al., "Targeting MYC dependence in cancer by inhibiting BET bromodomains," *Proc Natl Acad Sci USA* 108(40):16669-74 (2011); Ott, C. J., et al., "BET bromodomain inhibition targets both c-Myc and IL7R in highrisk acute lymphoblastic leukemia," *Blood* 120(14):2843-52 (2012); Zuber, J., et al., "RNAi screen identifies Brd4 as a therapeutic target in acute myeloid leukaemia," *Nature* 478(7370):524-8 (2011).

Embodiments of the invention include methods for treating human cancers that rely on BET proteins and pTEFb (Cdk9/CyclinT) to regulate oncogenes (Wang, S. and P. M. Fischer, "Cyclin-dependent kinase 9: a key transcriptional regulator and potential drug target in oncology, virology and cardiology," *Trends Pharmacol Sci* 29(6):302-13 (2008)), and cancers that can be treated by inducing apoptosis or senescence by inhibiting Bcl2, cyclin-dependent kinase 6 (CDK6)(Dawson, M. A., et al., "Inhibition of BET recruitment to chromatin as an effective treatment for MLL-fusion leukaemia," *Nature* 478(7370):529-33 (2011)), or human telomerase reverse transcriptase (hTERT). Delmore, J. E., et al., "BET bromodomain inhibition as a therapeutic strategy to target c-Myc," *Cell* 146(6):904-17 (2010); Ruden, M. and N. Puri, "Novel anticancer therapeutics targeting telomerase," *Cancer Treat Rev* (2012).

BET inhibitors may be useful in the treatment of cancers including, but not limited to, adrenal cancer, acinic cell carcinoma, acoustic neuroma, acral lentiginous melanoma, acrospiroma, acute eosinophilic leukemia, acute erythroid leukemia, acute lymphoblastic leukemia, acute megakaryoblastic leukemia, acute monocytic leukemia, acute myeloid leukemia (Dawson, M. A., et al., "Inhibition of BET recruitment to chromatin as an effective treatment for MLL-fusion leukaemia," *Nature* 478(7370):529-33 (2011); Mertz, J. A., et al., "Targeting MYC dependence in cancer by inhibiting BET bromodomains," *Proc Natl Acad Sci USA* 108(40): 16669-74 (2011); Zuber, J., et al., "RNAi screen identifies Brd4 as a therapeutic target in acute myeloid leukaemia," *Nature* 478(7370):524-8 (2011)), adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell acute lymphoblastic leukemia (Ott, C. J., et al., "BET bromodomain inhibition targets both c-Myc and IL7R in highrisk acute lymphoblastic leukemia," *Blood* 120(14):2843-52 (2012)), B-cell chronic lymphocytic leukemia, B-cell prolymphocytic leukemia, B-cell lymphoma (Greenwald, R. J., et al., "E mu-BRD2 transgenic mice develop B-cell lymphoma and leukemia,". *Blood* 103(4):1475-84 (2004)), basal cell carcinoma, biliary tract cancer, bladder cancer, blastoma, bone cancer, Brenner tumor, Brown tumor, Burkitt's lymphoma (Mertz, J. A., et al., "Targeting MYC dependence in cancer by inhibiting BET bromodomains," *Proc Natl Acad Sci USA* 108(40):16669-74 (2011)), breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, Leydig cell tumor, liposarcoma, lung cancer, lymphangioma, lymphanglosarcoma, lymphoepithelioma, lymphoma, acute lymphocytic leukemia, acute myelogenous leukemia (Mertz, J. A., et al., "Targeting MYC dependence in cancer by inhibiting BET bromodomains," *Proc Natl Acad Sci USA* 108(40):16669-74 (2011)), chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma (Miguel F. Segura, et al, "BRD4 is a novel therapeutic target in melanoma," *Cancer Research.* 72(8): Supplement 1 (2012)), meningioma, Merkel cell cancer, mesothelioma, metastatic urothelial carcinoma, mixed Mullerian tumor, mixed lineage leukemia (Dawson, M. A., et al., "Inhibition of BET recruitment to chromatin as an effective treatment for MLL-fusion leukaemia," *Nature* 478(7370): 529-33 (2011)), mucinous tumor, multiple myeloma (Delmore, J. E., et al., "BET bromodomain inhibition as a therapeutic strategy to target c-Myc," *Cell* 146(6):904-17 (2010)), muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, NUT-midline carcinoma (Filippakopoulos, P., et al., "Selective inhibition of BET bromodomains," *Nature* 468(7327):1067-73 (2010)), ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, primary peritoneal cancer, prostate cancer, pancreatic cancer, pharyngeal cancer, pseudomyxoma peritonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor. Thus, one aspect of the inventions provides compounds, compositions, and methods for treating such cancers.

BET inhibitors may be useful in the treatment of benign proliferative and fibrotic disorders, including benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, juvenile polyposis syndrome, idiopathic pulmonary fibrosis, renal fibrosis, post-operative stricture, keloid formation, scleroderma, and cardiac fibrosis. Tang, X et al., "Assessment of Brd4 Inhibition in Idiopathic Pulmonary Fibrosis Lung Fibroblasts and in Vivo Models of Lung Fibrosis,"*Am J Pathology in press* (2013). Thus, one aspect of the invention provides compounds, compositions, and methods for treating such benign proliferative and fibrotic disorders.

Cardiovascular disease (CVD) is the leading cause of mortality and morbidity in the United States. Roger, V. L., et al., "Heart disease and stroke statistics—2012 update: a report from the American Heart Association," *Circulation* 125(1):e2-e220 (2012). Atherosclerosis, an underlying cause of CVD, is a multifactorial disease characterized by dyslipidemia and inflammation. BET inhibitors are expected to be efficacious in atherosclerosis and associated conditions because of aforementioned anti-inflammatory effects as well as ability to increase transcription of ApoA-1, the major constituent of HDL. Mirguet, O., et al., "From ApoA1 upregulation to BET family bromodomain inhibition: discovery of I-BET151," *Bioorg Med Chem Lett* 22(8):2963-7 (2012); Chung, C. W., et al., "Discovery and characterization of small molecule inhibitors of the BET family bromodomains," *J Med Chem* 54(11):3827-38 (2011). Accordingly, one aspect of the invention provides compounds, compositions, and methods for treating cardiovascular disease, including but not limited to atherosclerosis.

Up-regulation of ApoA-I is considered to be a useful strategy in treatment of atherosclerosis and CVD. Degoma, E. M. and D. J. Rader, "Novel HDL-directed pharmaco-therapeutic strategies," *Nat Rev Cordial* 8(5):266-77 (2011) BET inhibitors have been shown to increase ApoA-I transcription and protein expression. Mirguet, O., et al., "From ApoA1 upregulation to BET family bromodomain inhibition: discovery of I-BET151," *Bioorg Med Chem Lett* 22(8):2963-7 (2012); Chung, C. W., et al., "Discovery and characterization of small molecule inhibitors of the BET family bromodomains," *J Med Chem* 54(11):3827-38 (2011). It has also been shown that BET inhibitors bind directly to BET proteins and inhibit their binding to acetylated histones at the ApoA-1 promoter, suggesting the presence of a BET protein repression complex on the ApoA-1 promoter, which can be functionally disrupted by BET inhibitors. It follows that, BET inhibitors may be useful in the treatment of disorders of lipid metabolism via the regulation of ApoA-1 and HDL such as hypercholesterolemia, dyslipidemia, atherosclerosis (Degoma, E. M. and D. J. Rader, "Novel HDL-directed pharmacotherapeutic strategies," *Nat Rev Cardiol* 8(5):266-77 (2011)), and Alzheimer's disease and other neurological disorders. Elliott, D. A., et al., "Apolipoproteins in the brain: Implications for neurological and psychiatric disorders," *Clin Lipidol* 51(4):555-573 (2010). Thus, one aspect of the invention provides compounds, compositions, and methods for treating cardiovascular disorders by upregulation of ApoA-1.

BET inhibitors may be useful in the prevention and treatment of conditions associated with ischemia-reperfusion injury such as, but not limited to, myocardial infarction, stroke, acute coronary syndromes (Prinjha, R. K., J. Witherington, and K. Lee, "Place your BETs: the therapeutic potential of bromodomains," *Trends Pharmacol Sci* 33(3): 146-53 (2012)), renal reperfusion injury, organ transplantation, coronary artery bypass grafting, cardio-pulmonary bypass procedures, hypertension, pulmonary, renal, hepatic, gastro-intestinal, or peripheral limb embolism. Accordingly, one aspect of the invention provides compounds, compositions, and methods for prevention and treatment of conditions described herein that are associated with ischemia-reperfusion injury.

Obesity-associated inflammation is a hallmark of type II diabetes, insulin resistance, and other metabolic disorders. Belkina, A. C. and G. V. Denis, "BET domain co-regulators in obesity, inflammation and cancer," *Nat Rev Cancer* 12(7): 465-77 (2012); Denis, G. V., "Bromodomain coactivators in cancer, obesity, type 2 diabetes, and inflammation," *Discov Med* 10(55):489-99 (2010). Consistent with the ability of BET inhibitors to inhibit inflammation, gene disruption of Brd2 In mice ablates inflammation and protects animals from obesity-induced insulin resistance. Wang, F., et al., "Brd2 disruption in mice causes severe obesity without Type 2 diabetes," *Biochem J* 425(1):71-83 (2010). It has been shown that Brd2 interacts with PPAR☐☐ and opposes its transcriptional function. Knockdown of Brd2 in vitro promotes transcription of PPAR☐-regulated networks, including those controlling adipogenesis. Denis, G. V., et al, "An emerging role for bromodomain-containing proteins in chromatin regulation and transcriptional control of adipogenesis," *FEBS Lett* 584(15):3260-8 (2010). In addition Brd2 is highly expressed in pancreatic ☐-cells and regulates proliferation and insulin transcription. Wang, F., et al., "Brd2 disruption in mice causes severe obesity without Type 2 diabetes," *Biochem J* 425(1):71-83 (2010). Taken together, the combined effects of BET inhibitors on inflammation and metabolism decrease insulin resistance and may be useful in the treatment of pre-diabetic and type II diabetic individuals as well as patients with other metabolic complications. Belkina, A. C. and G. V. Denis, "BET domain co-regulators in obesity, inflammation and cancer," *Nat Rev Cancer* 12(7): 465-77 (2012). Accordingly, one aspect of the invention provides compounds, compositions, and methods for treatment and prevention of metabolic disorders, including but not limited to obesity-associated inflammation, type II diabetes, and insulin resistance.

Host-encoded BET proteins have been shown to be important for transcriptional activation and repression of viral promoters. Brd4 interacts with the E2 protein of human papilloma virus (HPV) to enable E2 mediated transcription of E2-target genes. Gagnon, D., et al., "Proteasomal degradation of the papillomavirus E2 protein is inhibited by overexpression of bromodomain-containing protein 4," *J Virol* 83(9):4127-39 (2009). Similarly, Brd2, Brd3, and Brd4 all bind to latent nuclear antigen 1 (LANA1), encoded by Kaposi's sarcoma-associated herpes virus (KSHV), promoting LANA-dependent proliferation of KSHV-infected cells. You, J., et al., "Kaposi's sarcoma-associated herpesvirus latency-associated nuclear antigen interacts with bromodomain protein Brd4 on host mitotic chromosomes," *J Virol* 80(18):8909-19 (2006). A BET inhibitor has been shown to inhibit the Brd4-mediated recruitment of the transcription elongation complex pTEFb to the Epstein-Barr virus (EBV) viral C promoter, suggesting therapeutic value for EBV-associated malignancies. Palermo, R. D., et al., "RNA polymerase II stalling promotes nucleosome occlusion and pTEFb recruitment to drive immortalization by Epstein-Barr virus," *PLoS Pathog* 7(10):e1002334 (2011). Also, a BET inhibitor reactivated HIV in models of latent T cell infection and latent monocyte infection, potentially allowing for viral eradication by complementary anti-retroviral therapy. Zhu, J., et al., "Reactivation of Latent HIV-1 by Inhibition of BRD4," *Cell Rep* (2012); Banerjee, C., et al., "BET bromodomain inhibition as a novel strategy for reactivation of HIV-1," *J Leukoc Biol* (2012); Bartholomeeusen, K., et al., "BET bromodomain inhibition activates transcription via a transient release of P-TEFb from 7SK snRNP," *J Biol Chem* (2012); Li, Z., et al., "The BET bromodomain inhibitor JQ1 activates HIV latency through antagonizing Brd4 inhibition of Tat-transactivation," *Nucleic Acids Res* (2012).

BET inhibitors may be useful in the prevention and treatment of episome-based DNA viruses including, but not limited to, human papillomavirus, herpes virus, Epstein-Barr virus, human immunodeficiency virus (Belkina, A. C. and G. V. Denis, "BET domain co-regulators in obesity, inflammation and cancer," *Nat Rev Cancer* 12(7):465-77 (2012)), adenovirus, poxvirus, hepatitis B virus, and hepatitis C virus. Thus, the invention also provides compounds, compositions, and methods for treatment and prevention of episome-based DNA virus infections described herein.

Some central nervous system (CNS) diseases are characterized by disorders in epigenetic processes. Brd2 haploinsufficiency has been linked to neuronal deficits and epilepsy. Velisek, L., et al., "GABAergic neuron deficit as an idiopathic generalized epilepsy mechanism: the role of BRD2 haploinsufficiency in juvenile myoclonic epilepsy," *PLoS One* 6(8): e23656 (2011) SNPs in various bromodomain-containing proteins have also been linked to mental disorders including schizophrenia and bipolar disorders. Prinjha, R. K., J. Witherington, and K. Lee, "Place your BETs: the therapeutic potential of bromodomains," *Trends Pharmacol Sci* 33(3):146-53 (2012). In addition, the ability of BET inhibitors to increase ApoA-I transcription may make BET inhibitors useful in Alzheimer's disease therapy considering the suggested relationship between increased ApoA-I and Alzheimer's disease and other neurological disorders. Elliott, D. A., et al., "Apolipoproteins in the brain: implications for neurological and psychiatric disorders," *Clin Lipidol* 51(4):555-573 (2010). Accordingly, one aspect of the invention provides compounds, compositions, and methods for treating such CNS diseases and disorders.

BRDT is the testis-specific member of the BET protein family which is essential for chromatin remodeling during spermatogenesis. Gaucher, J., et al., "Bromodomain-dependent stage-specific male genome programming by Brdt," *EMBO J* 31(19):3809-20 (2012); Shang, E., et al., "The first bromodomain of Brdt, a testis-specific member of the BET sub-family of double-bromodomain-containing proteins, is essential for male germ cell differentiation," *Development* 134(19):3507-15 (2007). Genetic depletion of BRDT or inhibition of BRDT interaction with acetylated histones by a BET inhibitor resulted in a contraceptive effect in mice, which was reversible when small molecule BET inhibitors were used. Matzuk, M. M., et al., "Small-Molecule inhibition of BRDT for Male Contraception," *Cell* 150(4): 673-684 (2012); Berkovits, B. D., et al., "The testis-specific double bromodomain-containing protein BRDT forms a complex with multiple spliceosome components and is required for mRNA splicing and 3'-UTR truncation in round spermatids," *Nucleic Acids Res* 40(15):7162-75 (2012). These data suggest potential utility of BET inhibitors as a novel and efficacious approach to male contraception. Thus, another aspect of the invention provides compounds, compositions, and methods for male contraception.

Monocyte chemotactic protein-1 (MCP-1, CCL2) plays an important role in cardiovascular disease. Niu, J. and P. E. Kolattukudy, "Role of MCP-1 in cardiovascular disease: molecular mechanisms and clinical implications," *Clin Sci (Lond)* 117(3):95-109 (2009). MCP-1, by its chemotactic activity, regulates recruitment of monocytes from the arterial lumen to the subendothelial space, where they develop into macrophage foam cells, and initiate the formation of fatty streaks which can develop into atherosclerotic plaque. Dawson, J., et al., "Targeting monocyte chemoattractant protein-1 signalling in disease," *Expert Opin Ther Targets* 7(1):35-48 (2003). The critical role of MCP-1 (and its cognate receptor CCR2) in the development of atherosclerosis has been examined in various transgenic and knockout mouse models on a hyperlipidemic background. Boring, L., et al., "Decreased lesion formation in CCR2−/− mice reveals a role for chemokines in the initiation of atherosclerosis," *Nature* 394(6696):894-7 (1998); Gosling, J., et al., "MCP-1 deficiency reduces susceptibility to atherosclerosis in mice that overexpress human apolipoprotein B," *J Clin Invest* 103(6):773-8 (1999); Gu, L., et al., "Absence of monocyte chemoattractant protein-1 reduces atherosclerosis in low density lipoprotein receptor-deficient mice," *Mol Cell* 2(2):275-81 (1998); Aiello, R. J., et al., "Monocyte chemoattractant protein-1 accelerates atherosclerosis in apolipoprotein E-deficient mice," *Arterioscler Thromb Vasc Biol* 19(6):1518-25 (1999). These reports demonstrate that abrogation of MCP-1 signaling results in decreased macrophage infiltration to the arterial wall and decreased atherosclerotic lesion development.

The association between MCP-1 and cardiovascular disease in humans is well-established. Niu, J. and P. E. Kolattukudy, "Role of MCP-1 in cardiovascular disease: molecular mechanisms and clinical implications," *Clin Sci (Lond)* 117(3):95-109 (2009). MCP-1 and its receptor are overexpressed by endothelial cells, smooth muscle cells, and infiltrating monocytes/macrophages in human atherosclerotic plaque. Nelken, N. A., et al., "Monocyte chemoattractant protein-1 in human atheromatous plaques," *J Clin Invest* 88(4):1121-7 (1991). Moreover, elevated circulating levels of MCP-1 are positively correlated with most cardiovascular risk factors, measures of coronary atherosclerosis burden, and the incidence of coronary heart disease (CHD). Deo, R., et al., "Association among plasma levels of monocyte chemoattractant protein-1, traditional cardiovascular risk factors, and subclinical atherosclerosis," *J Am Coll Cardiol*

44(9):1812-8 (2004). CHD patients with among the highest levels of MCP-1 are those with acute coronary syndrome (ACS). de Lemos, J. A., et al., "Association between plasma levels of monocyte chemoattractant protein-1 and long-term clinical outcomes in patients with acute coronary syndromes," *Circulation* 107(5):690-5 (2003). In addition to playing a role in the underlying inflammation associated with CHD, MCP-1 has been shown to be involved in plaque rupture, ischemic/reperfusion injury, restenosis, and heart transplant rejection. Niu, J. and P. E. Kolattukudy, "Role of MCP-1 in cardiovascular disease: molecular mechanisms and clinical implications," *Clin Sci (Lond)* 117(3):95-109 (2009).

MCP-1 also promotes tissue inflammation associated with autoimmune diseases including rheumatoid arthritis (RA) and multiple sclerosis (MS). MCP-1 plays a role in the infiltration of macrophages and lymphocytes into the joint in RA, and is overexpressed in the synovial fluid of RA patients. Koch, A. E., et al., "Enhanced production of monocyte chemoattractant protein-1 in rheumatoid arthritis," *J Clin Invest* 90(3):772-9 (1992). Blockade of MCP-1 and MCP-1 signaling in animal models of RA have also shown the importance of MCP-1 to macrophage accumulation and proinflammatory cytokine expression associated with RA. Brodmerkel, C. M., et al., "Discovery and pharmacological characterization of a novel rodent-active CCR2 antagonist, INCB3344," *J Immunol* 175(8):5370-8 (2005); Bruhl, H., et al., "Dual role of CCR2 during initiation and progression of collagen-induced arthritis: evidence for regulatory activity of CCR2+ T cells," *J Immunol* 172(2):890-8 (2004); Gong, J. H., et al., "An antagonist of monocyte chemoattractant protein 1 (MCP-1) inhibits arthritis in the MRL-lpr mouse model," *J Exp Med* 186(1):131-7 (1997); 65. Gong, J. H., et al., "Post-onset inhibition of murine arthritis using combined chemokine antagonist therapy," *Rheumatology* (Oxford 43(1): 39-42 (2004).

Overexpression of MCP-1, in the brain, cerebrospinal fluid (CSF), and blood, has also been associated with chronic and acute MS in humans. Mahad, D. J. and R. M. Ransohoff, "The role of MCP-1 (CCL2) and CCR2 in multiple sclerosis and experimental autoimmune encephalomyelitis (EAE)," *Semin Immunol* 15(1):23-32 (2003). MCP-1 is overexpressed by a variety of cell types in the brain during disease progression and contributes to the infiltration of macrophages and lymphocytes which mediate the tissue damage associated with MS. Genetic depletion of MCP-1 or CCR2 in the experimental autoimmune encephalomyelitis (EAE) mouse model, a model resembling human MS, results in resistance to disease, primarily because of decreased macrophage infiltration to the CNS. Fife, B. T., et al., "CC chemokine receptor 2 is critical for induction of experimental autoimmune encephalomyelitis," *J Exp Med* 192(6):899-905 (2000); Huang, D. R., et al., "Absence of monocyte chemoattractant protein 1 in mice leads to decreased local macrophage recruitment and antigen-specific T helper cell type 1 immune response in experimental autoimmune encephalomyelitis," *J Exp Med* 193(6):713-26 (2001).

Preclinical data have suggested that small- and large-molecule inhibitors of MCP-1 and CCR2 have potential as therapeutic agents in inflammatory and autoimmune indications. Thus, one aspect of the invention provides compounds, compositions, and methods for treating cardiovascular, inflammatory, and autoimmune conditions associated with MCP-1 and CCR2.

Accordingly, the invention provides compounds that are useful for inhibition of BET protein function by binding to bromodomains, pharmaceutical compositions comprising one or more of those compounds, and use of these compounds or compositions in the treatment and prevention of diseases and conditions, including, but not limited to, cancer, autoimmune, and cardiovascular diseases.

The compounds of the invention are defined by Formula I:

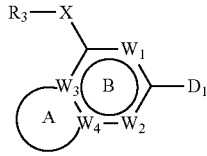

Formula I or a stereoisomer, tautomer, pharmaceutically acceptable salt, or hydrate thereof,
wherein:
  A is selected from a 5- or 6-membered monocyclic carbocycle or monocyclic heterocycle
    fused to ring B to form an A-B bicyclic ring,
  B is a six-membered carbocycle or heterocycle;
  $W_1$ is selected from N and $CR_1$;
  $W_2$ is selected from N and $CR_2$;
  $W_3$ and $W_4$ are independently selected from N, CH, and C,
    with the proviso that $W_3$ and $W_4$ cannot both be nitrogen;
  $W_1$ and $W_2$ may be the same or different from each other;
  $R_1$ and $R_2$ are independently selected from hydrogen, deuterium, alkyl, —OH, —NH$_2$, -thioalkyl, and alkoxy, ketone, ester, carboxylic acid, urea, carbamate, amino, amide, halogen, carbocycle, heterocycle, sulfone, sulfoxide, sulfide, sulfonamide, and —CN;
  X is optionally present, and if present, is selected from —O—, —(NH)—, —NHCR$_x$R$_y$—, —NHCR$_x$R$_y$-CR$_x$R$_y$—, —N(CR$_x$R$_y$CR$_x$R$_y$)$_2$—, —CH$_2$CH$_2$—, —CH═CH—, and —NHC(O)—, —NHSO$_2$—, —CR$_x$R$_y$NH—, —OCR$_x$R$_y$—, —CR$_x$R$_y$O—, —SCR$_x$R$_y$—, —CR$_x$R$_y$S—, where S might be oxidized to sulfoxide or sulfone;
  $R_x$ and $R_y$ are each independently selected from hydrogen, alkyl(C$_{1-5}$), halogen, —OH, —CF$_3$, deuterium, amino, alkoxy(C$_{1-5}$), or two substituents selected from R$_x$, R$_y$, and R$_1$ may be connected in a 5- or 6-membered ring to form a bicyclic carbocycle or bicyclic heterocycle;
  $R_3$ is selected from a 4-7 membered carbocycle, 4-7 membered heterocycle, bicyclic carbocycle, and bicyclic heterocycle;
  $D_1$ is selected from 5-membered monocyclic carbocycles and heterocycles connected to the B-ring via a carbon-carbon bond,
    with the proviso that $D_1$ cannot be a substituted or unsubstituted furan, thiophene, cyclopentane, tetrahydrofurane, and tetrahydrothiophene,
  with the proviso that A is not a substituted or unsubstituted

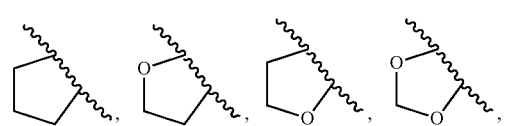

-continued

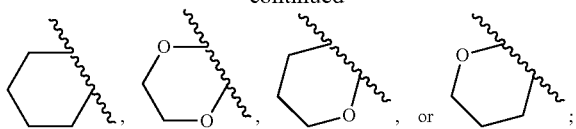

with the proviso that if A is a substituted or unsubstituted

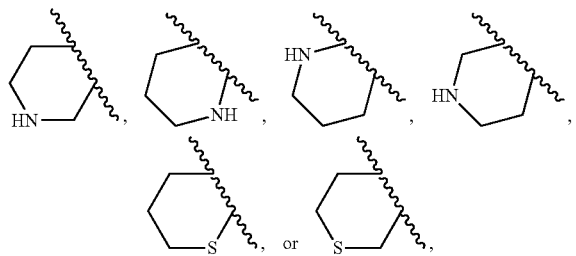

then $W_1$ and $W_2$ are not N.

In certain embodiments, the compounds of Formula I exclude compounds of Formula II:

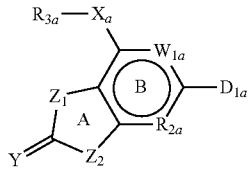

Formula II or a stereoisomer, tautomer, pharmaceutically acceptable salt, or hydrate thereof,
wherein:
$W_{1a}$ is selected from N and $CR_{1a}$;
$R_{1a}$ and $R_{2a}$ are independently selected from hydrogen, deuterium, alkyl, —OH, —$NH_2$, -thioalkyl, and alkoxy;
Y is selected from O and S;
$Z_1$ and $Z_2$ are independently selected from oxygen and —N—$R_{a1}$;
Each $R_{a1}$ is independently selected from hydrogen, deuterium, and alkyl($C_{1-5}$) (methyl, ethyl, propyl, cyclopropyl);
$X_a$ is optionally present, and if present, is selected from —(NH)—, —$NHCR_{xa}R_{ya}$—, —$NHSO_2$—, oxygen, —$CH_2CH_2$—, —CH=CH—, —$CR_{xa}R_{ya}NH$—, —$OCR_{xa}R_{ya}$—, —$CR_{xa}R_{ya}O$—, —$SCR_{xa}R_{ya}$—, —$CR_{xa}R_{ya}S$—, where S might be oxidized to sulfoxide or sulfone, or —NHC(O)—, wherein the nitrogen is connected to the B ring;
$R_{xa}$ and $R_{ya}$ are each independently selected from hydrogen, alkyl($C_{1-5}$), halogen, —OH, —$CF_3$, deuterium, amino, alkoxy($C_{1-5}$), or two substituents selected from $R_{xa}$, $R_{ya}$, and $R_{1a}$ may be connected in a 5- or 6-membered ring to form a bicyclic carbocycle or bicyclic heterocycle;
$R_{3a}$ is selected from hydrogen, 4-7 membered carbocycles, 4-7-membered heterocycles, bicyclic carbocycles, and bicyclic heterocycles;
with the proviso that $R_{3a}$ cannot be hydrogen if Xa is different from —NH—, and
$D_{1a}$ is selected from 5-membered monocyclic carbocycles and heterocycles connected to the B-ring via a carbon-carbon bond,
with the proviso that $D_{1a}$ cannot be a substituted or unsubstituted furan, thiophene, cyclopentane, tetrahydrofurane, and tetrahydrothiophene.

In some embodiments, the compounds of Formula I exclude compounds disclosed in "Novel Substituted Bicyclic Compounds as Bromodomain Inhibitors," PCT Application No. PCT/US2014/043383, filed Jun. 20, 2014.

In another aspect of the invention, a pharmaceutical composition comprising a compound of Formula I, or stereoisomer, tautomer, pharmaceutically acceptable salt, or hydrate thereof and one or more pharmaceutically acceptable carriers, diluents or excipients is provided.

In yet another aspect of the invention there is provided a compound of Formula I, or a stereoisomer, tautomer, pharmaceutically acceptable salt, or hydrate thereof for use in therapy, in particular in the treatment of diseases or conditions for which a bromodomain inhibitor is indicated.

In yet another aspect of the invention there is provided a compound of Formula I, or a stereoisomer, tautomer, pharmaceutically acceptable salt, or hydrate thereof in the manufacture of a medicament for the treatment of diseases or conditions for which a bromodomain inhibitor is indicated.

Definitions

As used in the present specification, the following words, phrases and symbols are generally intended to have the meanings as set forth below, except to the extent that the context in which they are used indicates otherwise. The following abbreviations and terms have the indicated meanings throughout.

As used herein, "cardiovascular disease" refers to diseases, disorders and conditions of the heart and circulatory system that are mediated by BET inhibition. Exemplary cardiovascular diseases, including cholesterol- or lipid-related disorders, include, but are not limited to, acute coronary syndrome, angina, arteriosclerosis, atherosclerosis, carotid atherosclerosis, cerebrovascular disease, cerebral infarction, congestive heart failure, congenital heart disease, coronary heart disease, coronary artery disease, coronary plaque stabilization, dyslipidemias, dyslipoproteinemias, endothelium dysfunctions, familial hypercholesterolemia, familial combined hyperlipidemia, hypoalphalipoproteinemia, hypertriglyceridemia, hyperbetalipoproteinemia, hypercholesterolemia, hypertension, hyperlipidemia, intermittent claudication, ischemia, ischemia reperfusion injury, ischemic heart diseases, cardiac ischemia, metabolic syndrome, multi-infarct dementia, myocardial infarction, obesity, peripheral vascular disease, reperfusion injury, restenosis, renal artery atherosclerosis, rheumatic heart disease, stroke, thrombotic disorder, transitory ischemic attacks, and lipoprotein abnormalities associated with Alzheimer's disease, obesity, diabetes mellitus, syndrome X, impotence, multiple sclerosis, Parkinson's disease, and inflammatory diseases.

As used herein, "inflammatory diseases" refers to diseases, disorders, and conditions that are mediated by BET inhibition. Exemplary inflammatory diseases, include, but are not limited to, arthritis, asthma, dermatitis, psoriasis, cystic fibrosis, post transplantation late and chronic solid organ rejection, multiple sclerosis, systemic lupus erythematosus, inflammatory bowel diseases, autoimmune diabetes, diabetic retinopathy, diabetic nephropathy, diabetic vasculopathy, ocular inflammation, uveitis, rhinitis, ischemia-reperfusion injury, post-angioplasty restenosis, chronic obstructive pulmonary disease (COPD), glomerulonephritis, Graves disease, gastrointestinal allergies, conjunctivitis, atherosclerosis, coronary artery disease, angina, and small artery disease.

As used herein, "cancer" refers to diseases, disorders, and conditions that are mediated by BET inhibition. Exemplary cancers, include, but are not limited to, chronic lymphocytic leukemia and multiple myeloma, follicular lymphoma, diffuse large B cell lymphoma with germinal center phenotype, Burkitt's lymphoma, Hodgkin's lymphoma, follicular lymphomas and activated, anaplastic large cell lymphoma, neuroblastoma and primary neuroectodermal tumor, rhabdomyosarcoma, prostate cancer, breast cancer, NMC (NUT-midline carcinoma), acute myeloid leukemia (AML), acute B lymphoblastic leukemia (B-ALL), Burkitt's Lymphoma, B-cell lymphoma, melanoma, mixed lineage leukemia, multiple myeloma, pro-myelocytic leukemia (PML), non-Hodgkin's lymphoma, neuroblastoma, medulloblastoma, lung carcinoma (NSCLC, SCLC), and colon carcinoma.

"Subject" refers to an animal, such as a mammal, that has been or will be the object of treatment, observation, or experiment. The methods described herein may be useful for both human therapy and veterinary applications. In one embodiment, the subject is a human.

As used herein, "treatment" or "treating" refers to an amelioration of a disease or disorder, or at least one discernible symptom thereof. In another embodiment, "treatment" or "treating" refers to an amelioration of at least one measurable physical parameter, not necessarily discernible by the patient. In yet another embodiment, "treatment" or "treating" refers to inhibiting the progression of a disease or disorder, either physically, e.g., stabilization of a discernible symptom, physiologically, e.g., stabilization of a physical parameter, or both. In yet another embodiment, "treatment" or "treating" refers to delaying the onset of a disease or disorder. For example, treating a cholesterol disorder may comprise decreasing blood cholesterol levels.

As used herein, "prevention" or "preventing" refers to a reduction of the risk of acquiring a given disease or disorder.

A dash ("-") that Is not between two letters or symbols is used to indicate a point of attachment for a substituent. For example, —CONH$_2$ is attached through the carbon atom.

By "optional" or "optionally" is meant that the subsequently described event or circumstance may or may not occur, and that the description includes instances where the event or circumstance occurs and instances in which is does not. For example, "optionally substituted aryrl" encompasses both "aryl" and "substituted aryl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, the term "hydrate" refers to a crystal form with either a stoichiometric or non-stoichiometric amount of water is incorporated into the crystal structure.

The term "alkenyl" as used herein refers to an unsaturated straight or branched hydrocarbon having at least one carbon-carbon double bond, such as a straight or branched group of 2-8 carbon atoms, referred to herein as $(C_2-C_8)$alkenyl. Exemplary alkenyl groups include, but are not limited to, vinyl, allyl, butenyl, pentenyl, hexenyl, butadienyl, pentadienyl, hexadienyl, 2-ethylhexenyl, 2-propyl-2-butenyl, and 4-(2-methyl-3-butene)-pentenyl.

The term "alkoxy" as used herein refers to an alkyl group attached to an oxygen (—O-alkyl-). "Alkoxy" groups also include an alkenyl group attached to an oxygen ("alkenyloxy") or an alkynyl group attached to an oxygen ("alkynyloxy") groups. Exemplary alkoxy groups include, but are not limited to, groups with an alkyl, alkenyl or alkynyl group of 1-8 carbon atoms, referred to herein as $(C_1-C_8)$alkoxy. Exemplary alkoxy groups include, but are not limited to methoxy and ethoxy.

The term "alkyl" as used herein refers to a saturated straight or branched hydrocarbon, such as a straight or branched group of 1-8 carbon atoms, referred to herein as $(C_1-C_8)$alkyl. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, and octyl.

The term "alkynyl" as used herein refers to an unsaturated straight or branched hydrocarbon having at least one carbon-carbon triple bond, such as a straight or branched group of 2-8 carbon atoms, referred to herein as $(C_2-C_8)$alkynyl. Exemplary alkynyl groups include, but are not limited to, ethynyl, propynyl, butynyl, pentynyl, hexynyl, methylpropynyl, 4-methyl-1-butynyl, 4-propyl-2-pentynyl, and 4-butyl-2-hexynyl.

The term "amide" as used herein refers to the form —NR$_a$C(O)(R$_b$)— or —C(O)NR$_b$R$_c$, wherein R$_a$, R$_b$ and R$_c$ are each independently selected from alkyl, alkenyl, alkynyl, aryl, arylalkyl, cycloalkyl, haloalkyl, heteroaryl, heterocyclyl, and hydrogen. The amide can be attached to another group through the carbon, the nitrogen, R$_b$, or R$_c$. The amide also may be cyclic, for example R$_b$ and R$_c$, may be joined to form a 3- to 8-membered ring, such as 5- or 6-membered ring. The term "amide" encompasses groups such as sulfonamide, urea, ureido, carbamate, carbamic acid, and cyclic versions thereof. The term "amide" also encompasses an amide group attached to a carboxy group, e.g., -amide-COOH or salts such as -amide-COONa, an amino group attached to a carboxy group (e.g., -amino-COOH or salts such as -amino-COONa).

The term "amine" or "amino" as used herein refers to the form —NR$_d$R$_e$ or —N(R$_d$)R$_e$—, where R$_d$ and R$_e$ are independently selected from alkyl, alkenyl, alkynyl, aryl, arylalkyl, carbamate, cycloalkyl, haloalkyl, heteroaryl, heterocycle, and hydrogen. The amino can be attached to the parent molecular group through the nitrogen. The amino also may be cyclic, for example any two of R$_d$ and R$_e$ may be joined together or with the N to form a 3- to 12-membered ring (e.g., morpholino or piperidinyl). The term amino also includes the corresponding quaternary ammonium salt of any amino group. Exemplary amino groups include alkylamino groups, wherein at least one of R$_d$ or R$_e$ is an alkyl group. In some embodiments R$_d$ and R$_e$ each may be optionally substituted with hydroxyl, halogen, alkoxy, ester, or amino.

The term "aryl" as used herein refers to a mono-, bi-, or other multi-carbocyclic, aromatic ring system. The aryl group can optionally be fused to one or more rings selected from aryls, cycloalkyls, and heterocyclyls. The aryl groups of this present disclosure can be substituted with groups selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone. Exemplary aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. Exemplary aryl groups also include, but are not limited to a monocyclic aromatic ring system, wherein the ring comprises 6 carbon atoms, referred to herein as "($C_6$)aryl."

The term "arylalkyl" as used herein refers to an alkyl group having at least one aryl substituent (e.g., -aryl-alkyl-). Exemplary arylalkyl groups include, but are not limited to, arylalkyls having a monocyclic aromatic ring system, wherein the ring comprises 6 carbon atoms, referred to herein as "($C_6$)arylalkyl."

The term "carbamate" as used herein refers to the form —$R_g$OC(O)N($R_h$)—, —$R_g$OC(O)N($R_h$)$R_i$—, or —OC(O)N$R_h$R_i$, wherein $R_g$, $R_h$ and $R_i$ are each independently selected from alkyl, alkenyl, alkynyl, aryl, arylalkyl, cycloalkyl, haloalkyl, heteroaryl, heterocyclyl, and hydrogen. Exemplary carbamates include, but are not limited to, arylcarbamates or heteroaryl carbamates (e.g., wherein at least one of $R_g$, $R_h$ and $R_i$ are independently selected from aryl or heteroaryl, such as pyridine, pyridazine, pyrimidine, and pyrazine).

The term "carbocycle" as used herein refers to an aryl or cycloalkyl group.

The term "carboxy" as used herein refers to —COOH or its corresponding carboxylate salts (e.g., —COONa). The term carboxy also includes "carboxycarbonyl," e.g. a carboxy group attached to a carbonyl group, e.g., —C(O)—COOH or salts, such as —C(O)—COONa.

The term "cyano" as used herein refers to —CN.

The term "cycloalkoxy" as used herein refers to a cycloalkyl group attached to an oxygen.

The term "cycloalkyl" as used herein refers to a saturated or unsaturated cyclic, bicyclic, or bridged bicyclic hydrocarbon group of 3-12 carbons, or 3-8 carbons, referred to herein as "($C_3$-$C_8$)cycloalkyl," derived from a cycloalkane. Exemplary cycloalkyl groups include, but are not limited to, cyclohexanes, cyclohexenes, cyclopentanes, and cyclopentenes. Cycloalkyl groups may be substituted with alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Cycloalkyl groups can be fused to other cycloalkyl saturated or unsaturated, aryl, or heterocyclyl groups.

The term "dicarboxylic acid" as used herein refers to a group containing at least two carboxylic acid groups such as saturated and unsaturated hydrocarbon dicarboxylic acids and salts thereof. Exemplary dicarboxylic acids include alkyl dicarboxylic acids. Dicarboxylic acids may be substituted with alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone. Dicarboxylic acids include, but are not limited to succinic acid, glutaric acid, adipic acid, suberic acid, sebacic acid, azelaic acid, maleic acid, phthalic acid, aspartic acid, glutamic acid, malonic acid, fumaric acid, (+)/(−)-malic acid, (+)/(−) tartaric acid, isophthalic acid, and terephthalic acid. Dicarboxylic acids further include carboxylic acid derivatives thereof, such as anhydrides, imides, hydrazides (for example, succinic anhydride and succinimide).

The term "ester" refers to the structure —C(O)O—, —C(O)O—$R_j$-, —$R_k$C(O)O—$R_j$-, or —$R_k$C(O)O—, where O is not bound to hydrogen, and $R_j$ and $R_k$ can independently be selected from alkoxy, aryloxy, alkyl, alkenyl, alkynyl, amide, amino, aryl, arylalkyl, cycloalkyl, ether, haloalkyl, heteroaryl, and heterocyclyl. $R_k$ can be a hydrogen, but $R_j$ cannot be hydrogen. The ester may be cyclic, for example the carbon atom and $R_j$, the oxygen atom and $R_k$, or $R_j$ and $R_k$ may be joined to form a 3- to 12-membered ring. Exemplary esters include, but are not limited to, alkyl esters wherein at least one of $R_j$ or $R_k$ is alkyl, such as —O—C(O)-alkyl, —C(O)—O-alkyl-, and -alkyl-C(O)—O-alkyl-. Exemplary esters also include aryl or heteoaryl esters, e.g. wherein at least one of $R_j$ or $R_k$ is a heteroaryl group such as pyridine, pyridazine, pyrimidine and pyrazine, such as a nicotinate ester. Exemplary esters also include reverse esters having the structure —$R_k$C(O)O—, where the oxygen is bound to the parent molecule. Exemplary reverse esters include succinate, D-argininate, L-argininate, L-lysinate and D-lysinate. Esters also include carboxylic acid anhydrides and acid halides.

The terms "halo" or "halogen" as used herein refer to F, Cl, Br, or I.

The term "haloalkyl" as used herein refers to an alkyl group substituted with one or more halogen atoms. "Haloalkyls" also encompass alkenyl or alkynyl groups substituted with one or more halogen atoms.

The term "heteroaryl" as used herein refers to a mono-, bi-, or multi-cyclic, aromatic ring system containing one or more heteroatoms, for example 1-3 heteroatoms, such as nitrogen, oxygen, and sulfur. Heteroaryls can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Heteroaryls can also be fused to non-aromatic rings. Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3)- and (1,2,4)-triazolyl, pyrazinyl, pyrimidilyl, tetrazolyl, furyl, thienyl, isoxazolyl, thiazolyl, furyl, phenyl, isoxazolyl, and oxazolyl. Exemplary heteroaryl groups include, but are not limited to, a monocyclic aromatic ring, wherein the ring comprises 2-5 carbon atoms and 1-3 heteroatoms, referred to herein as "($C_2$-$C_5$)heteroaryl."

The terms "heterocycle," "heterocyclyl," or "heterocyclic" as used herein refer to a saturated or unsaturated 3-, 4-, 5-, 6- or 7-membered ring containing one, two, or three heteroatoms independently selected from nitrogen, oxygen, and sulfur. Heterocycles can be aromatic (heteroaryls) or non-aromatic. Heterocycles can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Heterocycles also include bicyclic, tricyclic, and tetracyclic groups in which any of the above heterocyclic rings is fused to one or two rings independently selected from aryls, cycloalkyls, and heterocycles. Exemplary heterocycles include acridinyl, benzimidazolyl, benzofuryl, benzothiazolyl, benzothienyl, benzoxazolyl, biotinyl, cinnolinyl, dihydrofuryl, dihydroindolyl, dihydropyranyl, dihydrothienyl, dithiazolyl, furyl, homopiperidinyl, imidazolidinyl, imidazolinyl, imidazolyl, indolyl, isoquinolyl, isothiazolidinyl, isothiazolyl, isoxazolidinyl, isoxazolyl, morpholinyl, oxadiazolyl, oxazolldinyl, oxazolyl, piperazinyl, piperidinyl, pyranyl, pyrazolidinyl, pyrazinyl, pyrazolyl, pyrazolinyl, pyridazinyl, pyridyl, pyrimidinyl, pyrimidyl, pyrrolidinyl, pyrrolidin-2-onyl, pyrrolinyl, pyrrolyl, quinolinyl, quinoxaloyl, tetrahydrofuryl, tetrahydroisoquinolyl, tetrahydropyranyl, tetrahydroquinolyl, tetrazolyl, thiadiazolyl, thiazolidinyl, thiazolyl, thienyl, thiomorpholinyl, thiopyranyl, and triazolyl.

The terms "hydroxy" and "hydroxyl" as used herein refer to —OH.

The term "hydroxyalkyl" as used herein refers to a hydroxy attached to an alkyl group.

The term "hydroxyaryl" as used herein refers to a hydroxy attached to an aryl group.

The term "ketone" as used herein refers to the structure —C(O)—Rn (such as acetyl, —C(O)CH$_3$) or —R$_n$—C(O)—R$_o$—. The ketone can be attached to another group through R$_n$ or R$_o$. R$_n$ or R$_o$ can be alkyl, alkenyl, alkynyl, cycloalkyl, heterocyclyl or aryl, or R$_n$ or R$_o$ can be joined to form a 3- to 12-membered ring.

The term "monoester" as used herein refers to an analogue of a dicarboxylic acid wherein one of the carboxylic acids is functionalized as an ester and the other carboxylic acid is a free carboxylic acid or salt of a carboxylic acid. Examples of monoesters include, but are not limited to, to monoesters of succinic acid, glutaric acid, adipic acid, suberic acid, sebacic acid, azelaic acid, oxalic and maleic acid.

The term "phenyl" as used herein refers to a 6-membered carbocyclic aromatic ring. The phenyl group can also be fused to a cyclohexane or cyclopentane ring. Phenyl can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, phosphate, sulfide, sulfinyl, sulfonyl, sulfonic acid, sulfonamide and thioketone.

The term "thioalkyl" as used herein refers to an alkyl group attached to a sulfur (—S— alkyl-).

"Alkyl," "alkenyl," "alkynyl", "alkoxy", "amino" and "amide" groups can be optionally substituted with or interrupted by or branched with at least one group selected from alkoxy, aryloxy, alkyl, alkenyl, alkynyl, amide, amino, aryl, arylalkyl, carbamate, carbonyl, carboxy, cyano, cycloalkyl, ester, ether, formyl, halogen, haloalkyl, heteroaryl, heterocyclyl, hydroxyl, ketone, phosphate, sulfide, sulfinyl, sulfonyl, sulfonic acid, sulfonamide, thioketone, ureido and N. The substituents may be branched to form a substituted or unsubstituted heterocycle or cycloalkyl.

As used herein, a suitable substitution on an optionally substituted substituent refers to a group that does not nullify the synthetic or pharmaceutical utility of the compounds of the present disclosure or the intermediates useful for preparing them. Examples of suitable substitutions include, but are not limited to: $C_{14}$ alkyl, alkenyl or alkynyl; $C_{14}$ aryl, $C_{2-5}$ heteroaryl; $C_{37}$ cycloalkyl; $C_{1-8}$ alkoxy; $C_6$ aryloxy; —CN; —OH; oxo; halo, carboxy; amino, such as —NH ($C_{1-8}$ alkyl), —N($C_{1-8}$ alkyl)$_2$, —NH(($C_6$)aryl), or —N(($C_6$) aryl)$_2$; formyl; ketones, such as —CO($C_{1-8}$ alkyl), —CO(($C_6$ aryl) esters, such as —CO$_2$($C_{1-8}$ alkyl) and —CO$_2$ ($C_6$ aryl). One of skill in art can readily choose a suitable substitution based on the stability and pharmacological and synthetic activity of the compound of the present disclosure.

The term "pharmaceutically acceptable carrier" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutically acceptable composition" as used herein refers to a composition comprising at least one compound as disclosed herein formulated together with one or more pharmaceutically acceptable carriers.

The term "pharmaceutically acceptable prodrugs" as used herein represents those prodrugs of the compounds of the present disclosure that are, within the scope of sound medical judgment, suitable for use in contact with the tissues of humans and lower animals without undue toxicity, irritation, allergic response, commensurate with a reasonable benefit/risk ratio, and effective for their intended use, as well as the zwitterionic forms, where possible, of the compounds of the present disclosure. A discussion is provided in Higuchi et al., "Prodrugs as Novel Delivery Systems," *ACS Symposium Series*, Vol. 14, and in Roche, E. B., ed. *Bioreversible Carriers in Drug Design*, American Pharmaceutical Association and Pergamon Press, 1987, both of which are incorporated herein by reference.

The term "pharmaceutically acceptable salt(s)" refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfate, citrate, matate, acetate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions, that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present disclosure encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly.

Individual stereoisomers of compounds of the present disclosure can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, or (3) direct separation of the mixture of optical enantiomers on chiral chromatographic columns. Stereoisomeric mixtures can also be resolved into their component stereoisomers by well-known methods, such as chiral-phase gas chromatography, chiral-phase high performance liquid chromatography, crystallizing the compound as a chiral salt complex, or crystallizing the compound in a chiral solvent. Stereoisomers can also be obtained from stereomerically-pure intermediates, reagents, and catalysts by well-known asymmetric synthetic methods.

Geometric isomers can also exist in the compounds of the present disclosure. The present disclosure encompasses the various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the E and Z isomers.

Substituents around a carbon-carbon double bond alternatively can be referred to as "cis" or "trans," where "cis" represents substituents on the same side of the double bond and "trans" represents substituents on opposite sides of the double bond. The arrangements of substituents around a carbocyclic ring are designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The compounds disclosed herein may exist as tautomers and both tautomeric forms are intended to be encompassed by the scope of the present disclosure, even though only one tautomeric structure is depicted.

EXEMPLARY EMBODIMENTS OF THE INVENTION

The invention provides compounds and pharmaceutical compositions comprising one or more of those compounds wherein the structure of the compound is defined by Formula I:

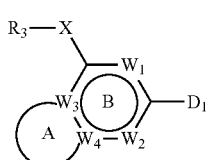

Formula I or a stereoisomer, tautomer, pharmaceutically acceptable salt, or hydrate thereof,
wherein:
A is selected from a 5- or 6-membered monocyclic carbocycle or monocyclic heterocycle fused to ring B to form an A-B bicyclic ring,
B is a six-membered carbocycle or heterocycle;

$W_1$ is selected from N and $CR_2$;
$W_2$ is selected from N and $CR_2$;
$W_3$ and $W_4$ are independently selected from N, CH, and C, with the proviso that $W_3$ and $W_4$ cannot both be nitrogen;
$W_1$ and $W_2$ may be the same or different from each other;
$R_1$ and $R_2$ are independently selected from hydrogen, deuterium, alkyl, —OH, —NH$_2$, -thioalkyl, and alkoxy, ketone, ester, carboxylic acid, urea, carbamate, amino, amide, halogen, carbocycle, heterocycle, sulfone, sulfoxide, sulfide, sulfonamide, and —CN;

X is optionally present, and if present, is selected from —O—, —(NH)—, —NHCR$_x$R$_y$—, —NHCR$_x$R$_y$CR$_x$R$_y$—, —N(CR$_x$R$_y$CR$_x$R$_y$)$_2$—, —CH$_2$CH$_2$—, —CH=CH—, and —NHC(O)—, —NHSO$_2$—, —CR$_x$R$_y$NH—, —OCR$_x$R$_y$—, —CR$_x$R$_y$O—, —SCR$_x$R$_y$—, —CR$_x$R$_y$S—, where S might be oxidized to sulfoxide or sulfone;

R$_x$ and R$_y$ are each independently selected from hydrogen, alkyl(C$_{1-5}$), halogen, —OH, —CF$_3$, deuterium, amino, alkoxy(C$_{1-5}$), or two substituents selected from R$_x$, R$_y$, and R$_1$ may be connected in a 5- or 6-membered ring to form a bicyclic carbocycle or bicyclic heterocycle;

R$_3$ is selected from a 4-7 membered carbocycle, 4-7 membered heterocycle, bicyclic carbocycle, and bicyclic heterocycle;

D$_1$ is selected from 5-membered monocyclic carbocycles and heterocycles connected to the B-ring via a carbon-carbon bond, with the proviso that D$_1$ cannot be a substituted or unsubstituted furan, thiophene, cyclopentane, tetrahydrofurane, and tetrahydrothiophene, with the proviso that A is not a substituted or unsubstituted

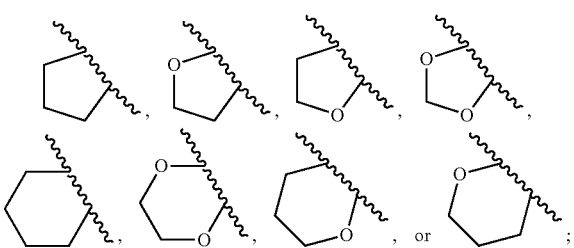

with the proviso that if A is a substituted or unsubstituted

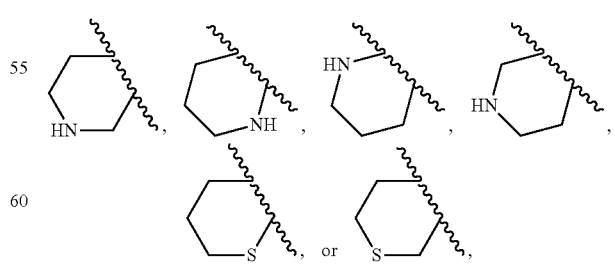

then $W_1$ and $W_2$ are not N;
and with the proviso that Formula I excludes compounds of Formula II:

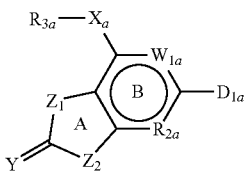

Formula II or a stereoisomer, tautomer, pharmaceutically acceptable salt, or hydrate thereof,
wherein:
$W_{1a}$ is selected from N and $CR_{1a}$;
$R_{1a}$ and $R_{2a}$ are independently selected from hydrogen, deuterium, alkyl, —OH, —$NH_2$, -thioalkyl, and alkoxy;
Y is selected from O and S;
$Z_1$ and $Z_2$ are independently selected from oxygen and —N—$R_{a1}$;
Each $Ra_1$ is independently selected from hydrogen, deuterium, and alkyl($C_{1-5}$) (methyl, ethyl, propyl, cyclopropyl);
$X_a$ is optionally present, and if present, is selected from —(NH)—, —$NHCR_{xa}R_{ya}$—, —$NHSO_2$—, oxygen, —$CH_2CH_2$—, —CH=CH—, —$CR_{xa}R_{ya}NH$—, —$OCR_{xa}R_{ya}$—, —$CR_{xa}R_{ya}O$—, —$SCR_{xa}R_{ya}$—, —$CR_{xa}R_{ya}S$—, where S might be oxidized to sulfoxide or sulfone, or —NHC(O)—, wherein the nitrogen is connected to the B ring;
$R_{xa}$ and $R_{ya}$ are each independently selected from hydrogen, alkyl($C_{1-5}$), halogen, —OH, —$CF_3$, deuterium, amino, alkoxy($C_{1-5}$), or two substituents selected from $R_{xa}$, $R_{ya}$, and $R_{1a}$ may be connected in a 5- or 6-membered ring to form a bicyclic carbocycle or bicyclic heterocycle; $R_{3a}$ is selected from hydrogen, 4-7 membered carbocycles, 4-7-membered heterocycles, bicyclic carbocycles, and bicyclic heterocycles;
with the proviso that $R_{3a}$ cannot be hydrogen if Xa is different from —NH—, and
$D_{1a}$ is selected from 5-membered monocyclic carbocycles and heterocycles connected to the B-ring via a carbon-carbon bond,
with the proviso that $D_{1a}$ cannot be a substituted or unsubstituted furan, thiophene, cyclopentane, tetrahydrofurane, and tetrahydrothiophene.

In some embodiments of Formula I, the A-B bicyclic ring is selected from

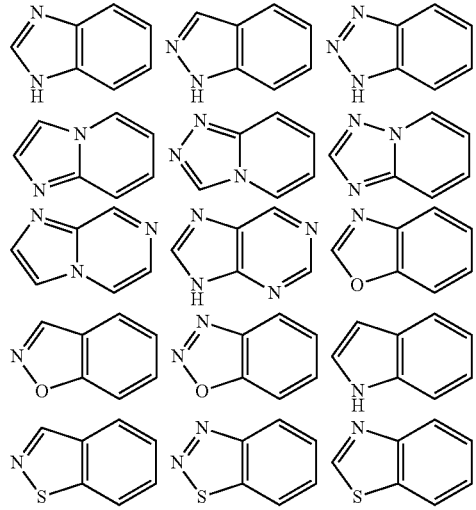

-continued

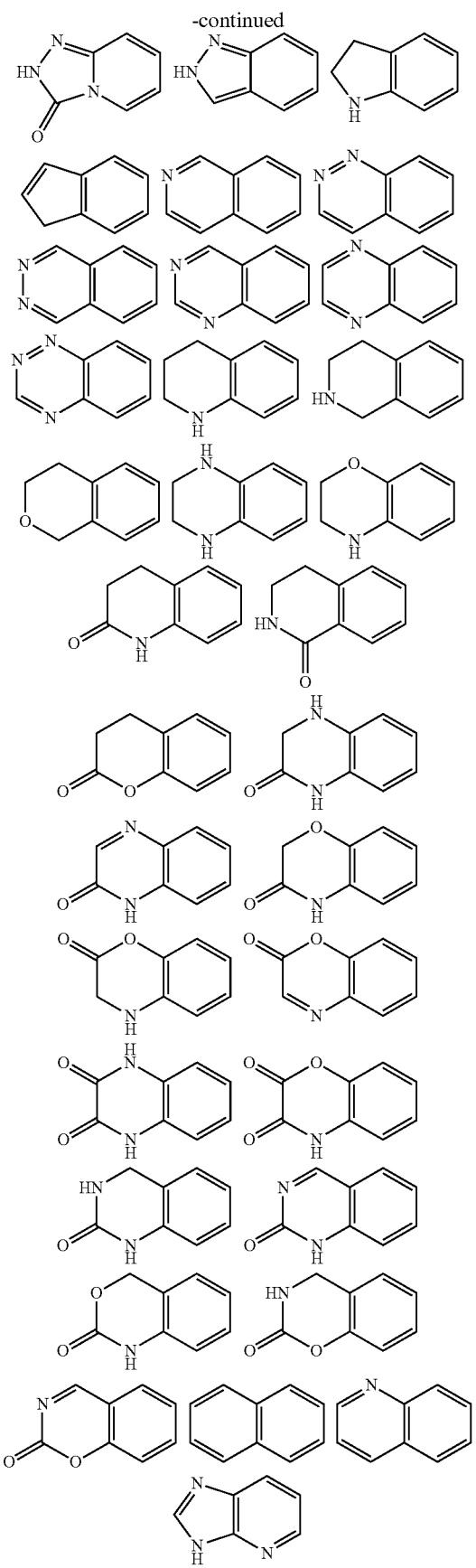

which may be optionally substituted with one or more groups independently selected from deuterium, —NH$_2$, amino (such as —NH(C$_1$-C$_5$), —N(C$_1$-C$_5$)$_2$, —NHPh, —NHBn, —NHpyridyl, —NHheterocycle(C$_4$-C$_7$), —NHcarbocycle(C$_4$-C$_7$), —NHCH$_2$pyridyl, —NHCH$_2$CH$_2$OH), heterocycle(C$_4$-C$_7$), carbocycle(C$_4$-C$_7$), halogen, —CN, —OH, —CF$_3$, —CH$_2$CF$_3$, sulfone, sulfoxide, alkyl(C$_1$-C$_6$), thioalkyl(C$_1$-C$_6$), alkoxy(C$_1$-C$_6$), and ketone(C$_1$-C$_6$).

In some embodiments of Formula I, the A-B bicyclic ring is selected from

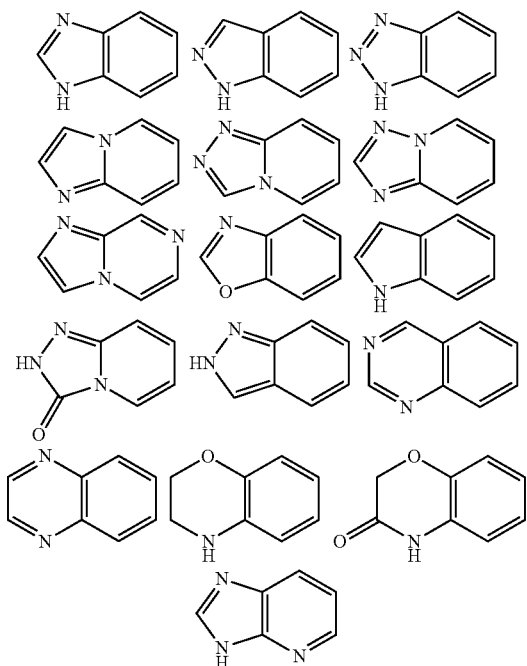

which may be optionally substituted with one or more groups independently selected from deuterium, —NH$_2$, amino (such as —NH(C$_1$-C$_5$), —N(C$_1$-C$_5$)$_2$, —NHPh, —NHBn, —NHpyridyl, —NHheterocycle(C$_4$-C$_7$), —NHcarbocycle(C$_4$-C$_7$), —NHCH$_2$pyridyl, —NHCH$_2$CH$_2$OH), heterocycle(C$_4$-C$_7$), carbocycle(C$_4$-C$_7$), halogen, —CF$_3$, —CH$_2$CF$_3$, sulfone, sulfoxide, alkyl (C$_1$-C$_6$), thioalkyl(C$_1$-C$_6$), alkoxy(C$_1$-C$_6$), and ketone(C$_1$-C$_6$).

In some embodiments of Formula I, the A-B bicyclic ring is selected from

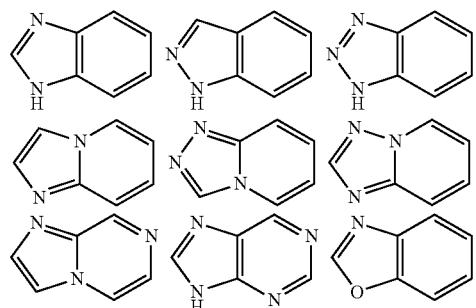

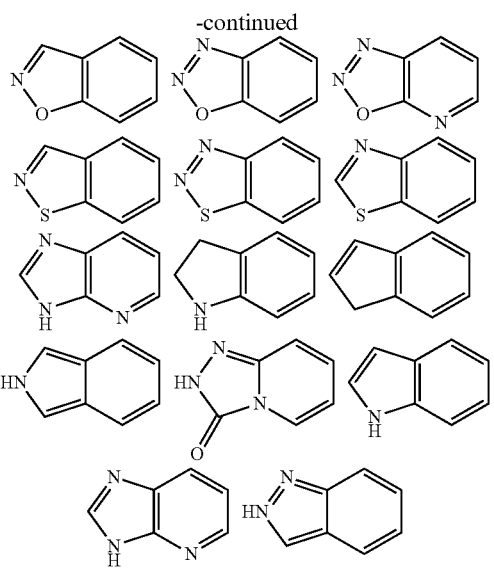

which may be optionally substituted with one or more groups independently selected from deuterium, —NH$_2$, amino (such as —NH(C$_1$-C$_5$), —N(C$_1$-C$_5$)$_2$, —NHPh, —NHBn, —NHpyridyl, —NHheterocycle(C$_4$-C$_7$), —NHcarbocycle(C$_4$-C$_7$)), heterocycle(C$_4$-C$_7$), carbocycle (C$_4$-C$_7$), halogen, —CN, —OH, —CF$_3$, sulfone, sulfoxide, alkyl(C$_1$-C$_6$), thioalkyl(C$_1$-C$_6$), Alkenyl(C$_1$-C$_6$), alkoxy(C$_1$-C$_6$), ketone(C$_1$-C$_6$), ester, urea, carboxylic acid, carbamate, and amide(C$_1$-C$_6$).

In other embodiments of Formula I, the A-B bicyclic ring is selected from

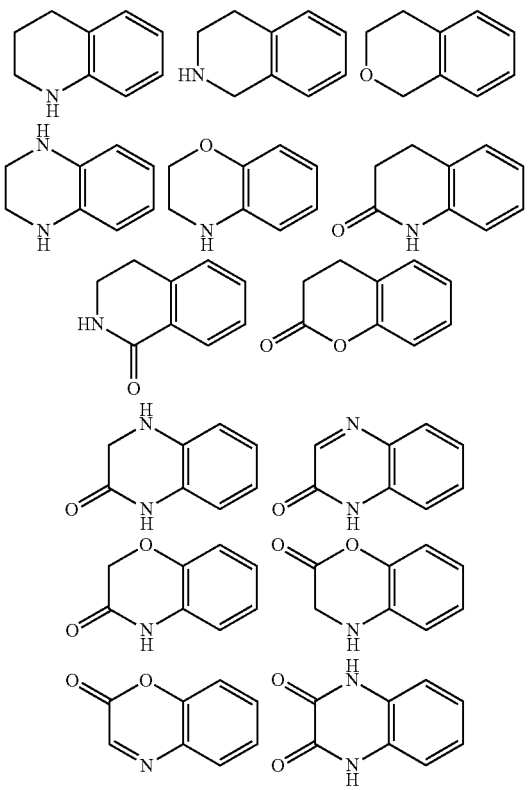

-continued

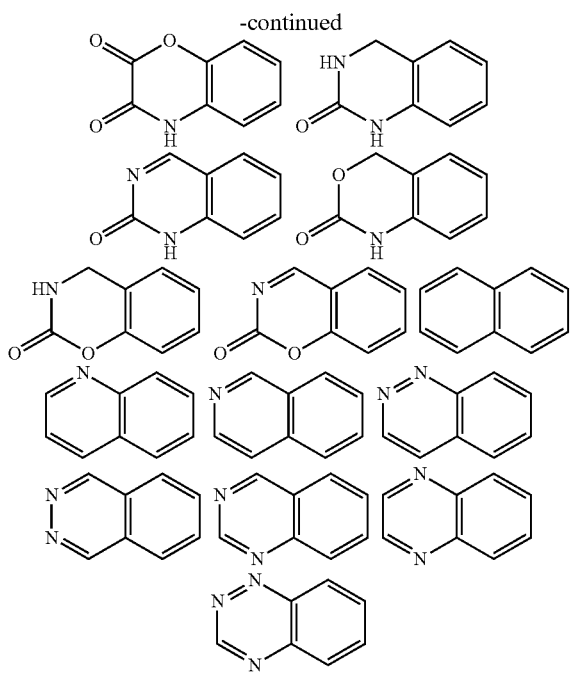

where either ring may be the A or B ring, and which may be optionally substituted with one or more groups independently selected from deuterium, —NH$_2$, amino (such as —NH(C$_1$-C$_5$), —N(C$_1$-C$_5$)$_2$, —NHPh, —NHBn, —NHpyridyl, —NHheterocycle(C$_4$-C$_7$), —NHcarbocycle (C$_4$-C$_7$)), heterocycle(C$_4$-C$_7$), carbocycle(C$_4$-C$_7$), halogen, —CN, —OH, —CF$_3$, sulfone, sulfoxide, alkyl(C$_1$-C$_6$), thioalkyl(C$_1$-C$_6$), Alkenyl(C$_1$-C$_6$), alkoxy(C$_1$-C$_6$), ketone(C$_1$-C$_6$), ester, urea, carboxylic acid, carbamate, and amide(C$_1$-C$_6$).

In other embodiments of Formula I, the A-B bicyclic ring is selected from

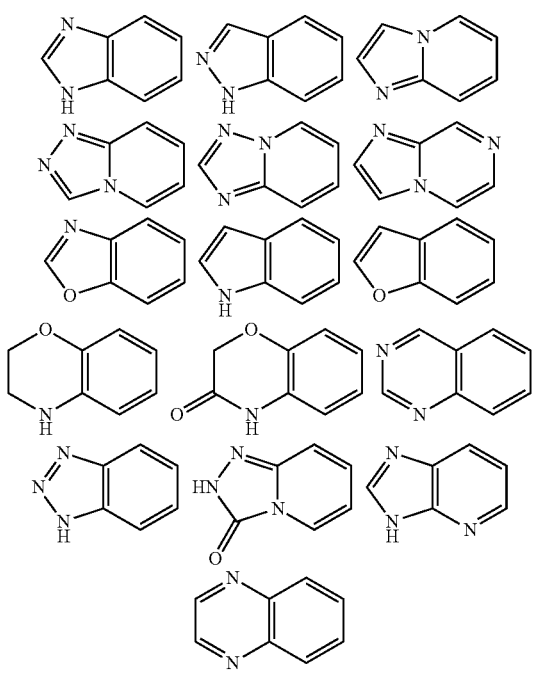

which may be optionally substituted with one or more groups independently selected from hydrogen, deuterium, —NH$_2$, amino (such as —NH(C$_1$-C$_5$), —N(C$_1$-C$_5$), —NHPh, —NHBn, —NHpyridyl, —NHheterocycle(C$_4$-C$_7$), —NHcarbocycle(C$_4$-C$_7$)), heterocycle(C$_4$-C$_7$), halogen, —CN, —OH, —CF$_3$, sulfone, sulfoxide, sulfonamide, alkyl(C$_1$-C$_6$), thioalkyl(C$_1$-C$_6$), and alkoxy(C$_1$-C$_6$).

In certain embodiments of Formula I, the A-B bicyclic ring is selected from

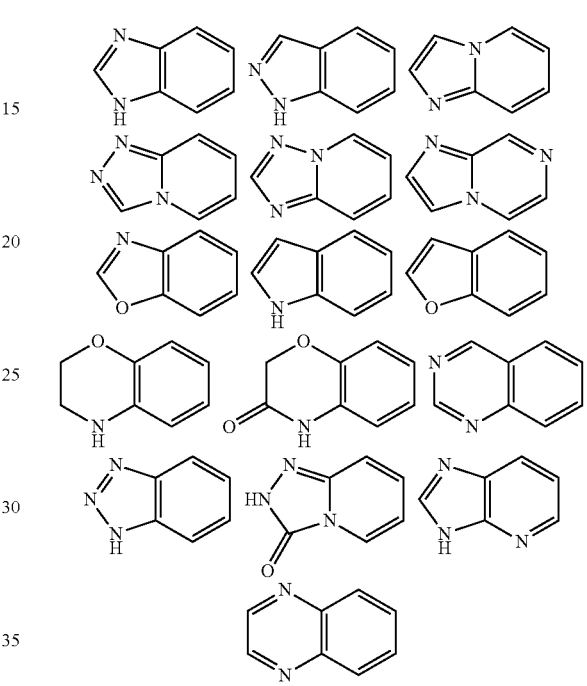

which may be optionally substituted with one or more groups independently selected from hydrogen, deuterium, methyl, ethyl, propyl, isopropyl, methoxy, ethoxy, propoxy, isopropoxy, halogen, —CF$_3$, —CN, —NH$_2$, —NHMe, —NHEt, —NHPr, —NHiPr, pyrrolidino, morpholino, and piperidino.

In some embodiments of Formula I, the A-B bicyclic ring is substituted with groups independently selected from deuterium, methyl, ethyl, propyl, isopropyl, methoxy, ethoxy, propoxy, isopropoxy, halogen, —CF$_3$, —CN, —NH$_2$, —NHMe, —NHEt, —NHPr, —NHiPr, pyrrolidino, morpholino, and piperidino.

In certain embodiments of Formula I, the A-B bycyclic ring is selected from

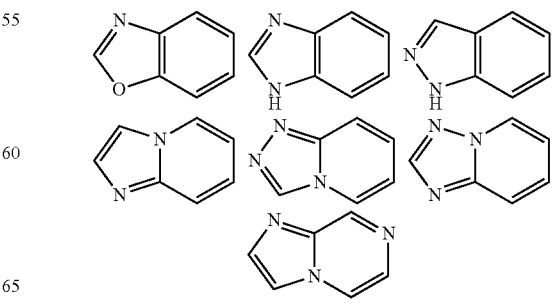

which may be optionally substituted with one or more groups independently selected from deuterium, —NH$_2$, amino (such as —NH(C$_1$-C$_5$), —N(C$_1$-C$_5$)$_2$, —NHPh, —NHBn, —NHpyridyl, —NHheterocycle(C$_4$-C$_7$), —NHcarbocycle(C$_4$-C$_7$)), heterocycle(C$_4$-C$_7$), carbocycle (C$_4$-C$_7$), halogen, —CN, —OH, —CF$_3$, sulfone, sulfoxide, sulfonamide, alkyl(C$_1$-C$_6$), thioalkyl(C$_1$-C$_6$), and alkoxy (C$_1$-C$_6$).

In certain embodiments of Formula I, the A-B bicyclic ring is

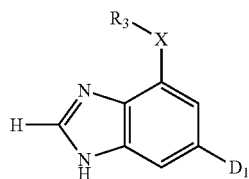

which may be optionally substituted with one or more groups independently selected from deuterium, —NH$_2$, —OH, alkyl(C$_1$-C$_6$), thioalkyl(C$_1$-C$_6$), and alkoxy(C$_1$-C$_6$).

In certain embodiments of Formula I, the A-B bicyclic ring is

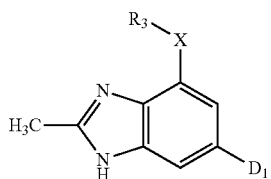

which may be optionally substituted with one or more groups independently selected from deuterium, —NH$_2$, —OH, alkyl(C$_1$-C$_6$), thioalkyl(C$_1$-C$_6$), and alkoxy(C$_1$-C$_6$).

In some embodiments of Formula I, the A-B bicyclic ring is selected from

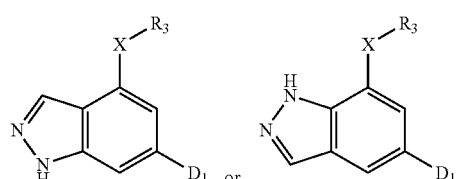

which may be optionally substituted with one or more groups independently selected from deuterium, —NH$_2$, —OH, alkyl(C$_1$-C$_6$), thioalkyl(C$_1$-C$_6$), and alkoxy(C$_1$-C$_6$).

In some embodiments of Formula I, one or more of the hydrogens of the A-B bicyclic ring is replaced by deuterium.

In some embodiments of Formula I, the A-B bicyclic ring is optionally substituted with one or more groups independently selected from deuterium, and alkyl(C$_1$-C$_6$).

In some embodiments of Formula I, the A-B bicyclic ring is optionally substituted with one or more groups independently selected from deuterium, and alkyl(C$_1$-C$_6$).

In some embodiments of Formula I, D$_1$ is selected from a 5-membered monocyclic heterocycle selected from

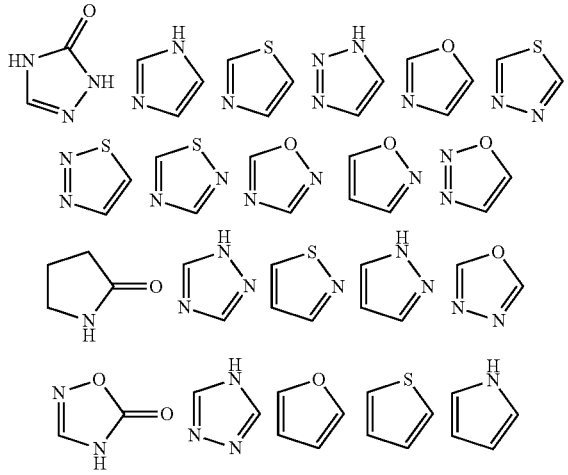

optionally substituted with one or more deuterium, alkyl (C$_1$-C$_4$) (such as methyl, ethyl, propyl, isopropyl, butyl), alkoxy(C$_1$-C$_4$) (such as methoxy, ethoxy, isopropoxy), amino (such as —NH$_2$, —NHMe, —NHEt, —NHiPr, —NHBu —NMe$_2$, NMeEt, —NEt$_2$, —NEtBu, —NHC(O) NHalkyl), halogen (such as F, Cl), amide (such as —NHC (O)Me, —NHC(O)Et, —C(O)NHMe, —C(O)NEt$_2$, —C(O) NiPr), —CF$_1$, CN, —N$_3$, ketone (C$_1$-C$_4$) (such as acetyl, —C(O)Et, —C(O)Pr), —S(O)Alkyl(C$_1$-C$_4$) (such as —S(O) Me, —S(O)Et), —SO$_2$alkyl(C$_1$-C$_4$) (such as —SO$_2$Me, —SO$_2$Et, —SO$_2$Pr), -thioalkyl(C$_1$-C$_4$) (such as —SMe, —SEt, —SPr, —SBu), —COOH, and/or ester (such as —C(O)OMe, —C(O)OEt, —C(O)OBu), wherein said alkyl (C$_1$-C$_4$), alkoxy(C$_1$-C$_4$), amino, amide, ketone (C$_1$-C$_4$), —S(O)Alkyl(C$_1$-C$_4$), —SO$_2$alkyl(C$_1$-C$_4$), -thioalkyl(C$_1$-C$_4$), and ester may be optionally substituted with F, Cl, Br, —OH, —NH$_2$, —NHMe, —OMe, and —SMe.

In certain embodiments of Formula I, D$_1$ is selected from a 5-membered monocyclic heterocycle selected from

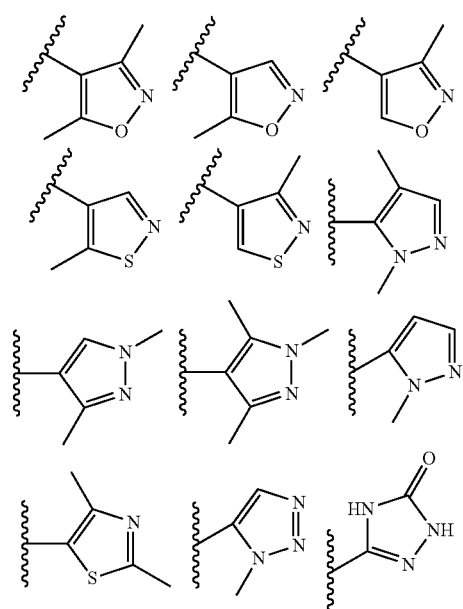

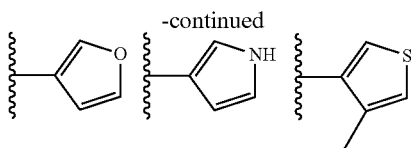

optionally substituted with one or more deuterium, alkyl (C$_1$-C$_4$)(such as methyl, ethyl, propyl, isopropyl, butyl), alkoxy(C$_1$-C$_4$) (such as methoxy, ethoxy, isopropoxy), amino (such as —NH$_2$, —NHMe, —NHEt, —NHiPr, —NHBu —NMe$_2$, NMeEt, —NEt$_2$, —NEtBu, —NHC(O)NHalkyl), halogen (such as F, Cl), amide (such as —NHC(O)Me, —NHC(O)Et, —C(O)NHMe, —C(O)NEt$_2$, —C(O)NiPr), —CF$_3$, CN, —N$_3$, ketone (C$_1$-C$_4$) (such as acetyl, —C(O)Et, —C(O)Pr), —S(O)Alkyl(C$_1$-C$_4$) (such as —S(O)Me, —S(O)Et), —SOzalkyl(C$_1$-C$_4$) (such as —SO$_2$Me, —SO$_2$Et, —SO$_2$Pr), -thioalkyl(C$_1$-C$_4$) (such as —SMe, —SEt, —SPr, —SBu), —COOH, and/or ester (such as —C(O)OMe, —C(O)OEt, —C(O)OBu), wherein said alkyl (C$_1$-C$_4$), alkoxy(C$_1$-C$_4$), amino, amide, ketone (C$_1$-C$_4$), —S(O)Alkyl(C$_1$-C$_4$), —SO$_2$alkyl(C$_1$-C$_4$), -thioalkyl(C$_1$-C$_4$), and ester may be optionally substituted with F, Cl, Br, —OH, —NH$_2$, —NHMe, —OMe, and —SMe.

In certain embodiments of Formula I, D$_1$ is selected from a 5-membered monocyclic heterocycle selected from

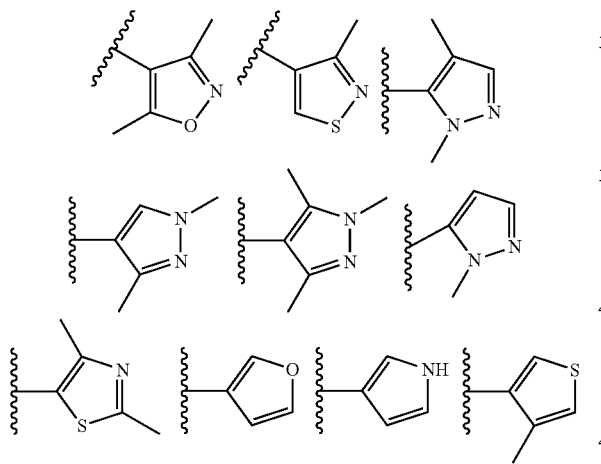

optionally substituted with one or more deuterium, alkyl (C$_1$-C$_4$)(such as methyl, ethyl, propyl, isopropyl, butyl), alkoxy(C$_1$-C$_4$) (such as methoxy, ethoxy, isopropoxy), amino (such as —NH$_2$, —NHMe, —NHEt, —NHiPr, —NHBu —NMe$_2$, NMeEt, —NEt$_2$, —NEtBu, —NHC(O)NHalkyl), halogen (such as F, Cl), amide (such as —NHC(O)Me, —NHC(O)Et, —C(O)NHMe, —C(O)NEt$_2$, —C(O)NiPr), —CF$_3$, CN, —N$_3$, ketone (C$_1$-C$_4$) (such as acetyl, —C(O)Et, —C(O)Pr), —S(O)Alkyl(C$_1$-C$_4$) (such as —S(O)Me, —S(O)Et), —SO$_2$alkyl(C$_1$-C$_4$) (such as —SO$_2$Me, —SO$_2$Et, —SO$_2$Pr), -thioalkyl(C$_1$-C$_4$) (such as —SMe, —SEt, —SPr, —SBu), —COOH, and/or ester (such as —C(O)OMe, —C(O)OEt, —C(O)OBu), wherein said alkyl (C$_1$-C$_4$), alkoxy(C$_1$-C$_4$), amino, amide, ketone (C$_1$-C$_4$), —S(O)Alkyl(C$_1$-C$_4$), —SO$_2$alkyl(C$_1$-C$_4$), -thioalkyl(C$_1$-C$_4$), and ester may be optionally substituted with F, Cl, Br, —OH, —NH$_2$, —NHMe, —OMe, and —SMe.

In certain embodiments of Formula I, D$_1$ is optionally substituted with one or more deuterium, alkyl(C$_1$-C$_4$)(such as methyl, ethyl, propyl, isopropyl, butyl), alkoxy(C$_1$-C$_4$) (such as methoxy, ethoxy, isopropoxy, wherein said alkyl (C$_1$-C$_4$) and alkoxy(C$_1$-C$_4$) may be optionally substituted with F, Cl, Br, —OH, and —NH$_2$, In certain embodiments of Formula I, D$_1$ is selected from a 5-membered monocyclic heterocycle containing one oxygen and one or two nitrogens, where the heterocycle is connected to the rest of the molecule via a carbon-carbon bond, optionally substituted with one or more deuterium, alkyl(C$_1$-C$_4$) (such as methyl, ethyl, propyl, isopropyl, butyl) optionally substituted with F, Cl, Br, —OH, and —NH$_2$, In certain embodiments of Formula I, D$_1$ is an isoxazole optionally substituted with one or more deuterium, alkyl (C$_1$-C$_4$)(such as methyl, ethyl, propyl, isopropyl, butyl) which may be optionally substituted with F, Cl, Br, —OH, and —NH$_2$.

In certain embodiments of Formula I, D$_1$ is an isoxazole optionally substituted with one or two groups independently selected from deuterium, alkyl(C$_1$-C$_4$)(such as methyl, ethyl, propyl, isopropyl, butyl) which may be optionally substituted with F, Cl, Br, —OH, and —NH$_2$.

In some embodiments of Formula I, D$_1$ is

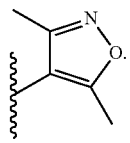 [SMILES: *c1c(C)noc1C]

In some embodiments of Formula I, W$_1$ is CR$_1$.
In some embodiments of Formula I, W$_2$ is CR$_2$.
In some embodiments of Formula I, W$_3$ and W$_4$ are C.
In other embodiments of Formula I, at least one of W$_1$ and W$_2$ is nitrogen.
In some embodiments of Formula I, either W$_3$ or W$_4$ is nitrogen.
In certain embodiments of Formula I, the A-B bicyclic ring is

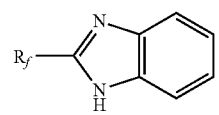

wherein R$_f$ is selected from hydrogen, deuterium, —NH$_2$, amino (such as —NH(C$_1$-C$_5$), —N(C$_1$-C$_5$)$_2$, —NHPh, —NHBn, —NHpyridyl, —NHheterocycle(C$_4$-C$_7$), —NHcarbocycle(C$_4$-C$_7$)), heterocycle(C$_4$-C$_7$), carbocycle (C$_4$-C$_7$), halogen, —CN, —OH, —CF$_3$, sulfone, sulfoxide, sulfonamide, alkyl(C$_1$-C$_6$), thioalkyl(C$_1$-C$_6$), alkenyl(C$_1$-C$_6$), alkoxy(C$_1$-C$_6$), ketone(C$_1$-C$_6$), ester, urea, carboxylic acid, carbamate, and amide(C$_1$-C$_6$).

In some embodiments of Formula I, R$_f$ is selected from hydrogen, deuterium, —NH$_2$, amino (such as —NH(C$_1$-C$_5$), —N(C$_1$-C$_5$)$_2$, —NHPh, —NHBn, —NHpyridyl, —NHheterocycle(C$_4$-C$_7$), —NHcarbocycle(C$_4$-C$_7$)), heterocycle(C$_4$-C$_7$), carbocycle(C$_4$-C$_7$), —CF$_3$, alkyl(C$_1$-C$_6$), and alkoxy (C$_1$-C$_6$).

In some embodiments of Formula I, R$_f$ is selected from hydrogen, deuterium, amino (such as —NH(C$_1$-C$_5$), —N(C$_1$-C$_5$)$_2$, —NHPh, —NHBn, —NHpyridyl, —NHheterocycle(C$_4$-C$_7$), —NHcarbocycle(C$_4$-C$_7$)), heterocycle(C$_4$-C$_7$), carbocycle(C$_4$-C$_7$), —CF$_3$, and alkyl(C$_1$-C$_6$).

In some embodiments of Formula I, $R_f$ is selected from hydrogen, deuterium,
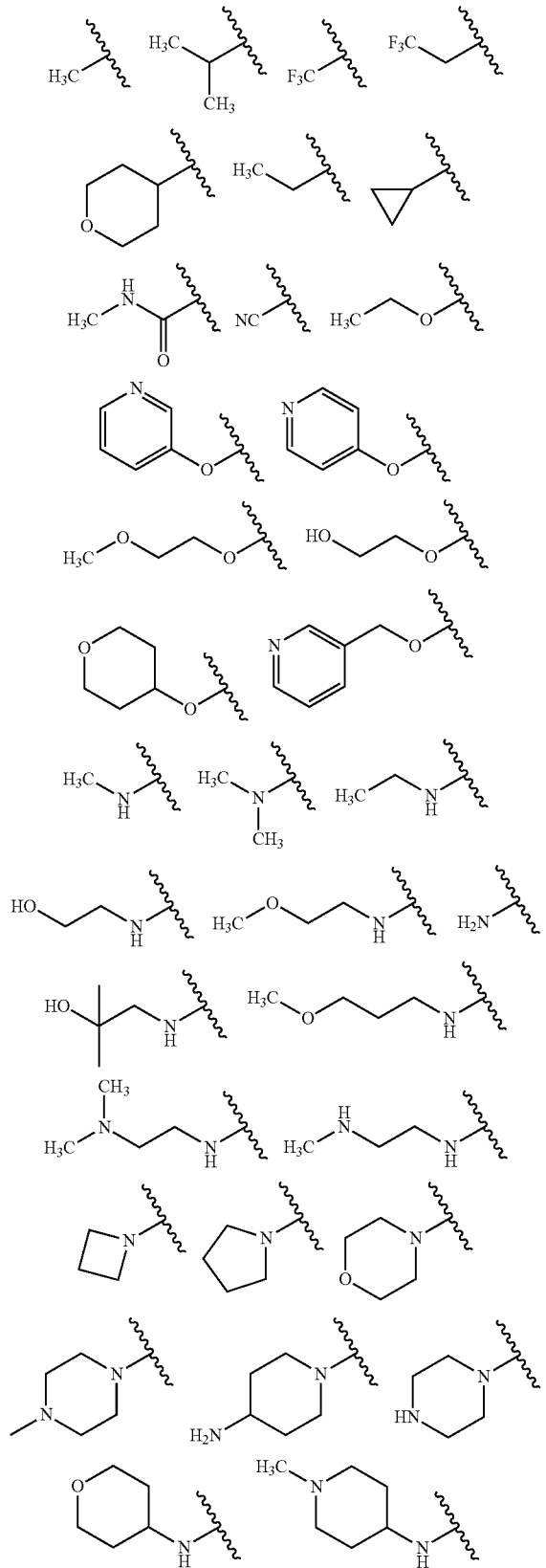
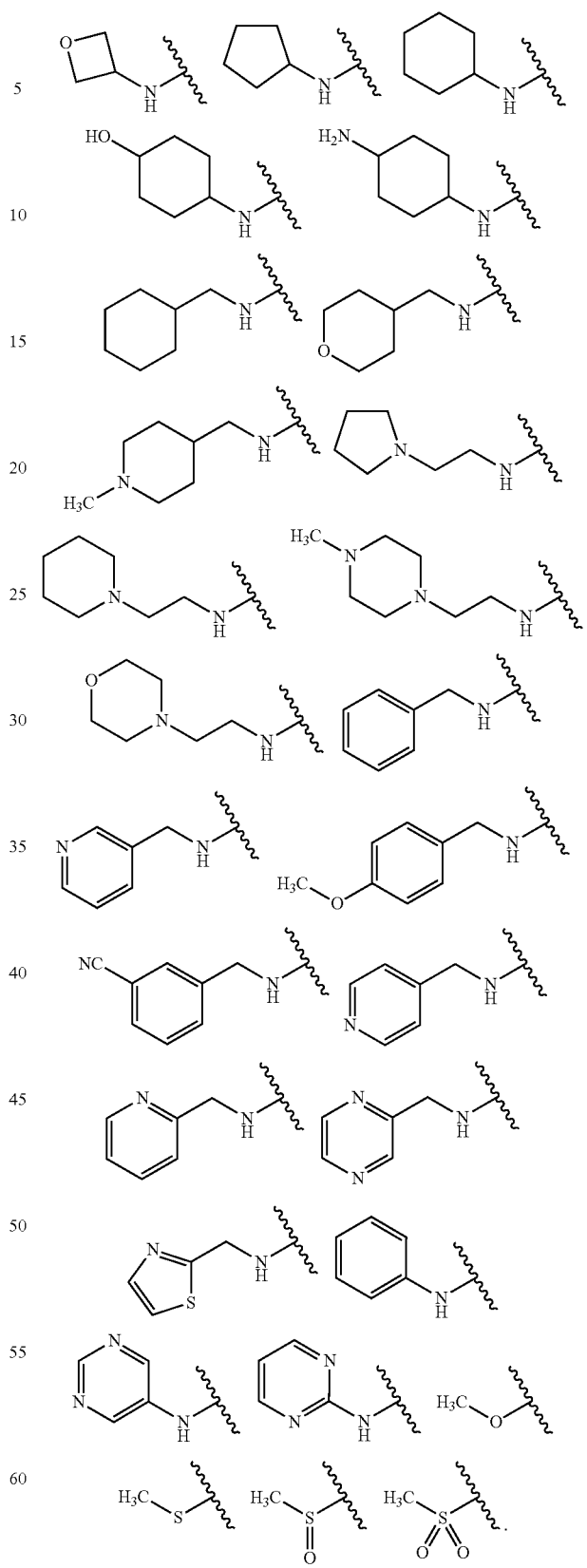
In certain embodiments of Formula I, $R_f$ is selected from hydrogen, deuterium,

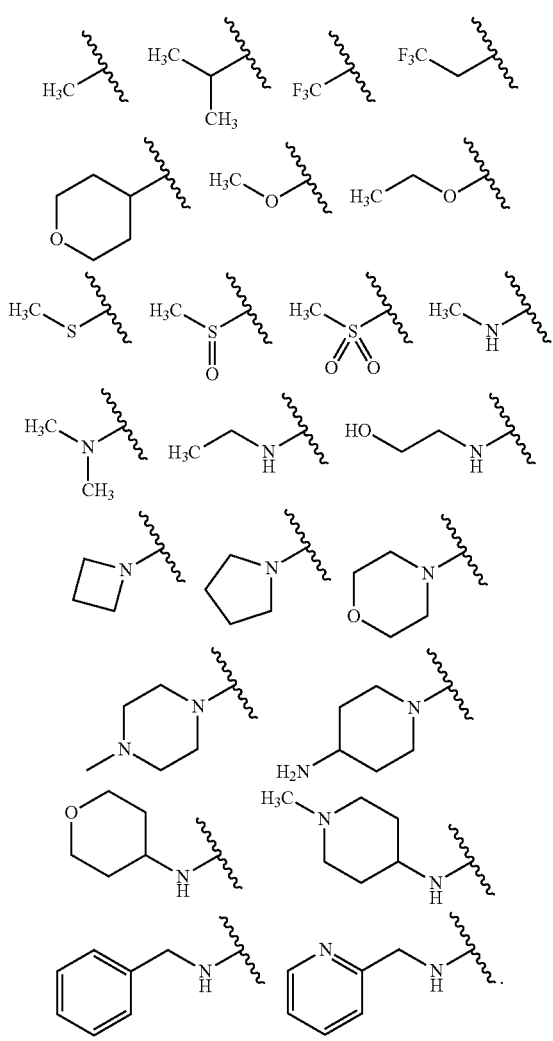

In other embodiments of Formula I, X is optionally present, and if present, is selected from —O—, —(NH)—, —NHCR$_x$R$_y$—, —NHCR$_x$R$_y$CR$_x$R$_y$—, —N(CR$_x$R$_y$CR$_x$R$_y$)$_2$—, —CH$_2$CH$_2$—, —CH=CH—, and —NHC(O)—, —NHSO$_2$—, —CR$_x$R$_y$NH—, —OCR$_x$R$_y$—, —CR$_x$R$_y$O—, —SCR$_x$R$_y$—, —CR$_x$R$_y$S—, where S might be oxidized to sulfoxide or sulfone.

In certain embodiments of Formula I, X is optionally present, and if present, is selected from —(NH)—, —NHCR$_x$R$_y$—, —CR$_x$R$_y$NH—.

In some embodiments of Formula I, X is —NH— and R$_3$ is hydrogen.

In some embodiments of Formula I, R$_x$ and R$_y$ are each independently selected from hydrogen, alkyl(C$_{1-5}$), halogen, —OH, —CF$_3$, deuterium, amino, and alkoxy(C$_{1-5}$).

In certain embodiments of Formula I, R$_x$ and R$_y$ are each independently selected from hydrogen, alkyl(C$_{1-5}$), halogen, —OH, —CF$_3$, and deuterium.

In some embodiments of Formula I, R$_x$ and R$_y$ are each independently selected from hydrogen, alkyl(C$_{1-5}$), deuterium, alkoxy(C$_{1-5}$), or two substituents selected from R$_x$, R$_y$, and R$_1$ may be connected in a 5- or 6-membered ring to form a bicyclic carbocycle or bicyclic heterocycle.

In some embodiments of Formula I, X is not present.

In some embodiments of Formula I, R$_1$ is selected from hydrogen, deuterium, alkyl, —OH, and —NH$_2$ In some embodiments of Formula I, R$_2$ is selected from hydrogen, deuterium, alkyl, —OH, and —NH$_2$, In some embodiments of Formula I, R$_1$ and R$_2$ are independently selected from hydrogen, deuterium, alkyl, and —NH$_2$ In other embodiments of Formula I, R$_3$ is selected from 5-6 membered carbocycles and heterocycles.

In some embodiments of Formula I, R$_3$ is selected from 5-6 membered heterocycles.

In certain embodiments of Formula I, R$_3$ is selected from 5-6 membered heterocycles containing 1 or 2 nitrogens, such as unsubstituted and substituted pyrimidyl rings.

In certain embodiments of Formula I, R$_3$ is selected from 6-membered heterocycles containing at least one nitrogen, such as unsubstituted and substituted pyridyl rings.

In some embodiments of Formula I, R$_3$ is selected from

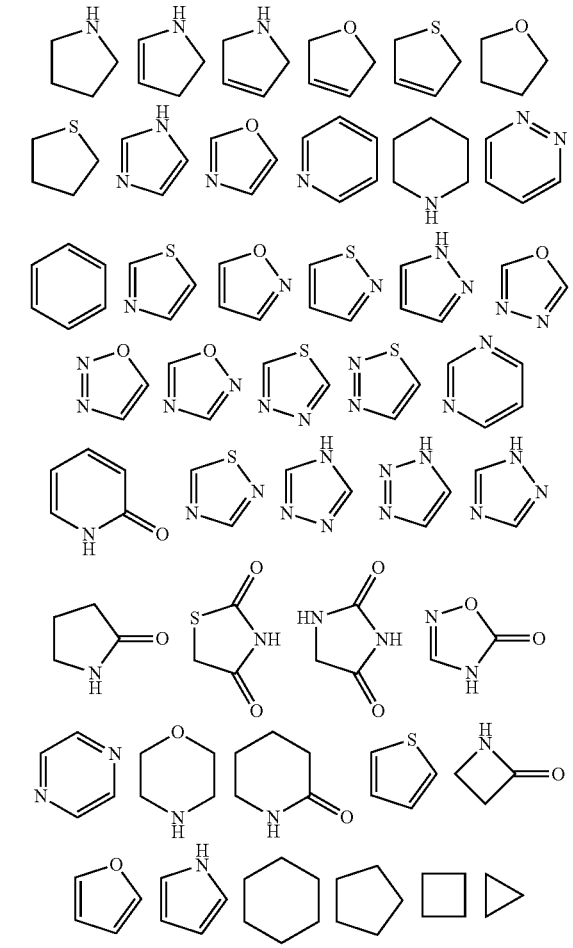

optionally substitued with one or more groups independently selected from deuterium, alkyl(C$_3$-C$_4$)(such as methyl, ethyl, propyl, isopropyl, butyl), —OH, alkoxy(C$_1$-C$_4$) (such as methoxy, ethoxy, isopropoxy), amino (such as —NH$_2$, —NHMe, —NHEt, —NHiPr, —NHBu —NMe$_2$NMeEt, —NEt$_2$, —NEtBu, —NHC(O)NHalkyl), halogen (such as F, Cl), amide (such as —NHC(O)Me, —NHC(O)Et, —C(O)NHMe, —C(O)NH$_2$, C(O)NEt$_2$, —C(O)NIPr, —C(O)N(cyclopentyl)), —CF$_3$, CN, —OCf$_3$, —N$_3$, ketone (C$_1$-C$_4$) (such as acetyl, —C(O)Et, —C(O)Pr), —S(O)Alkyl(C$_1$-C$_4$) (such as —S(O)Me, —S(O)Et), —SO$_2$alkyl(C$_1$-C$_4$)) such as —SO$_2$Me, —SO$_2$Et, —SO$_2$Pr), thioalkyl($C_1$-$C_4$)) (such as —SMe, —SEt, —SPr, —SBu), carboxyl (such as —COOH), and/or ester (such as —C(O)OMe, —C(O)OEt, —C(O)OBu), wherein said alkyl($C_1$-$C_4$), alkoxy($C_1$-$C_4$), amino, amide, ketone ($C_1$-$C_4$), —S(O)Alkyl ($C_1$-$C_4$), —$SO_2$alkyl($C_1$-$C_4$), -thioalkyl($C_1$-$C_4$), and ester may be optionally substituted with F, Cl, Br, —OH, —$NH_2$, —NHMe, —$NMe_2$, —OMe, —SMe, oxo, and/or thio-oxo.

In some embodiments of Formula I, $R_3$ is selected from

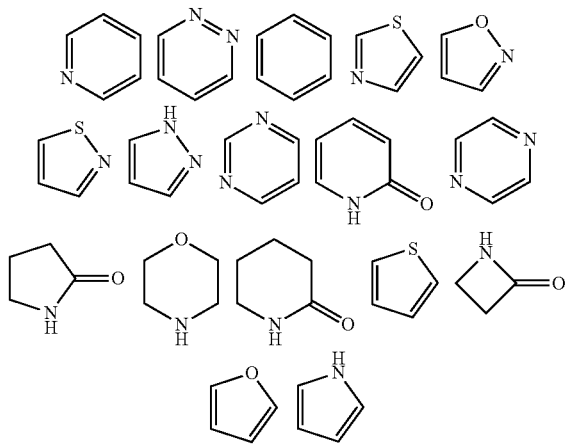

optionally substituted with one or more groups independently selected from deuterium, alkyl($C_1$-$C_4$)(such as methyl, ethyl, propyl, isopropyl, butyl), alkoxy($C_1$-$C_4$) (such as methoxy, ethoxy, isopropoxy), amino (such as —$NH_2$, —NHMe, —NHEt, —NHiPr, —NHBu —$NMe_2$, NMeEt, —$NEt_2$, —NEtBu, —NHC(O)NHalkyl), halogen (such as F, Cl), amide (such as —NHC(O)Me, —NHC(O)Et, —C(O)NHMe, —C(O)$NH_2$, —C(O)$NEt_2$, —C(O)NiPr, —C(O)N(cyclopentyl)), —$CF_3$, CN, —$OCF_3$, —$SO_2$alkyl($C_1$-$C_4$) (such as —$SO_2$Me, —$SO_2$Et, —$SO_2$Pr), and carboxyl (such as —COOH), wherein said alkyl($C_1$-$C_4$), alkoxy($C_1$-$C_4$), amino, amide, and —$SO_2$alkyl($C_1$-$C_4$), may be optionally substituted with F, Cl, Br, —OH, —$NH_2$, —NHMe, —$NMe_2$, —OMe, —SMe, oxo, and/or thio-oxo.

In some embodiments of Formula I, $R_3$ is an isoxazole or pyrazole optionally substituted with one or more groups independently selected from deuterium, alkyl($C_1$-$C_4$)(such as methyl, ethyl, propyl, isopropyl, butyl), —OH, alkoxy ($C_1$-$C_4$) (such as methoxy, ethoxy, isopropoxy), amino (such as —$NH_2$, —NHMe, —NHEt, —NHiPr, —NHBu —$NMe_2$, NMeEt, —$NEt_2$, —NEtBu, —NHC(O)NHalkyl), halogen (such as F, Cl), amide (such as —NHC(O)Me, —NHC(O)Et, —C(O)NHMe, —C(O)$NH_2$, —C(O)$NEt_2$, —C(O)NiPr, —C(O)N(cyclopentyl)), —$CF_3$, CN, —$OCF_3$, —$N_3$, ketone ($C_1$-$C_4$) (such as acetyl, —C(O)Et, —C(O)Pr), —S(O)Alkyl ($C_1$-$C_4$) (such as —S(O)Me, —S(O)Et), —$SO_2$alkyl($C_1$-$C_4$) (such as —$SO_2$Me, —$SO_2$Et, —$SO_2$Pr), -thioalkyl($C_1$-$C_4$) (such as —SMe, —SEt, —SPr, —SBu), carboxyl (such as —COOH), and/or ester (such as —C(O)OMe, —C(O)OEt, —C(O)OBu), wherein said alkyl($C_1$-$C_4$), alkoxy($C_1$-$C_4$), amino, amide, ketone ($C_1$-$C_4$), —S(O)Alkyl($C_1$-$C_4$), —$SO_2$alkyl($C_1$-$C_4$), -thioalkyl($C_1$-$C_4$), and ester may be optionally substituted with F, Cl, Br, —OH, —$NH_2$, —NHMe, —$NMe_2$, —OMe, —SMe, oxo, and/or thio-oxo.

In some embodiments of Formula I, $R_3$ is selected from 5-6 membered carbocycles, such as a substituted or unsubstituted phenyl ring.

In some embodiments of Formula I, $R_3$ is an isoxazolyl, oxazolyl, pyrazolyl, pyridyl, pyridonyl, thiazolyl, isothiaz-olyl, pyrimidinyl, thiozolyl, pyrazinyl, pyridazinyl, azetidi-nyl, pyrrolidyl, piperidinyl, morpholinyl, cyclopropyl, cyclobutyl, cyclopentyl, cyclohexyl, or phenyl optionally substituted with one or more groups independently selected from deuterium, alkyl($C_1$-$C_4$)(such as methyl, ethyl, propyl, isopropyl, butyl), —OH, alkoxy($C_1$-$C_4$) (such as methoxy, ethoxy, isopropoxy), amino (such as —$NH_2$, —NHMe, —NHEt, —NHiPr, —NHBu —$NMe_2$, NMeEt, —$NEt_2$, —NEtBu, —NHC(O)NHalkyl), halogen (such as F, Cl), amide (such as —NHC(O)Me, —NHC(O)Et, —C(O)NHMe, —C(O)$NH_2$, —C(O)$NEt_2$, —C(O)NiPr, —C(O)N(cyclopentyl)), —$CF_3$, CN, —$OCF_3$, —$N_3$, ketone ($C_1$-$C_4$) (such as acetyl, —C(O)Et, —C(O)Pr), —S(O)Alkyl($C_1$-$C_4$) (such as —S(O)Me, —S(O)Et), —$SO_2$alkyl($C_1$-$C_4$) (such as —$SO_2$Me, —$SO_2$Et, —$SO_2$Pr), -thioalkyl($C_1$-$C_4$) (such as —SMe, —SEt, —SPr, —SBu), carboxyl (such as —COOH), and/or ester (such as —C(O)OMe, —C(O)OEt, —C(O)OBu), wherein said alkyl($C_1$-$C_4$), alkoxy($C_1$-$C_4$), amino, amide, ketone ($C_1$-$C_4$), —S(O)Alkyl($C_2$-$C_4$), —$SO_2$alkyl($C_1$-$C_4$), -thioalkyl($C_1$-$C_4$), and ester may be optionally substituted with F, Cl, Br, —OH, —$NH_2$, —NHMe, —$NMe_2$, —OMe. —SMe, oxo, and/or thio-oxo.

In certain embodiments of Formula I, $R_3$ is selected from

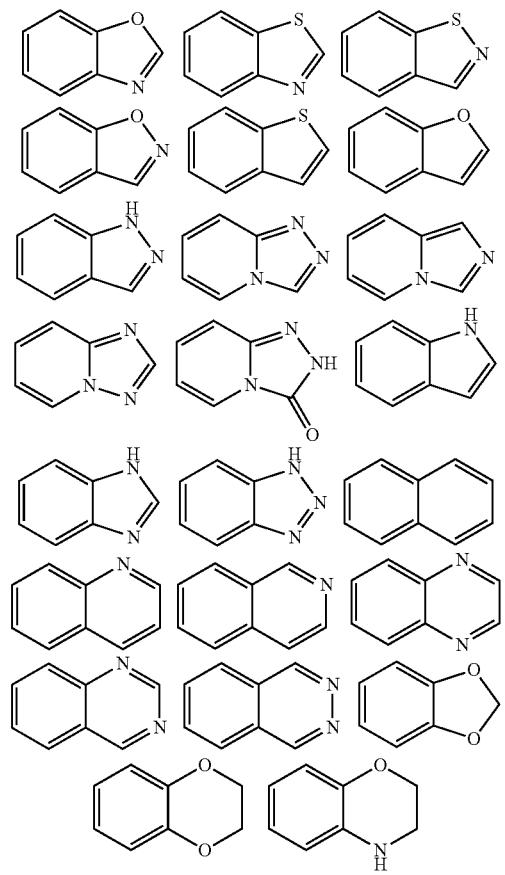

optionally substituted with one or more groups independently selected from deuterium, alkyl($C_1$-$C_4$)(such as methyl, ethyl, propyl, isopropyl, butyl), —OH, alkoxy($C_1$-$C_4$) (such as methoxy, ethoxy, isopropoxy), amino (such as —$NH_2$, —NHMe, —NHEt, —NHiPr, —NHBu —NMez, NMeEt, —$NEt_2$, —NEtBu, —NHC(O)NHalkyl), halogen (such as F, Cl), amide (such as —NHC(O)Me, —NHC(O)

Et, —C(O)NHMe, —C(O)NH$_2$, —C(O)NEt$_2$, —C(O)NiPr, —C(O)N(cyclopentyl)), —CF$_3$, CN, —OCF$_3$, —N$_3$, ketone (C$_1$-C$_4$) (such as acetyl, —C(O)Et, —C(O)Pr), —S(O)Alkyl (C$_1$-C$_4$) (such as —S(O)Me, —S(O)Et), —SO$_2$alkyl(C$_1$-C$_4$) (such as —SO$_2$Me, —SO$_2$Et, —SO$_2$Pr), -thioalkyl(C$_1$-C$_4$) (such as —SMe, —SEt, —SPr, —SBu), carboxyl (such as —COOH), and/or ester (such as —C(O)OMe, —C(O)OEt, —C(O)OBu), wherein said alkyl(C$_1$-C$_4$), alkoxy(C$_1$-C$_4$), amino, amide, ketone (C$_1$-C$_4$), —S(O)Alkyl(C$_1$-C$_4$), —SO$_2$alkyl(C$_1$-C$_4$), -thioalkyl(C$_1$-C$_4$), and ester may be optionally substituted with F, Cl, Br, —OH, —NH$_2$, —NHMe, —NMe$_2$, —OMe, —SMe, oxo, and/or thio-oxo.

In some embodiments of Formula I, R$_3$ is selected from

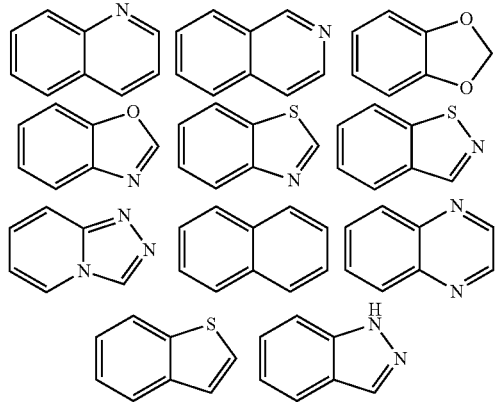

optionally substituted with one or more groups independently selected from deuterium, alkyl(C$_1$-C$_4$)(such as methyl, ethyl, propyl, isopropyl, butyl), alkoxy(C$_1$-C$_4$) (such as methoxy, ethoxy, isopropoxy), amino (such as —NH$_2$, —NHMe, —NHEt, —NHiPr, —NHBu —NMe$_2$, NMeEt, —NEt$_2$, —NEtBu, —NHC(O)NHalkyl), halogen (such as F, Cl), amide (such as —NHC(O)Me, —NHC(O)Et, —C(O)NHMe, —C(O)NH$_2$, —C(O)NEt$_2$, —C(O)NiPr, —C(O)N(cyclopentyl)), —CF$_3$, CN, —OCF$_3$, —SO$_2$alkyl(C$_1$-C$_4$) (such as —SO$_2$Me, —SO$_2$Et, —SO$_2$Pr), and carboxyl (such as —COOH), wherein said alkyl(C$_1$-C$_4$), alkoxy(C$_1$-C$_4$), amino, amide, and —SO$_2$alkyl(C$_1$-C$_4$), may be optionally substituted with F, Cl, Br, —OH, —NH$_2$, —NHMe, —NMe$_2$, —OMe, —SMe, oxo, and/or thio-oxo.

In certain embodiments of Formula I, R$_3$ is selected from

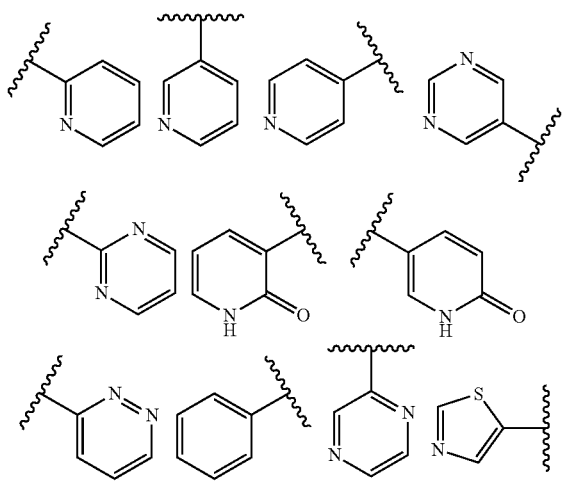

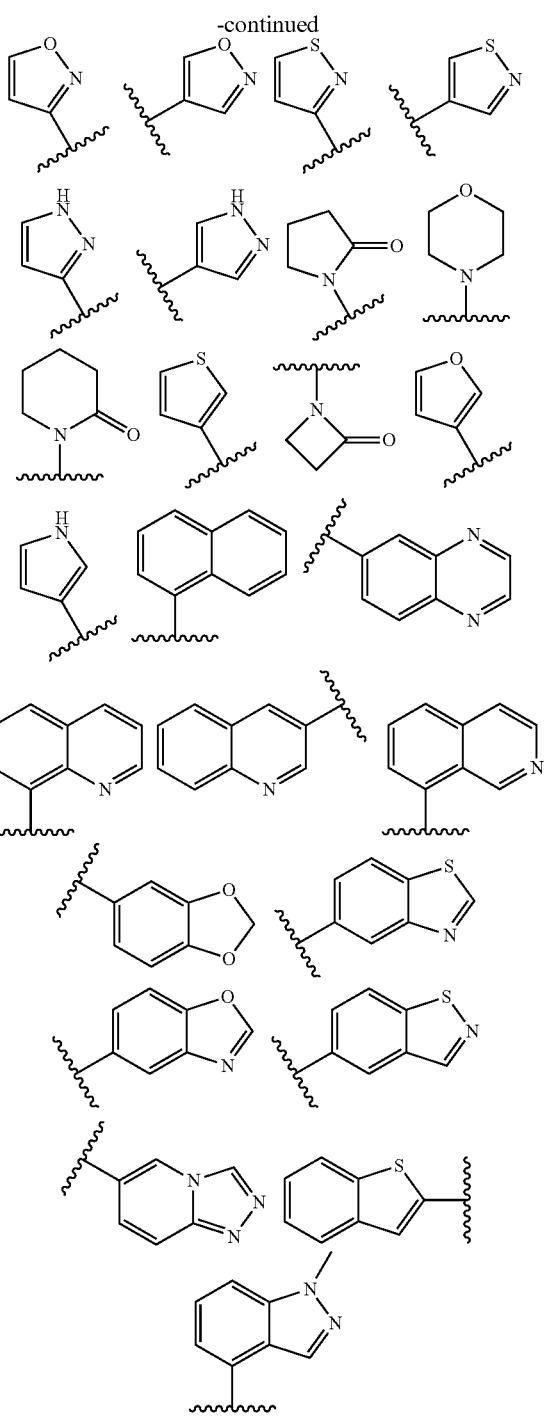

optionally substituted with one or more groups independently selected from deuterium, alkyl(C$_1$-C$_4$)(such as methyl, ethyl, propyl, isopropyl, butyl), alkoxy(C$_1$-C$_4$) (such as methoxy, ethoxy, isopropoxy), amino (such as —NH$_2$, —NHEt, —NHiPr, —NHBu —NMe$_2$, NMeEt, —NEt$_2$, —NEtBu, —NHC(O)NHalkyl), halogen (such as F, Cl), amide (such as —NHC(O)Me, —NHC(O)Et, —C(O)NHMe, —C(O)NH$_2$, —C(O)NEt$_2$, —C(O)NiPr, —C(O)N(cyclopentyl)), —CF$_3$, CN, —OCF$_3$, —SO$_2$alkyl(C$_1$-C$_4$) (such as SO$_2$Me, —SO$_2$Et, —SO$_2$Pr), and carboxyl (such as —COOH), wherein said alkyl(C$_1$-C$_4$), alkoxy(C$_1$-C$_4$), amino, amide, and —SO$_2$alkyl(C$_1$-C$_4$), may be optionally substituted with F, Cl, Br, —OH, —NH$_2$, —NHMe, —NMe$_2$, —OMe, —SMe, oxo, and/or thio-oxo.

In other embodiments of Formula I, —X—R$_3$ is selected from —NHAryl.

In some embodiments of Formula I, R$_3$ is pyridyl.

In certain embodiments of Formula I, the A-B bicyclic ring is selected from

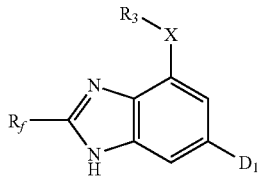

which may be optionally substituted with one or more groups independently selected from deuterium, —NH$_2$, —OH, alkyl(C$_1$-C$_6$), thioalkyl(C$_1$-C$_6$), and alkoxy(C$_1$-C$_6$).

D$_1$ is an isoxazole or pyrazole optionally substituted with one or more groups independently selected from deuterium, alkyl(C$_1$-C$_4$)(such as methyl, ethyl, propyl, isopropyl, butyl), —OH, alkoxy(C$_1$-C$_4$) (such as methoxy, ethoxy, isopropoxy), amino (such as —NH$_2$, —NHMe, —NHEt, —NHiPr, —NHBu —NMe$_2$, NMeEt, —NEt$_2$, —NEtBu, —NHC(O)NHalkyl), halogen (such as F, Cl), amide (such as —NHC(O)Me, —NHC(O)Et, —C(O)NHMe, —C(O)NH$_2$, —C(O)NEt$_2$, —C(O)NiPr, —C(O)N(cyclopentyl)), —CF$_3$, CN, —OCF$_3$, —N$_3$, ketone (C$_1$-C$_4$) (such as acetyl, —C(O)Et, —C(O)Pr), —S(O)Alkyl(C$_1$-C$_4$) (such as —S(O)Me, —S(O)Et), —SO$_2$alkyl(C$_1$-C$_4$) (such as —SO$_2$Me, —SOzEt, —SO$_2$Pr), -thioalkyl(C$_1$-C$_4$) (such as —SMe, —SEt, —SPr, —SBu), carboxyl (such as —COOH), and/or ester (such as —C(O)OMe, —C(O)OEt, —C(O)OBu), wherein said alkyl(C$_1$-C$_4$), alkoxy(C$_1$-C$_4$), amino, amide, ketone (C$_1$-C$_4$), —S(O)Alkyl(C$_1$-C$_4$), —SO$_2$alkyl(C$_2$-C$_4$), -thioalkyl(C$_1$-C$_4$), and ester may be optionally substituted with F, Cl, Br, —OH, —NH$_2$, —NHMe, —NMe$_2$, —OMe, —SMe, oxo, and/or thio-oxo;

X is optionally present, and if present, is selected from —(NH)—, —O—, —NHCR$_x$R$_y$—, —NHSO$_2$—, —CR$_x$R$_y$NH—, or —NH$_2$ and R$_a$ is absent; and R$_3$ is selected from 5-6 membered carbocycles and heterocycles, such as, an isoxazolyl, oxazolyl, pyrazolyl, pyridyl, pyridonyl, thiazolyl, isothiazolyl, pyrimidinyl, thiozolyl, pyrazinyl, pyridazinyl, azetidinyl, pyrrolidyl, piperidinyl, morpholinyl, cyclopropyl, cyclobutyl, cyclopentyl, cyclohexyl, or phenyl optionally substituted with one or more groups independently selected from deuterium, alkyl (C$_1$-C$_4$)(such as methyl, ethyl, propyl, isopropyl, butyl), —OH, alkoxy(C$_1$-C$_4$) (such as methoxy, ethoxy, isopropoxy), amino (such as —NH$_2$, —NHMe, —NHEt, —NHiPr, —NHBu —NMe$_2$, NMeEt, —NEt$_2$, —NEtBu, —NHC(O)NHalkyl), halogen (such as F, Cl), amide (such as —NHC(O)Me, —NHC(O)Et, —C(O)NHMe, —C(O)NH$_2$, —C(O)NEt$_2$, —C(O)NiPr, —C(O)N(cyclopentyl)), —CF$_3$, CN, —OCF$_3$, —N$_3$, ketone (C$_1$-C$_4$) (such as acetyl, —C(O)Et, —C(O)Pr), —S(O)Alkyl(C$_1$-C$_4$) (such as —S(O)Me, —S(O)Et), —SO$_2$alkyl(C$_1$-C$_4$) (such as —SO$_2$Me, —SO$_2$Et, —SO$_2$Pr), -thioalkyl(C$_1$-C$_4$) (such as —SMe, —SEt, —SPr, —SBu), carboxyl (such as —COOH), and/or ester (such as —C(O)OMe, —C(O)OEt, —C(O)OBu), wherein said alkyl(C$_1$-C$_4$), alkoxy(C$_1$-C$_4$), amino, amide, ketone (C$_1$-C$_4$), —S(O)Alkyl(C$_1$-C$_4$), —SO$_2$alkyl(C$_1$-C$_4$), -thioalkyl(C$_1$-C$_4$), and ester may be optionally substituted with F, Cl, Br, —OH, —NH$_2$, —NHMe, —NMe$_2$, —OMe, —SMe, oxo, and/or thio-oxo.

In certain embodiments of Formula I, the A-B bicyclic ring is selected from

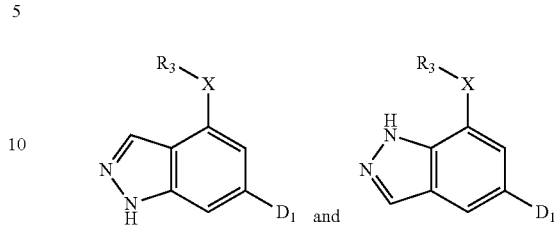

which may be optionally substituted with one or more groups independently selected from deuterium, —NH$_2$, —OH, alkyl(C$_1$-C$_6$), thioalkyl(C$_1$-C$_6$), and alkoxy(C$_1$-C$_6$);

D$_1$ is an isoxazole or pyrazole optionally substituted with one or more groups independently selected from deuterium, alkyl(C$_1$-C$_4$)(such as methyl, ethyl, propyl, isopropyl, butyl), —OH, alkoxy(C$_1$-C$_4$) (such as methoxy, ethoxy, isopropoxy), amino (such as —NH, —NHMe, —NHEt, —NHiPr, —NHBu —NMe$_2$, NMeEt, —NEt$_2$, —NEtBu, —NHC(O)NHalkyl), halogen (such as F, Cl), amide (such as —NHC(O)Me, —NHC(O)Et, —C(O)NHMe, —C(O)NH$_2$, —C(O)NEt$_2$, —C(O)NiPr, —C(O)N(cyclopentyl)), —CF$_3$, CN, —OCF$_3$, —N$_3$, ketone (C$_1$-C$_4$) (such as acetyl, —C(O)Et, —C(O)Pr), —S(O)Alkyl(C$_1$-C$_4$) (such as —S(O)Me, —S(O)Et), —SO$_2$alkyl(C$_1$-C$_4$) (such as —SO$_2$Me, —SO$_2$Et, —SOzPr), -thioalkyl(C$_1$-C$_4$) (such as —SMe, —SEt, —SPr, —SBu), carboxyl (such as —COOH), and/or ester (such as —C(O)OMe, —C(O)OEt, —C(O)OBu), wherein said alkyl(C$_1$-C$_4$), alkoxy(C$_1$-C$_4$), amino, amide, ketone (C$_1$-C$_4$), —S(O)Alkyl(C$_1$-C$_4$), —SO$_2$alkyl(C$_1$-C$_4$), -thioalkyl(C$_1$-C$_4$), and ester may be optionally substituted with F, Cl, Br, —OH, —NH$_2$, —NHMe, —NMe$_2$, —OMe, —SMe, oxo, and/or thio-oxo;

X is optionally present, and if present, is selected from —(NH)—, —NHCR$_x$R$_y$—, —NHSO$_2$—, —CR$_x$R$_y$NH—, or —NH$_2$ and R$_3$ is absent;

R$_3$ is selected from 5-6 membered carbocycles and heterocycles, such as, an isoxazolyl, oxazolyl, pyrazolyl, pyridyl, pyridonyl, thiazolyl, isothiazolyl, pyrimidinyl, thiozolyl, pyrazinyl, pyridazinyl, azetidinyl, pyrrolidyl, piperidinyl, morpholinyl, cyclopropyl, cyclobutyl, cyclopentyl, cyclohexyl, or phenyl optionally substituted with one or more groups independently selected from deuterium, alkyl (C$_1$-C$_4$)(such as methyl, ethyl, propyl, isopropyl, butyl), —OH, alkoxy(C$_1$-C$_4$) (such as methoxy, ethoxy, isopropoxy), amino (such as —NH$_2$, —NHMe, —NHEt, —NHiPr, —NHBu —NMe$_2$, NMeEt, —NEt$_2$, —NEtBu, —NHC(O)NHalkyl), halogen (such as F, Cl), amide (such as —NHC(O)Me, —NHC(O)Et, —C(O)NHMe, —C(O)NH$_2$, —C(O)NEt$_2$, —C(O)NiPr, —C(O)N(cyclopentyl)), —CF$_3$, CN, —OCF$_3$, —N$_3$, ketone (C$_1$-C$_4$) (such as acetyl, —C(O)Et, —C(O)Pr), —S(O)Alkyl(C$_1$-C$_4$) (such as —S(O)Me, —S(O)Et), —SO$_2$alkyl(C$_1$-C$_4$) (such as —SO$_2$Me, —SO$_1$Et, —SO$_2$Pr), -thioalkyl(C$_1$-C$_4$) (such as —SMe, —SEt, —SPr, —SBu), carboxyl (such as —COOH), and/or ester (such as —C(O)OMe, —C(O)OEt, —C(O)OBu), wherein said alkyl(C$_1$-C$_4$), alkoxy(C$_1$-C$_4$), amino, amide, ketone (C$_1$-C$_4$), —S(O)Alkyl(C$_1$-C$_4$), —SO$_2$alkyl(C$_1$-C$_4$), -thioalkyl(C$_1$-C$_4$), and ester may be optionally substituted with F, Cl,. Br, —OH, —NH$_2$, —NHMe, —NMe$_2$, —OMe, —SMe, oxo, and/or thio-oxo.

In certain embodiments of Formula I, the A-B bicyclic ring is selected from

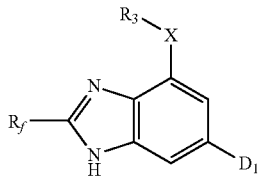

which may be optionally substituted with one or more groups Independently selected from deuterium, —NH$_2$, —OH, alkyl(C$_1$-C$_6$), thioalkyl(C$_1$-C$_6$), and alkoxy(C$_1$-C$_6$).

D$_1$ is

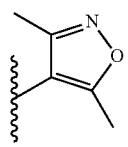

X is absent;

R$_3$ is selected from 5-6 membered carbocycles and heterocycles, such as, but not limited to, an isoxazolyl, oxazolyl, pyrazolyl, pyridyl, pyridonyl, thiazolyl, isothiazolyl, pyrimidinyl, thiozolyl, pyrazinyl, pyridazinyl, azetidinyl, pyrrolidyl, piperidinyl, morpholinyl, cyclopropyl, cyclobutyl, cyclopentyl, cyclohexyl, or phenyl optionally substituted with one or more groups independently selected from deuterium, alkyl(C$_1$-C$_4$)(such as methyl, ethyl, propyl, isopropyl, butyl), —OH, alkoxy(C$_1$-C$_4$) (such as methoxy, ethoxy, isopropoxy), amino (such as —NH$_2$, —NHMe, —NHEt, —NHiPr, —NHBu —NMe$_2$, NMeEt, —NEt$_2$, —NEtBu, —NHC(O)NHalkyl), halogen (such as F, Cl), amide (such as —NHC(O)Me, —NHC(O)Et, —C(O)NHMe, —C(O)NH$_2$, —C(O)NEt$_2$, —C(O)NiPr, —C(O)N(cyclopentyl)), —CF$_3$, CN, —OCF$_3$, —N$_3$, ketone (C$_1$-C$_4$) (such as acetyl, —C(O)Et, —C(O)Pr), —S(O)Alkyl(C$_1$-C$_4$) (such as —S(O)Me, —S(O)Et), —SO$_2$alkyl(C$_1$-C$_4$) (such as —SO$_2$Me, —SO$_2$Et, —SO$_2$Pr), -thioalkyl(C$_1$-C$_4$) (such as —SMe, —SEt, —SPr, —SBu), carboxyl (such as —COOH), and/or ester (such as —C(O)OMe, —C(O)OEt, —C(O)OBu), wherein said alkyl(C$_1$-C$_4$), alkoxy(C$_1$-C$_4$), amino, amide, ketone (C$_1$-C$_4$), —S(O)Alkyl(C$_1$-C$_4$), —SO$_2$alkyl(C$_1$-C$_4$), -thioalkyl(C$_1$-C$_4$), and ester may be optionally substituted with F, Cl, Br, —OH, —NH$_2$, —NHMe, —NMe, —OMe, —SMe, oxo, and/or thio-oxo.

In certain embodiments of Formula I, the A-B-D$_1$ system in the compound of Formula I or stereoisomer, tautomer, pharmaceutically acceptable salt, or hydrate thereof, is selected from

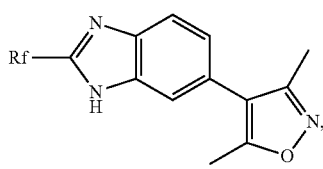

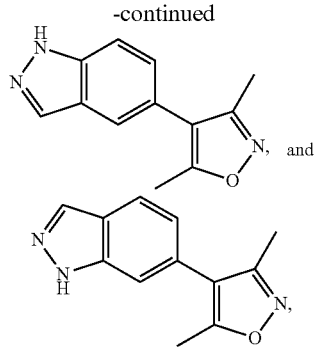

wherein the A-B bicyclic ring system may be optionally substituted with one or more groups independently selected from deuterium, —NH$_2$, —OH, alkyl(C$_1$-C$_6$), thioalkyl(C$_1$-C$_6$), and alkoxy(C$_1$-C$_4$).

X is absent;

R$_3$ is selected from 5-6 membered carbocycles and heterocycles, such as, but not limited to, an isoxazolyl, oxazolyl, pyrazolyl, pyridyl, pyridonyl, thiazolyl, isothiazolyl, pyrimidinyl, thiozolyl, pyrazinyl, pyridazinyl, azetidinyl, pyrrolidyl, piperidinyl, morpholinyl, cyclopropyl, cyclobutyl, cyclopentyl, cyclohexyl, or phenyl optionally substituted with one or more groups independently selected from deuterium, alkyl(C$_1$-C$_4$)(such as methyl, ethyl, propyl, isopropyl, butyl), —OH, alkoxy(C$_1$-C$_4$) (such as methoxy, ethoxy, isopropoxy), amino (such as —NH$_2$, —NHMe, —NHEt, —NHiPr, —NHBu —NMe$_2$, NMeEt, —NEt$_2$, —NEtBu, —NHC(O)NHalkyl), halogen (such as F, Cl), amide (such as —NHC(O)Me, —NHC(O)Et, —C(O)NHMe, —C(O)NH$_2$, —C(O)NEt$_2$, —C(O)NiPr, —C(O)N(cyclopentyl)), —CF$_3$, CN, —OCF$_3$, —N$_3$, ketone (C$_1$-C$_4$) (such as acetyl, —C(O)Et, —C(O)Pr), —S(O)Alkyl(C$_1$-C$_4$) (such as —S(O)Me, —S(O)Et), —SO$_2$alkyl(C$_1$-C$_4$) (such as —SO$_2$Me, —SO$_2$Et, —SO$_2$Pr), -thioalkyl(C$_1$-C$_4$) (such as —SMe, —SEt, —SPr, —SBu), carboxyl (such as —COOH), and/or ester (such as —C(O)OMe, —C(O)OEt, —C(O)OBu), wherein said alkyl(C$_1$-C$_4$), alkoxy(C$_1$-C$_4$), amino, amide, ketone (C$_1$-C$_4$), —S(O)Alkyl(C$_1$-C$_4$), —SO$_2$alkyl(C$_2$-C$_4$), -thioalkyl(C$_1$-C$_4$), and ester may be optionally substituted with F, Cl, Br, —OH, —NH$_2$, —NHMe, —NMe$_2$, —OMe, —SMe, oxo, and/or thio-oxo.

In some embodiments of Formula I, the compound of Formula I is selected from:

4,4'-(1H-benzo[d]imidazole-4,6-diyl)bis(3,5-dimethylisoxazole);
3-(6-(3,5-dimethylisoxazol-4-yl)-1H-benzo[d]imidazol-4-yl)benzonitrile;
4,4'-(quinazoline-2,4-diyl)bis(3,5-dimethylisoxazole);
N-benzyl-6-(3,5-dimethylisoxazol-4-yl)-1H-benzo[d]imidazol-4-amine;
N-benzyl-2-(3,5-dimethylisoxazol-4-yl)quinazolin-4-amine;
4,4'-(2-methyl-1H-benzo[d]imidazole-4,6-diyl)bis(3,5-dimethylisoxazole);
6-(3,5-dimethylisoxazol-4-yl)-N-phenyl-1H-benzo[d]imidazol-4-amine;
4,4'-(imidazo[1,2-a]pyridine-6,8-diyl)bis(3,5-dimethylisoxazole);
3,5-dimethyl-4-(4-(1,3,5-trimethyl-1H-pyrazol-4-yl)-1H-benzo[d]imidazol-6-yl)isoxazole;
4,4'-(imidazo[1,2-a]pyrazine-6,8-diyl)bis(3,5-dimethylisoxazole);

6,8-bis(3,5-dimethylisoxazol-4-yl)-2H-benzo[b][1,4]ox-azin-3(4H)-one;
2-(3,5-dimethylisoxazol-4-yl)-6,7-dimethoxy-N-phenylquinazolin-4-amine;
6,8-bis(3,5-dimethylisoxazol-4-yl)-3,4-dihydro-2H-benzo[b][1,4]oxazine;
3,5-dimethyl-4-(6-(1,3,5-trimethyl-1H-pyrazol-4-yl)-1H-benzo[d]imidazol-4-yl)isoxazole;
6-(3,5-dimethylisoxazol-4-yl)-N-phenyl-[1,2,4]triazolo[4,3-a]pyridin-8-amine;
3,5-dimethyl-4-(4-(1-methyl-1H-pyrazol-5-yl)-1H-benzo[d]imidazol-6-yl)isoxazole;
4,4'-([1,2,4]triazolo[1,5-a]pyridine-6,8-diyl)bis(3,5-dimethylisoxazole);
4-(4-(1,3-dimethyl 1H-pyrazol-4-yl)-1H-benzo[d]imidazol-6-yl)-3,5-dimethylisoxazole;
3,5-dimethyl-4-(4-(2-(trifluoromethyl)phenyl)-1H-benzo[d]imidazol-6-yl)isoxazole;
3,5-dimethyl-4-(4-(4-methylpyridin-3-yl)-1H-benzo[d]imidazol-6-yl)isoxazole;
4,4'-(1H-indazole-5,7-diyl)bis(3,5-dimethylisoxazole);
3,5-dimethyl-4-(4-(pyrimidin-5-yl)-1H-benzo[d]imidazol-6-yl)isoxazole;
3,5-dimethyl-4-(4-(1-methyl-1H-indazol-4-yl)-1H-benzol[d]imidazol-6-yl)isoxazole;
N-benzyl-6-(3,5-dimethylisoxazol-4-yl)-[1,2,4]triazolo[4,3-a]pyridin-8-a mine;
6-(3,5-dimethylisoxazol-4-yl)-N-(4-methoxyphenyl)-1H-benzo[d]imidazol-4-amine;
3,5-dimethyl-4-(4-(4-methylthiazol-5-yl)-1H-benzo[d]imidazol-6-yl)isoxazole;
3,5-dimethyl-4-(4-(2-methylpyridin-3-yl)-1H-benzo[d]imidazol-6-yl)isoxazole;
1-(2-(6-(3,5-dimethylisoxazol-4-yl)-1H-benzo[d]imidazol-4-yl)phenyl)-N,N-dimethylmethanamine;
3,5-dimethyl-4-(4-(1-methyl-1H-pyrazol-4-yl)-1H-benzo[d]imidazol-6-yl)isoxazole;
4,6-bis(3,5-dimethylisoxazol-4-yl)-N-methyl-1H-benzo[d]imidazol-2-amine;
N-benzyl-4,6-bis(3,5-dimethylisoxazo-4-yl)-1H-benzo[d]imidazol-2-amine;
6-(3,5-dimethylisoxazol-4-yl)-N-(3-fluorophenyl)-1H-benzo[d]imidazol-4-amine;
6-(3,5-dimethylisoxazol-4-yl)-N-(3-methoxyphenyl)-1H-benzo[d]imidazol-4-amine;
4,4'-(2-(trifluoromethyl)-1H-benzo[d]imidazol-4,6-diyl)bis(3,5-dimethylisoxazole);
6-(3,5-dimethylisoxazol-4-yl)-N-(pyridin-3-ylmethyl)-1H-benzo[d]imidazol-4-amine;
3-(6-(3,5-dimethylisoxazol-4-yl)-1H-benzo[d]imidazol-4-yl)benzamide;
6-(3,5-dimethylisoxazol-4-yl)-N—((1,3,5-trimethyl-1H-pyrazol-4-yl)methyl)-1H-benzo[d]imidazol-4-amine;
6-(3,5-dimethylisoxazol-4-yl)-N-(4-fluorobenzyl)-1H-benzo[d]imidazol-4-amine;
6-(3,5-dimethylisoxazol-4-yl)-N-((3,5-dimethylisoxazo-4-yl)methy)-H-benzo[d]imidazol-4-amine;
N-(4-chlorophenyl)-6-(3,5-dimethylisoxazol-4-yl)-1H-benzo[d]imidazol-4-8 mine;
3,5-dimethyl-4-(2-methyl-4-(2-methylpyridin-3-yl)-1H-benzo[d]imidazol-6-yl)isoxazole;
N-(6-(3,5-dimethylisoxazol-4-yl)-1H-benzo[d]imidazol-4-yl)-3,5-dimethylisoxazol-4-amine;
6-(3,5-dimethylisoxazol-4-yl)-N-pyrimidin-2-yl)-1H-benzo[d]imidazol-4-amine;
N-(6-(3,5-dimethylisoxazol-4-yl)-1H-benzo[d]imidazol-4-yl)-4-methyloxazol-3-amine;
4,4'-(2-isopropyl-1H-benzo[d]imidazole-4,6-diyl)bis(3,5-dimethyloxazole);
4,4'-(2-ethoxy-1H-benzo[d]imidazole-4,6-diyl)bis(3,5-dimethylisoxazole);
6-(3,5-dimethylisoxazol-4-yl)-N-(pyridin-2-ylmethyl)-1H-benzo[d]imidazol-4-amine;
4-(4-(2-methoxypyridin-3-yl)-1H-benzo[d]imidazol-6-yl)-3,5-dimethylisoxazole;
3,5-dimethyl-4-(2-methyl-4-(1,3,5-trimethyl-1H-pyrazol-4-yl)-1H-benzo[d]imidazol-6-yl)isoxazole;
3,5-dimethyl-4-(2-methy-4-(4-(trifluoromethyl)pyridin-3-yl)-1H-benzo[d]imidazol-6-yl)isoxazole;
4-(4-(2-methoxy-5-methylphenyl)-1H-benzo[d]imidazol-6-yl)-3,5-dimethylisoxazole;
3,5-dimethyl-4-(2-methyl-7-(3-methylisothiazol-4-yl)-1H-benzo[d]imidazol-5-yl)isoxazole;
3,5-dimethyl-4-(2-methyl-4-(4-methylpyridin-3-yl)-1H-benzo[d]imidazol-6-yl)isoxazole;
4,4'-(1-methyl-1H-indazole-5,7-diyl)bis(3,5-dimethylisoxazole);
4,4'-(2-methyl-2H-indazole-5,7-diyl)bis(3,5-dimethylisoxazole);
3-(6-(3,5-dimethylisoxazol-4-yl)-1H-benzo[d]imidazo-4-yl)pyridyl-2(1H)-one;
3-(6-(3,5-dimethylisoxazol-4-yl)-1H-benzo[d]imidazol-4-yl)-2-methylbenzonitrile;
3-(6-(3,5-dimethylisoxazol-4-yl)-2-methyl-1H-benzo[d]imidazol-4-yl)-4-methylbenzonitrile;
3,5-dimethyl-4-(2-methyl-4-(2-(trifluoromethyl)pyridin-3-yl)-1H-benzo[d]imidazol-6-yl)isoxazole;
4-(4-(1,3-dimethyl-1H-pyrazol-4-yl)-2-methyl-1H-benzo[d]imidazol-6-yl)-3,5-dimethylisoxazole;
3-(6-(3,5-dimethylisoxazol-4-yl)-2-methy-H-benzo[d]imidazo-4-yl)isonicotinonitrile;
6-(3,5-dimethylisoxazol-4-yl)-N-(pyrazin-2-yl)-1H-benzo[d]imidazol-4-amine;
6-(3,5-dimethylisoxazol-4-yl)-2-methyl-N-(3-methylpyridin-2-yl)-1H-benzo[d]imidazol-4-amine;
N-(2-(6-(3,5-dimethylisoxazol-4-yl)-2-methyl-1H-benzo[d]imidazol-4-yl)phenyl)acetamide;
4,6-bis(3,5-dimethylisoxazol-4-yl)-N-(pyridin-3-ylmethyl)-1H-benzo[d]imidazol-2-amine;
4-(4-(1,5-dimethyl-3-(trifluoromethyl)-1H-pyrazol-4-yl)-2-methyl-1H-benzo[d]imidazol-6-yl)-3,5-dimethylisoxazole;
4-(5-(3,5-dimethylisoxazol-4-yl)-2-methyl-1H-benzo[d]imidazol-7-yl)-N,3-dimethylisoxazole-5-carboxamide;
5-(6-(3,5-dimethylisoxazol-4-yl)-2-methy-1H-benzo[d]imidazol-4-yl)-6-methylpyridyl-2-amine;
3,5-dimethyl-4-(2-methyl-4-(2-(methylsulfonyl)phenyl)-1H-benzo[d]imidazol-6-yl)isoxazole;
3,5-dimethyl-4-(7-(2-methylpyridin-3-yl)-1H-Indazol-5-yl)isoxazole;
2-(6-(3,5-dimethylisoxazol-4-yl)-2-methyl-1H-benzo[d]imidazol-4-yl)benzonitrile;
4-(4-(4-methoxypyridin-3-yl)-2-methyl-1H-benzo[d]imidazol-6-yl)-3,5-dimethylisoxazole;
3-(6-(3,5-dimethylisoxazol-4-yl)-1H-benzo[d]imidazol-4-yl)-2-methylbenzamide;
3-(6-(3,5-dimethylisoxazol-4-yl)-2-methyl-1H-benzo[d]imidazol-4-yl)-4-methylbenzamide;
3-(6-(3,5-dimethylisoxazol-4-yl)-2-methyl-1H-benzoimidazol-4-yl)-4-methylbenzoic acid;
4,4'-(2-(2,2,2-trifluoroethyl)-1H-benzo[d]imidazole-5,7-diyl)bis(3,5-dimethylisoxazole);
3,5-dimethyl-4-(2-methyl-4-(2-(trifluoromethoxy)phenyl)-1H-benzo[d]imidazol-6-yl)isoxazole;

3,5-dimethyl-4-(2-methyl-4-(2-(trifluoromethyl)phenyl)-1H-benzo[d]imidazol-6-yl)isoxazole;
3,5-dimethyl-4-(2-methyl-4-(pyridin-3-yl)-1H-benzo[d]imidazol-6-yl)isoxazole;
4-(4-(5-fluoro-2-(trifluoromethyl)phenyl)-2-methyl-1H-benzo[(d)imidazol-6-yl)-3,5-dimethylisoxazole;
4-(2-ethoxy-4-(2-methylpyridin-3-yl)-1H-benzo[d]imidazol-6-yl)-3,5-dimethylisoxazole;
3-(6-(3,5-dimethylisoxazol-4-yl)-2-methyl-1H-benzo[d]imidazo-4-yl)pyridin-2-amine;
2-(6-(3,5-dimethylisoxazol-4-yl)-2-methyl-1H-benzo[d]imidazol-4-yl)-6-fluorobenzonitrile;
3,5-dimethyl-4-(2-methyl-4-(3-methylpyridin-2-yl)-1H-benzo[d]imidazol-6-yl)isoxazole;
3,5-dimethyl-4-(2-methyl-4-(pyrazin-2-yl)-1H-benzo[d]imidazol-6-yl)isoxazole;
3,5-dimethyl-4-(2-methyl-4-(6-methylpyrazin-3-yl)-1H-benzo[d]imidazol-6-yl)isoxazole;
4,4'-(1H-indazole-4,6-diyl)bis(3,5-dimethylisoxazole);
3,5-dimethyl-4-(2-methyl-4-phenyl-1H-benzo[d]imidazol-6-yl)isoxazole;
3,5-dimethyl-4-(2-methyl-4-(o-tolyl)-1H-benzo[d]imidazol-6-yl)isoxazole;
4-(4-(4-chloro-2-methylphenyl)-2-methyl-1H-benzo[d]imidazol-6-yl)-3,5-dimethylisoxazole;
4-(4-(2-fluorophenyl)-2-methyl-1H-benzo[d]imidazol-6-yl)-3,5-diethylisoxazole;
4-(4-(5-fluoro-2-methylphenyl)-2-methyl-1H-benzo[d]imidazol-6-yl)-3,5-dimethylisoxazole;
4,4'-(1-methyl-1H-benzo[d]imidazole-5,7-diyl)bis(3,5-dimethylisoxazole);
2-(6-(3,5-dimethylisoxazol-4-yl)-2-methyl-1H-benzo[d]imidazol-4-yl)-4-fluorobenzonitrile;
4,4'-(1H-benzo[d][1,2,3]triazole-4,6-diyl)bis(3,5-dimethylisoxazole);
3,5-dimethyl-4-(2-methyl-4-(3-(trifluoromethoxy)phenyl)-1H-benzo[d]imidazol-6-yl)isoxazole;
4-(4-(3,5-dimethylpyridin-4-yl)-2-methyl-1H-benzo[d]imidazol-6-yl)-3,5-dimethylisoxazole;
4-(4-(4,6-dimethylpyrimidin-5-yl)-2-methyl-1H-benzo[d]imidazol-6-yl)-3,5-dimethylisoxazole;
5-(6-(3,5-dimethylisoxazol-4-yl)-2-methyl-1H-benzo[d]imidazol-4-yl)-4,6-dimethylpyrimidin-2-amine;
6-(3,5-dimethylisoxazol-4-yl)-N-ethyl-4-(2-methylpyridin-3-yl)-1H-benzo[d]imidazol-2-amine;
5,7-bis(3,5-dimethylisoxazol-4-yl)-2-methylbenzo[d]oxazole;
N-(6-(3,5-dimethylisoxazol-4-yl)-1H-benzo[d]imidazol-4-yl)-2-methoxybenzenesulfonamide;
4-(4-(benzo[d][1,3]dioxol-5-yl)-2-methyl-1H-benzo[d]imidazol-6-yl)-3,5-dimethylisoxazole;
3,5-dimethyl-4(2-methyl-4-(4-methylthiazol-5-yl)-H-benzo[d]imidazo-6-yl)isoxazole;
4-(4-(5-chloro-2-methylphenyl)-2-methyl-1H-benzo[d]imidazol-6-yl)-35-dimethylisoxazole;
4-(4-(2-fluoro-3-methylphenyl)-2-methyl-1H-benzo[d]imidazol-6-yl)-35-dimethylisoxazole;
4-(4-(5-chloro-2-methoxyphenyl)-2-methyl-1H-benzo[d]imidazol-6-yl)-3,5-dimethylisoxazole;
4-(4-(2-fluoro-5-methoxyphenyl)-2-methyl-1H-benzo[d]imidazol-6-yl)-3,5-dimethylisoxazole;
4-(4-(2-ethoxypyridin-3-yl)-2-methyl-1H-benzo[d]imidazol-6-yl)-3,5-dimethylisoxazole;
4-(4-(isoquinolin-8-yl)-2-methyl-1H-benzo[d]imidazol-6-yl)-3,5-dimethylisoxazole;
3,5-dimethyl-4-(2-methyl-4-(quinolin-8-yl)-1H-benzo[d]imidazol-6-yl)isoxazole;
4-(4-(5-fluoro-2-methoxyphenyl)-2-methyl-1H-benzo[d]imidazol-6-yl)-3,5-dimethylisoxazole;
3,5-dimethyl-4-(2-methyl-4-(5-methylthiazol-4-yl)-1H-benzo[d]imidazol-6-yl)isoxazole;
4-(4-(2-methoxy-4-methylpyridin-3-yl)-2-methyl-1H-benzo[d]imidazol-6-yl)-3,5-dimethylisoxazole;
3,5-dimethyl-4-(2-methyl-4-(1-methyl-3-(trifluormethyl)-1H-pyrazol-4-yl)-1H-benzo[d]imidazol-6-yl)isoxazole;
4,6-bis(3,5-dimethylisoxazol-4-yl)-N,N-dimethyl-1H-benzo[d]imidazol-2-amine;
4-(4-(2-(methoxymethyl)phenyl)-2-methyl-1H-benzo[d]imidazol-6-yl)-3,5-dimethylisoxazole;
4-(4-(2-methoxypyridin-3-yl)-2-methyl-H-benzo[d]imidazol-6-yl)-3,5-dimethylisoxazole;
3,5-dimethyl-4-(7-(4-methylpyridin-3-yl)-1H-indazol-5-yl)isoxazole;
4-(7-(1,3-dimethyl-1H-pyrazol-4-yl)-1H-indazol-5-yl)-3,5-dimethylisoxazole;
1-(6-(3,5-dimethylisoxazol-4-yl)-2-methy-1H-benzo[d]imidazol-4-yl)-5-methylpyrrolidin-2-one;
1-(6-(3,5-dimethylisoxazol-4-yl)-2-methyl-1H-benzo[d]imidazol-4-yl)piperidin-2-one;
3-(6-(3,5-dimethylisoxazol-4-yl)-2-methyl-1H-benzo[d]imidazol-4-yl)-2-methylbenzonitrile;
4-(4-(benzo[d]thiazol-5-yl)-2-methyl-1H-benzo[d]imidazol-6-yl)-3,5-dimethylisoxazole;
4-(4-(5-fluoro-4-methylpyridin-3-yl)-2-methyl-1H-benzo[d]imidazol-6-yl)-3,5-dimethylisoxazole;
3-(6-(3,5-dimethylisoxazol-4-yl)-2-methyl-1H-benzo[d]imidazol-4-yl)-2-methylbenzamide;
3,5-dimethyl-4-(7-(1,3,5-trimethyl-1H-pyrazol-4-yl)-1H-indazol-5-yl)isoxazole;
3,5-dimethyl-4-(7-(2-(trifluoromethyl)pyridin-3-yl)-1H-indazol-5-yl)isoxazole;
3,5-dimethyl-4-(7-(4-(trifluormethyl)pyridin-3-yl)-1H-indazol-5-yl)isoxazole;
4-(4-(3,5-dichloropyridin-4-yl)-2-methyl-1H-benzo[d]imidazol-6-yl)-3,5-dimethylisoxazole;
4-(4-(5-fluoro-2-methoxypyridin-3-yl)-2-methyl-1H-benzo[d]imidazol-6-yl)-3,5-dimethylisoxazole;
4-(4-(3,4-difluoro-2-methylphenyl)-2-methyl-1H-benzo[d]imidazol-6-yl)-3,5-dimethylisoxazole;
4,6-bis(1,3-dimethyl-1H-pyrazol-4-yl)-2-methyl-1H-benzo[d]imidazole;
2-methyl-4,6-bis(1-methyl-1H-pyrazol-5-yl)-1H-benzo[d]imidazole;
4-(4-(2-methoxy-6-methylpyridin-3-yl)-2-methyl-1H-benzo[d]imidazol-6-yl)-3,5-dimethylisoxazole;
5-(6-(3,5-dimethylisoxazol-4-yl)-2-methyl-1H-benzo[d]imidazol-4-yl)benzo[d]oxazole;
4-(4-(benzo[d]isothiazol-5-yl)-2-methyl-1H-benzo[d]imidazol-6-yl)-3,5-dimethylisoxazole;
3,5-dimethyl-4-(2-methyl-4-(naphthalen-1-yl)-1H-benzo[d]imidazol-6-yl) isoxazole;
4,4'-(2-methyl-1H-benzo[d]imidazole-4,6-diyl)bis(3-methylisothiazole);
4,4'-(3-methyl-1H-indole-4,6-diyl)bis(3,5-dimethylisoxazole);
2-methyl-4,6-bis(4-methylthiophen-3-yl)-1H-benzo[d]imidazole;
6-(3,5-dimethylisoxazol-4-yl)-N-phenethyl-1H-benzo[d]imidazol-4-amine;
6-(3,5-dimethylisoxazol-4-yl)-2-methyl-N-(2-methylpyridin-3-yl)-1H-benzo[d]imidazol-4-amine;
4-(4-(2-chlorophenyl)-2-methyl-1H-benzo[d]imidazol-6-yl)-3,5-dimethylisoxazole;

4-(4-(benzo[b]thiophen-2-yl)-2-methyl-1H-benzo[d]imidazo-6-yl)-3,5-dimethylisoxazole;
6-(3,5-dimethylisoxazol-4-yl)-2-methyl-N-(1,3,5-trimethyl-1H-pyrazol-4-yl)-1H-benzo[d]imidazol-4-amine;
1-(6-(3,5-dimethylisoxazol-4-yl)-2-methyl-1H-benzo[d]imidazol-4-yl)azetidin-2-one;
3,5-dimethyl-4-(2-methyl-4-phenoxy-1H-benzo[d]imidazol-6-yl)isoxazole;
6,8-bis(3,5-dimethylisoxazol-4-yl)-[1,2,4]triazolo[4,3-a]pyridin-3(2H)-one;
2-((4,6-bis(3,5-dimethylisoxazol-4-yl)-1H-benzo[d]imidazol-2-yl)amino)ethanol;
6-(3,5-dimethylisoxazol-4-yl)-N,N-diphenethyl-1H-benzo[d]imidazol-4-amine;
4-(4-(2-fluoro-3-methoxyphenyl)-2-methyl-1H-benzo[d]imidazol-6-yl)-3,5-dimethylisoxazole;
3,5-dimethyl-4-(2-methyl-4-quinoxalin-6-yl)-1H-benzo[d]imidazol-6-yl)isoxazole;
3,5-dimethyl-4-(2-methyl-4-(3-(methylsulfonyl)phenyl)-1H-benzo[d]imidazol-6-yl)isoxazole;
3,5-dimethyl-4-(2-methyl-4-((2-methylpyridin-3-yl)oxy)-1H-benzo[d]imidazol-6-yl)isoxazole;
4-(4-([1,2,4]triazolo[4,3-a]pyridin-6-yl)-2-methyl-1H-benzo[d]imidazol-6-yl)-3,5-dimethylisoxazole;
4-(4-(2-fluoro-5-(trifluoromethyl)phenyl)-2-methyl-1H-benzo[d]imidazol-6-yl)-3,5-dimethylisoxazole;
(E)-3,5-dimethyl-4-(2-methyl-4-styryl-1H-benzo[d]imidazol-6-yl)isoxazole;
4,4'-(quinoxaline-5,7-diyl)bis(3,5-dimethylisoxazole);
4,6-di(furan-3-yl)-2-methyl-1H-benzo[d]imidazole;
3,5-dimethyl-4-(2-methyl-4-phenethyl-1H-benzo[d]imidazol-6-yl)isoxazole;
4-(4-(2-chloro-5-(trifluoromethyl)phenyl)-2-ethyl-H-benzo[d]imidazol-6-yl)-3,5-dimethylisoxazole;
3,5-dimethyl-4-(2-methyl-4-(quinolin-3-yl)-1H-benzo[d]imidazol-6-yl)isoxazole;
2-methyl-4,6-di(1H-pyrrol-3-yl)-1H-benzo[d]imidazole;
N-(6-(3,5-dimethylisoxazol-4-yl)-2-methyl-1H-benzo[d]imidazol-4-yl)benzamide;
3,5-dimethyl-4-(2-methyl-4-(4-methylthiophen-3-yl)-1H-benzo[d]imidazol-6-yl)isoxazole;
4,6-bis(1,4-dimethyl-1H-pyrazol-5-yl)-2-methyl-1H-benzo[d]imidazole;
5,5'-(2-methyl-1H-benzo[d]imidazole-4,6-diyl)bis(2,4-dimethylthiazole);
4-(4-(1,4-dimethyl-1H-pyrazol-5-yl)-2-methyl-1H-benzo[d]imidazol-6-yl)-3,5-dimethylisoxazole;
4-(4-(2,4-dimethylthiazol-5-yl)-2-methyl-1H-benzo[d]imidazol-6-yl)-3,5-dimethylisoxazole;
4-(4-((4-methoxypyridin-3-yl)oxy)-2-methyl-1H-benzo[d]imidazol-6-yl)-3,5-dimethylisoxazole;
3-((6-(3,5-dimethylisoxazol-4-yl)-2-methyl-1H-benzo[d]imidazol-4-yl)oxy)-4-methylbenzonitrile;
4-(6-(3,5-dimethylisoxazol-4-yl)-2-methyl-1H-benzoimidazol-4-yl)morpholine;
3-((6-(3,5-dimethylisoxazol-4-yl)-2-methyl-1H-benzo[d]imidazol-4-yl)oxy)-4-methylbenzamide;
3-((6-(3,5-dimethylisoxazol-4-yl)-2-methyl-1H-benzo[d]imidazol-4-yl)oxy)-4-methylbenzoic acid;
4,4'-(2-methyl-3H-imidazo[4,5-b]pyridine-5,7-diyl)bis(3,5-dimethylisoxazole);
4-(6-(3,5-dimethylisoxazol-4-yl)-2-methyl-1H-benzo[d]imidazol-4-yl)-3-methylmorpholine;
4-(6-(1,4-dimethyl-1H-pyrazol-5-yl)-2-methyl-1H-benzo[d]imidazol-4-yl)-3,5-dimethylisoxazole;
4,4'-(3-methyl-1H-Indazole-4,6-diyl)bis(3,5-dimethylisoxazole);
4-(4-(3,5-dimethyl-1H-pyrazol-4-yl)-3-methyl-1H-indazol-6-yl)-3,5-dimethylisoxazole;
3,5-dimethyl-4-(2-(4-methylpiperazin-1-yl)-4-(1,3,5-trimethyl-1H-pyrazol-4-yl)-1H-benzo[d]imidazol-6-yl)isoxazole;
3,5-dimethyl-4-(1-methyl-7-(1,3,5-trimethyl-1H-pyrazol-4-yl)-1H-benzo[d]imidazol-5-yl)isoxazole;
3,5-dimethyl-4-(2-(4-methylpiperazin-1-yl)-4-(2-methylpyridin-3-yl)-1H-benzo[d]imidazol-6-yl)isoxazole;
4-(6-(3,5-dimethylisoxazol-4-yl)-4-(1,3,5-trimethyl-1H-pyrazol-4-yl)-1H-benzo[d]imidazol-2-yl)morpholine;
6-(3,5-dimethylisoxazol-4-yl)-N-(1-methylpiperidin-4-yl)-4-(1,3,5-trimethyl-1H-pyrazol-4-yl)-1H-benzo[d]imidazol-2-amine;
3-(6-(3,5-dimethylisoxazol-4-yl)-2-(4-methylpiperazin-1-yl)-1H-benzo[d]imidazol-4-yl)-4-methylbenzonitrile;
3,5-dimethyl-4-(2-(methylthio)-4-(1,3,5-trimethyl-1H-pyrazol-4-yl)-1H-benzo[d]imidazol-6-yl)isoxazole;
3,5-dimethyl-4-(1-methyl-2-(methylthio)-4-(1,3,5-trimethyl-1H-pyrazol-4-yl)-1H-benzo[d]imidazol-6-yl)isoxazole;
3-(6-(3,5-dimethylisoxazol-4-yl)-2-(4-methylpiperazin-1-yl)-1H-benzo[d]imidazol-4-yl)-4-methylbenzamide;
6-(3,5-dimethylisoxazol-4-yl)-N-(tetrahydro-2H-pyran-4-yl)-4-(1,3,5-trimethyl-1H-pyrazol-4-yl)-1H-benzo[d]imidazol-2-amine;
3,5-dimethyl-4-(1-methyl-2-(methylthio)-7-(1,3,5-trimethyl-1H-pyrazol-4-yl)-1H-benzo[d]imidazol-5-yl)isoxazole;
4,4'-(7-bromo-1H-benzo[d]imidazole-4,6-diyl)bis(3,5-dimethylisoxazole);
3-(6-(3,5-dimethylisoxazol-4-yl)-2-morpholino-H-benzo[d]imidazol-4-yl)-4-methylbenzonitrile;
3,5-dimethyl-4-(2-(methylsulfinyl)-7-(1,3,5-trimethyl-1H-pyrazol-4-yl)-1H-benzo[d]imidazol-5-yl)isoxazole;
3,5-dimethyl-4-(2-(methylsulfonyl)-7-(1,3,5-trimethyl-1H-pyrazol-4-yl)-1H-benzo[d]imidazol-5-yl)isoxazole;
4-(6-(3,5-dimethylisoxazol-4-yl)-4-(4-methylpyridin-3-yl)-H-benzo[d]imidazol-2-yl)morpholine;
3-(6-(3,5-dimethylisoxazol-4-yl)-2-morpholino-1H-benzo[d]imidazol-4-yl)-4-methylbenzamide;
3-(6-(3,5-dimethylisoxazol-4-yl)-2-((tetrahydro-2H-pyran-4-yl)amino)-1H-benzo[d]imidazol-4-yl)-4-methylbenzonitrile;
3,5-dimethyl-4-(2-(4-methylpiperazin-1-yl)-4-(4-methylpyridin-3-yl)-1H-benzo[d]imidazol-6-yl)isoxazole;
3-(6-(3,5-dimethylisoxazol-4-yl)-2-((tetrahydro-2H-pyran-4-yl)amino)-1H-benzo[d]imidazol-4-yl)-4-methylbenzamide;
6-(3,5-dimethylisoxazol-4-yl)-4-(4-methylpyridin-3-yl)-N-(tetrahydro-2H-pyran-4-yl)-1H-benzo[d]imidazol-2-amine;
3-(6-(3,5-dimethylisoxazol-4-yl)-2-(4-methylpiperazin-1-yl)-H-benzo[d]imidazo-4-yl)-2-methylbenzonitrile;
3-(6-(3,5-dimethylisoxazol-4-yl)-2-morpholino-H-benzo[d]imidazol-4-yl)-2-methylbenzonitrile;
3-(6-(3,5-dimethylisoxazol-4-yl)-2-((tetrahydro-2H-pyran-4-yl)amino)-1H-benzo[d]imidazol-4-yl)-2-methylbenzonitrile;
3-(6-(3,5-dimethylisoxazol-4-yl)-2-((1-methylpiperidin-4-yl)amino)-1H-benzo[d]imidazol-4-yl)-4-methylbenzonitrile;
3-(6-(3,5-dimethylisoxazol-4-yl)-2-(4-methylpiperazin-1-yl)-1H-benzo[d]imidazol-4-yl)-2-methylbenzamide;
3-(6-(3,5-dimethylisoxazol-4-yl)-2-((tetrahydro-2H-pyran-4-yl)amino)-1H-benzo[d]imidazol-4-yl)-2-methylbenzamide;

3-(6-(3,5-dimethylisoxazol-4-yl)-2-morpholino-1H-benzo[d]imidazol-4-yl)-2-methylbenzamide;
3-(2-(4-aminopiperidin-1-yl)-6-(3,5-dimethylisoxazol-4-yl)-1H-benzo[d]imidazol-4-yl)-2-methylbenzonitrile;
3-(2-(benzylamino)-6-(3,5-dimethylisoxazol-4-yl)-1H-benzo[d]imidazol-4-yl)-4-methylbenzonitrile;
3-(6-(3,5-dimethylisoxazol-4-yl)-2-((pyridin-3-ylmethyl)amino)-1H-benzo[d]imidazol-4-yl)-4-methylbenzonitrile;
N-benzyl-6-(3,5-dimethylisoxazol-4-yl)-4-(1,3,5-trimethyl-1H-pyrazol-4-yl)-1H-benzo[d]imidazol-2-amine;
3,5-dimethyl-4-(2-(pyrrolidin-1-yl)-4-(1,3,5-trimethyl-1H-pyrazol-4-yl)-1H-benzo[d]imidazol-6-yl)isoxazole;
6-(3,5-dimethylisoxazol-4-yl)-N-methy-4-(4-methylpyridin-3-yl)-1H-benzo[d]imidazol-2-amine;
3-(6-(3,5-dimethylisoxazol-4-yl)-2-(pyrrolidin-1-yl)-1H-benzo[d]imidazol-4-yl)-4-methylbenzonitrile;
3-(6-(3,5-dimethylisoxazol-4-yl)-2-((1-methylpiperidin-4-yl)amino)-1H-benzo[d]imidazol-4-yl)-2-methylbenzonitrile;
4-(2-(azetidin-1-yl)-4-(1,3,5-trimethyl-1H-pyrazol-4-yl)-1H-benzo[d]imidazol-6-yl)-3,5-dimethylisoxazole;
(3-(6-(3,5-dimethylisoxazol-4-yl)-2-(pyrrolidin-1-yl)-1H-benzo[d]imidazol-4-yl)-4-methylphenyl)(pyrrolidin-1-yl)methanone;
3-(6-(3,5-dimethylisoxazol-4-yl)-2-((pyridin-3-ylmethyl)amino)-1H-benzo[d]imidazol-4-yl)-4-methylbenzamide;
3-(2-(benzylamino)-6-(3,5-dimethylisoxazol-4-yl)-1H-benzo[d]imidazol-4-yl)-4-methylbenzamide;
6-(3,5-dimethylisoxazol-4-yl)-N-(pyridin-3-ylmethyl)-4-(1,3,5-trimethyl-1H-pyrazol-4-yl)-1H-benzo[d]imidazol-2-amine;
N-benzyl-6-(3,5-dimethylisoxazol-4-yl)-4-(4-methylpyridin-3-yl)-1H-benzo[d]imidazol-2-amine;
6-(3,5-dimethylisoxazol-4-yl)-4-(4-methylpyridin-3-yl)-N-(pyridin-3-ylmethyl)-1H-benzo[d]imidazol-2-amine;
3,5-dimethyl-4-(4-(4-methylpyridin-3-yl)-2-(pyrrolidin-1-yl)-1H-benzo[d]imidazol-6-yl)isoxazole;
3-amino-5-(6-(3,5-dimethylisoxazol-4-yl)-1H-benzo[d]imidazol-4-yl)-1-methylpyridin-2(1H)-one;
4-(4,6-bis(3,5-dimethylisoxazol-4-yl)-1H-benzo[d]imidazol-2-yl) morpholine;
4,4'-(5-methoxy-2-methyl-1H-benzo[d]imidazole-4,6-diyl)bis(3,5-dimethylisoxazole);
4,4'-(2-(tetrahydro-2H-pyran-4-yl)-1H-benzo[d]imidazole-4,6-diyl)bis(3,5-dimethylisoxazole);
4,6-bis(3,5-dimethylisoxazol-4-yl)-N-(tetrahydro-2H-pyran-4-yl)-1H-benzo[d]imidazol-2-amine;
3,5-dimethyl-4-(5-(1-methyl-1H-pyrazol-5-yl)-1H-benzo[d]imidazol-7-yl)isoxazole;
4,4'-(2-(4-methylpiperazin-1-yl)-1H-benzo[d]imidazole-4,6-diyl)bis(3,5-dimethylisoxazole);
4,6-bis(3,5-dimethylisoxazol-4-yl)-N-(1-methylpiperidin-4-yl)-1H-benzo[d]imidazol-2-amine; and
4,6-bis(3,5-dimethylisoxazol-4-yl)-N-(piperidin-4-yl)-1H-benzo[d]imidazol-2-amine, or a stereoisomer, tautomer, pharmaceutically acceptable salt, or hydrate thereof.

Another aspect of the invention provides a method for inhibition of BET protein function by binding to bromodomains, and their use in the treatment and prevention of diseases and conditions in a mammal (e.g., a human) comprising administering a therapeutically effective amount of a compound of Formula I.

In one embodiment, because of potent effects of BET inhibitors in vitro on IL-6 and IL-17 transcription, BET inhibitor compounds of Formula I may be used as therapeutics for inflammatory disorders in which IL-6 and/or IL-17 have been implicated in disease. The following autoimmune diseases are amenable to therapeutic use of BET inhibition by administration of a compound of Formula I or stereoisomer, tautomer, pharmaceutically acceptable salt, or hydrate thereof because of a prominent role of IL-6 and/or IL-17: Acute Disseminated Encephalomyelitis (Ishizu, T., et al., "CSF cytokine and chemokine profiles in acute disseminated encephalomyelitis," *J Neuroimmunol* 175(1-2): 52-8 (2006)), Agammaglobulinemia (Gonzalez-Serrano, M. E., et al., "Increased Pro-inflammatory Cytokine Production After Lipopolysaccharide Stimulation in Patients with X-linked Agammaglobulinemia," *J Clin Immunol* 32(5):967-74 (2012)), Allergic Disease (McKinley, L., et al., "TH17 cells mediate steroid-resistant airway inflammation and airway hyperresponsiveness in mice," *J Immunol* 181(6):4089-97 (2008)), Ankylosing spondylitis (Taylan, A., et al., "Evaluation of the T helper 17 axis in ankylosing spondylitis," *Rheumatol Int* 32(8):2511-5 (2012)), Anti-GBM/Anti-TBM nephritis (Ito, Y., et al., "Pathogenic significance of interleukin-6 in a patient with antiglomerular basement membrane antibody-induced glomerulonephritis with multinucleated giant cells," *Am J Kidney Dis* 26(1):72-9 (1995)), Anti-phospholipid syndrome (Soltesz, P., et al., "Immunological features of primary anti-phospholipid syndrome in connection with endothelial dysfunction," *Rheumatology* (Oxford) 47(11):1628-34 (2008)), Autoimmune aplastic anemia (Gu, Y., et al., "Interleukin (IL)-17 promotes macrophages to produce IL-8, IL-6 and tumour necrosis factor-alpha in aplastic anaemia," *Br J Haematol* 142(1):109-14 (2008)), Autoimmune hepatitis (Zhao, L., et al., "Interleukin-17 contributes to the pathogenesis of autoimmune hepatitis through inducing hepatic interleukin-6 expression," *PLoS One* 6(4):e18909 (2011)), Autoimmune inner ear disease (Gloddek, B., et al., "Pharmacological influence on inner ear endothelial cells in relation to the pathogenesis of sensorineural hearing loss," *Adv Otorhinolaryngol* 59:75-83 (2002)), Autoimmune myocarditis (Yamashita, T., et al., "IL-6-mediated Th17 differentiation through RORgammat is essential for the initiation of experimental autoimmune myocarditis," *Cordiovasc Res* 91(4):640-8 (2011)), Autoimmune pancreatitis (Ni, J., et al., "Involvement of Interleukin-17A in Pancreatic Damage in Rat Experimental Acute Necrotizing Pancreatitis," *Inflammation* (2012)), Autoimmune retinopathy (Hohki, S., et al., "Blockade of interleukin-6 signaling suppresses experimental autoimmune uveoretinitis by the inhibition of inflammatory Th17 responses," *Exp Eye Res* 91(2):162-70 (2010)), Autoimmune thrombocytopenic purpura (Ma, D., et al., "Profile of Th17 cytokines (IL-17, TGF-beta, IL-6) and Th1 cytokine (IFN-gamma) in patients with immune thrombocytopenic purpura," *Ann Hematol* 87(11):899-904 (2008)), Behcet's Disease (Yoshimura, T., et al., "Involvement of Th17 cells and the effect of anti-IL-6 therapy in autoimmune uveitis," *Rheumatology* (Oxford) 48(4):347-54 (2009)), Bullous pemphigoid (D'Auria, L., P. et al., "Cytokines and bullous pemphigoid," *Eur Cytokine Netw* 10(2):123-34 (1999)), Castleman's Disease (El-Osta, H. E. and R. Kurzrock, "Castleman's disease: from basic mechanisms to molecular therapeutics," *Oncologist* 16(4):497-511 (2011)), Celiac Disease (Lahdenpera, A. I., et al., "Up-regulation of small intestinal interleukin-17 immunity in untreated coeliac disease but not in potential coeliac disease or in type 1 diabetes," *Clin Exp Immunol* 167(2):226-34 (2012)), Churg-Strauss syndrome (Fujioka, A., et al., "The analysis of mRNA expression of cytokines from skin lesions in Churg-Strauss syndrome," *J Dermatol* 25(3):171-7 (1998)), Crohn's Disease (Holtta, V., et al., "IL-23/IL-17 immunity as a hallmark of Crohn's disease," *Inflamm Bowel Dis* 14(9):1175-84 (2008)), Cogan's syndrome (Shibuya, M., et al., "Successful treatment with tocilizumab in a case of Cogan's syndrome complicated with aortitis," *Mod Rheumatol* (2012)), Dry eye syndrome (De Paiva, C. S., et al., "IL-17 disrupts corneal barrier following desiccating stress," *Mucosal Immunol* 2(3):243-53 (2009)), Essential mixed cryoglobulinemia (Antonelli, A., et al., "Serum levels of proinflammatory cytokines interleukin-ibeta, interleukin-6, and tumor necrosis factor alpha in mixed cryoglobulinemia," *Arthritis Rheum* 60(12):3841-7 (2009)), Dermatomyositis (Chevrel, G., et al., "Interleukin-17 increases the effects of IL-1 beta on muscle cells: arguments for the role of T cells in the pathogenesis of myositis," *J Neuroimmunol* 137(1-2):125-33 (2003)), Devic's Disease (Linhares, U. C., et al., "The Ex Vivo Production of IL-6 and IL-21 by CD4(+) T Cells is Directly Associated with Neurological Disability in Neuromyelitis Optica Patients," *J Clin Immunol* (2012)), Encephalitis (Kyburz, D. and M. Corr, "Th17 cells generated in the absence of TGF-beta induce experimental allergic encephalitis upon adoptive transfer," *Expert Rev Clin Immunol* 7(3):283-5 (2011)), Eosinophlic esophagitis (Dias, P. M. and G. Banerjee, "The Role of Th17/IL-17 on Eosinophilic Inflammation," *J Autoimmun* (2012)), Eosinophilic fasciitis (Dias, P. M. and G. Banerjee, "The Role of Th17/IL-17 on Eosinophilic Inflammation," *J Autoimmun* (2012)), Erythema nodosum (Kahawita, I. P. and D. N. Lockwood, "Towards understanding the pathology of erythema nodosum leprosum," *Trans R Soc Trop Med Hyg* 102(4):329-37 (2008)), Giant cell arteritis (Deng, J., et al., "Th17 and Th1 T-cell responses in giant cell arteritis," *Circulation* 121(7):906-15 (2010)), Glomerulonephritis (Ooi, J. D., et al., "Review: T helper 17 cells: their role in glomerulonephritis," *Nephrology* (Carlton) 15(5):513-21 (2010)), Goodpasture's syndrome (Ito, Y., et al., "Pathogenic significance of interleukin-6 in a patient with antiglomerular basement membrane antibody-induced glomerulonephritis with multinucleated giant cells," *Am J Kidney Dis* 26(1):72-9 (1995)), Granulomatosis with Polyangiitis (Wegener's) (Nakahama, H., et al., "Distinct responses of interleukin-6 and other laboratory parameters to treatment in a patient with Wegener's granulomatosis," *Intern Med* 32(2):189-92 (1993)), Graves' Disease (Kim, S. E., et al., "Increased serum interleukin-17 in Graves' ophthalmopathy," *Graefes Arch Clin Exp Ophthalmol* 250(10):1521-6 (2012)), Guillain-Barre syndrome (Lu, M. O. and J. Zhu, "The role of cytokines in Guillain-Barre syndrome," *J Neurol* 258(4):533-48 (2011)), Hashimoto's thyroiditis (Figueroa-Vega, N., et al., "Increased circulating pro-inflammatory cytokines and Th17 lymphocytes in Hashimoto's thyroiditis," *J Clin Endocrinol Metab* 95(2):953-62 (2009)), Hemolytic anemia (Xu, L., et al., "Critical role of Th17 cells in development of autoimmune hemolytic anemia," *Exp Hematol* (2012)), Henoch-Schonlein purpura (Jen, H. Y., et al., "Increased serum interleukin-17 and peripheral Th17 cells in children with acute Henoch-Schonlein purpura," *Pediatr Allergy Immunol* 22(8):862-8 (2011)), IgA nephropathy (Lin, F. J., et al., "Imbalance of regulatory T cells to Th17 cells in IgA nephropathy," *Scand J Clin Lab Invest* 72(3):221-9 (2012)), Inclusion body myositis (Baron, P., et al., "Production of IL-6 by human myoblasts stimulated with Abeta: relevance in the pathogenesis of IBM," *Neurology* 57(9):1561-5 (2001)), Type I diabetes (Belkina, A. C. and G. V. Denis, "BET domain co-regulators in obesity, inflammation and cancer," *Nat Rev Cancer* 12(7):465-77 (2012)), Interstitial cystitis (Lamale, L. M., et al., "Interleukin-6, histamine, and methylhistamine as diagnostic markers for interstitial cystitis," *Urology* 68(4):702-6 (2006)), Kawasaki's Disease (Jia, S., et al., "The T helper type 17/regulatory T cell imbalance in patients with acute Kawasaki disease," *Clin Exp Immunol* 162(1):131-7 (2010)), Leukocytoclastic vasculitis (Min, C. K., et al., "Cutaneous leucoclastic vasculitis (LV) following bortezomib therapy in a myeloma patient; association with pro-inflammatory cytokines," *Eur J Hoematol* 76(3):265-8 (2006)), Lichen planus (Rhodus, N. L., et al., "Proinflammatory cytokine levels in saliva before and after treatment of (erosive) oral lichen planus with dexamethasone," *Oral Dis* 12(2):112-6 (2006)), Lupus (SLE) (Mok, M. Y., et al., "The relation of interleukin 17 (IL-17) and L-23 to Th1/Th2 cytokines and disease activity in systemic lupus erythematosus," *J Rheumatol* 37(10):2046-52 (2010)), Microscopic polyangitis (Muller Kobold, A. C., et al., "In vitro up-regulation of E-selectin and induction of interleukin-6 in endothelial cells by autoantibodies in Wegener's granulomatosis and microscopic polyangiitis," *Clin Exp Rheumatol* 17(4):433-40 (1999)), Multiple sclerosis (Jadidi-Niaragh, F. and Mirshafiey A., "Th17 cell, the new player of neuroinflammatory process in multiple sclerosis," *Scand J Immunol* 74(1):1-13 (2011)), Myasthenia gravis (Aricha, R., et al., "Blocking of IL-6 suppresses experimental autoimmune myasthenia gravis," *J Autoimmun* 36(2):135-41 (2011)), myositis (Chevrel, G., et al., "Interleukin-17 Increases the effects of IL-1 beta on muscle cells: arguments for the role of T cells in the pathogenesis of myositis," *J Neuroimmunol* 137(1-2):125-33 (2003)), Optic neuritis (Icoz, S., et al., "Enhanced IL-6 production in aquaporin-4 antibody positive neuromyelitis optica patients," *Int J Neurosci* 120(1):71-5 (2010)), Pemphigus (Lopez-Robles, E., et al., "TNFalpha and IL-6 are mediators in the blistering process of pemphigus," *Int J Dermatol* 40(3):185-8 (2001)), POEMS syndrome (Kallen, K J., et al., "New developments in IL-6 dependent biology and therapy: where do we stand and what are the options?" *Expert Opin Investig Drugs* 8(9):1327-49 (1999)), Polyarteritis *nodosa* (Kawakami, T., et al., "Serum levels of interleukin-6 in patients with cutaneous polyarteritis nodosa," *Acta Derm Venereol* 92(3):322-3 (2012)), Primary biliary cirrhosis (Harada, K., et al., "Periductal interleukin-17 production in association with biliary innate immunity contributes to the pathogenesis of cholangiopathy in primary biliary cirrhosis," *Clin Exp Immunol* 157(2):261-70 (2009)), Psoriasis (Fujishima, S., et al., "Involvement of IL-17F via the induction of IL-6 in psoriasis," *Arch Dermatol Res* 302(7):499-505 (2010)), Psoriatic arthritis (Raychaudhuri, S. P., et al., IL-17 receptor and its functional significance in psoriatic arthritis," *Mol Cell Biochem* 359 (1-2):419-29 (2012)), Pyoderma gangrenosum (Kawakami, T., et al., "Reduction of interleukin-6, interleukin-8, and anti-phosphatidylserine-prothrombin complex antibody by granulocyte and monocyte adsorption apheresis in a patient with pyoderma gangrenosum and ulcerative colitis," *Am J Gastroenterol* 104(9):2363-4 (2009)), Relapsing polychondritis (Kawai, M., et al., "Sustained response to tocilizumab, anti-interleukin-6 receptor antibody, in two patients with refractory relapsing polychondritis," *Rheumatology* (Oxford) 48(3):318-9 (2009)), Rheumatoid arthritis (Ash, Z. and P. Emery, "The role of tocilizumab in the management of rheumatoid arthritis," *Expert Opin Biol Ther,* 12(9):1277-89 (2012)), Sarcoidosis (Belli, F., et al., "Cytokines assay in peripheral blood and bronchoalveolar lavage in the diagnosis and staging of pulmonary granulomatous diseases," *Int J Immunopathol Pharmacol* 13(2):61-67 (2000)), Scleroderma (Radstake, T. R., et al., "The pronounced Th17 profile in systemic sclerosis (SSc) together with intracellular expression of TGFbeta and IFNgamma distinguishes SSc phenotypes," *PLoS One,* 4(6): e5903 (2009)), Sjogren's syndrome (Katsifis, G. E., et al., "Systemic and local interleukin-17 and linked cytokines associated with Sjogren's syndrome mmunopathogenesis," *Am J Pathol* 175(3):1167-77 (2009)), Takayasu's arteritis (Sun, Y., et al., "MMP-9 and IL-6 are potential biomarkers for disease activity in Takayasu's arteritis," *Int J Cordiol* 156(2):236-8 (2012)), Transverse myelitis (Graber, J. J., et al., "Interleukin-17 in transverse myelitis and multiple sclerosis," J Neuroimmunol 196(1-2):124-32 (2008)), Ulcerative colitis (Mudter, J. and M. F. Neurath, "11-6 signaling in inflammatory bowel disease: pathophysiological role and clinical relevance," *Inflamm Bowel Dis* 13(8):1016-23 (2007)), Uveitis (Haruta, H., et al., "Blockade of interleukin-6 signaling suppresses not only th17 but also interphotoreceptor retinoid binding protein-specific Th1 by promoting regulatory T cells in experimental autoimmune uveoretinitis," *Invest Ophthalmol Vis Sci* 52(6):3264-71 (2011)), and Vitiligo (Bassiouny, D. A. and O. Shaker, "Role of interleukin-17 in the pathogenesis of vitiligo," *Clin Exp Dermatol* 36(3):292-7 115. (2011)). Thus, the invention includes compounds of Formula I, stereoisomers, tautomers, pharmaceutically acceptable salts, or hydrates thereof; pharmaceutical compositions comprising one or more of those compounds; and methods of using those compounds or compositions for treating these diseases.

Acute and chronic (non-autoimmune) inflammatory diseases characterized by increased expression of pro-inflammatory cytokines, including IL-6, MCP-1, and IL-17, would also be amenable to therapeutic BET inhibition. These include, but are not limited to, sinusitis (Bradley, D. T. and S. E. Kountakis, "Role of interleukins and transforming growth factor-beta in chronic rhinosinusitis and nasal polyposis," *Laryngoscope* 115(4):684-6 (2005)), pneumonitis (Besnard, A. G., et al., "Inflammasome-IL-1-Th1 7 response in allergic lung inflammation" *J Mol Cell Biol* 4(1):3-10 (2012)), osteomyelitis (Yoshii, T., et al., "Local levels of interleukin-ibeta, -4, -6 and tumor necrosis factor alpha in an experimental model of murine osteomyelitis due to *staphylococcus aureus,*" *Cytokine* 19(2):59-65 2002), gastritis (Bayraktaroglu, T., et al., "Serum levels of tumor necrosis factor-alpha, interleukin-6 and interleukin-8 are not increased in dyspeptic patients with *Helicobacter pylori*-associated gastritis," *Mediators Inflamm* 13(1):25-8 (2004)), enteritis (Mitsuyama, K., et al., "STAT3 activation via interleukin 6 trans-signalling contributes to ileitis in SAMP1/Yit mice," *Gut* 55(9):1263-9. (2006)), gingivitis (Johnson, R. B., et al., "Interleukin-11 and IL-17 and the pathogenesis of periodontal disease," *J Periodontol* 75(1):37-43 (2004)), appendicitis (Latifi, S. Q., et al., "Persistent elevation of serum interleukin-6 in intraabdominal sepsis identifies those with prolonged length of stay," *J Pediatr Surg* 39(10):1548-52 (2004)), irritable bowel syndrome (Ortiz-Lucas, M., et al., "Irritable bowel syndrome immune hypothesis. Part two: the role of cytokines," *Rev Esp Enferm Dig* 102(12):711-7 (2010)), tissue graft rejection (Kappel, L. W., et al., "IL-17 contributes to CD4-mediated graft-versus-host disease," *Blood* 113(4):945-52 (2009)), chronic obstructive pulmonary disease (COPD) (Traves, S. L. and L. E. Donnelly, "Th17 cells in airway diseases," *Curr Mol Med* 8(5):416-26 (2008)), septic shock (toxic shock syndrome, SIRS, bacterial sepsis, etc) (Nicodeme, E., et al., "Suppression of Inflammation by a synthetic histone mimic," *Nature* 468(7327):1119-23 (2010)), osteoarthritis (Chen, L., et al., "IL-17RA aptamer-mediated repression of IL-6 inhibits synovium inflammation in a murine model of osteoarthritis," *Osteoarthritis Cartilage* 19(6):711-8 (2011)), acute gout (Urano, W., et al., "The inflammatory process in the mechanism of decreased serum uric acid concentrations during acute gouty arthritis," *J Rheumotol* 29(9):1950-3 (2002)), acute lung injury (Traves, S. L. and L. E. Donnelly, "Th17 cells in airway diseases," *Curr Mol Med* 8(5):416-26 (2008)), acute renal failure (Simmons, E. M., et al., "Plasma cytokine levels predict mortality in patients with acute renal failure," *Kidney int* 65(4):1357-65 (2004)), burns (Paquet, P. and G. E. Pierard, "Interleukin-6 and the skin," *Int Arch Allergy Immunol* 109(4):308-17 (1996)), Herxheimer reaction (Kaplanski, G., et al., "Jarisch-Herxheimer reaction complicating the treatment of chronic Q fever endocarditis: elevated TNFalpha and IL-6 serum levels," *J Infect* 37(1):83-4 (1998)), and SIRS associated with viral infections (Belkina, A. C. and G. V. Denis, "BET domain co-regulators in obesity, inflammation and cancer," *Nat Rev Cancer* 12(7):465-77 (2012)). Thus, the invention includes compounds of Formula I, stereoisomers, tautomers, pharmaceutically acceptable salts, or hydrates thereof; pharmaceutical compositions comprising one or more of those compounds; and methods of using those compounds or compositions for treating these diseases.

In one embodiment, BET inhibitor compounds of Formula I, stereoisomers, tautomers, pharmaceutically acceptable salts, or hydrates thereof, or compositions comprising one or more of those compounds may be used for treating rheumatoid arthritis (RA) and multiple sclerosis (MS). Strong proprietary data exist for the utility of BET inhibitors in preclinical models of R A and M S. R. Jahagirdar. S. M. et al., "An Orally Bioavailable Small Molecule RVX-297 Significantly Decreases Disease in a Mouse Model of Multiple Sclerosis," *World Congress of Inflammation,* Paris, France (2011). Both RA and MS are characterized by a dysregulation of the IL-6 and IL-17 inflammatory pathways (Kimura, A. and T. Kishimoto, "IL-6: regulator of Treg/Th17 balance," *Eur J Immunol* 40(7):1830-5 (2010)) and thus would be especially sensitive to BET inhibition. In another embodiment, BET inhibitor compounds of Formula I may be used for treating sepsis and associated afflictions. BET inhibition has been shown to inhibit development of sepsis, in part, by inhibiting IL-6 expression, in preclinical models in both published (Nicodeme, E., et al., "Suppression of inflammation by a synthetic histone mimic," *Nature* 468 (7327):1119-23 (2010)) and proprietary data.

In one embodiment, BET inhibitor compounds of Formula I, stereoisomers, tautomers, pharmaceutically acceptable salts, or hydrates thereof, or compositions comprising one or more of those compounds may be used to treat cancer. Cancers that have an overexpression, translocation, amplification, or rearrangement c-myc or other myc family oncoproteins (MYCN, L-myc) are particularly sensitive to BET inhibition. Delmore, J. E., et al., "BET bromodomain inhibition as a therapeutic strategy to target c-Myc," *Cell* 146(6):904-17 (2010); Mertz, J. A., et al., "Targeting MYC dependence in cancer by inhibiting BET bromodomains," *Proc Natl Acad Sci USA* 108(40):16669-74 (2011). These cancers include, but are not limited to, B-acute lymphocytic leukemia, Burkitt's lymphoma, Diffuse large cell lymphoma, Multiple myeloma, Primary plasma cell leukemia, Atypical carcinoid lung cancer, Bladder cancer, Breast cancer, Cervix cancer, Colon cancer, Gastric cancer, Glioblastoma, Hepatocellular carcinoma, Large cell neuroendocrine carcinoma, Medulloblastoma, Melanoma, nodular, Melanoma, superficial spreading, Neuroblastoma, esophageal squamous cell carcinoma, Osteosarcoma, Ovarian cancer, Prostate cancer, Renal clear cell carcinoma, Retinoblastoma, Rhabdomyosarcoma, and Small cell lung carcinoma. Vita, M. and M. Henriksson, "The Myc oncoprotein as a therapeutic target for human cancer," *Semin Cancer Biol* 16(4): 318-30 (2006).

In one embodiment, BET inhibitor compounds of Formula I, stereoisomers, tautomers, pharmaceutically acceptable salts, or hydrates thereof, or compositions comprising one or more of those compounds may be used to treat cancers that result from an aberrant regulation (overexpression, translocation, etc) of BET proteins. These include, but are not limited to, NUT midline carcinoma (Brd3 or Brd4 translocation to nutlin 1 gene) (French, C. A., "NUT midline carcinoma," *Cancer Genet Cytogenet* 203(1):16-20 (2010)), B-cell lymphoma (Brd2 overexpression) (Greenwald, R. J., et al., "E mu-BRD2 transgenic mice develop B-cell lymphoma and leukemia,". *Blood* 103(4):1475-84 (2004)), nonsmall cell lung cancer (BrdT overexpression) (Grunwald, C., et al., "Expression of multiple epigenetically regulated cancer/germline genes in nonsmall cell lung cancer," *Int J Cancer* 118(10):2522-8 (2006)), esophageal cancer and head and neck squamous cell carcinoma (BrdT overexpression) (Scanlan, M. J., et al., "Expression of cancer-testis antigens in lung cancer: definition of bromodomain testis-specific gene (BRDT) as a new CT gene, CT9," *Cancer Lett* 150(2):55-64 (2000)), and colon cancer (Brd4) (Rodriguez, R. M., et al., "Aberrant epigenetic regulation of bromodomain BRD4 in human colon cancer," *J Mol Med* (Berl) 90(5):587-95 (2012)).

In one embodiment, because BET inhibitors decrease Brd-dependent recruitment of pTEFb to genes involved in cell proliferation, BET inhibitor compounds of Formula I, stereoisomers, tautomers, pharmaceutically acceptable salts, or hydrates thereof, or compositions comprising one or more of those compounds may be used to treat cancers that rely on pTEFb (Cdk9/cyclin T) and BET proteins to regulate oncogenes. These cancers include, but are not limited to, chronic lymphocytic leukemia and multiple myeloma (Tong, W. G., et al., "Phase I and pharmacologic study of SNS-032, a potent and selective Cdk2, 7, and 9 inhibitor, in patients with advanced chronic lymphocytic leukemia and multiple myeloma," *J Clin Oncol* 28(18):3015-22 (2010)), follicular lymphoma, diffuse large B cell lymphoma with germinal center phenotype, Burkitt's lymphoma, Hodgkin's lymphoma, follicular lymphomas and activated, anaplastic large cell lymphoma (Bellan, C., et al., "CDK9/CYCLIN T1 expression during normal lymphoid differentiation and malignant transformation," *J Pathol* 203(4):946-52 (2004)), neuroblastoma and primary neuroectodermal tumor (De Falco, G., et al., "Cdk9 regulates neural differentiation and its expression correlates with the differentiation grade of neuroblastoma and PNET tumors," *Cancer Biol Ther* 4(3): 277-81 (2005)), rhabdomyosarcoma (Simone, C. and A. Giordano, "Abrogation of signal-dependent activation of the cdk9/cyclin T2a complex in human RD rhabdomyosarcoma cells," *Cell Death Differ* 14(1):192-5 (2007)), prostate cancer (Lee, D. K., et al., "Androgen receptor interacts with the positive elongation factor P-TEFb and enhances the efficiency of transcriptional elongation," *J Biol Chem* 276(13): 9978-84 (2001)), and breast cancer (Bartholomeeusen, K., et al., "BET bromodomain inhibition activates transcription via a transient release of P-TEFb from 7SK snRNP," *J Biol Chem* (2012)).

In one embodiment, BET inhibitor compounds of Formula I, stereolsomers, tautomers, pharmaceutically acceptable salts, or hydrates thereof, or compositions comprising one or more of those compounds may be used to treat cancers in which BET-responsive genes, such as CDK6, Bcl2, TYRO3, MYB, and hTERT are up-regulated. Dawson, M. A., et al., "Inhibition of BET recruitment to chromatin as an effective treatment for MLL-fusion leukaemia," *Nature* 478(7370):529-33 (2011); Delmore, J. E., et al., "BET bromodomain inhibition as a therapeutic strategy to target c-Myc," *Cell* 146(6):904-17 (2010). These cancers include, but are not limited to, pancreatic cancer, breast cancer, colon cancer, glioblastoma, adenoid cystic carcinoma, T-cell pro-lymphocytic leukemia, malignant glioma, bladder cancer, medulloblastoma, thyroid cancer, melanoma, multiple myeloma, Barret's adenocarcinoma, hepatoma, prostate cancer, pro-myelocytic leukemia, chronic lymphocytic leukemia, mantle cell lymphoma, diffuse large B-cell lymphoma, small cell lung cancer, and renal carcinoma. Ruden, M. and N. Purl, "Novel anticancer therapeutics targeting telomerase," *Cancer Treat Rev* (2012); Kelly, P. N. and A. Strasser, "The role of Bcl-2 and its pro-survival relatives in tumourigenesis and cancer therapy" *Cell Death Differ* 18(9): 1414-24 (2011); Uchida, T., et al., "Antitumor effect of bcl-2 antisense phosphorothioate oligodeoxynucleotides on human renal-cell carcinoma cells in vitro and in mice," *Mol Urol* 5(2):71-8 (2001).

Published and proprietary data have shown direct effects of BET inhibition on cell proliferation in various cancers. In one embodiment, BET inhibitor compounds of Formula I, stereoisomers, tautomers, pharmaceutically acceptable salts, or hydrates thereof, or compositions comprising one or more of those compounds may be used to treat cancers for which exist published and, for some, proprietary, in vivo and/or in vitro data showing a direct effect of BET inhibition on cell proliferation. These cancers include NMC (NUT-midline carcinoma), acute myeloid leukemia (AML), acute B lymphoblastic leukemia (B-ALL), Burkitt's Lymphoma, B-cell Lymphoma, Melanoma, mixed lineage leukemia, multiple myeloma, pro-myelocytic leukemia (PML), and non-Hodgkin's lymphoma. Filippakopoulos, P., et al., "Selective inhibition of BET bromodomains," *Nature* 468(7327):1067-73 (2010); Dawson, M. A., et al., "Inhibition of BET recruitment to chromatin as an effective treatment for MLL-fusion leukaemia," *Nature* 478(7370):529-33 (2011); Zuber, J., et al., "RNAi screen identifies Brd4 as a therapeutic target in acute myeloid leukaemia," Nature 478(7370):524-8 (2011); Miguel F. Segura, et al, "BRD4 is a novel therapeutic target in melanoma," *Cancer Research.* 72(8):Supplement 1 (2012). The compounds of the invention have a demonstrated BET inhibition effect on cell proliferation in vitro for the following cancers: Neuroblastoma, Medulloblastoma, lung carcinoma (NSCLC, SCLC), and colon carcinoma.

In one embodiment, because of potential synergy or additive effects between BET inhibitors and other cancer therapy, BET inhibitor compounds of Formula I, stereoisomers, tautomers, pharmaceutically acceptable salts, or hydrates thereof, or compositions comprising one or more of those compounds may be combined with other therapies, chemotherapeutic agents, or anti-proliferative agents to treat human cancer and other proliferative disorders. The list of therapeutic agents which can be combined with BET inhibitors in cancer treatment includes, but is not limited to, ABT-737, Azacitidine (Vidaza), AZD1152 (Barasertib), AZD2281 (Olaparib), AZD6244 (Setumetinib), BEZ235, Bleomycin Sulfate, Bortezomib (Velcade), Busulfan (Myleran), Camptothecin, Cisplatin, Cyclophosphamide (Clafen), CYT387, Cytarabine (Ara-C), Dacarbazine, DAPT (GSI-IX), Decitabine, Dexamethasone, Doxorubicin (Adriamycin), Etoposide, Everolimus (RAD001), Flavopiridol (Alvocidib), Ganetespib (STA-9090), Gefitinib (Iressa), Idarubicin, Ifosfamide (Mitoxana), IFNa2a (Roferon A), Melphalan (Alkeran), Methazolastone (temozolomide), Metformin, Mitoxantrone (Novantrone), Paclitaxel, Phenformin, PKC412 (Midostaurin), PLX4032 (Vemurafenib), Pomalidomide (CC-4047), Prednisone (Deltasone), Rapamycin, Revlimid (Lenalidomide), Ruxolitinib (INCB018424), Sorafenib (Nexavar), SU11248 (Sunitinib), SU11274, Vinblastine, Vincristine (Oncovin), Vinorelbine (Navelbine), Vorinostat (SAHA), and WP1130 (Degrasyn).

In one embodiment, BET inhibitor compounds of Formula I, stereoisomers, tautomers, pharmaceutically acceptable salts, or hydrates thereof, or compositions comprising one or more of those compounds may be used to treat benign proliferative and fibrotic disorders, including benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, juvenile polyposis syndrome, idiopathic pulmonary fibrosis, renal fibrosis, post-operative stricture, keloid formation, scleroderma, and cardiac fibrosis. Tang, X et al., "Assessment of Brd4 Inhibition in Idiopathic Pulmonary Fibrosis Lung Fibroblasts and in Vivo Models of Lung Fibrosis," *Am J Pathology in press* (2013).

In one embodiment, because of their ability to up-regulate ApoA-1 transcription and protein expression (Mirguet, O., et al., "From ApoA1 upregulation to BET family bromodomain inhibition: discovery of I-BET151," *Bioorg Med Chem Lett* 22(8):2963-7 (2012); Chung, C. W., et al., "Discovery and characterization of small molecule inhibitors of the BET family bromodomains," *J Med Chem* 54(11):3827-38 (2011)), BET inhibitor compounds of Formula I, stereoisomers, tautomers, pharmaceutically acceptable salts, or hydrates thereof, or compositions comprising one or more of those compounds may be used to treat cardiovascular diseases that are generally associated with including dyslipidemia, atherosclerosis, hypercholesterolemia, and metabolic syndrome (Belkina, A. C. and G. V. Denis, "BET domain co-regulators in obesity, inflammation and cancer," *Nat Rev Cancer* 12(7):465-77 (2012); Denis, G. V., "Bromodomain coactivators in cancer, obesity, type 2 diabetes, and inflammation," *Discov Med* 10(55):489-99 (2010)). In another embodiment, BET inhibitor compounds of Formula I may be used to treat non-cardiovascular disease characterized by deficits in ApoA-1, including Alzheimer's disease. Elliott, D. A., et al., "Apolipoproteins in the brain: implications for neurological and psychiatric disorders," *Clin Lipidol* 51(4): 555-573 (2010).

In one embodiment, BET inhibitor compounds of Formula I, stereoisomers, tautomers, pharmaceutically acceptable salts, or hydrates thereof, or compositions comprising one or more of those compounds may be used in patients with insulin resistance and type II diabetes. Belkina, A. C. and G. V. Denis, "BET domain co-regulators in obesity, inflammation and cancer," *Nat Rev Cancer* 12(7):465-77 (2012); Denis, G. V., "Bromodomain coactivators in cancer, obesity, type 2 diabetes, and inflammation," *Discov Med* 10(55):489-99 (2010); Wang, F., et al., "Brd2 disruption in mice causes severe obesity without Type 2 diabetes," *Biochem J* 425(1):71-83 (2010); Denis, G. V., et al, "An emerging role for bromodomain-containing proteins in chromatin regulation and transcriptional control of adipogenesis," *FEBS Lett* 584(15):3260-8 (2010). The anti-inflammatory effects of BET inhibition would have additional value in decreasing inflammation associated with diabetes and metabolic disease. Alexandraki, K., et al., "Inflammatory process in type 2 diabetes: The role of cytokines," *Ann N Y Acad Sci* 1084:89-117 (2006).

In one embodiment, because of their ability to down-regulate viral promoters, BET inhibitor compounds of Formula I, stereoisomers, tautomers, pharmaceutically acceptable salts, or hydrates thereof, or compositions comprising one or more of those compounds may be used as therapeutics for cancers that are associated with viruses including Epstein-Barr Virus (EBV), hepatitis virus (HBV, HCV), Kaposi's sarcoma associated virus (KSHV), human papilloma virus (HPV), Merkel cell polyomavirus, and human cytomegalovirus (CMV). Gagnon, D., et al., "Proteasomal degradation of the papillomavirus E2 protein is inhibited by overexpression of bromodomain-containing protein 4," *J Viral* 83(9):4127-39 (2009); You, J., et al., "Kaposi's sarcoma-associated herpesvirus latency-associated nuclear antigen interacts with bromodomain protein Brd4 on host mitotic chromosomes," *J Virol* 80(18):8909-19 (2006); Palermo, R. D., et al., "RNA polymerase II stalling promotes nucleosome occlusion and pTEFb recruitment to drive immortalization by Epstein-Barr virus," *PLoS Pathog* 7(10): e1002334 (2011); Poreba, E., et al., "Epigenetic mechanisms in virus-induced tumorigenesis," *Clin Epigenetics* 2(2):233-47. 2011. In another embodiment, because of their ability to reactivate HIV-1 in models of latent T cell infection and latent monocyte infection, BET inhibitors could be used in combination with anti-retroviral therapeutics for treating HIV. Zhu, J., et al., "Reactivation of Latent HIV-1 by Inhibition of BRD4," *Cell Rep* (2012); Banerjee, C., et al., "BET bromodomain inhibition as a novel strategy for reactivation of HIV-1," *J Leukoc Biol* (2012); Bartholomeeusen, K., et al., "BET bromodomain inhibition activates transcription via a transient release of P-TEFb from 7SK snRNP," *J Biol Chem* (2012); Li, Z., et al., "The BET bromodomain inhibitor JQ1 activates HIV latency through antagonizing Brd4 inhibition of Tat-transactivation," *Nucleic Acids Res* (2012.)

In one embodiment, because of the role of epigenetic processes and bromodomain-containing proteins in neurological disorders, BET inhibitor compounds of Formula I, stereoisomers, tautomers, pharmaceutically acceptable salts, or hydrates thereof, or compositions comprising one or more of those compounds may be used to treat diseases including, but not limited to, Alzheimer's disease, Parkinson's disease, Huntington disease, bipolar disorder, schizophrenia, Rubinstein-Taybi syndrome, and epilepsy. Prinjha, R. K., J. Witherington, and K. Lee, "Place your BETs: the therapeutic potential of bromodomains," *Trends Pharmacol Sci* 33(3): 146-53 (2012); Muller, S., et al., "Bromodomains as therapeutic targets," *Expert Rev Mol Med* 13:e29 (2011).

In one embodiment, because of the effect of BRDT depletion or inhibition on spermatid development, BET inhibitor compounds of Formula I, stereoisomers, tautomers, pharmaceutically acceptable salts, or hydrates thereof, or compositions comprising one or more of those compounds may be used as reversible, male contraceptive agents. Matzuk, M. M., et al., "Small-Molecule Inhibition of BRDT for Male Contraception," *Cell* 150(4): p. 673-684 (2012); Berkovits, B. D., et al., "The testis-specific double bromodomain-containing protein BRDT forms a complex with multiple spliceosome components and is required for mRNA splicing and 3'-UTR truncation in round spermatids," *Nucleic Acids Res* 40(15):7162-75 (2012).

Pharmaceutical Compositions

Pharmaceutical compositions of the present disclosure comprise at least one compound of Formula I, or tautomer, stereoisomer, pharmaceutically acceptable salt or hydrate thereof formulated together with one or more pharmaceutically acceptable carriers. These formulations include those suitable for oral, rectal, topical, buccal and parenteral (e.g., subcutaneous, intramuscular, intradermal, or intravenous) administration. The most suitable form of administration in any given case will depend on the degree and severity of the condition being treated and on the nature of the particular compound being used.

Formulations suitable for oral administration may be presented in discrete units, such as capsules, cachets, lozenges, or tablets, each containing a predetermined amount of a compound of the present disclosure as powder or granules; as a solution or a suspension in an aqueous or non-aqueous liquid; or as an oil-in-water or water-in-oil emulsion. As indicated, such formulations may be prepared by any suitable method of pharmacy which includes the step of bringing into association at least one compound of the present disclosure as the active compound and a carrier or excipient (which may constitute one or more accessory ingredients). The carrier must be acceptable in the sense of being compatible with the other ingredients of the formulation and must not be deleterious to the recipient. The carrier may be a solid or a liquid, or both, and may be formulated with at least one compound described herein as the active compound in a unit-dose formulation, for example, a tablet, which may contain from about 0.05% to about 95% by weight of the at least one active compound. Other pharmacologically active substances may also be present including other compounds. The formulations of the present disclosure may be prepared by any of the well-known techniques of pharmacy consisting essentially of admixing the components.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmacologically administrable compositions can, for example, be prepared by, for example, dissolving or dispersing, at least one active compound of the present disclosure as described herein and optional pharmaceutical adjuvants in an excipient, such as, for example, water, saline, aqueous dextrose, glycerol, ethanol, and the like, to thereby form a solution or suspension. In general, suitable formulations may be prepared by uniformly and intimately admixing the at least one active compound of the present disclosure with a liquid or finely divided solid carrier, or both, and then, if necessary, shaping the product. For example, a tablet may be prepared by compressing or molding a powder or granules of at least one compound of the present disclosure, which may be optionally combined with one or more accessory ingredients. Compressed tablets may be prepared by compressing, in a suitable machine, at least one compound of the present disclosure in a freeflowing form, such as a powder or granules, which may be optionally mixed with a binder, lubricant, inert diluent and/or surface active/dispersing agent(s). Molded tablets may be made by molding, in a suitable machine, where the powdered form of at least one compound of the present disclosure is moistened with an inert liquid diluent.

Formulations suitable for buccal (sub-lingual) administration include lozenges comprising at least one compound of the present disclosure in a flavored base, usually sucrose and acacia or tragacanth, and pastilles comprising the at least one compound in an inert base such as gelatin and glycerin or sucrose and acacia.

Formulations of the present disclosure suitable for parenteral administration comprise sterile aqueous preparations of at least one compound of Formula I or tautomers, stereoisomers, pharmaceutically acceptable salts, and hydrates thereof, which are approximately isotonic with the blood of the intended recipient. These preparations are administered intravenously, although administration may also be effected by means of subcutaneous, intramuscular, or intradermal injection. Such preparations may conveniently be prepared by admixing at least one compound described herein with water and rendering the resulting solution sterile and isotonic with the blood. Injectable compositions according to the present disclosure may contain from about 0.1 to about 5% w/w of the active compound.

Formulations suitable for rectal administration are presented as unit-dose suppositories. These may be prepared by admixing at least one compound as described herein with one or more conventional solid carriers, for example, cocoa butter, and then shaping the resulting mixture.

Formulations suitable for topical application to the skin may take the form of an ointment, cream, lotion, paste, gel, spray, aerosol, or oil. Carriers and excipients which may be used include Vaseline, lanoline, polyethylene glycols, alcohols, and combinations of two or more thereof. The active compound (i.e., at least one compound of Formula I or tautomers, stereoisomers, pharmaceutically acceptable salts, and hydrates thereof) is generally present at a concentration of from about 0.1% to about 15% w/w of the composition, for example, from about 0.5 to about 2%.

The amount of active compound administered may be dependent on the subject being treated, the subject's weight, the manner of administration and the judgment of the prescribing physician. For example, a dosing schedule may involve the daily or semi-daily administration of the encapsulated compound at a perceived dosage of about 1 μg to about 1000 mg. In another embodiment, intermittent administration, such as on a monthly or yearly basis, of a dose of the encapsulated compound may be employed. Encapsulation facilitates access to the site of action and allows the administration of the active ingredients simultaneously, in theory producing a synergistic effect. In accordance with standard dosing regimens, physicians will readily determine optimum dosages and will be able to readily modify administration to achieve such dosages.

A therapeutically effective amount of a compound or composition disclosed herein can be measured by the therapeutic effectiveness of the compound. The dosages, however, may be varied depending upon the requirements of the patient, the severity of the condition being treated, and the compound being used. In one embodiment, the therapeutically effective amount of a disclosed compound is sufficient to establish a maximal plasma concentration. Preliminary doses as, for example, determined according to animal tests, and the scaling of dosages for human administration is performed according to art-accepted practices.

Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferable.

Data obtained from the cell culture assays or animal studies can be used in formulating a range of dosage for use in humans. Therapeutically effective dosages achieved in one animal model may be converted for use in another animal, including humans, using conversion factors known in the art (see, e.g., Freireich et al., *Cancer Chemother. Reports* 50(4):219-244 (1966) and the following Table for Equivalent Surface Area Dosage Factors).

| Equivalent Surface Area Dosage Factors: | | | | | |
|---|---|---|---|---|---|
| | To: | | | | |
| From: | Mouse (20 g) | Rat (150 g) | Monkey (3.5 kg) | Dog (8 kg) | Human (60 kg) |
| Mouse | 1 | ½ | ¼ | ⅙ | 1/12 |
| Rat | 2 | 1 | ½ | ¼ | 1/7 |
| Monkey | 4 | 2 | 1 | ⅗ | ⅓ |
| Dog | 6 | 4 | ⅗ | 1 | ½ |
| Human | 12 | 7 | 3 | 2 | 1 |

The dosage of such compounds lies preferably within a range of circulating concentrations that include the $ED_{50}$ with little or no toxicity. The dosage may vary within this range depending upon the dosage form employed and the route of administration utilized. Generally, a therapeutically effective amount may vary with the subject's age, condition, and gender, as well as the severity of the medical condition in the subject. The dosage may be determined by a physician and adjusted, as necessary, to suit observed effects of the treatment.

In one embodiment, a compound of Formula I or a tautomer, stereoisomer, pharmaceutically acceptable salt or hydrate thereof, is administered in combination with another therapeutic agent. The other therapeutic agent can provide additive or synergistic value relative to the administration of a compound of the present disclosure alone. The therapeutic agent can be, for example, a statin; a PPAR agonist, e.g., a thiazolidinedione or fibrate; a niacin, a RVX, FXR or LXR agonist; a bile-acid reuptake inhibitor; a cholesterol absorption inhibitor; a cholesterol synthesis inhibitor; a cholesteryl ester transfer protein (CETP), an ion-exchange resin; an antioxidant; an inhibitor of AcylCoA cholesterol acyltransferase (ACAT inhibitor); a tyrophostine; a sulfonylurea-based drug; a biguanide; an alpha-glucosidase inhibitor; an apolipoprotein E regulator; a HMG-CoA reductase inhibitor, a microsomal triglyceride transfer protein; an LDL-lowing drug; an HDL-raising drug; an HDL enhancer; a regulator of the apolipoprotein A-IV and/or apolipoprotein genes; or any cardiovascular drug.

In another embodiment, a compound of Formula I or a tautomer, stereoisomer, pharmaceutically acceptable salt or hydrate thereof, is administered in combination with one or more anti-inflammatory agents. Anti-inflammatory agents can include immunosuppressants, TNF inhibitors, corticosteroids, non-steroidal anti-inflammatory drugs (NSAIDs), disease-modifying anti-rheumatic drugs (DMARDS), and the like. Exemplary anti-inflammatory agents include, for example, prednisone; methylprenisolone (Medrol®), triamcinolone, methotrexate (Rheumatrex®, Trexall®), hydroxychloroquine (Plaquenil®), sulfasalzine (Azulfidine®), leflunomide (Arava®), etanercept (Enbrel®), infliximab (Remicade®), adalimumab (Humira®), rituximab (Rituxan®), abatacept (Orencia®), interleukin-1, anakinra (Kineret®), ibuprofen, ketoprofen, fenoprofen, naproxen, aspirin, acetominophen, indomethacin, sulindac, meloxicam, piroxicam, tenoxicam, lornoxicam, ketorolac, etodolac, mefenamic acid, meclofenamic acid, flufenamic acid, tolfenamic acid, diclofenac, oxaprozin, apazone, nimesulide, nabumetone, tenidap, etanercept, tolmetin, phenylbutazone, oxyphenbutazone, diflunisal, salsalate, olsalazine, or sulfasalazine.

EXAMPLES

General Methods:

Unless otherwise noted, reagents and solvents were used as received from commercial suppliers. Proton nuclear magnetic resonance spectra were obtained on a Bruker AVANCE 300 spectrometer at 300 MHz or Bruker AVANCE 500 spectrometer at 500 MHz. Spectra are given in ppm (δ) and coupling constants, J values, are reported in hertz (Hz). Tetramethylsilane was used as an internal standard for $^1$H nuclear magnetic resonance. Mass spectra analyses were performed on Waters Aquity UPLC Mass Spectrometer in ESI or APCI mode when appropriate, Agilent 6130A Mass Spectrometer in ESI, APCI, or MultiMode mode when appropriate or Applied Biosystems API-150EX Spectrometer in ESI or APCI mode when appropriate. Silica gel chromatographys were in general performed on a Teledyne Isco CombiFlash® Rf 200 system or a Teledyne Isco CombiFlash® Companion system.

General Procedure A:

4,4'-(2-methyl-1H-benzo[d]imidazole-4,6-diyl)bis(3,5-dimethylisoxazole) (Example Compound 6)

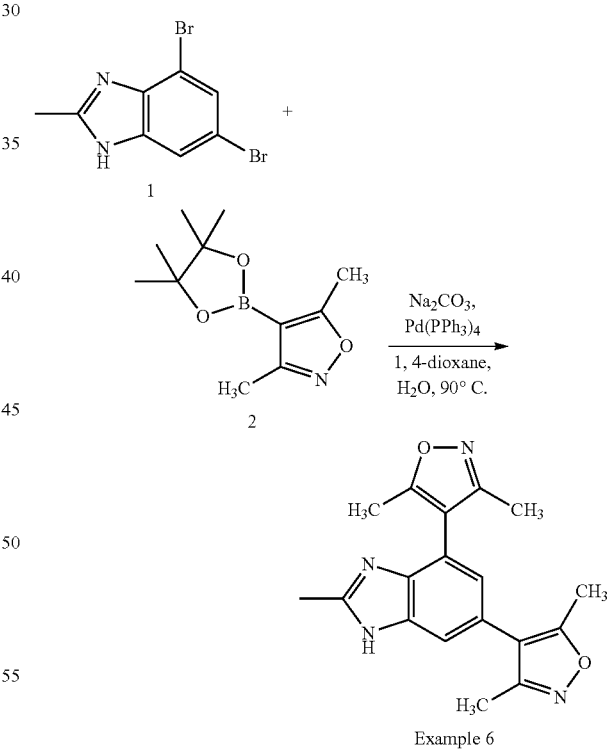

Example 6

To a solution of 1 (250 mg, 0.86 mmol) in 1,4-dioxane (15 mL) and water (2 mL) was added 3,5-dimethyl-4-(4,4,5,5-tetramethyl-1,3,2-dioxaborolan-2-yl)isoxazole (540 mg, 2.41 mmol), sodium carbonate (180 mg, 1.70 mmol) and tetrakis(triphenylphosphine)palladium(0) (50 mg, 0.043 mmol). The reaction mixture was purged with nitrogen for 5 min and heated to 90° C. for 16 h. The mixture was diluted with methylene chloride (20 mL) and washed with brine (15 mL). The organic layer was dried over sodium sulfate, filtered and concentrated. Purification by chromatography (silica gel, 0-100% ethyl acetate/hexanes) afforded Example Compound 6 (166 mg, 60%) as an off-white solid: $^1$H NMR (300 MHz, CD$_3$OD) δ 7.47 (s, 1H), 7.05 (d, J=1.5 Hz, 1H), 2.58 (s, 3H), 2.44 (s, 3H), 2.37 (s, 3H), 2.29 (s, 3H), 2.22 (s, 3H); ESI MS m/z 323 [M+H]$^+$.

General Procedure B:

Preparation of N-benzyl-2-(3,5-dimethylisoxazol-4-yl)quinazolin-4-amine (Example Compound 5)

cation by chromatography (silica gel, 0-100% ethyl acetate/hexanes) afforded Example Compound 5 (54 mg, 82%) as a white solid: $^1$H NMR (500 MHz, CDCl$_3$) δ 7.85 (d, J=7.5 Hz, 1H), 7.75-7.68 (m, 2H), 7.44-7.36 (m, 5H), 7.34-7.31 (m, 1H), 5.93 (s, 1H), 4.91 (d, J=5.0 Hz, 2H), 2.80 (s, 3H), 2.64 (s, 3H); ESI m/z 331 [M+H]$^+$.

General Procedure C:

Preparation of N-benzyl-6-(3,5-dimethylisoxazol-4-yl)-[1,2,4]triazolo[4,3-o]pyridin-8-amine (Example Compound 24)

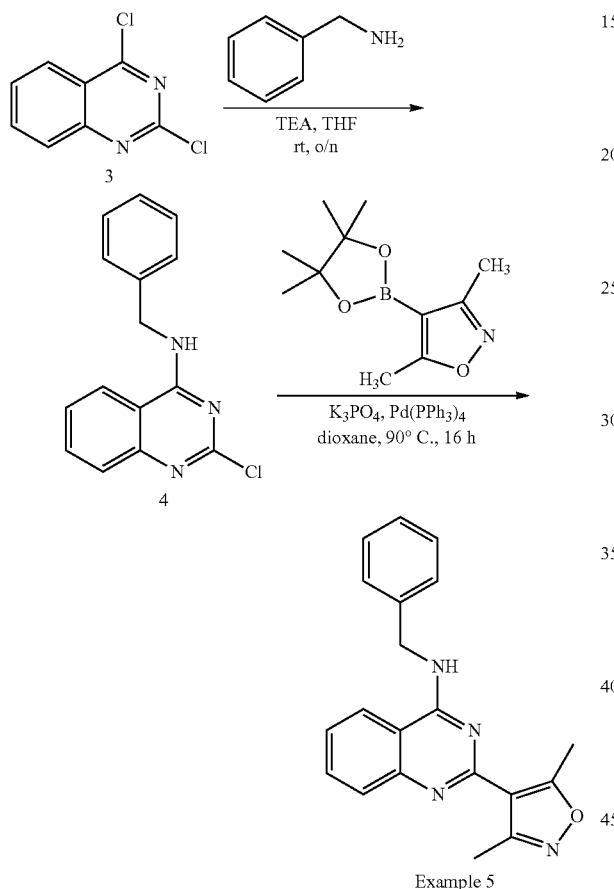

Example 5

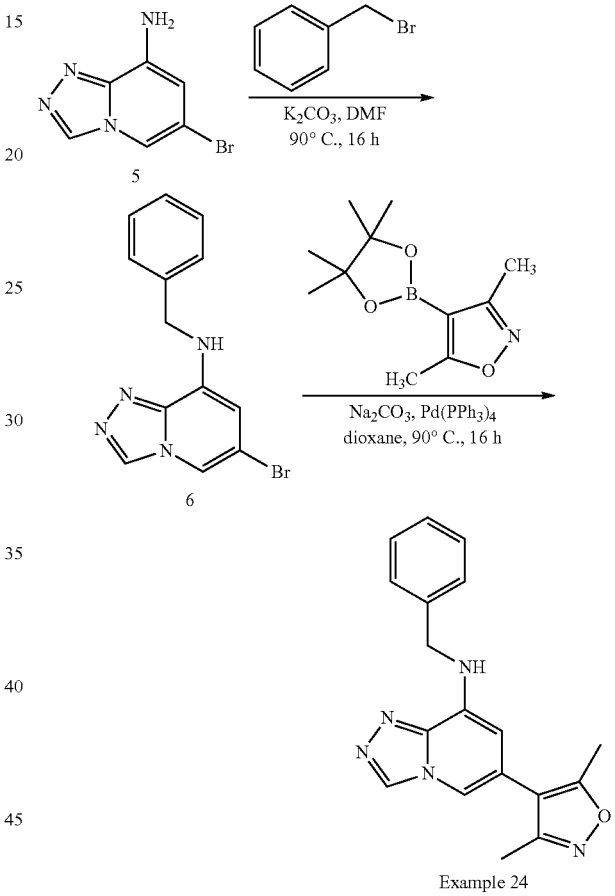

Example 24

Step 1:

To a solution of 3 (100 mg, 0.50 mmol) in THF (2 mL) was added triethylamine (0.08 mL, 0.6 mmol) and benzylamine (53 mg, 0.50 mmol). The mixture was stirred at room temperature for 16 h, concentrated and purified by chromatography (silica gel, 0-100% ethyl acetate/hexanes) to give 4 (122 mg, 90%) as a yellow solid: ESI m/z 270 [M+H]$^+$.

Step 2:

To a solution of 4 (54 mg, 0.20 mmol) in 1,4-dioxane (2 mL) was added 3,5-dimethyl-4-(4,4,5,5-tetramethyl-1,3,2-dioxaborolan-2-yl)isoxazole (67 mg, 0.30 mmol), potassium phosphate (85 mg, 0.40 mmol) and tetrakis(triphenylphosphine)palladium(0) (22 mg, 0.02 mmol). The reaction mixture was purged with nitrogen and heated at 90° C. for 16 h. The mixture was diluted with methylene chloride (30 mL) and washed with brine (2×10 mL). The organic layer was dried over sodium sulfate, filtered and concentrated. Purifi- Step 1:

To a solution of 5 (86 mg, 0.40 mmol) in DMF (2 mL) was added potassium carbonate (124 mg, 0.9 mmol) and benzyl bromide (68 mg, 0.40 mmol). The mixture was heated at 90° C. in a sealed tube for 16 h. After cooling to room temperature, the mixture was filtered through a celite plug, concentrated and purified by chromatography (silica gel, 0-100% ethyl acetate/hexanes) to give 6 (41 mg, 90%) as a white solid: ESI m/z 303 [M+H]$^+$.

Step 2:

To a solution of 6 (36 mg, 0.20 mmol) in 1,4-dioxane (1 mL) was added 3,5-dimethyl-4-(4,4,5,5-tetramethyl-1,3,2-dioxaborolan-2-yl)isoxazole (38 mg, 0.14 mmol), sodium carbonate (2.0 M in H$_2$O, 0.1 mL, 0.2 mmol) and tetrakis (triphenylphosphine)palladium(0) (9 mg, 0.01 mmol). The reaction mixture was purged with nitrogen and heated at 90° C. for 16 h. The mixture was diluted with methylene chloride (30 mL) and washed with brine (2×10 mL). The organic layer was dried over sodium sulfate, filtered and concentrated. Purification by chromatography (silica gel, 0-100% ethyl acetate/hexanes) afforded Example Compound 24 (11 mg, 29%) as a white solid: $^1$H NMR (500 MHz, CDCl$_3$) δ 8.30 (s, 1H), 7.88 (s, 1H), 7.40-7.34 (m, 4H), 7.31-7.28 (m, 1H), 6.12 (s, 1H), 4.55 (s, 2H), 2.28 (s, 3H), 2.10 (s, 3H); ESI m/z 320 [M+H]$^+$.

General Procedure D:

Preparation of 3,5-dimethyl-4-(4-(1-methyl-1H-pyrazol-5-yl)-1H-benzo[d]imidazol-6-yl)isoxazole (Example Compound 16)

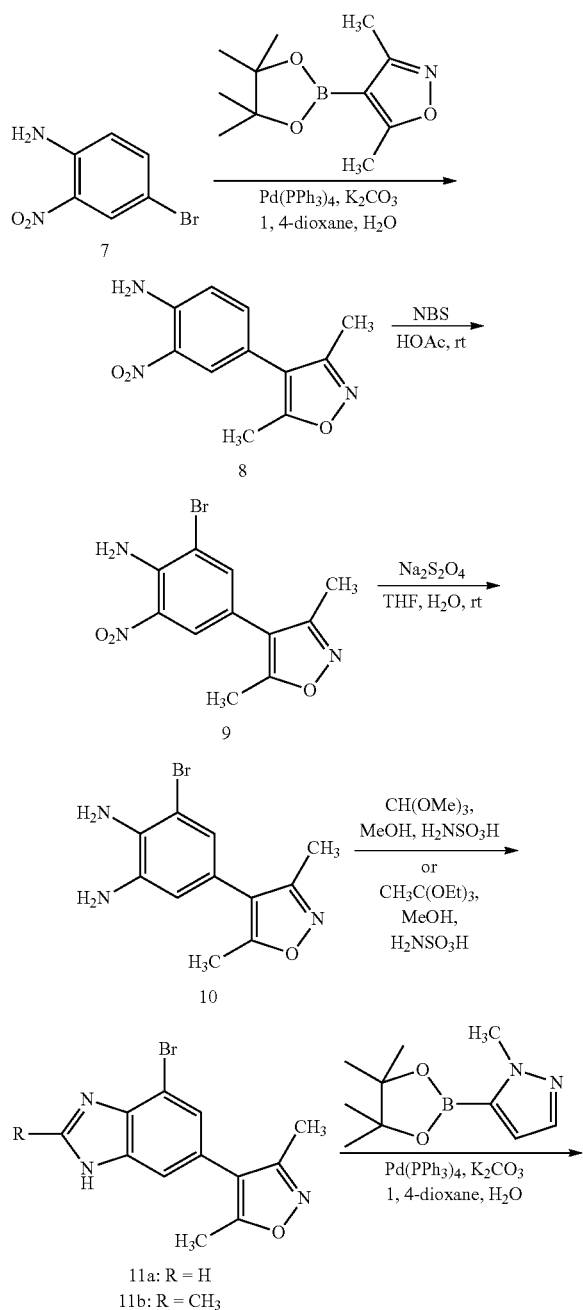

Example 16: R = H

Step 1:

To a solution of 7 (1.00 g, 4.61 mmol) in 1,4-dioxane (40 mL) and water (4 mL) was added 3,5-dimethyl-4-(4,4,5,5-tetramethyl-1,3,2-dioxaborolan-2-yl)isoxazole (1.23 g, 5.53 mmol), potassium carbonate (1.27 g, 9.22 mmol), and tetrakis(triphenylphosphine)palladium(0) (266 mg, 0.231 mmol). The reaction mixture was purged with nitrogen and heated at 90° C. for 16 h. The reaction mixture was cooled to room temperature, concentrated and purified by chromatography (silica gel, 0-30% ethyl acetate/hexanes) to give 8 (950 mg, 88%) as a yellow solid: $^1$H NMR (500 MHz, CDCl$_3$) δ 8.02 (d, J=2.1 Hz, 1H), 7.26 (dd, J=2.1 Hz, 8.5 Hz, 1H), 6.89 (d, J=8.6 Hz, 1H), 6.14 (s, 2H), 2.40 (s, 3H), 2.26 (s, 3H); ESI m/z 234 [M+H]$^+$.

Step 2:

To a solution of 8 (940 mg, 4.03 mmol) in acetic acid (15 mL) at 0° C. was added N-bromosuccinimide (753 mg, 4.23 mmol). The reaction was warmed to room temperature and stirred for 16 h. The mixture was concentrated in vacuo. The residue was suspended in hot MeOH, cooled to room temperature and was basified with 10% aq. NaHCO$_3$. The mixture was diluted with water and filtered. The solid was washed with water and dried in vacuo to afford 9 (1.10 g, 87%) as a yellow solid: $^1$H NMR (500 MHz, CDCl$_3$) δ 8.04 (d, J=2.1 Hz, 1H), 7.61 (d, J=2.1 Hz, 1H), 6.69 (bs, 2H), 2.40 (s, 3H), 2.26 (s, 3H); ESI m/z 312 [M+H]$^+$.

Step 3:

To a solution of 9 (1.09 g, 3.49 mmol) in tetrahydrofuran (30 mL) was added sodium dithionite (4.86 g, 28.0 mmol) in water (15 mL). The reaction mixture was stirred at room temperature for 16 h and concentrated under vacuum. The residue was dissolved in MeOH/water (1:1, 150 mL) and the solid was precipitated by removing some MeOH under vacuum. The solid was filtered, washed with water and dried under vacuum to afford 10 (440 mg, 45%) as a yellow solid: $^1$H NMR (500 MHz, CDCl$_3$) δ 6.85 (d, J=1.8 Hz, 1H), 6.51 (d, J=1.8 Hz, 1H), 4.00-3.60 (bs, 2H), 3.60-3.30 (bs, 2H), 2.36 (s, 3H), 2.23 (s, 3H); ESI m/z 282 [M+H]$^+$.

Step 4:

To a solution of 10 (490 mg, 1.74 mmol) in methanol (15 mL) was added trimethyl orthoformate (276 mg, 2.61 mmol) and sulfamic acid (9 mg, 0.09 mmol). The reaction was stirred at room temperature for 5 h. The reaction mixture was diluted with water (50 mL), basified with NaHCO$_3$ and filtered. The solid was washed with water and dried in vacuo to give 11a (440 mg, 87%) as a yellow solid: $^1$H NMR (500 MHz, DMSO-d$_6$) δ 12.99 (s, 0.3H), 12.84 (s, 0.7H), 8.35 (s, 1H), 7.67 (s, 0.3H), 7.51 (s, 0.7H), 7.43 (s, 0.3H), 7.74 (s, 0.7H), 2.40 (s, 3H), 2.22 (s, 3H); ESI m/z 292 [M+H]$^+$.

11b was prepared by following the similar method as 11a using triethylorthoacetate: $^1$H NMR (300 MHz, DMSO-d$_6$)

δ 12.82 (br.s, 1H), 7.42 (d, J=1.5 Hz, 1H), 7.31 (d, J=1.5 Hz, 1H), 2.52 (s, 3H), 2.40 (s, 3H), 2.24 (s, 3H).

Step 5:

To a solution of 11a (60 mg, 0.21 mmol) in 1,4-dioxane (10 mL) and water (1 mL) was added 1-methyl-5-(4,4,5,5-tetramethyl-1,3,2-dioxaborolan-2-yl)-1H-pyrazole (66 mg, 0.32 mmol), potassium carbonate (58 mg, 0.42 mmol), and tetrakis(triphenylphosphine)palladium(0) (12 mg, 0.011 mmol). The reaction mixture was purged with nitrogen and heated at 90° C. for 16 h. The reaction mixture was cooled to room temperature, concentrated and purified by chromatography (silica gel, 0-20% ethyl acetate/MeOH). It was further purified by reverse phase HPLC eluting with 10-90% CH₃CN in H₂O to give Example Compound 16 (49 mg, 80%) as an off-white solid: $^1$H NMR (500 MHz, DMSO-d₆) δ 12.90-12.40 (bs, 1H), 8.33 (s, 1H), 7.90-7.50 (m, 2H), 7.22 (s, 1H), 6.54 (d, J=1.7 Hz, 1H), 3.87 (s, 3H), 2.44 (s, 3H), 2.27 (s, 3H); ESI m/z 294 [M+H]⁺.

General Procedure E:

Preparation of 6-(3,5-dimethylisoxazol-4-yl)-N-(4-methoxyphenyl)-1H-benzo[d]imidazol-4-amine (Example Compound 25)

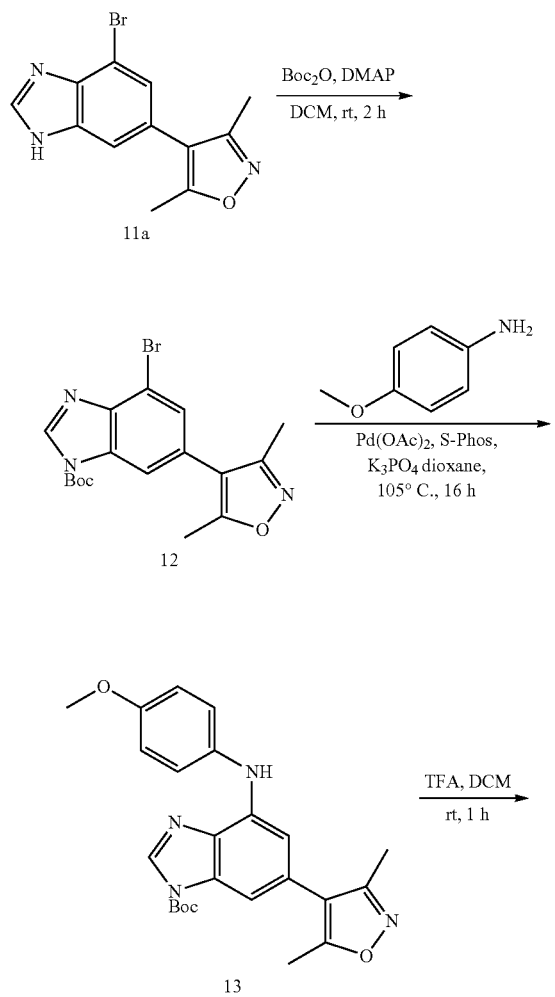

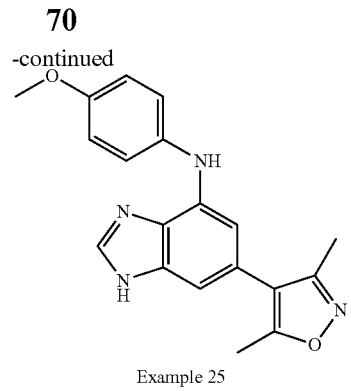

Example 25

Step 1:

To a suspension of 11a (1.30 g, 4.47 mmol) in DCM (40 mL) was added di-tert-butyl dicarbonate (1.17 g, 5.36 mmol) and DMAP (54 mg, 0.45 mmol). The mixture was stirred at rt for 2 h, concentrated and purified by chromatography (silica gel, 0-100% ethyl acetate/hexanes) to give 12 (1.64 g, 94%) as a white foam: $^1$H NMR (500 MHz, CDCl₃) δ 8.50 (s, 1H), 7.88 (s, 1H), 7.89 (d, J=1.5 Hz, 1H), 7.44 (d, J=1.5 Hz, 1H), 2.45 (s, 3H), 2.30 (s, 3H), 1.70 (s, 1H).

Step 2:

To a solution of 12 (100 mg, 0.25 mmol) in dioxane (3 mL) was added 4-methoxyaniline (61 mg, 0.50 mmol), BINAP (31 mg, 0.05 mmol), cesium carbonate (163 mg, 0.5 mmol) and palladium acetate (17 mg, 0.025 mmol). The reaction mixture was purged with nitrogen for five minutes and heated at 105° C. for 16 h. The mixture was diluted with methylene chloride (30 mL) and washed with brine (2×10 mL). The organic layer was dried over sodium sulfate, filtered and concentrated. Purification by chromatography (silica gel, 0-100% ethyl acetate/hexanes) afforded 13 (45 mg, 42%) as a white solid: ESI m/z 435 [M+H]⁺.

Step 3:

To a solution of 13 (45 mg, 0.10 mmol) in DCM (1 mL) was added TFA (1 mL). The reaction mixture was stirred at rt for 1 h. The mixture was concentrated, neutralized with 2 N NaOH (3 mL), and extracted with methylene chloride. The extracts were dried over sodium sulfate, filtered and concentrated. Purification by chromatography (silica gel, 0-10% methanol/methylene chloride) afforded Example Compound 25 (8 mg, 24%) as a white solid: $^1$H NMR (500 MHz, CDCl₃) δ 8.55 (s, 1H), 7.21 (d, J=9.0 Hz, 2H), 6.88 (d, J=9.0 Hz, 2H), 6.74 (s, 1H), 6.73 (s, 1H), 3.20 (s, 3H), 2.36 (s, 3H), 2.22 (s, 3H); ESI m/z 335 [M+H]⁺.

General Procedure F:

Preparation of 4-(4,6-bis(3,5-dimethylisoxazol-4-yl)-1H-benzo[d]imidazol-2-yl)morpholine (Example Compound 226)

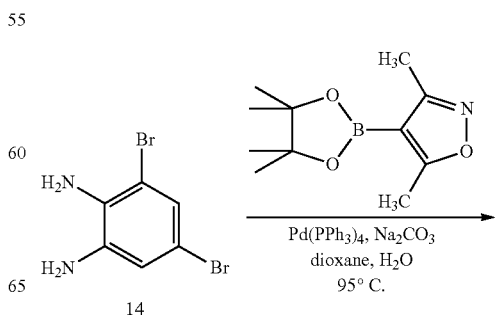

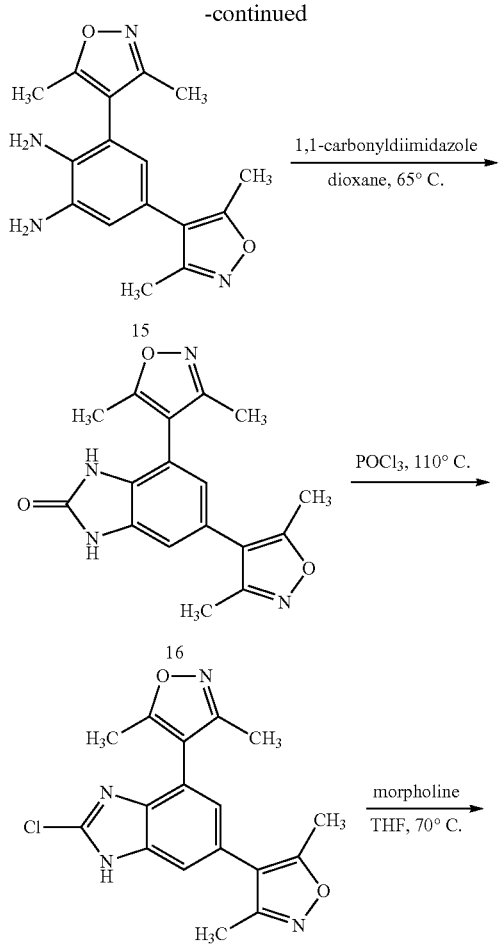

Step 1:

To a solution of 14 (2.67 g, 10.08 mmol) in 1,4-dioxane (80 mL) and water (20 mL) was added 3,5-dimethyl-4-(4,4,5,5-tetramethyl-1,3,2-dioxaborolan-2-yl)isoxazole (6.69 g, 30.0 mmol), tetrakis(triphenylphosphine)palladium(0) (1.16 mg, 1.0 mmol) and sodium carbonate (4.24 g, 40.0 mmol). The reaction mixture was purged with nitrogen and was heated at 95° C. for 16 h. The mixture was diluted with methylene chloride (200 mL) and washed with brine (2×50 mL). The organic layer was dried over sodium sulfate, filtered and concentrated. Purification by chromatography (silica gel, 40-90% ethyl acetate/hexanes) afforded 15 (1.71 g, 57%) as an off-white solid: $^1$H NMR (300 MHz, DMSO-$d_6$) δ 6.58 (d, J=2.1 Hz, 1H), 6.25 (d, J=2.1 Hz, 1H), 4.78 (s, 2H), 4.35 (s, 2H), 2.36 (s, 3H), 2.26 (s, 3H), 2.20 (s, 3H), 2.10 (s, 3H).

Step 2:

To a solution of 15 (1.27 g, 4.26 mmol) in 1,4-dioxane (30 mL) was added 1,1'-carbonyldiimidazole (897 mg, 5.54 mmol). The reaction was heated at 65° C. for 8 h. The reaction mixture was cooled to room temperature and concentrated in vacuo. Purification by trituration with EtOAc afforded 16 (910 mg, 66%) as a white solid: $^1$H NMR (300 MHz, DMSO-$d_6$) δ 10.85 (s, 1H), 10.72 (s, 1H), 6.91 (s, 1H), 6.83 (d, J=1.5 Hz, 1H), 2.41 (s, 3H), 2.31 (s, 3H), 2.24 (s, 3H), 2.15 (s, 3H); ESI m/z 325 [M+H]$^+$.

Step 3:

A mixture of 16 (324 mg, 1.0 mmol) in POCl$_3$ (5 mL) was heated at 110° C. for 3 h. The reaction mixture was concentrated, the residue was dissolved in CH$_2$Cl$_2$ (100 mL) and washed with saturated NaHCO$_3$ (2×50 mL) and brine (50 mL). The organic layer was dried over sodium sulfate, filtered and concentrated to afford 17 (350 mg, 100%) as an off-white solid: ESI m/z 343 [M+H]$^+$.

Step 4:

To a solution of 17 (103 mg, 0.3 mmol) in THF (3 mL) was added morpholine (261 mg, 3.0 mmol). The reaction mixture was heated at 70° C. for 16 h. The reaction mixture was concentrated and purified by chromatography (silica gel, 0-5% MeOH/CH$_2$Cl$_2$) to afford Example Compound 226 (26 mg, 22%) as an off-white solid: $^1$H NMR (300 MHz, MeOD) δ 7.21 (s, 1H), 6.88 (s, 1H), 3.82 (t, J=5.1 Hz, 4H), 3.54 (t, J=5.1 Hz, 4H), 2.43 (s, 3H), 2.38 (s, 3H), 2.28 (s, 3H), 2.24 (s, 3H); ESI m/z 394 [M+H]$^+$.

General Procedure G:

Preparation of 6-(3,5-dimethylisoxazol-4-yl)-1H-benzo[d]imidazol-4-amine (Example Compound 4)

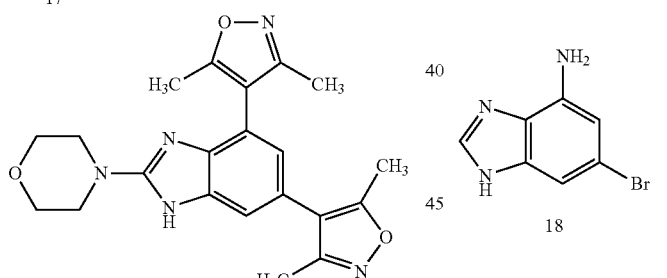

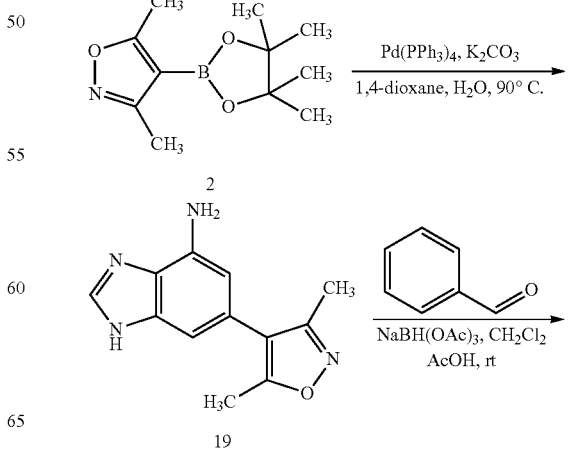

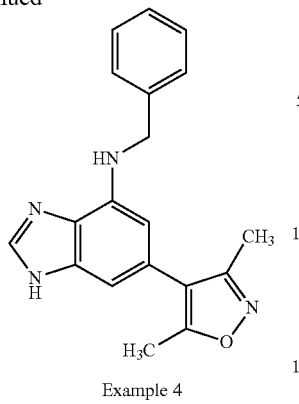

Example 4

Step 1:

A mixture of 18 (1.0 g 4.7 mmol), 2 (4.5 g 6.6 mmmol), K₂CO₃ (1.3 g, 9.4 mmol), 1,4-dioxane (48 mL) and water (3.5 mL) was degassed with nitrogen for 20 minutes followed by addition of tetrakis(triphenylphosphine)palladium (0) (550 mg, 0.94 mmol). The mixture was heated at 90° C. for 18 hours then cooled to room temperature. The crude reaction mixture was then adsorbed onto silica gel and purified by chromatography (silica gel, 0-10% methanol/dichloromethane) to provide 19 (760 mg, 68%) as an off-white solid: ¹H NMR (500 MHz, CDCl₃) δ 7.98 (s, 1H), 6.74 (s, 1H), 6.40 (s, 1H), 4.45 (s, 2H), 2.38 (s, 3H), 2.25 (s, 3H); ESI m/z 229 [M+H]⁺.

Step 2:

A solution of Example 30 (600 mg, 2.63 mmol), benzaldehyde (420 mg, 3.95 mmol), AcOH (1 mL) and CH₂Cl₂ (30 mL) was stirred at room temperature for 2 hours. NaBH(OAc)₃ (3.4 g, 15.8 mmol) was added portionwise over a 4 hour period. The reaction mixture was stirred 18 hours at room temperature and then diluted with CH₂Cl₂ (50 mL). A saturated solution of sodium bicarbonate was slowly added and the layers were separated. The organic phase was dried over sodium sulfate, filtered and concentrated under reduced pressure. The crude reaction mixture was purified by chromatography (silica gel, 0-10% methanol/dichloromethane). The product was further purified by preparative HPLC (CH₃CN/H₂O) to provide Example Compound 4 (218 mg, 26%) as an off-white solid: ¹H NMR (500 MHz, CD₃OD) δ 8.06 (s, 1H), 7.32 (m, 2H), 7.31 (m, 2H), 7.22 (m, 1H), 6.74 (s, 1H), 6.12 (s, 1H), 4.53 (s, 2H), 2.22 (s, 3H), 2.05 (s, 3H); ESI m/z 319 [M+H]⁺.

Preparation of 6,8-bis(3,5-dimethylisoxazol-4-yl)-2H-benzo[b][1,4]oxazin-3(4H)-one (Example Compound 11)

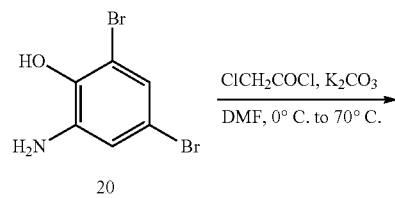

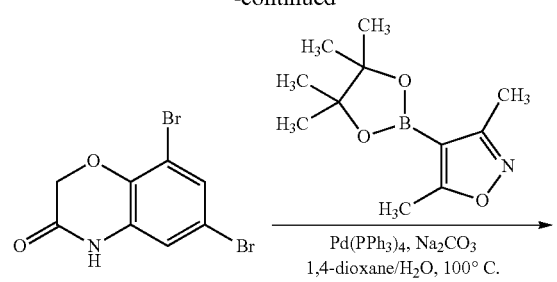

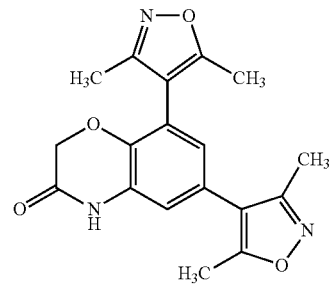

Example 11

Step 1:

To a stirred mixture of 20 (2.13 g, 7.98 mmol) and potassium carbonate (2.76 g, 19.97 mmol) in DMF (50 ml) at 0° C. under nitrogen was added a solution of 2-chloroacetyl chloride (0.904 g, 8.00 mmol) in 1,4-dioxane (20 mL) dropwise over 30 minutes. The reaction mixture was then stirred at 0° C. for 1 h and was stirred at 70° C. for 16 h. After cooling to room temperature, the reaction mixture was diluted with ethyl acetate (400 mL), washed with water (2×350 mL) and brine (100 mL). The solution was dried over sodium sulfate, filtered and concentrated. Purification by chromatography (silica gel, 0-100% ethyl acetate/heptane) afforded 21 (1.87 g, 76%) as a brown solid: ¹H NMR (300 MHz, DMSO-d₆) δ 10.96 (s, 1H), 7.41 (d, J=2.4 Hz, 1H), 7.02 (d, J=2.4 Hz, 1H), 4.72 (s, 2H); MM m/z 306 [M+H]⁺.

Step 2:

A stirred mixture of 21 (522 mg, 1.70 mmol), 3,5-dimethyl-4-(4,4,5,5-tetramethyl-1,3,2-dioxaborolan-2-yl)isoxazole (1.25 g, 5.60 mmol) and sodium carbonate (890 mg, 8.40 mmol) in 1,4-dioxane (15 mL)/water (4 mL) was purged with nitrogen for 4 minutes. Tetrakis(triphenylphosphine)palladium(0) (236 mg, 0.204 mmol) was added and the reaction mixture stirred for 16 h at 100° C. under nitrogen atmosphere. After cooling to room temperature, the mixture was mixed with silica gel (6 g) and concentrated. The resulting residue was purified by chromatography (silica gel, 0-60% ethyl acetate/heptane) followed by trituration with methylene chloride/heptane to afford Example Compound 11 (254 mg, 44%) as a white solid: ¹H NMR (300 MHz, DMSO-d₆) δ 10.84 (s, 1H), 6.94-6.91 (m, 2H), 4.66 (s, 2H), 2.42 (s, 3H), 2.33 (s, 3H), 2.24 (s, 3H), 2.17 (s, 3H); MM m/z 340 [M+H]⁺.

75

Preparation of 6,8-bis(3,5-dimethylisoxazol-4-yl)-3,4-dihydro-2H-benzo[b][1,4]oxazine (Example Compound 13)

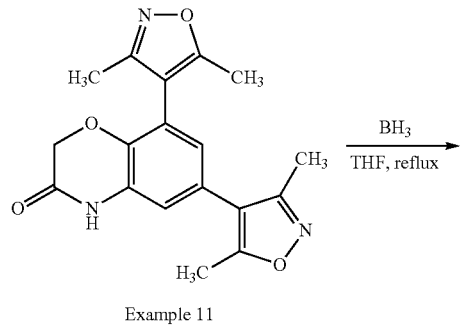

Example 11

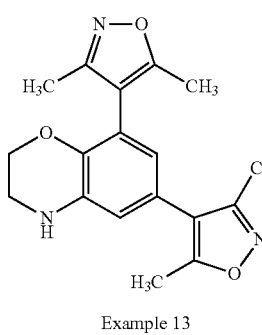

Example 13

Step 1:

To a stirred solution of Example Compound 11 (188 mg, 0.554 mmol) in THF (10 mL) at room temperature under nitrogen was added a solution of borane (5.00 mL, 1.0 M in THF, 5.00 mmol) dropwise over 5 minutes. The reaction mixture was then refluxed under nitrogen atmosphere for 8 h. After cooling to 0° C., the reaction was slowly quenched with methanol (25 mL), followed with aqueous hydrochloric acid (1.0 M, 10 mL). The mixture was concentrated and the resulting residue was slowly basified with saturated sodium bicarbonate (40 mL). The aqueous phase was extracted with methylene chloride (50 mL×2). The combined organic layers were dried over sodium sulfate, filtered, and concentrated. The residue was purified by chromatography (silica gel, 0-90% ethyl acetate/heptane) followed by trituration with methylene chloride/hexanes to afford Example Compound 13 (145 mg, 71%) as an off-white solid: $^1$H NMR (300 MHz, CDCl$_3$) δ 6.48 (d, J=2.1 Hz, 1H), 6.35 (d, J=2.1 Hz, 1H), 4.28 (t, J=4.4 Hz, 2H), 3.95 (br s, 1H), 3.51-3.47 (m, 2H), 2.40 (s, 3H), 2.35 (s, 3H), 2.27 (s, 3H), 2.23 (s, 3H); MM m/z 326 [M+H]$^+$.

76

Preparation of 4,4'-(2-(trifluoromethyl)-1H-benzo[d]imidazole-4,6-diyl)bis(3,5-dimethylixaole) (Example Compound 34)

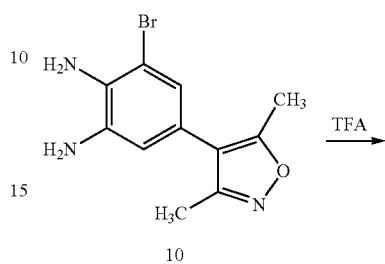

10

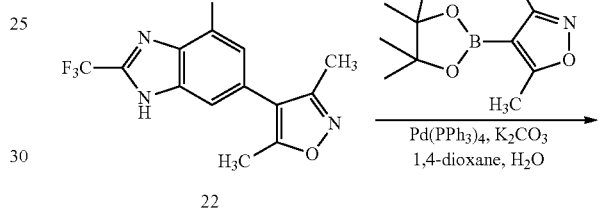

22

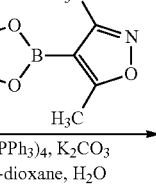

Example 34

Step 1:

A mixture of 10 (75 mg, 0.27 mmol) and trifluoroacetic acid (0.53 ml) was heated at 75° C. for 5 hours. After removing the solvent in vacuo, 22 was obtained as an off-white solid (140 mg): ESI MS m/z 360, 362 [M+H]$^+$.

Step 2:

Using Step 5 in General Procedure D employing 3,5-dimethyl-4-(4,4,5,5-tetramethyl-1,3,2-dioxaborolan-2-yl)isoxazole instead afforded Example Compound 34 as an off-white solid: $^1$H NMR (500 MHz, CD$_3$OD) δ 7.65 (s, 1H), 7.27 (s, 1H), 2.47 (s, 3H), 2.40 (s, 3H), 2.31 (s, 3H), 2.25 (s, 3H); MM m/z 377 [M+H].

General Procedure H:

Preparation of 4,4'-(1H-indazole-4,6-diyl)bis(3,5-dimethylisoxazole) (Example Compound 70)

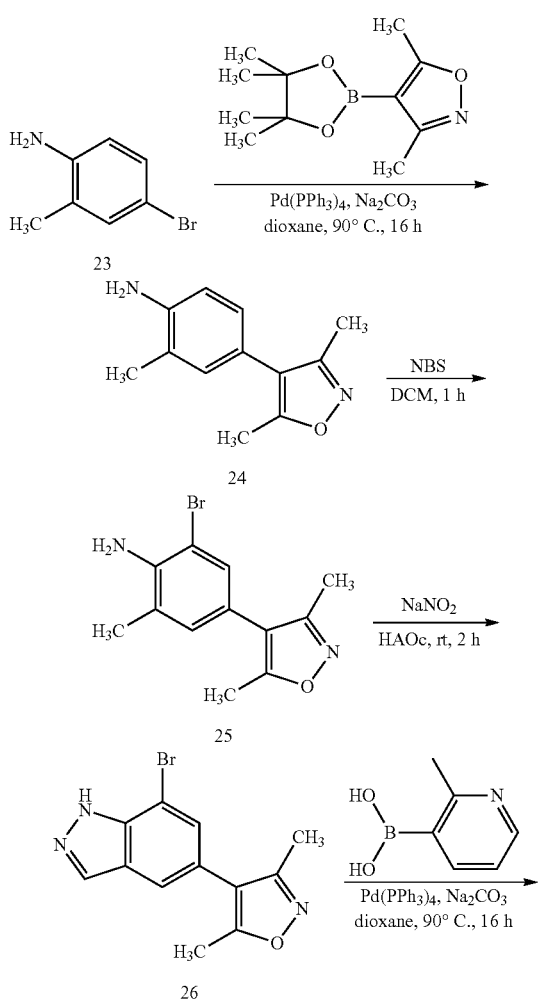

Example 70

Step 1:

To a solution of 23 (1.86 g, 10.0 mmol) in 1,4-dioxane (50 mL) was added 3,5-dimethyl-4-(4,4,5,5-tetramethyl-1,3,2-dioxaborolan-2-yl)isoxazole (2.23 g, 12.0 mmol), 2 M $Na_2CO_3$ (7.5 mL, 15.0 mmol) and tetrakis(triphenylphosphine)palladium(0) (577 mg, 0.5 mmol). The reaction mixture was purged with nitrogen and heated at 90° C. for 16 h. The mixture was filtered through celite and concentrated. Purification by chromatography (silica gel, 0-100% ethyl acetate/hexanes) afforded 24 (1.72 g, 85%) as a yellow oil: 1H NMR (500 MHz, $CDCl_3$) δ 6.93-6.92 (m, 2H), 6.76-6.75 (m, 1H), 3.98 (br s, 2H), 2.37 (s, 3H), 2.24 (s, 3H), 2.22 (s, 3H); ESI m/z 203 $[M+H]^+$.

Step 2:

To a solution of 24 (315 mg, 1.56 mmol) in DCM (5 mL) was added NBS (278 mg, 1.56 mmol) in portions at room temperature. After 1 h, the reaction mixture was concentrated and purified by chromatography (silica gel, 0-100% ethyl acetate/hexanes) to afford 25 (152 mg, 35%) as a brown solid: 1H NMR (500 MHz, $CDCl_3$) δ 7.19 (d, J=1.5 Hz, 1H), 6.88 (d, J=1.5 Hz, 1H), 2.36 (s, 3H), 2.27 (s, 3H), 2.23 (s, 3H); ESI m/z 282 $[M+H]^+$.

Step 3:

To a solution of 25 (144 mg, 0.5 mmol) in HOAc (2 mL) was added $NaNO_2$ (140 mg, 1.0 mmol) in portions at room temperature. After 2 h, 6 N NaOH was added to adjust to pH~10. The reaction mixture was extracted with ethyl acetate, dried, concentrated and purified by chromatography (silica gel, 0-100% ethyl acetate/hexanes) to afford 26 (96 mg, 66%) as a brown solid: 1H NMR (500 MHz, $CDCl_3$) δ 8.22 (s, 1H), 7.58 (d, J=1.5 Hz, 1H), 7.45 (d, J=1.5 Hz, 1H), 2.42 (s, 3H), 2.32 (s, 3H); ESI m/z 293 $[M+H]^+$.

Step 4:

To a solution of 26 (90 mg, 0.31 mmol) in 1,4-dioxane (3 mL) was added (2-methylpyridin-3-yl)boronic acid (110 mg, 0.46 mmol), 2 M $Na_2CO_3$ (0.31 mL, 0.62 mmol) and tetrakis(triphenylphosphine)palladium(0) (36 mg, 0.031 mmol). The reaction mixture was purged with nitrogen and heated at 90° C. for 16 h. The mixture was diluted with methylene chloride (15 ml) and washed with brine (2×3 mL). The organic layer was dried over sodium sulfate, filtered and concentrated. Purification by chromatography (silica gel, 0-100% ethyl acetate/hexanes) afforded Example Compound 70 (51 mg, 52%) as a light brown solid: 1H NMR (500 MHz, $CDCl_3$) δ 8.58-8.57 (m, 1H), 8.21 (s, 1H), 7.75-7.74 (m, 1H), 7.69 (d, J=1.5 Hz, 1H), 7.35-7.33 (m, 1H), 7.15 (d, J=1.5 Hz, 1H), 2.51 (s, 1H), 2.46 (s, 3H), 2.10 (s, 3H); ESI m/z 305 $[M+H]^+$.

General Procedure I:

Preparation of 4,4'-(2-isopropyl-1H-benzo[d]imidazole-4,6-diyl)bis(3,5-dimethylisoxazole) (Example Compound 45)

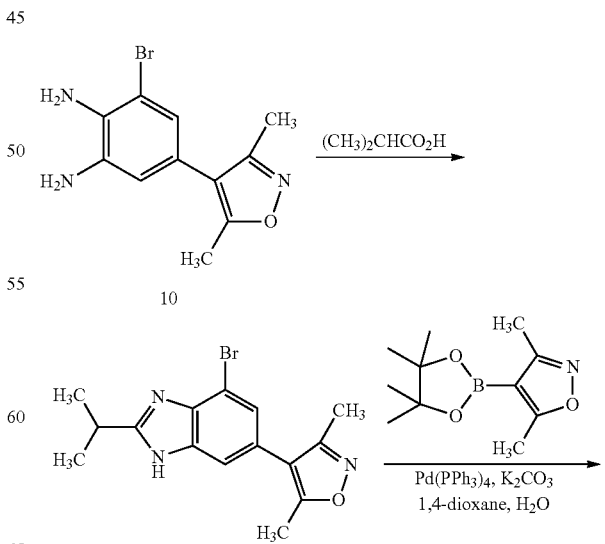

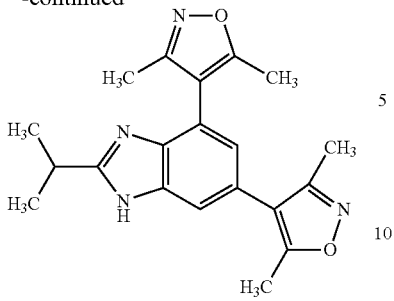

Example 45

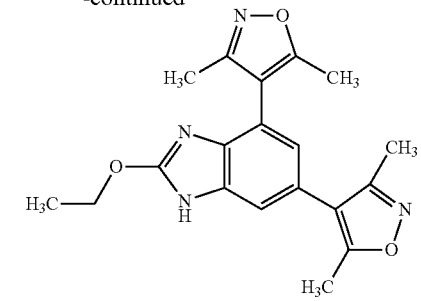

Example 46

Step 1:
A mixture of 10 (75 mg, 0.27 mmol) in isobutyric acid (1.0 mL) was heated at 130° C. for 5 h. The reaction mixture was concentrated under vacuum and used in the next step without purification.

Step 2:
To a solution of 27 (crude, 0.27 mmol) in 1,4-dioxane (10 mL) and water (1 mL) was added 3,5-dimethyl-4-(4,4,5,5-tetramethyl-1,3,2-dioxaborolan-2-yl)isoxazole (90 mg, 0.41 mmol), potassium carbonate (149 mg, 1.08 mmol), and tetrakis(triphenylphosphine)palladium(0) (16 mg, 0.014 mmol). The reaction mixture was purged with nitrogen and heated at 90° C. for 16 h. The reaction mixture was cooled to room temperature, concentrated and purified by chromatography (silica gel, 0-50% ethyl acetate in hexanes). It was further purified by reverse phase HPLC on a Polaris column eluting with 10-90% CH$_3$CN in H$_2$O to give Example Compound 45 (9 mg, 10%) as an off-white solid: $^1$H NMR (500 MHz, CD$_3$OD) δ 7.69 (d, J=1.4 Hz, 1H), 7.40 (d, J=1.4 Hz, 1H), 3.55-3.40 (m, 1H), 2.46 (s, 3H), 2.38 (s, 3H), 2.30 (s, 3H) 2.21 (s, 3H), 1.53 (d, J=7.0 Hz, 6H); ESI m/z 351 [M+H]$^+$.

General Procedure J:

Preparation of 4,4'-(2-Isopropyl-1H-benzo[d]imidazole-4,6-diyl)bis(3,5-dimethylisoxazole) (Example Compound 46)

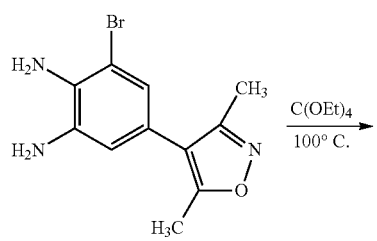

Step 1:
A mixture of 10 (200 mg, 0.709 mmol) in tetraethoxymethane (340 mg, 1.77 mmol) was heated at 100° C. for 4 h. The reaction mixture was cooled to room temperature, concentrated and purified by chromatography (silica gel, 0-50% ethyl acetate in hexanes) to afford 28 (177 mg, 74%) as a yellow solid: $^1$H NMR (500 MHz, CD$_3$OD) δ 7.30-7.15 (m, 2H), 4.57 (q, J=7.0 Hz, 2H), 2.39 (s, 3H), 2.23 (s, 3H), 1.47 (t, J=7.0 Hz, 3H); ESI m/z 336 [M+H].

Step 2:
To a solution of 28 (90, 0.27 mmol) in 1,4-dioxane (10 mL) and water (1 mL) was added 3,5-dimethyl-4-(4,4,5,5-tetramethyl-1,3,2-dioxaborolan-2-yl)isoxazole (90 mg, 0.41 mmol), potassium carbonate (74 mg, 0.54 mmol), and tetrakis(triphenylphosphine)palladium(0) (15 mg, 0.013 mmol). The reaction mixture was purged with nitrogen and heated at 90° C. for 16 h. The reaction mixture was cooled to room temperature, concentrated and purified by chromatography (silica gel, 0-50% ethyl acetate in hexanes). It was further purified by reverse phase HPLC on a Polaris column eluting with 10-90% CH$_3$CN in H$_2$O to give Example Compound 46 (27 mg, 29%) as an off-white solid: $^1$H NMR (500 MHz, CD$_3$OD) δ 7.50-7.10 (m, 1H), 6.94 (d, J=1.5 Hz, 1H), 4.53 (q, J=7.1 Hz, 2H), 2.42 (s, 3H), 2.38 (s, 3H), 2.27 (s, 3H), 2.24 (s, 3H), 1.45 (d, J=7.1 Hz, 3H); ESI m/z 353 [M+H]$^+$.

Preparation of 3,5-dimethyl-4-(6-(1,3,5-trimethyl-1H-pyrazol-4-yl)-1H-benzo[d]imidazol-4-yl)isoxazole (Example Compound 14)

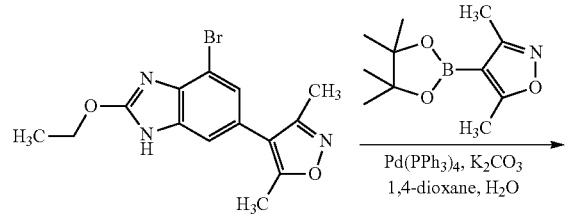

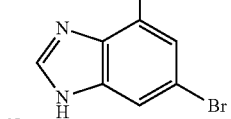

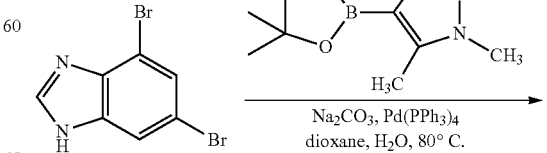

-continued

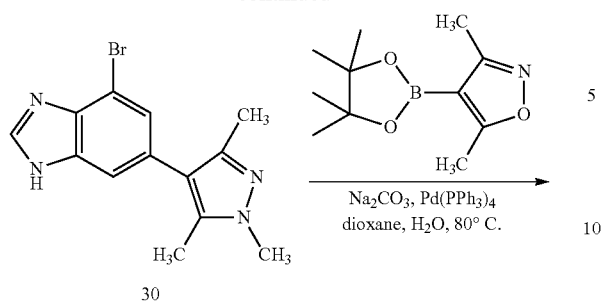

30

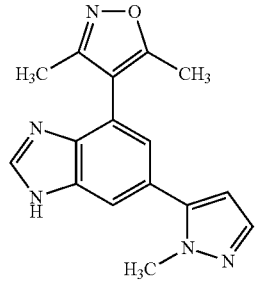

Example 14

Step 1:

To a solution of 4,6-dibromo-1H-benzo[d]imidazole 29 (466 mg, 1.69 mmol) in 1,4-dioxane (25 mL) and H₂O (2 mL) was added 1,3,5-trimethyl-4-(4,4,5,5-tetramethyl-1,3,2-dioxaborolan-2-yl)-1H-pyrazole (1.0 g, 4.23 mmol), sodium carbonate (360 mg, 3.38 mmol) and tetrakis(triphenylphosphine)palladium(0) (195 mg, 0.17 mmol). The reaction mixture was purged with nitrogen and heated at 90° C. for 16 h. The mixture was diluted with methylene chloride (20 mL) and filtered through a layer of Celite. The filtrate was concentrated and purified by chromatography (silica gel, 0-10% CH₃OH/CH₂Cl₂) to afford 30 (87 mg, 17%) as a yellow solid: ¹H NMR (300 MHz, CD₃OD) δ 8.26 (s, 1H), 7.42 (s, 1H), 7.33 (d, J=1.2 Hz, 1H), 3.77 (s, 3H), 2.26 (s, 3H), 2.19 (s, 3H); ESI m/z 307 [M+H]⁺.

Step 2:

To a solution of 4-bromo-6-(1,3,5-trimethyl-1H-pyrazol-4-yl)-1H-benzo[d]imidazole 30 (87 mg, 0.29 mmol) in 1,4-dioxane (5 mL) and H₂O (0.5 mL) was added 3,5-dimethyl-4-(4,4,5,5-tetramethyl-1,3,2-dioxaborolan-2-yl)isoxazole (127 mg, 0.57 mmol), sodium carbonate (60 mg, 0.57 mmol) and tetrakis(triphenylphosphine)palladium(O) (33 mg, 0.029 mmol). The reaction mixture was purged with nitrogen and heated at 90° C. for 16 h. The mixture was diluted with methylene chloride (10 mL) and filtered through a layer of Celite. The filtrate was concentrated and purified by chromatography (silica gel, 0-10% CH₃OH/CH₂Cl₂) to afford Example Compound 14 (32 mg, 35%) as a pale yellow solid: ¹H NMR (300 MHz, CD₃OD) δ 8.23 (s, 1H), 7.51 (s, 1H), 7.07 (d, J=1.5 Hz, 1H), 3.80 (s, 3H), 2.40 (s, 3H), 2.32 (s, 3H), 2.25 (s, 6H); ESI m/z 322 [M+H]⁺.

Preparation of 3,5-dimethyl-4-(6-(1-methyl-1H-pyrazol-5-yl)-1H-benzo[d]imidazol-4-yl)isoxazole (Example Compound 230)

Example 230

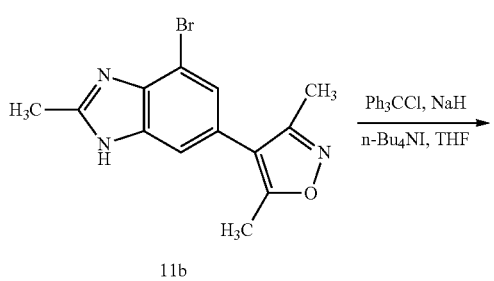

Example Compound 230 was prepared by following the similar method for the preparation of Example Compound 14 using 1-methyl-5-(4,4,5,5-tetramethyl-1,3,2-dioxaborolan-2-yl)-1H-pyrazole affording the product as an off-white solid: ¹H NMR (500 MHz, CD₃OD) δ 8.29 (s, 1H), 7.75 (br.s, 1H), 7.52 (d, J=2.0 Hz, 1H), 7.29 (s, 1H), 6.43 (d, J=2.0 Hz, 1H), 3.92 (s, 3H), 2.38 (s, 3H), 2.23 (s, 3H); ESI m/z 294 [M+H]⁺.

General Procedure K:

Preparation of 6-(3,5-dimethylisoxazol-4-yl)-2-methyl-N-(2-methylpyridin-3-yl)-1H-benzo[d]imidazol-4-amine (Example Compound 143)

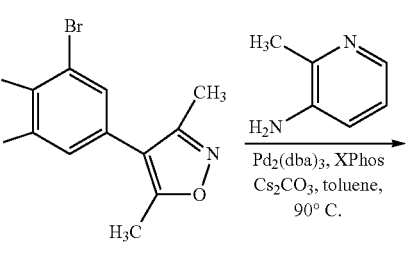

11b

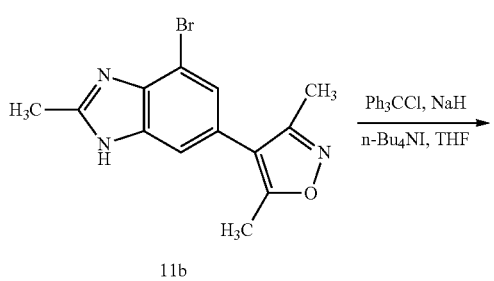

31

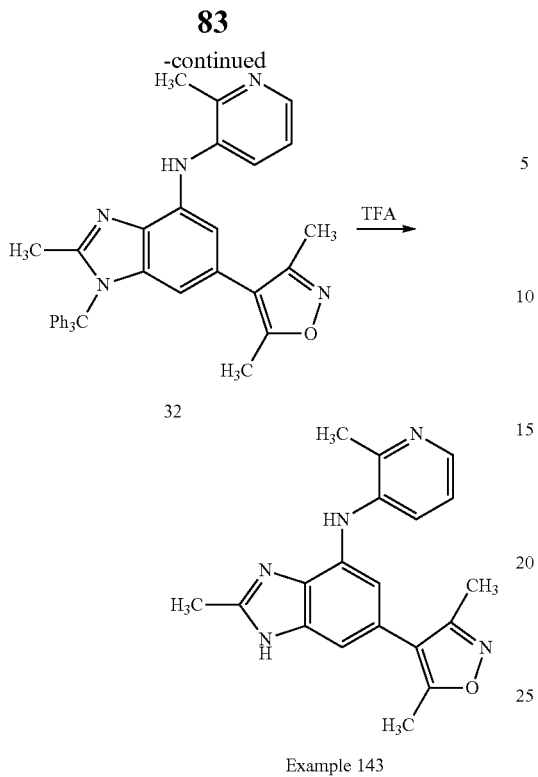

Example 143

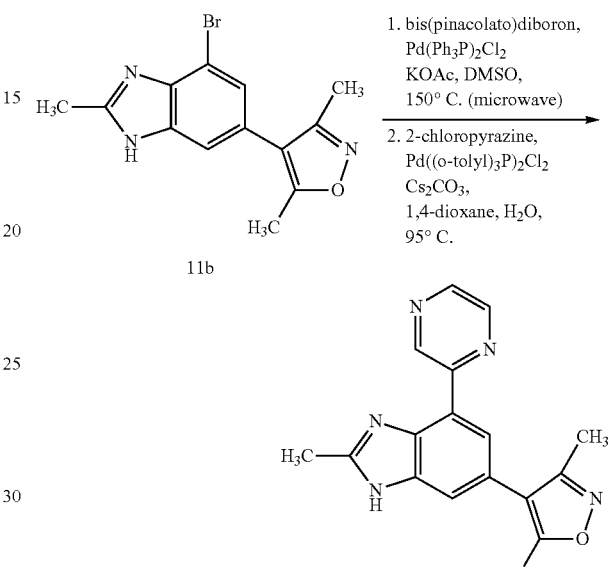

Example 85

7.30-7.80 (br.s, 1H), 7.05 (s, 1H), 7.90-7.30 (br.s, 1H), 6.60-6.90 (br.s, 1H), 2.58 (s, 3H), 2.57 (s, 3H), 2.39 (s, 3H), 2.24 (s, 3H); ESI m/z 334 [M+H]+.

General Procedure L:

Preparation of 3,5-dimethyl-4-(2-methyl-4-(pyrazin-2-yl)-1H-benzo[d]imidazol-6-yl)isoxazole (Example Compound 85)

Step 1:

To a solution of 11b (1.50 g, 5.07 mmol) in THF (100 mL) under nitrogen was added NaH (243 mg, 60% dispersion in mineral oil, 6.08 mmol) at room temperature. The mixture was stirred at room temperature for 30 min and trityl chloride (1.84 g, 6.59 mmol) was added followed by a catalytic amount of n-Bu$_4$NI (10 mg). The mixture was stirred at room temperature for 16 h. The mixture was concentrated and purified by chromatography (silica gel, 0-50% ethyl acetate/hexanes) to give 31 (1.05 g, 38%) as a yellow solid: $^1$H NMR (500 MHz, CD$_3$OD) δ 7.35-7.41 (m, 9H), 7.30-7.35 (m, 6H), 7.28 (d, J=1.3 Hz, 1H), 5.81 (d, J=1.3 Hz, 1H), 2.10 (s, 3H), 1.96 (s, 3H), 1.94 (s, 3H).

Step 2:

To a solution of 31 (100 mg, 0.182 mmol) in toluene (10 mL) under nitrogen atmosphere was added 2-methylpyridin-3-amine (30 mg, 0.27 mmol), cesium carbonate (118 mg, 0.364 mmol), 2-dicyclohexylphosphino-2',4',6'-tri-i-propyl-1,1'-biphenyl (13 mg, 0.027 mmol), and tris(dibenzylideneacetone)dipalladium(0) (16 mg, 0.018 mmol). The reaction mixture was heated at 90° C. for 16 h, cooled to room temperature, and purified by chromatography (silica gel, 0-100% ethyl acetate/hexanes) to give 32 (78 mg, 75%) as a light brown solid: $^1$H NMR (500 MHz, CD$_3$OD) δ 8.04 (dd, J=4.8, 1.4 Hz, 1H), 7.68 (dd, J=8.1, 1.4 Hz, 1H), 7.32-7.42 (m, 15H), 7.19 (dd, J=8.1, 4.9 Hz, 1H), 6.56 (d, J=1.3 Hz, 1H), 5.44 (d, J=1.3 Hz, 1H), 2.58 (s, 3H), 2.07 (s, 3H), 1.95 (s, 3H), 1.92 (s, 3H); ESI m/z 576 [M+H]+.

Step 3:

A mixture of 32 (78 mg, 0.14 mmol) and TFA (1 mL) were stirred at room temperature for 1 h. The reaction mixture was concentrated under vacuum. The residue was dissolved in MeOH and basified by concentrated NH$_4$OH. The mixture was concentrated under vacuum and purified by reverse phase HPLC on a Polaris column eluting with 10-90% CH$_3$CN in H$_2$O to give Example 143 (23 mg, 49%) as an off-white solid: $^1$H NMR (500 MHz, CD$_3$OD) δ 7.99 (s, 1H), A mixture of 11b (214 mg, 0.700 mmol), potassium acetate (208 mg, 2.12 mmol) and bis(pinacolato)diboron (356 mg, 1.40 mmol) in anhydrous DMSO (5 mL) was purged with nitrogen for 5 minutes. To the mixture was added trans-dichlorobis(triphenylphosphine)palladium(II) (71 mg, 0.101 mmol). Following the addition, the mixture was purged with nitrogen for 2 minutes. The vial was capped and heated at 150° C. by microwave irradiation for 1.5 h. After cooling to room temperature, 1,4-dioxane (8 mL)/water (3 mL) was added, followed by cesium carbonate (684 mg, 2.10 mmol) and 2-chloropyrazine (120 mg, 1.05 mmol). The resulting mixture was purged with nitrogen for 5 minutes. Then dichlorobis(tri(o-tolyl)phosphine)palladium (II) was added and the mixture was heated for 16 h at 95° C. under nitrogen atmosphere. After cooling to room temperature, the reaction mixture was diluted with water (60 mL). extracted with ethyl acetate (3×30 mL) and the organic extract was dried over sodium sulfate, filtered, and concentrated. The residue was purified by chromatography (silica gel, 100% heptane-1% Et$_3$N in 10% methanol/ethyl acetate), followed by trituration with methylene chloride/hexanes to afford Example 85 (77 mg, 36%) as a white solid: $^1$H NMR (300 MHz, CD$_3$OD) δ 9.36 (br s, 1H), 8.82 (br s, 1H), 8.57 (d, J=2.7 Hz, 1H), 7.87 (s, 1H), 7.60 (br s, 1H), 2.69 (s, 3H), 2.46 (s, 3H), 2.31 (s, 3H); MM m/z 306 [M+H]+.

General Procedure M:

Preparation of 3,5-dimethyl-4-(2-methyl-4-((2-methylpyridin-3-yl)oxy)-1H-benzo[d]imidazol-6-yl)isoxazole (Example Compound 155)

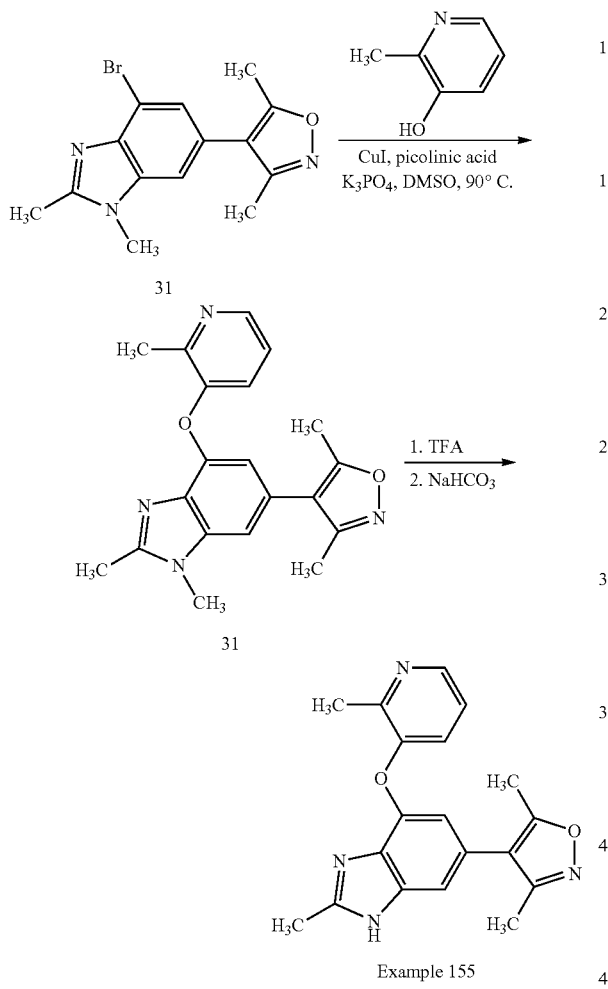

Step 1:

A mixture of 31 (150 mg, 0.273 mmol), 2-methylpyridin-3-ol (391 mg, 0.356 mmol), picolinic acid (7 mg, 0.054 mmol) and K₃PO₄ (145 mg, 0.683 mmol) in DMSO (3 mL) was purged with N₂ for 5 minutes. Then CuI (5 mg, 0.027 mmol) was added and the reaction mixture was heated to 90° C. for 16 h. The mixture was diluted with ethyl acetate (100 mL) and washed with brine (100 mL). The organic layer was dried over sodium sulfate, filtered and concentrated. The residue was purified by chromatography (silica gel, 50-100% ethyl acetate/hexanes) to afford 33 (90 mg, 35%) as a purple sticky solid: ¹H NMR (300 MHz, CDCl₃) δ 8.34 (dd, J=4.8, 1.2 Hz, 1H), 7.38-7.25 (m, 17H), 6.20 (br.s, 1H), 5.49 (s, 1H), 2.67 (s, 3H), 2.03 (s, 3H), 1.97 (s, 3H), 1.90 (s, 3H).

Step 2:

A solution of 33 (90 mg, 0.156 mmol) in TFA (2 mL) was stirred at rt for 1 h. The mixture was concentrated, the residue was dissolved in ethyl acetate (100 mL) and washed with saturated NaHCO₃ (2×50 mL). The organic layer was dried over sodium sulfate, filtered and concentrated. Purification by chromatography (silica gel, 0-10% methanol/ethyl acetate) afforded Example Compound 155 (38 mg, 73%) as a pink solid: ¹H NMR (300 MHz, CD₃OD) δ 8.20-8.17 (m, 1H), 7.27-7.21 (m, 3H), 6.61 (d, J=1.2 Hz, 1H), 2.60 (s, 3H), 2.58 (s, 3H), 2.37 (s, 3H), 2.21 (s, 3H); ESI m/z 335 [M+H]⁺.

General Procedure N:

Preparation of 4,4'-(1-methyl-1H-benzo[d]imidazole-5,7-diyl)bis(3,5-dimethylisoxazole) (Example Compound 93)

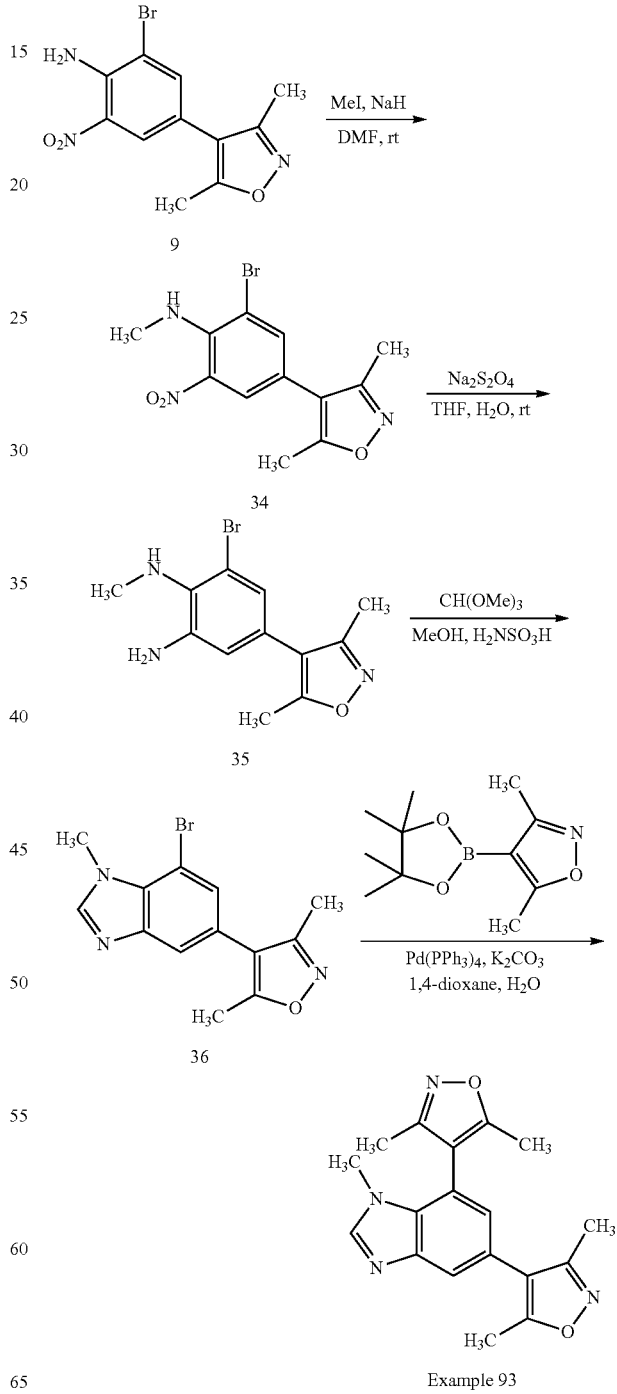

Step 1:

To a solution of 9 (1.00 g, 3.21 mmol) in DMF (10 mL) was added NaH (60% dispersion in mineral oil, 141 mg, 3.53 mmol) at room temperature under nitrogen. The mixture was stirred at room temperature for 30 min and iodomethane (410 mg, 2.98 mmol) was added. The reaction mixture was stirred at room temperature for 16 h. NH$_4$Cl/H$_2$O (10 mL) was added, the mixture was stirred for 30 min, concentrated and purified by chromatography (silica gel, 0-25% ethyl acetate/hexanes) to give 34 (370 mg, 35%) as a orange solid: $^1$H NMR (500 MHz, CDCl$_3$) δ 7.75 (d, J=2.1 Hz, 1H), 7.57 (d, J=2.1 Hz, 1H), 6.25 (d, J=4.6 Hz, 1H), 3.06 (d, J=5.5 Hz, 3H), 2.40 (s, 3H), 2.26 (s, 3H); ESI m/z 226 [M+H]$^+$.

Step 2:

To a solution of 34 (370 mg, 1.13 mmol) in tetrahydrofuran (20 mL) was added sodium dithionite (1.18 g, 6.78 mmol) in water (20 mL). The reaction mixture was stirred at room temperature for 16 h and concentrated under vacuum. The residue was dissolved in MeOH/water (1:1, 100 mL) and solid was precipitated by removing some MeOH under vacuum. The solid was filtered, washed with water, and dried under vacuum to afford 35 (180 mg, 54%) as a yellow solid: $^1$H NMR (500 MHz, CDCl$_3$) δ 7.26 (s, 1H), 6.79 (d, J=1.9 Hz, 1H), 6.50 (d, J=1.9 Hz, 1H), 4.09 (s, 2H), 3.29 (s, 1H), 2.71 (s, 3H), 2.38 (s, 3H), 2.24 (s, 3H); ESI m/z 296 [M+H]$^+$.

Step 3:

To a solution of 35 (180 mg, 0.608 mmol) in methanol (5 mL) was added trimethyl orthoformate (97 mg, 0.91 mmol) and sulfamic acid (3 mg, 0.03 mmol). The reaction was stirred at room temperature for 16 h. The mixture was concentrated and then purified by chromatography (silica gel, 0-100% ethyl acetate/hexanes) to give 36 (180 mg 97%) as an off-white solid: $^1$H NMR (500 MHz, CD$_3$OD) δ 8.20 (s, 1H), 7.57 (d, J=1.4 Hz, 1H), 7.43 (d, J=1.4 Hz, 1H), 4.20 (s, 3H), 2.41 (s, 3H), 2.25 (s, 3H); ESI m/z 306 [M+H]$^+$.

Step 4:

To a solution of 36 (100 mg, 0.327 mmol) in 1,4-dioxane (10 mL) and water (1 mL) was added 3,5-dimethyl-4-(4,4,5,5-tetramethyl-1,3,2-dioxaborolan-2-yl)isoxazole (109 mg, 0.490 mmol), tetrakis(triphenylphosphine)palladium(0) (19 mg, 0.016 mmol) and potassium carbonate (90 mg, 0.65 mmol). The reaction mixture was purged with nitrogen and heated at 90° C. for 16 h. The mixture was cooled to room temperature, concentrated and purified by chromatography (silica gel, 0-100% hexanes/ethyl acetate). It was further purified by reverse phase HPLC on a Polaris column eluting with 10-90% CH$_3$CN in H$_2$O to give Example Compound 93 (41 mg, 39%) as an off-white solid: $^1$H NMR (300 MHz, CD$_3$OD) δ 8.18 (s, 1H), 7.69 (d, J=1.6 Hz, 1H), 7.08 (d, J=1.6 Hz, 1H), 3.58 (s, 3H), 2.44 (s, 3H), 2.32 (s, 3H), 2.28 (s, 3H), 2.13 (s, 3H); ESI m/z 323 [M+H]$^+$.

Preparation of 4,4'-(2-methyl-1H-benzo[d]imidazole-4,6-diyl)bis(3-methylisothiazole) (Example Compound 139)

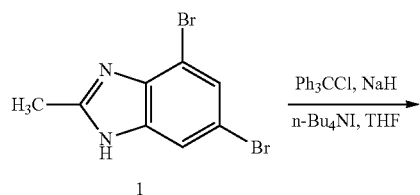

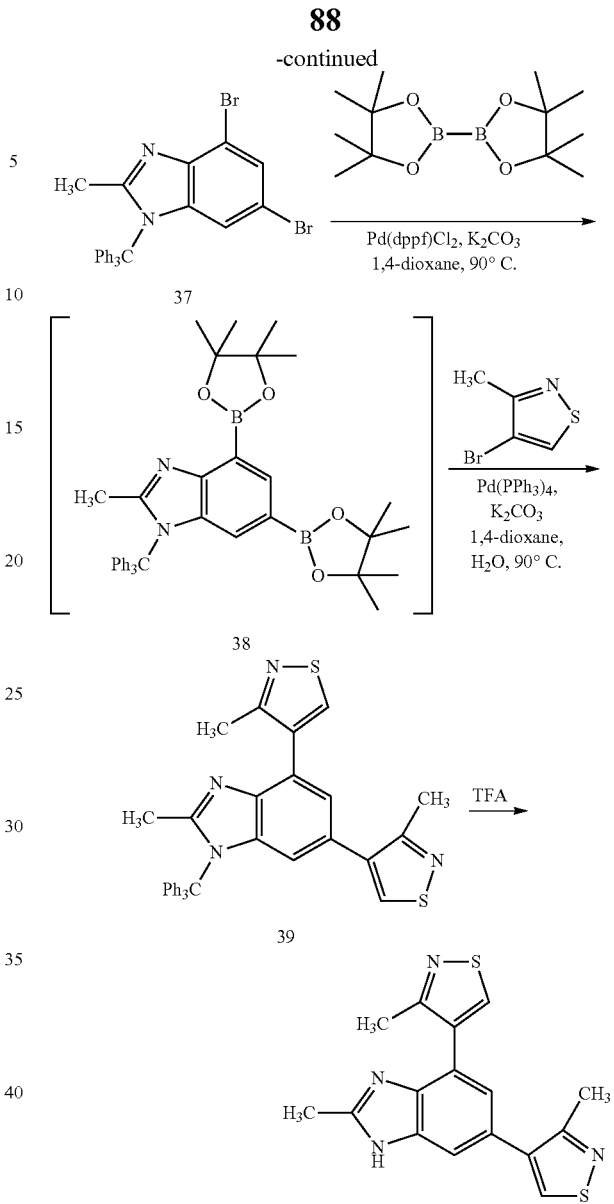

Example 139

Step 1:

To a solution of 1 (1.00 g, 3.45 mmol) in THF (50 mL) under nitrogen was added NaH (166 mg, 60% dispersion in mineral oil, 4.14 mmol) at room temperature. The mixture was stirred at room temperature for 30 min and trityl chloride was added followed by a catalytical amount of n-Bu$_4$NI (10 mg). The reaction was stirred at room temperature for 16 h and water and SiO$_2$ were added. The mixture was concentrated and purified by chromatography (silica gel, 0-100% ethyl acetate/hexanes) to give 37 (1.30 g, 71%) as an off-white solid: $^1$H NMR (500 MHz, CDCl$_3$) δ 7.44 (d, J=1.6 Hz, 1H), 7.32-7.40 (m, 9H), 7.25-7.30 (m, 6H), 5.52 (d, J=1.6 Hz, 1H), 1.93 (s, 3H).

Step 2:

To a solution of 37 (100 mg, 0.188 mmol) in 1,4-dioxane (10 mL) was added bis(pinacolato)diboron (105 mg, 0.414 mmol), potassium acetate (74 mg, 0.75 mmol), and [1,1'-bis(diphenylphosphino)ferrocene]dichloropalladium(II) (14 mg, 0.019 mmol). The reaction mixture was heated at 90° C.

for 16 h under nitrogen. The reaction mixture was cooled to room temperature and the material was used in the next step without purification.

Step 3:

To the crude reaction mixture from Step 2 (0.188 mmol) was added water (1 mL), 4-bromo-3-methylisothiazole (100 mg, 0.564 mmol), potassium carbonate (156 mg, 1.13 mmol), and tetrakis(triphenylphosphine)palladium(0) (22 mg, 0.019 mmol). The reaction mixture was heated at 90° C. for 16 h under nitrogen. The reaction was cooled to room temperature, concentrated and purified by chromatography (silica gel, 0-100% ethyl acetate/hexanes) to give 39 (50 mg, 47%) as a yellow solid: $^1$H NMR (500 MHz, CD$_3$OD) δ 8.90 (s, 1H), 8.43 (s, 1H), 7.25-7.45 (m, 15H), 7.15 (d, J=1.4 Hz, 1H), 6.00 (d, J=1.4 Hz, 1H), 2.47 (s, 3H), 2.17 (s, 3H), 1.93 (s, 3H).

Step 4:

A mixture of 39 (50 mg, 0.088 mmol) and TFA (2 mL) were stirred at room temperature for 1 h. The reaction mixture was concentrated under vacuum. The residue was dissolved in MeOH and basified by Et$_3$N. The mixture was concentrated under vacuum and purified by reverse phase HPLC on a Polaris column eluting with 10-90% CH$_3$CN in H$_2$O to give Example Compound 139 (9 mg, 31%) as an off-white solid: $^1$H NMR (500 MHz, CD$_3$OD) δ 8.91 (s, 1H), 8.80 (s, 1H), 7.58 (s, 1H), 7.22 (d, J=1.5 Hz, 1H), 2.57 (s, 3H), 2.54 (s, 3H), 2.44 (s, 3H); ESI m/z 327 [M+H]$^+$.

Preparation of 4,4'-(3-methyl-1H-indole-4,6-diyl)bis(3,5-dimethylisoxazole) (Example Compound 140)

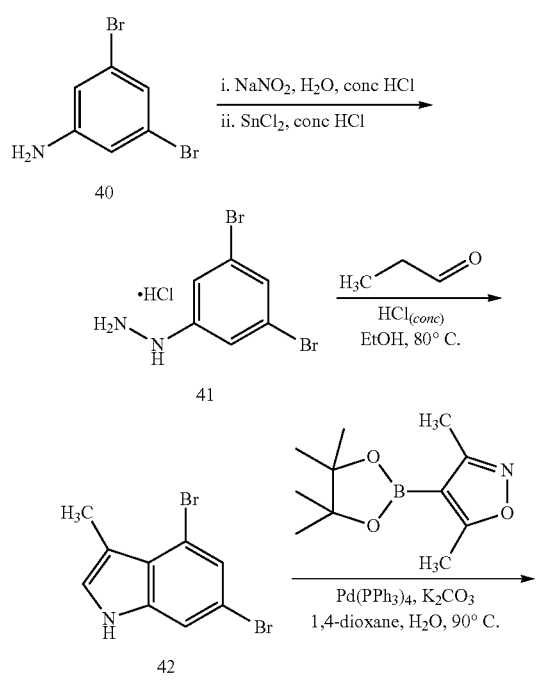

-continued

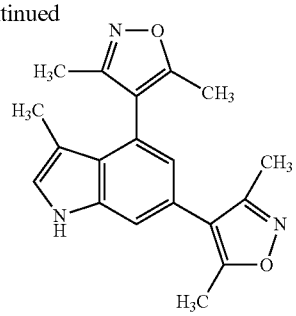

Example 140

Step 1:

To a solution of 40 (1.00 g 3.98 mmol) in concentrated HCl (8 mL) at 0° C. was added dropwise a solution of sodium nitrite (275 mg, 3.98 mmol) in water (1 mL). The mixture was stirred at 0° C. for 1 h. Tin (II) chloride (1.50 g, 7.96 mmol) in concentrated HCl (20 mL) was slowly added. The mixture was warmed to room temperature and stirred for 16 h. The solid was filtered, washed with EtOH, and dried under vacuum at 50° C. to give 41 (1.05 g, 87%) as a light brown solid: $^1$H NMR (500 MHz, CD$_3$OD) δ 7.36 (s, 1H), 7.12 (s, 2H).

Step 2:

To a solution of 41 (200 mg, 0.661 mmol) in ethanol (5 mL) was added propionaldehyde (58 mg, 0.99 mmol) at room temperature. The mixture was heated at 80° C. for 30 min and then cooled to room temperature. Concentrated hydrochloric acid (0.1 mL) was added and the reaction was heated at 80° C. for 5 h. The mixture was concentrated under vacuum. The residue was dissolved in MeOH and basified with sodium carbonate (20% in water). The mixture was concentrated and purified by chromatography (silica gel, 0-10% ethyl acetate/hexanes) to give 42 (45 mg, 23%) as an orange oil: $^1$H NMR (500 MHz, CD$_3$OD) δ 7.44 (d, J=1.6 Hz, 1H), 7.24 (d, J=1.6 Hz, 1H), 7.04 (d, J=1.0 Hz, 1H), 2.48 (d, J=1.0 Hz, 3H).

Step 3:

To a solution of 42 (170 mg, 0.588 mmol) in 1,4-dioxane (10 mL) and water (1 mL) was added 3,5-dimethyl-4-(4,4,5,5-tetramethyl-1,3,2-dioxaborolan-2-yl)isoxazole (525 mg, 2.35 mmol), potassium carbonate (487 mg, 3.53 mmol), and tetrakis(triphenylphosphine)palladium(0) (68 mg, 0.059 mmol). The reaction mixture was purged with nitrogen and heated at 90° C. for 16 h. The reaction mixture was cooled to room temperature, concentrated and purified by chromatography (silica gel, 0-30% ethyl acetate/hexanes). It was further purified by reverse phase HPLC on a Polaris column eluting with 10-90% CH$_3$CN in H$_2$O to give Example Compound 140 (63 mg, 33%) as an off-white solid: $^1$H NMR (500 MHz, CD$_3$OD) δ 7.33 (d, J=1.4 Hz, 1H), 7.09 (d, J=0.9 Hz, 1H), 6.72 (d, J=1.5 Hz, 1H), 2.43 (s, 3H), 2.28 (s, 3H), 2.27 (s, 3H), 2.08 (s, 3H), 1.93 (d, J=0.9 Hz, 3H); ESI m/z 322 [M+H]$^+$.

Preparation of 4,4'-(1H-indazole-4,6-diyl)bis(3,5-dimethylisoxazole) (Example Compound 87)

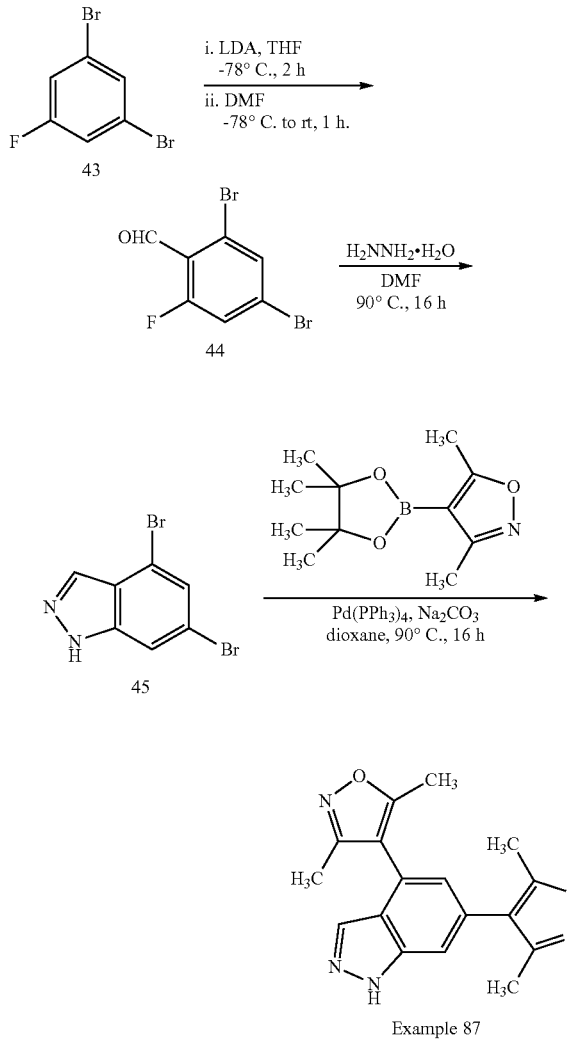

Example 87

Step 1:
To a solution of 43 (0.75 g, 2.95 mmol) in anhydrous THF (15 mL) under N$_2$ at −78° C. was added LDA (2 M in THF, 1.77 mL, 3.54 mmol) slowly. After the reaction mixture was stirred at this temperature for 2 h, DMF (438 mg, 6 mmol) was added slowly. The reaction temperature was allowed to rise to room temperature over 30 min and stirred for additional 30 min. The reaction was quenched by addition of water (5 mL) at 0° C. The mixture was diluted with ether (50 mL) and washed with brine (2×10 mL). The organic layer was dried over sodium sulfate, filtered and concentrated. Purification by chromatography (silica gel, 0-100% ethyl acetate/hexanes) afforded 44 as a yellow solid (309 mg, 37%): $^1$H NMR (500 MHz, CDCl$_3$) δ 10.29 (d, J=0.5 Hz, 1H), 7.69-7.68 (m, 1H); 7.37-7.34 (m, 1H).

Step 2:
To a solution of 44 (110 mg, 0.39 mmol) in DMF (1 mL) was added hydrazine monohydrate (1 mL). The reaction mixture was heated at 90° C. for 16 h, concentrated and purified by chromatography (silica gel, 0-100% ethyl acetate/hexanes) to give 45 as a white solid (110 mg, 70%): ESI m/z 276 [M+H]$^+$.

Step 3:
To a solution of 45 (49 mg, 0.18 mmol) in 1,4-dioxane (2 mL) was added 3,5-dimethyl-4-(4,4,5,5-tetramethyl-1,3,2-dioxaborolan-2-yl)isoxazole (120 mg, 0.54 mmol), 2 M Na$_2$CO$_3$ (0.18 mL, 0.36 mmol) and tetrakis(triphenylphosphine)palladium(0) (20 mg, 0.018 mmol). The reaction mixture was purged with nitrogen and heated at 90° C. for 16 h. The mixture was diluted with methylene chloride (30 mL) and washed with brine (2×10 mL). The organic layer was dried over sodium sulfate, filtered and concentrated. Purification by chromatography (silica gel, 0-100% ethyl acetate/hexanes) afforded Example Compound 87 (9 mg, 16%) as a white solid: $^1$H NMR (500 MHz, CDCl$_3$) δ 7.94 (s, 1H), 7.44 (s, 1H), 6.92 (d, J=1.0 Hz, 1H), 2.48 (s, 1H), 2.41 (s, 3H), 2.33 (s, 3H), 2.27 (s, 3H); ESI m/z 309 [M+H]$^+$.

Preparation of 4,4'-(1-methyl-1H-indazole-5,7-diyl)bis(3,5-dimethylisoxazole) (Example Compound 54) and 4,4'-(2-methyl-2H-indazole-5,7-diyl)bis(3,5-dimethylisoxazole) (Example Compound 55)

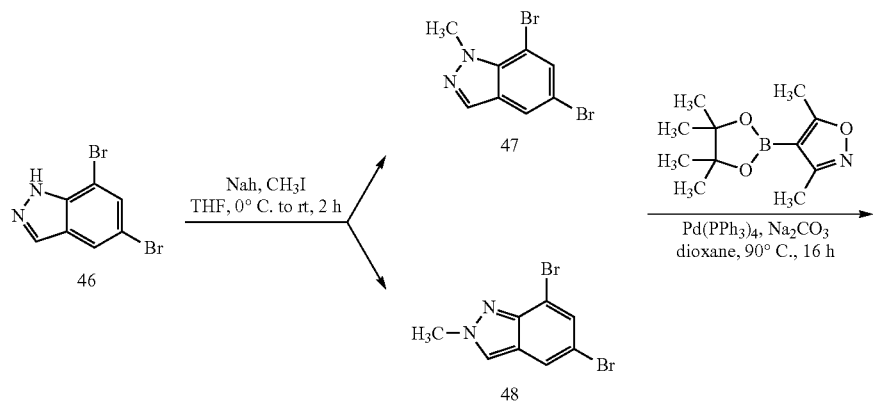

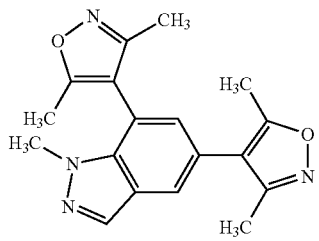

Example 54

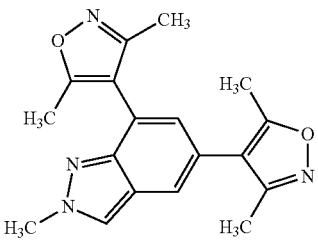

Example 55

Step 1:

To a solution of 46 (191 mg, 0.69 mmol) in anhydrous THF (2 mL) at 0° C. was added NaH (60% dispersion in mineral oil, 30 mg, 0.76 mmol) in portions. The reaction mixture was stirred at room temperature for 30 min, followed by addition of iodomethane (392 mg, 2.76 mmol). The reaction mixture was stirred for 2 h, concentrated, and purified by chromatography (silica gel, 0-100% ethyl acetate/hexanes) to afford two products 47 (49 mg, 25%): $^1$H NMR (500 MHz, CDCl$_3$) δ 7.89 (s, 1H), 7.79 (d, J=1.5 Hz, 1H), 7.65 (d, J=1.5 Hz, 1H), 4.40 (s, 3H); $^{13}$C NMR (125 MHz, DMSO-d$_6$) δ 135.7, 132.2, 132.1, 127.2, 123.1, 112.3, 103.5, 40.0; and 48 (110 mg, 56%): $^1$H NMR (500 MHz, CDCl$_3$) δ 7.94 (s, 1H), 7.76 (d, J=1.5 Hz, 1H), 7.59 (d, J=1.5 Hz, 1H), 4.25 (s, 3H); $^{13}$C NMR (125 MHz, DMSO-d$_6$) δ 145.0, 130.1, 126.3, 123.0, 122.5, 112.5, 111.2, 40.3.

Step 2:

To a solution of 47 (44 mg, 0.15 mmol) in 1,4-dioxane (2 mL) was added 3,5-dimethyl-4-(4,4,5,5-tetramethyl-1,3,2-dioxaborolan-2-yl)isoxazole (102 mg, 0.46 mmol), 2 M Na$_2$CO$_3$ (0.15 mL, 0.45 mmol) and tetrakis(triphenylphosphine)palladium(0) (20 mg, 0.018 mmol). The reaction mixture was purged with nitrogen for 5 min and heated at 90° C. for 16 h. The mixture was diluted with methylene chloride (20 mL) and washed with brine (2×5 mL). The organic layer was dried over sodium sulfate, filtered and concentrated. Purification by chromatography (silica gel, 0-100% ethyl acetate/hexanes) afforded Example 54 (34 mg, 71%) as a white solid: $^1$H NMR (500 MHz, CDCl$_3$) δ 8.08 (s, 1H), 7.64 (d, J=1.5 Hz, 1H), 7.0 (d, J=1.5 Hz, 1H), 3.80 (s, 3H), 2.44 (s, 3H), 2.34 (s, 3H), 2.30 (s, 3H), 2.16 (s, 3H); ESI m/z 323 [M+H]$^+$.

Example Compound 55 was synthesized in the same manner as Example Compound 54 as a white solid (67%): $^1$H NMR (500 MHz, CDCl$_3$) δ 8.01 (s, 1H), 7.53 (d, J=1.5 Hz, 1H), 6.98 (d, J=1.5 Hz, 1H), 4.26 (s, 3H), 2.45 (s, 3H), 2.44 (s, 3H), 2.31 (s, 6H); ESI m/z 323 [M+H]$^+$.

Preparation of 4,4'-(quinoxaline-5,7-diyl)bis(3,5-dimethylisoxazole) (Example Compound 159)

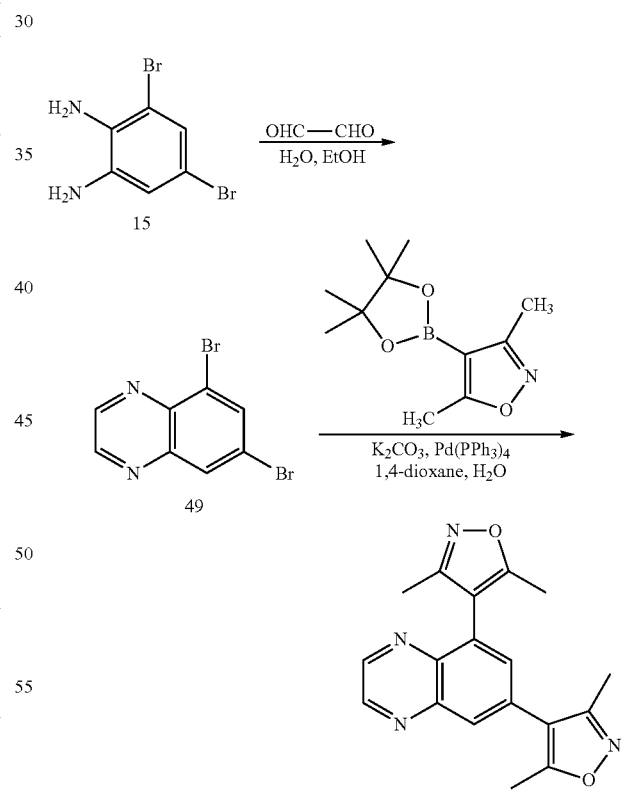

Example 159

Step 1:

Glyoxal (40%, 354 mg, 2.44 mmol) was added to a solution of 3,5-dibromobenzene-1,2-diamine (15, 500 mg, 1.88 mmol) and ethanol (10 mL) at room temperature. The solution was then heated at reflux for 3 hours and then cooled to room temperature. The solvent was removed under reduced pressure to provide a tan solid (173 mg, 32%) that was used without further purification: $^1$H NMR (500 MHz, DMSO-d$_6$) δ 9.08 (d, J=2.0 Hz, 1H), 9.05 (d, J=1.5 Hz, 1H), 8.46 (d, J=2.5 Hz, 1H), 8.40 (d, J=2.0 Hz, 1H).

Step 2:

Example Compound 159 was synthesized according to General Procedure A affording an 84% yield as a white solid: $^1$H NMR (500 MHz, CD$_3$OD) δ 8.95 (d, J=2.0 Hz, 1H), 8.92 (d, J=1.5 Hz, 1H), 8.13 (d, J=2.0 Hz, 1H), 7.81 (d, J=2.0 Hz, 1H), 2.54 (s, 3H), 2.39 (s, 3H), 2.35 (s, 3H), 2.17 (s, 3H); ESI m/z 321 [M+H]$^+$.

Preparation of 4,4'-(1H-benzo[d][1,2,3]triazole-4,6-diyl)bis(3,5-dimethylisoxazole) (Example Compound 95)

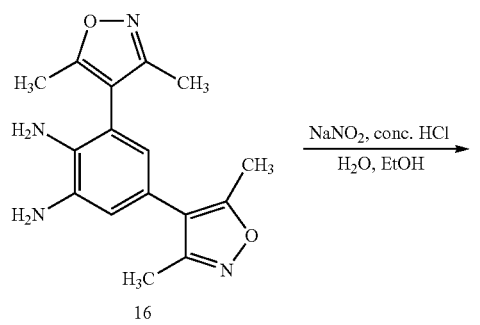

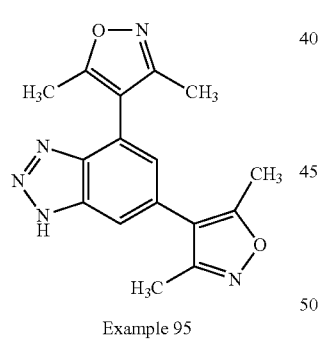

Example 95

A solution of 16 (55 mg, 0.18 mmol) in water (2 mL), concentrated HCl (47 µL) and absolute ethanol (0.62 mL) was cooled to 0° C. and a solution of sodium nitrite (20 mg, 0.29 mmol) in water (1 mL) was added. The reaction was allowed to warm to room temperature over 0.5 h and stirred at room temperature for 1 h. The precipitated solid was filtered and washed with hexanes (5 mL). The remaining material was dissolved in acetonitrile (3 mL) and was purified on the preparative HPLC. This afforded Example 95 (16 mg, 28%) as a white solid: $^1$H NMR (500 MHz, CD$_3$OD) δ 7.83 (s, 1H), 7.34 (s, 1H), 2.48 (s, 3H), 2.43 (s, 3H), 2.32 (s, 3H), 2.27 (s, 3H); ESI m/z 308 [M−H]$^-$.

Preparation of 5,7-bis(3,5-dimethylisoxazol-4-yl)-2-methylbenzo[d]oxazole (Example Compound 101)

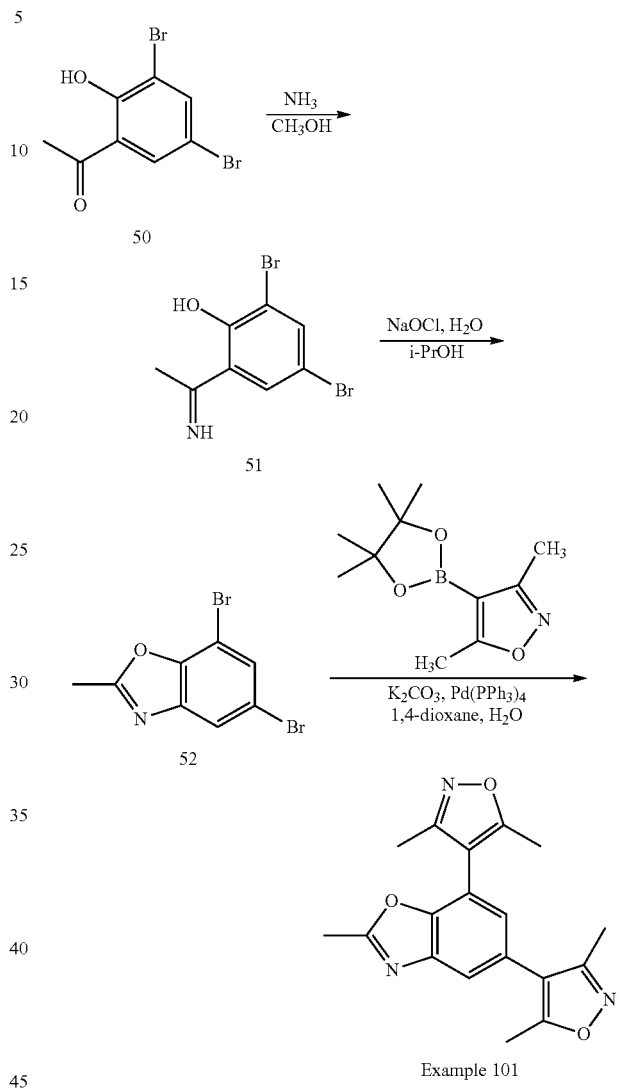

Example 101

Step 1: 50 (2.00 g, 6.80 mmol) and a solution of 7 N ammonia in methanol (4.76 mL, 33.3 mmol) were combined and stirred. After adding methanol (10 mL), the reaction stirred at room temperature for 1 h. The precipitate was filtered, washed with hexanes (20 mL) and air dried for 2 h, affording 51 as a yellow solid (1.95 g, 98%): $^1$H NMR (500 MHz, DMSO-d$_6$): δ 14.8 (s, 1H), 10.8 (s, 1H), 7.73 (d, J=2.5 Hz, 1H), 7.61 (d, J=2.5 Hz, 1H).

Step 2:

A solution of 51 (1.00 g, 3.40 mmol) in isopropanol (10 mL) was cooled to 0° C. under nitrogen, a solution of aqueous sodium hypochlorite (12.5%, 6.12 mL, 10.2 mmol) was added dropwise keeping the internal temperature<10° C. The reaction mixture was allowed to warm to room temperature over 0.5 h and water was added (20 mL). The organic layer was dried over Na$_2$SO$_4$, filtered and concentrated. The resulting solid residue was purified by flash chromatography (silica gel, 0-10% ethyl acetate/hexanes) affording 52 as a white solid (381 mg, 38%): $^1$H NMR (500 MHz, CDCl$_3$) δ 7.72 (d, J=1.5 Hz, 1H), 7.59 (d, J=2.0 Hz, 1H), 2.67 (s, 3H).

Step 3:

To a sealed tube was added 52 (200 mg, 0.68 mmol), potassium carbonate (380 mg, 2.75 mmol), 3,5-dimethyl-4-(4,4,5,5-tetramethyl-1,3,2-dioxaborolan-2-yl)isoxazole (460 mg, 2.06 mmol), water (1.5 mL) and 1,4-dioxane (7 mL). The mixture was sparged with nitrogen for 5 minutes and tetrakis(triphenylphosphine)palladium(0) (80 mg, 0.067 mmol) was added. The tube was sealed and the mixture heated at 90° C. for 16 h. The reaction mixture was concentrated to dryness and the residue was purified by flash chromatography (silica gel, 0-30% ethyl acetate/hexanes). Further purification on a preparative HPLC using a 10:90 acetonitrile:water to 100% acetonitrile over a 30 min gradient afforded Example Compound 101 as a white solid (125 mg, 56%): $^1$H NMR (500 MHz, CD$_3$OD) δ 7.61 (d, J=1.5 Hz, 1H), 7.26 (d, J=1.5 Hz, 1H), 2.67 (s, 3H), 2.45 (s, 3H), 2.44 (s, 3H), 2.29 (s, 3H), 2.28 (s, 3H); ESI m/z 324 [M+H]$^+$.

Preparation of 2-methyl-4,6-di(1H-pyrrol-3-yl)-1H-benzo[d]imidazole (Example Compound 164)

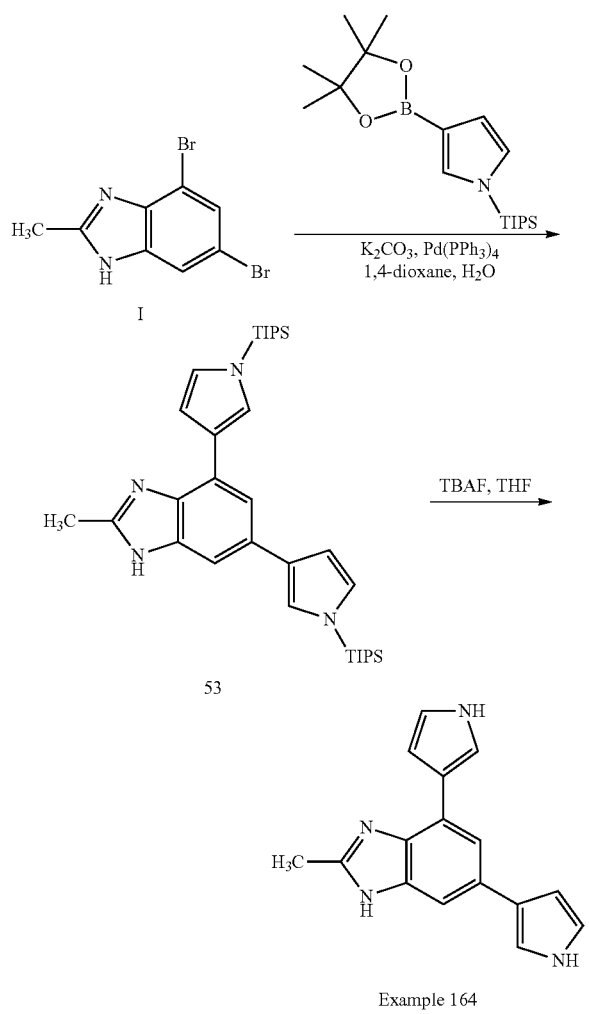

Step 1:

Compound 53 was synthesized according to General Procedure A affording a 40% yield as a beige solid: $^1$H NMR (500 MHz, CD$_3$OD) δ 7.51 (br s, 1H), 7.26 (br s), 7.25 (d, J=2.0 Hz, 1H), 7.07 (t, J=2.0 Hz, 1H), 6.89 (s, 1H), 6.67 (d, J=2.0 Hz, 1H), 6.78 (br s, 1H), 6.66 (d, J=2.0 Hz, 1H), 2.61 (s, 3H), 1.54-1.46 (m, 6H), 1.15 (d, J=7.5 Hz, 18H), 1.13 (d, J=7.5 Hz, 18H).

Step 2:

To a stirred solution of 53 (160 mg, 0.28 mmol) in anhydrous THF (5 mL) under nitrogen was added 1.0 M tetrabutylammonium fluoride in THF (0.556 mL, 0.556 mmol). The reaction was stirred at room temperature for 2 h and then was concentrated to dryness. After adding methanol (10 mL) and silica gel (10 g) the mixture was concentrated and chromatographed on silica gel eluting with 0-90% ethyl acetate in hexanes to afford the crude product. The material was further purified by reverse phase HPLC on a Polaris column eluting with 10-90% CH$_3$CN in H$_2$O to give Example 164 (26 mg, 35%) as a white solid: $^1$H NMR (500 MHz, CD$_3$OD) δ 7.50 (d, J=1.0 Hz, 1H), 7.52-7.20 (m, 2H), 7.09 (t, J=2.0 Hz, 1H), 6.83 (s, 1H), 6.77 (dd, J=2.5, 2.0 Hz, 1H), 6.60 (br s, 1H), 6.47 (dd, J=2.5, 1.5 Hz, 1H), 2.56 (s, 3H); ESI m/z 263 [M+H]$^+$.

Preparation of 6-(3,5-dimethylisoxazol-4-yl)-N-ethyl-4-(2-methylpyridin-3-yl)-1H-benzo[d]imidazol-2-amine (Example Compound 100)

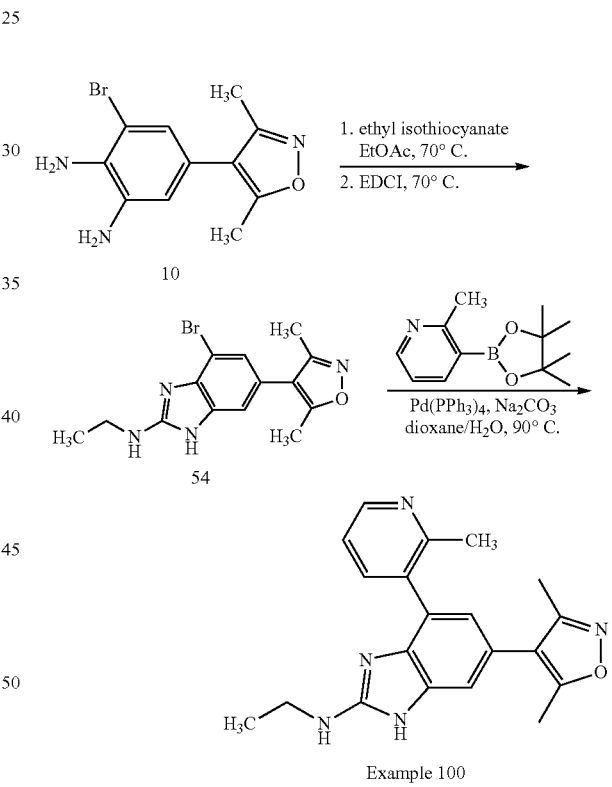

Example 100

Step 1:

A solution of 10 (300 mg, 1.06 mmol) and ethyl isothiocyanate (184 mg, 2.12 mmol) in ethyl acetate (5 mL) was heated at 70° C. for 3 h. The reaction mixture was concentrated, the residue was dissolved in ethyl acetate (10 mL), EDCI (305 mg, 1.59 mmol) was added and the mixture was heated at 70° C. for 1 h. The mixture was diluted with CH$_2$Cl$_2$ (100 mL), washed with brine (100 mL) and the organic layer was dried over sodium sulfate, filtered and concentrated. The residue was purified by chromatography (silica gel, 30-100% ethyl acetate/hexanes) to afford 54 (125 mg, 35%) as a white sticky solid: $^1$H NMR (300 MHz, CDCl$_3$) δ 7.07 (br.s, 2H), 3.44 (q, J=7.2 Hz, 2H), 2.40 (s, 3H), 2.24 (s, 3H), 1.29 (t, J=7.2 Hz, 3H).

Step 2:

To a solution of 54 (125 mg, 0.373 mmol) in 1,4-dioxane (8 mL) was added 2-methyl-3-(4,4,5,5-tetramethyl-1,3,2-dioxaborolan-2-yl)pyridine (163 mg, 0.746 mmol), 2 M aq. sodium carbonate (0.56 mL, 1.12 mmol) and tetrakis(triphenylphosphine)palladium(0) (43 mg, 0.037 mmol). The reaction mixture was purged with nitrogen and heated at 80° C. for 16 h. The mixture was diluted with ethyl acetate (100 mL) and washed with brine (50 mL). The organic layer was dried over sodium sulfate, filtered and concentrated. Purification by chromatography (silica gel, 0-8% methanol/ethyl acetate) followed by trituration with ethyl acetate afforded Example Compound 100 (72 mg, 56%) as a white solid: $^1$H NMR (300 MHz, CD$_3$OD) δ 8.45 (dd, J=5.1, 1.5 Hz, 1H), 7.78 (dd, J=7.8, 1.5 Hz, 1H), 7.38 (dd, J=7.8, 4.8 Hz, 1H), 7.19 (d, J=1.2 Hz, 1H), 6.79 (d, J=1.5 Hz, 1H), 3.40 (q, J=7.2 Hz, 2H), 2.44 (s, 3H), 2.43 (s, 3H), 2.28 (s, 3H), 1.26 (t, J=7.2 Hz, 3H); ESI m/z 348 [M+H]$^+$.

Preparation of 3-((6-(3,5-dimethylisoxazol-4-yl)-2-methyl-1H-benzo[d]imidazol-4-yl)oxy)-4-methylbenzamide (Example Compound 174) and 3-((6-(3,5-dimethylisoxazol-4-yl)-2-methyl-1H-benzo[d]imidazol-4-yl)oxy)-4-methylbenzoic acid (Example Compound 175)

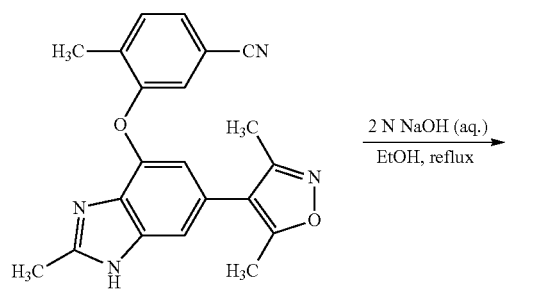

Example 172

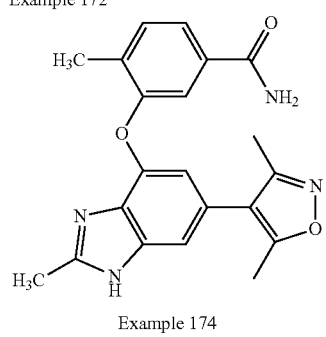

Example 174

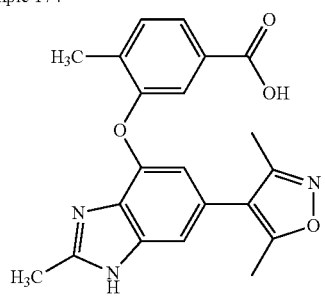

Example 175

To a solution of Example 172 (50 mg, 0.14 mmol) in EtOH (4 ml) was added 2 N NaOH (0.7 ml, 1.4 mmol). The reaction mixture was heated to reflux for 8 h. The reaction mixture was adjusted to pH 7 using 2 N HCl, then extracted with i-PrOH/CHCl$_3$ (1/9) (2×50 ml). The organic layer was concentrated, and the residue was purified by chromatography (silica gel, 3-10% MeOH/CH$_2$Cl$_2$) to afford Example 174 (32 mg, 60%) as a white solid and Example Compound 175 (11 mg, 21%) as a white solid; Example 174: $^1$H NMR (300 MHz, CD$_3$OD) δ 7.61 (dd, J=7.5, 1.2 Hz, 1H), 7.46 (d, J=1.2 Hz, 1H), 7.41 (d, J=7.8 Hz, 1H), 7.19 (br.s, 1H), 6.42 (s, 1H), 2.60 (s, 3H), 2.38 (s, 3H), 2.34 (s, 3H), 2.17 (s, 3H); APCI m/z 377 [M+H]$^+$; Example 175: $^1$H NMR (300 MHz, CD$_3$OD) δ 7.73 (dd, J=7.8, 1.2 Hz, 1H), 7.48 (d, J=1.2 Hz, 1H), 7.42 (d, J=7.8 Hz, 1H), 7.23 (s, 1H), 6.49 (d, J=1.2 Hz, 1H), 2.60 (s, 3H), 2.41 (s, 3H), 2.35 (s, 3H), 2.18 (s, 3H); APCI m/z 378 [M+H]$^+$.

Preparation of N-(6-(3,5-dimethylisoxazol-4-yl)-1H-benzo[d]imidazol-4-yl)-2-methoxybenzenesulfonamide (Example Compound 102)

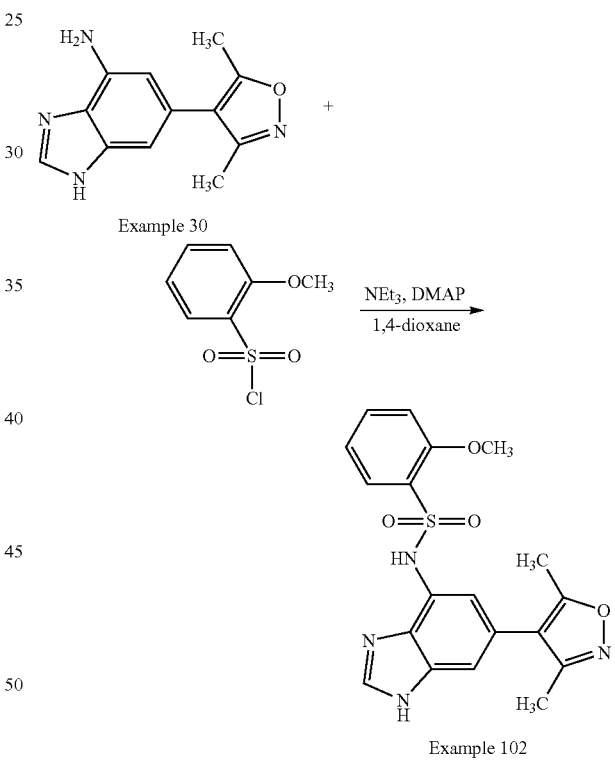

A mixture of Example 30 (83 mg, 0.25 mmol), NEt$_3$ (51 mg, 0.5 mmol), 2-methoxybenzene-1-sulfonyl chloride (63 mg, 0.3 mmol) and DMAP (10 mg, 0.08 mmol) in 1,4-dioxane (4 mL) was stirred at room temperature for 48 h. TFA (1 mL) was then added to the reaction mixture and the solution was stirred at room temperature for 2 h. After concentration, the resulting oil was dissolved in CH$_2$Cl$_2$ and Na$_2$CO$_3$ was added to the solution to reach pH 7. The mixture was filtered, concentrated and purified on silica gel to afford Example 102 as an off-white solid (25 mg, 25%). $^1$H NMR (300 MHz, CD$_3$OD) δ 8.73 (s, 1H), 7.72 (dd, J=7.8, 1.5 Hz, 1H), 7.59-7.53 (m, 1H), 7.38 (d, J=0.9 Hz, 1H), 7.17 (d, J=7.8 Hz, 1H), 6.98 (td, J=7.8, 0.9 Hz, 1H), 6.89 (d, J=1.5 Hz, 1H), 3.93 (s, 3H), 2.22 (s, 3H), 2.05 (s, 3H); ESI MS m/z 399 [M+H]⁺.

Preparation of 3,5-dimethyl-4-(2-methyl-4-phenethyl-1H-benzo[d]imidazol-6-yl)isoxazole (Example Compound 161)

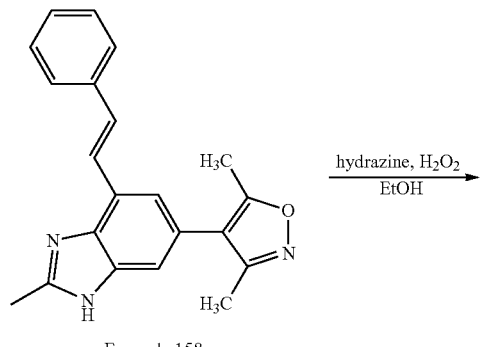

Example 158

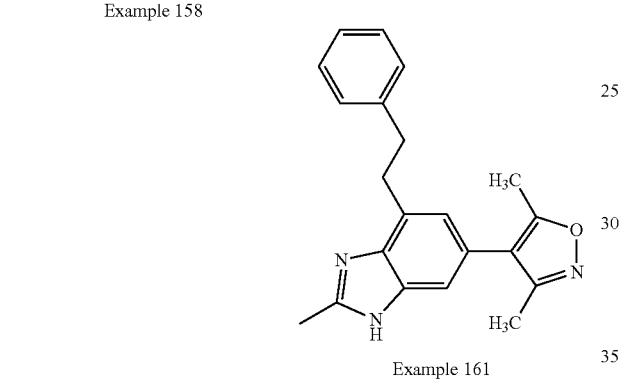

Example 161

A mixture of Example 158 (66 mg, 0.2 mmol), aqueous hydrazine (500 mg, 10 mmol) and H₂O₂(1.13 g, 10 mmol) in EtOH (2 ml) was stirred at room temperature for 64 h. The reaction mixture was concentrated and purified on silica gel to afford Example Compound 161 as an off-white solid (14 mg, 21%). ¹H NMR (300 MHz, CD₃OD) 1217.24-7.13 (m, 6H), 6.74 (s, 1H), 3.33-3.31 (m, 2H), 3.08-3.03 (m, 2H), 2.62 (s, 3H), 2.29 (s, 3H), 2.13 (s, 3H); ESI MS m/z 332 [M+H]⁺.

Preparation of 3-(6-(3,5-dimethylisoxazol-4-yl)-2-methyl-1H-benzo[d]imidazol-4-yl)-2-methylbenzamide (Example Compound 126)

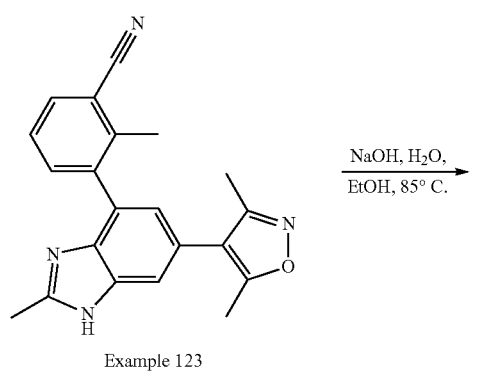

Example 123

-continued

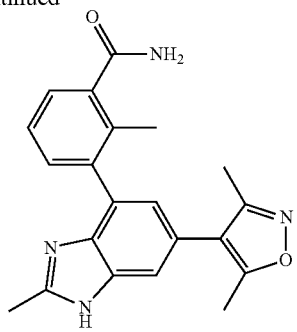

Example 126

To a solution of Example 123 (100 mg, 0.29 mmol) in ethanol (3 mL), was added 2 N NaOH (2.9 mL). The reaction mixture was heated to 80° C. and stirred for 16 h. The reaction was neutralized with acetic acid (1 mL), and concentrated. The residue was purified by chromatography (silica gel, 0-10% methanol/methylene chloride) to afford Example Compound 126 as an off-white solid (56 mg, 54%): ¹H NMR (500 MHz, CD₃OD) δ 7.48 (d, J=7.3 Hz, 2H), 7.40 (d, J=6.6 Hz, 1H), 7.37 (d, J=7.6 Hz, 1H), 6.99 (s, 1H), 2.55 (s, 3H), 2.44 (s, 3H), 2.29 (s, 3H), 2.23 (s, 3H); ESI m/z 361 [M+H]⁺.

Preparation of 1-(6-(3,5-dimethylisoxazol-4-yl)-2-methyl-1H-benzo[d]imidazol-4-yl)-5-methylpyrrolidin-2-one (Example Compound 121)

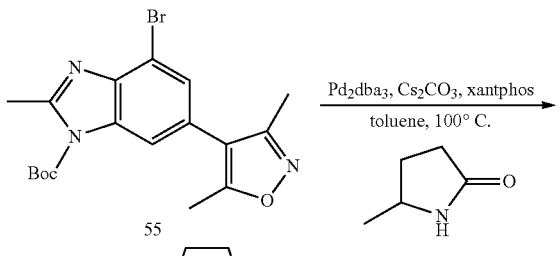

55

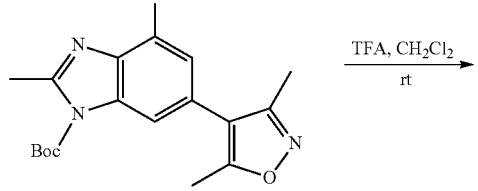

56

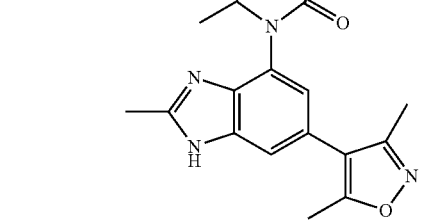

Example 121

Tert-butyl 4-bromo-6-(3,5-dimethylisoxazol-4-yl)-2-methyl-1H-benzo[d]imidazole-1-carboxylate (55) was synthesized using the same method as in Step 1 of General Procedure E instead using 4-(4-bromo-2-methyl-1H-benzo[d]imidazol-6-yl)-3,5-dimethylisoxazole (1).

Step 1:

A mixture of 55 (50 mg, 0.12 mmol), 5-methylpyrrolidin-2-one (14 mg, 0.14 mmol), xantphos (4 mg, 0.01 mmol), tris(dibenzylideneacetone)dipalladium (0) (2 mg, 0.003 mmol) and Cs$_2$CO$_3$ (55 mg, 0.17 mmol) in toluene (3 mL) was heated at 100° C. for 16 hours. The solvent was removed and the residue was purified by silica gel chromatography (eluting with 0 to 50% CMA (80% CH$_2$Cl$_2$, 18% methanol, 2% NH$_4$OH) in CH$_2$Cl$_2$) to provide 56 (48 mg, 94%) as a white solid: $^1$H NMR (500 MHz, CD$_3$OD) δ 7.62 (s, 1H), 7.21 (s, 1H), 4.81-4.79 (m, 1H), 2.85 (s, 3H), 2.58-2.44 (m, 3H), 2.34 (s, 3H), 2.25 (s, 3H), 2.03-1.84 (m, 1H), 1.21 (s, 3H), 1.12 (s, 9H); ESI m/z 425 [M+H]$^+$.

Step 2:

To a solution of 56 (48 mg, 0.11 mmol) in CH$_2$Cl$_2$ (2 mL) was added TFA (1 mL) at room temperature. The solution was stirred for 16 hours and the solvent was removed under reduced pressure. The residue was treated with a solution of saturated sodium bicarbonate and extracted with CH$_2$Cl$_2$. The organic layer was dried over sodium sulfate and filtered. The residue was purified by passing through a plug of silica gel (eluting with 10% MeOH in CH$_2$Cl$_2$) followed by semi-preparative HPLC to provide Example Compound 121 (12 ma 33%) as a white solid: $^1$H NMR (300 MHz, CD$_3$OD) δ 7.63 (s, 1H), 7.39 (s, 1H), 4.62-4.43 (m, 1H), 2.88 (s, 3H), 2.70-2.65 (m, 3H), 2.44 (s, 3H), 2.28 (s, 3H), 2.31-1.84 (m, 1H), 1.23 (d, J=6.2 Hz, 3H); ESI m/z 325 [M+H]$^+$.

Preparation of 1-(6-(3,5-dimethylisoxazol-4-yl)-2-methyl-1H-benzo[d]imidazol-4-yl)piperidin-2-one (Example Compound 122)

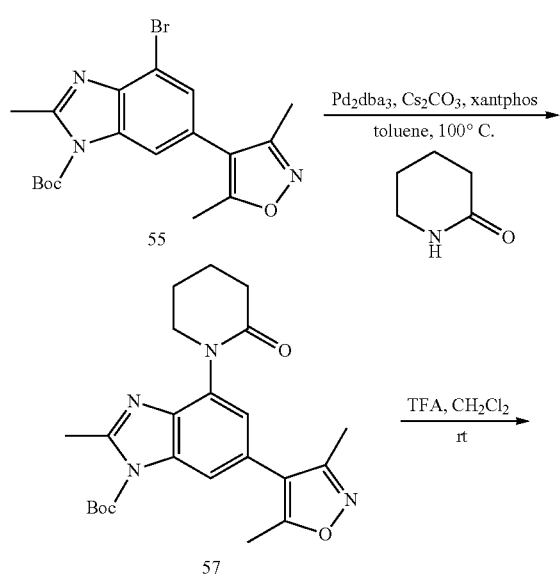

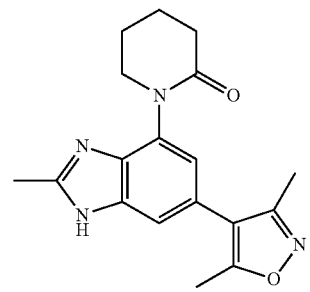

Example 122

Step 1:

A mixture 55 (50 mg, 0.12 mmol), piperidin-2-one (14 mg, 0.14 mmol), Cs$_2$CO$_3$ (55 mg, 0.17 mmol), xantphos (4 mg, 0.01 mmol) and tris(dibenzylideneacetone)dipalladium (0) (2 mg, 0.003 mmol) in toluene (3 mL) was heated at 100° C. for 16 hours. The solvent was removed and the residue was purified by combiflash (eluting with 0 to 50% CMA (80% CH$_2$Cl$_2$, 18% methanol, 2% NH$_4$OH) in CH$_2$Cl$_2$) to provide 57 (22 mg, 44%) as a white solid: $^1$H NMR (500 MHz, CDCl$_3$) δ 7.77 (s, 1H), 7.47 (s, 1H), 3.85-3.83 (m, 2H), 2.81 (s, 3H), 2.71-2.63 (m, 2H), 2.44 (s, 3H), 2.27 (s, 3H), 2.09-2.04 (m, 4H), 1.68 (s, 9H).

Step 2:

To a solution of 57 (22 mg, 0.05 mmol) and CH$_2$Cl$_2$ (2 mL) was added TFA (0.5 mL) at room temperature. The solution was stirred for 16 hours and the solvent was removed under reduced pressure. The residue was treated with saturated sodium bicarbonate solution and extracted into CH$_2$Cl$_2$. The organic layer was dried over sodium sulfate and filtered. The residue was purified by passing through a plug of silica gel (eluting with 10% MeOH in CH$_2$Cl$_2$) followed by semi-preparative HPLC to provide Example Compound 122 (4 mg, 25%): $^1$H NMR (300 MHz, CD$_3$OD) δ 7.62 (s, 1H), 7.48 (s, 1H), 3.90-3.81 (m, 2H), 2.87 (s, 3H), 2.69-2.61 (m, 2H), 2.44 (s, 3H), 2.28 (s, 3H), 2.07-2.05 (m, 4H); ESI m/z 325 [M+H]$^+$.

Preparation of 4,4'-(5-methoxy-2-methyl-1H-benzo[d]imidazole-4,6-diyl)bis(3,5-dimethylisoxazole) (Example Compound 227)

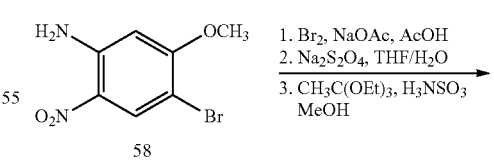

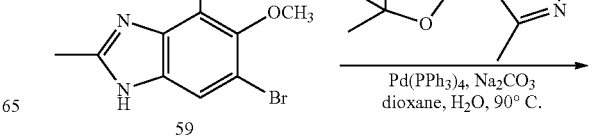

-continued

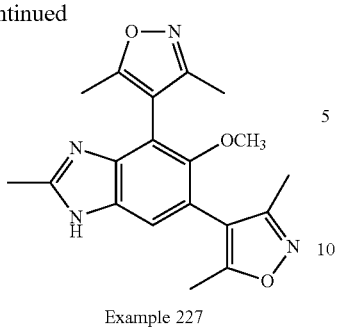

Example 227

Step 1:

To a suspension of 58 (760 mg, 308 mmol) and NaOAc (379 mg, 4.62 mmol) in acetic acid (10 mL) was added bromine (0.237 mL, 4.62 mmol) dropwise. The reaction was stirred at room temperature for 3h. The mixture was concentrated in vacuo. The residue was dissolved in EtOAc (100 mL), washed with saturated NaHCO$_3$ (2×50 mL), saturated Na$_7$S$_2$O$_3$ (3×50 mL) and brine (50 mL). The organic layer was dried over sodium sulfate, filtered and concentrated. The residue was dissolved in THF (50 mL) and water (40 mL), sodium dithionite (2.90 g, 16.68 mmol) was added. The reaction mixture was stirred at room temperature for 2 h. 1N HCl (10 mL) was added and the mixture was heated to reflux for 30 minutes, then cooled to room temperature. Saturated NaHCO$_3$ (100 mL) was added slowly. The mixture was extracted with EtOAc (150 mL), the organic layer was dried over sodium sulfate, filtered and concentrated. The residue was dissolved in MeOH (25 mL), and triethyl orthoacetate (666 mg, 4.11 mmol) and sulfamic acid (14 mg, 0.14 mmol) were added. The reaction was stirred at room temperature for 5 h. The reaction mixture was concentrated, the residue was suspended in EtOAc (100 mL) and washed with brine (50 mL). The organic layer was dried over sodium sulfate, filtered and concentrated to give 59 (880 mg, 90%) as a light brown solid: $^1$H NMR (300 MHz, DMSO-d$_6$) δ 12.65 (s, 0.3H), 12.60 (s, 0.7H), 7.76 (s, 0.3H), 7.69 (s, 0.7H), 3.79 (s, 3H), 2.50 (s, 3H).

Step 2:

To a solution of 59 (550 mg, 1.72 mmol) in 1,4-dioxane (10 mL) and water (3 mL) was added 3,5-dimethyl-4-(4,4,5,5-tetramethyl-1,3,2-dioxaborolan-2-yl)isoxazole (1.15 g, 5.16 mmol), Na$_2$CO$_3$ (729 mg, 6.88 mmol) and tetrakis(triphenylphosphine)palladium(0) (398 mg, 0.34 mmol). The reaction mixture was purged with nitrogen and heated at 90° C. overnight. The reaction mixture was cooled to room temperature, concentrated and purified by chromatography (silica gel, 0-5% MeOH/CH$_2$Cl$_2$) to give Example Compound 227 (49 mg, 80%) as a white solid: $^1$H NMR (300 MHz, CD$_3$OD) δ 7.40 (s, 1H), 3.17 (s, 3H), 2.55 (s, 3H), 2.39 (s, 3H), 2.34 (s, 3H), 2.22 (s, 3H), 2.20 (s, 3H); ESI m/z 353 [M+H]$^+$.

Preparation of 4,4'-(2-(tetrahydro-2H-pyran-4-yl)-1H-benzo[d]imidazole-4,6-dyl)bis(3,5-dimethylisoxazole) (Example Compound 228)

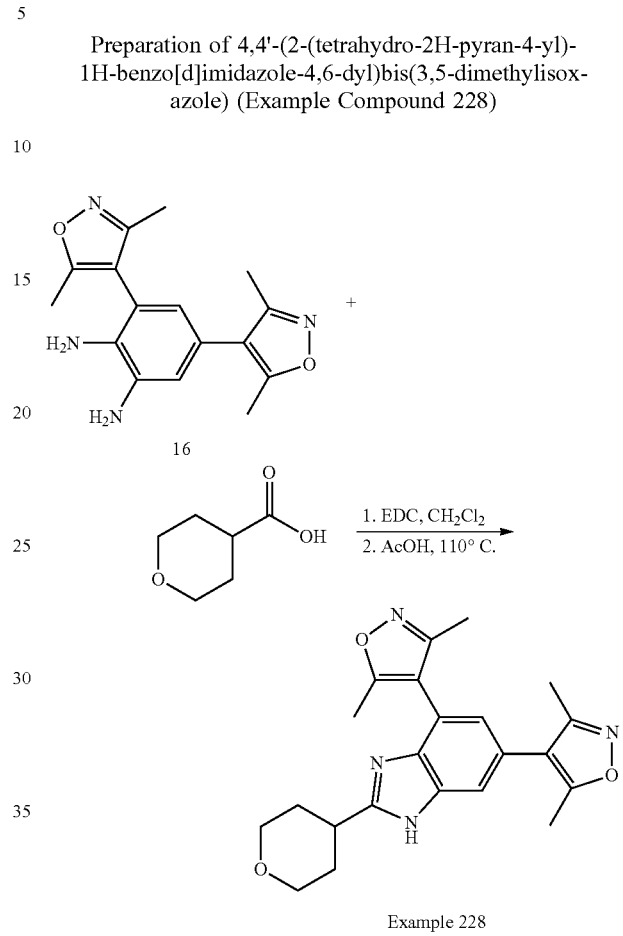

Example 228

To a solution of 16 (100 mg, 0.335 mmol) and tetrahydro-2H-pyran-4-carboxylic acid (47 mg, 0.369 mmol) in CH$_2$Cl$_2$ was added EDC (97 mg, 0.503 mmol). The reaction was stirred at rt for 16 h. The mixture was diluted with EtOAc (100 mL), washed with brine (50 mL) and saturated NaHCO$_3$ (50 mL). The organic layer was dried over sodium sulfate, filtered and concentrated. The residue was dissolved in AcOH (2 mL) and heated to reflux for 5 h. The mixture was concentrated, the residue was dissolved in EtOAc (100 mL), washed with saturated NaHCO$_3$ (2×50 mL) and brine (50 mL). The organic layer was dried over sodium sulfate, filtered and concentrated. The residue was purified by chromatography (silica gel, 0-5% MeOH/EtOAc) to give Example Compound 228 (50 mg, 38%) as an off-white solid: $^1$H NMR (300 MHz, DMSO-d$_6$) δ 12.49 (s, 0.7H), 12.18 (s, 0.3H), 7.60 (s, 0.3H), 7.41 (s, 0.7H), 7.06 (s, 1H), 3.96-3.93 (m, 2H), 3.51-3.45 (m, 2H), 3.21-3.01 (m, 1H), 2.44-2.33 (m, 6H), 2.28-2.17 (m, 6H), 1.93-1.82 (m, 4H); ESI m/z 393 [M+H]$^+$.

Preparation of 4,4'-(2-methyl-3H-imidazo[4,5-b]pyridine-5,7-diyl)bis(3,5-dimethylisoxazole) (Example Compound 176)

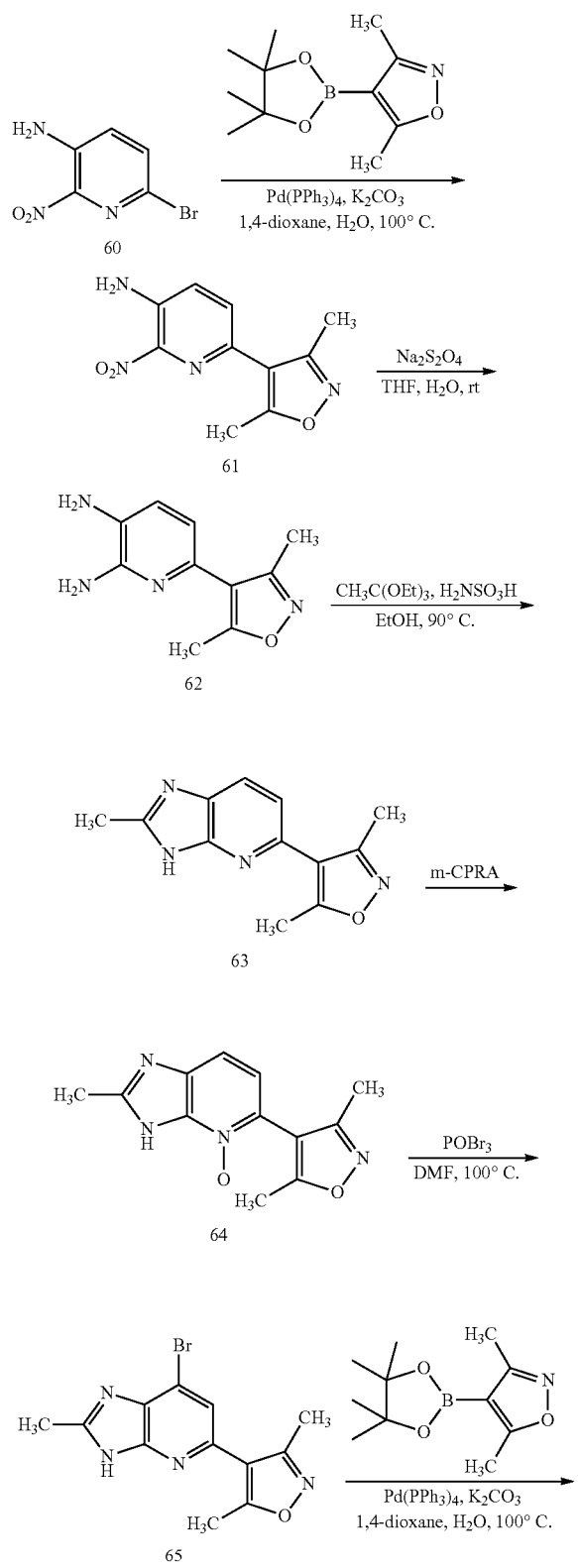

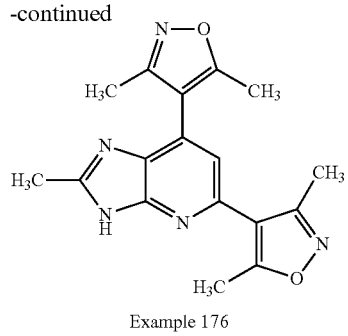

Example 176

Step 1:

To a solution of 60 (1.00 g, 4.59 mmol) in 1,4-dioxane (40 mL) and water (4 mL) was added 3,5-dimethyl-4-(4,4,5,5-tetramethyl-1,3,2-dioxaborolan-2-yl)isoxazole (1.53 g, 6.88 mmol), tetrakis(triphenylphosphine)palladium(0) (265 mg, 0.229 mmol) and potassium carbonate (1.27 g, 9.18 mmol). The reaction mixture was purged with nitrogen and heated at 90° C. for 16 h. The mixture was cooled to room temperature, concentrated and purified by chromatography (silica gel, 0-100% hexanes/ethyl acetate) to give 61 (1.01 g, 94%) as a yellow solid: $^1$H NMR (500 MHz, CDCl$_3$) δ 7.47 (d, J=8.5 Hz, 1H), 7.36 (d, J=8.5 Hz, 1H), 5.95 (s, 2H), 2.62 (s, 3H), 2.47 (s, 3H).

Step 2:

To a solution of 61 (500 mg, 2.14 mmol) in tetrahydrofuran (10 mL) was added sodium dithionite (2.23 g, 12.8 mmol) in water (10 mL). The reaction mixture was stirred at room temperature for 16 h and concentrated. The residue was suspended in MeOH and the solid was filtered, washed with MeOH, and the filtrate was concentrated. To the residue was added 2 N HCl and the mixture was heated to reflux for 10 minutes. The mixture was cooled to room temperature and concentrated. The residue was dissolved in MeOH and basified by 10% NaHCO$_3$. The mixture was concentrated, and the residue was purified by chromatography (silica gel, 0-100% hexanes/ethyl acetate) to afford 62 (335 mg, 77%) as an off-white solid: $^1$H NMR (500 MHz, CDCl$_3$) δ 6.95 (d, J=7.7 Hz, 1H), 6.64 (d, J=7.7 Hz, 1H), 4.25 (s, 2H), 3.34 (s, 2H), 2.50 (s, 3H), 2.37 (s, 3H); ESI m/z 205 [M+H]$^+$.

Step 3:

To a solution of 62 (330 mg, 1.62 mmol) in ethanol (5 mL) was added triethylorthoacetate (228 mg, 1.78 mmol) and sulfamic acid (3 mg, 0.03 mmol). The reaction was heated in a sealed tube at 90° C. for 16 h. The mixture was concentrated, and the residue was purified by chromatography (silica gel, 0-30% ethyl acetate in hexanes) to give 63 (340 mg, 92%) as a yellow solid: $^1$H NMR (500 MHz, CDCl$_3$) δ 10.92 (s, 1H), 8.03 (d, J=8.1 Hz, 1H), 7.23 (d, J=8.1 Hz, 1H), 2.56 (s, 3H), 2.51 (s, 3H), 2.42 (s, 3H); ESI m/z 229 [M+H]$^+$.

Step 4:

To a solution of 63 (191 mg, 0.838 mmol) in dichloromethane (5 mL) was added m-CPBA (375 mg, 1.68 mmol). The reaction mixture was stirred for 1 h, then additional m-CPBA (375 mg, 1.68 mmol) was added. The mixture was stirred for 1 h, concentrated, and the residue was purified by chromatography (silica gel, 0-20% methanol in ethyl acetate) to give 64 (128 mg, 62%) as an off-white solid: $^1$H NMR (500 MHz, CD$_3$OD) δ 7.71 (d, J=7.8 Hz, 1H), 7.34 (d, J=8.2 Hz, 1H), 2.66 (s, 3H), 2.40 (s, 3H), 2.26 (s, 3H); ESI m/z 245 [M+H]$^+$.

Step 5:

To a mixture of POBr₃ (422 mg, 1.48 mmol) in DMF (5 mL) was added a solution of 64 (120 mg, 0.492 mmol) in DMF (3 mL). The reaction mixture was stirred for 2 h, methanol (5 mL) was added slowly, and the mixture was basified by NaHCO₃ (10%). The mixture was concentrated, and the residue was purified by chromatography (silica gel, 0-100% ethyl acetate in hexanes) to give 65 (75 mg, 50%) as an off-white solid: $^1$H NMR (500 MHz, CD₃OD) δ 7.54 (s, 1H), 2.63 (s, 3H), 2.57 (s, 3H), 2.41 (s, 3H); ESI m/z 307 [M+H]⁺.

Step 6:

To a solution of 65 (60 mg, 0.20 mmol) in 1,4-dioxane (10 mL) and water (1 mL) was added 3,5-dimethyl-4-(4,4,5,5-tetramethyl-1,3,2-dioxaborolan-2-yl)isoxazole (134 mg, 0.60 mmol), tetrakis(triphenylphosphine)palladium(0) (24 mg, 0.02 mmol) and potassium carbonate (110 mg, 0.80 mmol). The reaction mixture was purged with nitrogen and heated at 90° C. for 20 h. The mixture was cooled to room temperature, concentrated and the residue was purified by chromatography (silica gel, 0-100% ethyl acetate in hexanes and then to 20% methanol in ethyl acetate). The desired product was further purified by reverse phase HPLC on a Polaris C₁₈ column eluting with 10-90% CH₃CN in H₂O to give Example Compound 176 (40 mg, 62%) as an off-white solid: $^1$H NMR (300 MHz, CD₃OD) δ 8.18 (s, 1H), 7.69 (d, J=1.6 Hz, 1H), 7.08 (d, J=1.6 Hz, 1H), 3.58 (s, 3H), 2.44 (s, 3H), 2.32 (s, 3H), 2.28 (s, 3H), 2.13 (s, 3H); ESI m/z 323 [M+H]⁺.

Preparation of 4-(6-(1,4-dimethyl-1H-pyrazol-5-yl)-2-methyl-1H-benzo[d]imidazol-4-yl)-3,5-dimethyl-isoxazole (Example Compound 178)

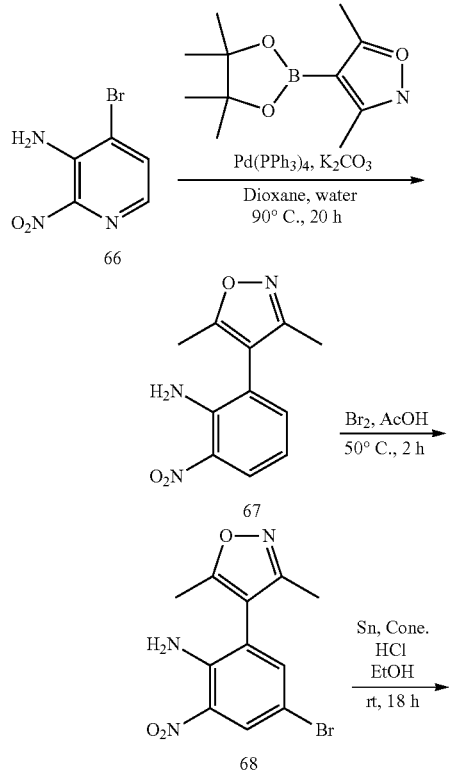

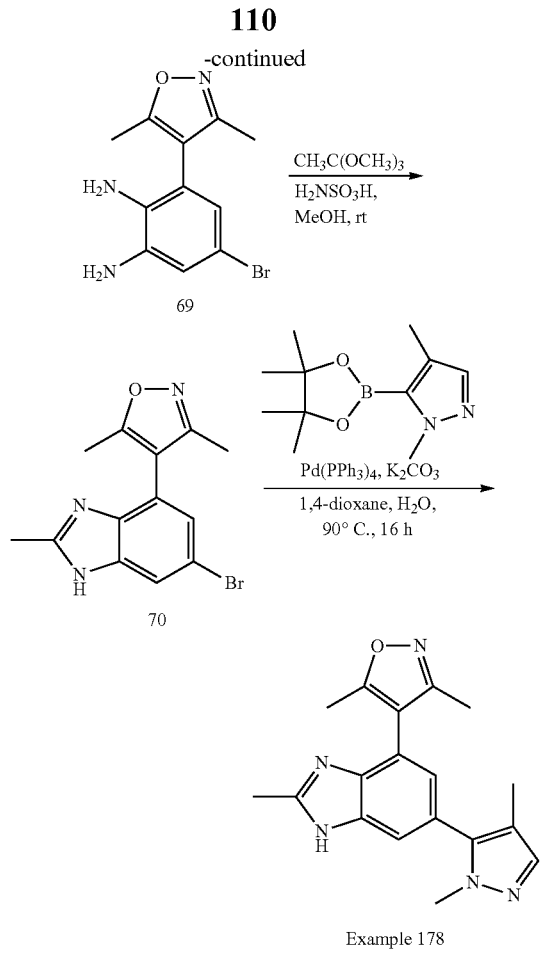

Example 178

Step 1:

To a degassed solution of 2-bromo-6-nitroaniline (10 g, 46.1 mmol), 3,5-dimethyl-4-(4,4,5,5-tetramethyl-1,3,2-dioxaborolan-2-yl)isoxazole (13.4 g, 59.9 mmol) and K₂CO₃ (19.1 g, 138 mmol) in 1,4-dioxane (200 mL) and water (70 mL) was added Pd(PPh₃)₄(7.9 g, 6.9 mmol) and the mixture was degassed again. The reaction was heated at 90° C. for 20 h under N₂. The reaction was cooled to rt, filtered and concentrated under reduced pressure. The residue was dissolved in ethyl acetate (300 mL) and washed with water (200 mL). The aqueous phase was extracted with additional ethyl acetate and the combined organics were dried over Na₂SO₄ and concentrated. The residue was triturated with diethyl ether to give 67 (8.2 g, 76%) as an orange solid: $^1$H NMR (400 MHz, CDCl₃) δ 8.22 (dd, J=8.8 Hz, 1.2 Hz, 1H), 7.23 (dd, J=7.6 Hz, 1.6 Hz, 1H), 6.78 (dd, J=8.8 Hz, 1.6 Hz, 1H), 6.14 (br.s, 2H), 2.32 (s, 3H), 2.16 (s, 3H); ESI MS m/z 232 [M−H]⁻.

Step 2:

To a solution of 67 (8.2 g, 35.2 mmol) in acetic acid (90 mL) was added dropwise a solution of bromine (1.7 mL, 32.2 mmol) in acetic acid (10 mL) at 50 SC. After the addition was complete the reaction was stirred an additional 2h. The reaction was carefully poured into crushed ice and stirred for 20 min. The resulting precipitate was collected by filtration, the filter cake was washed with water (2×50 mL) and dried at 50° C. under vacuum to give 68 (8.9 g, 81%) as a yellow solid: $^1$H NMR (400 MHz, CDCl₃) δ 8.37 (d, J=2.4 Hz, 1H), 7.33 (d, J=2.4 Hz, 1H), 6.17 (b.s, 2H), 2.34 (s, 3H), 2.17 (s, 3H); ESI MS m/z 312 [M+H]⁺.

Step 3:

Granular tin (10.3 g, 86.5 mmol) was added to a solution of 68 (9.0 g, 28.8 mmol) in ethanol (150 mL). To the resulting suspension, concentrated HCl (15 mL) was added dropwise over a period of 30 min. After the addition was complete the reaction was stirred at rt for 18 h. The reaction was concentrated under reduced pressure and the resulting residue treated with water (100 mL), cooled on an ice-water bath and neutralized with 3 N NaOH solution. Then aqueous saturated NaHCO$_3$ solution (150 mL) was added to adjust to pH 8-9. Dichloromethane (100 mL) and methanol (50 mL) were added and the mixture was stirred for 30 min at rt. The resulting emulsion was filtered, the organic phase was separated, washed with water (500 mL), dried over Na$_2$SO$_4$ and concentrated under reduced pressure. The residue was purified by flash column chromatography (silica gel, 1-5% methanol/dichloromethane) to afford 69 (7.6 g, 93%) as a white solid: $^1$H NMR (400 MHz, CDCl$_3$) δ 6.89 (d, J=2.0 Hz, 1H), 6.67 (d, J=2.4 Hz, 1H), 3.49 (br.s. 2H), 3.32 (br.s, 2H), 2.30 (s, 3H), 2.16 (s, 3H); ESI MS m/z 282 [M+H]$^+$.

Step 4:

Trimethyl orthoacetate (6.5 g, 53.9 mmol) and sulfamic acid (0.523 g, 5.4 mmol) were added to a solution of 69 (7.6 g, 26.9 mmol) in methanol (150 mL). The reaction was stirred at rt for 5 h. The mixture was concentrated under reduced pressure, treated with ice cold water (150 mL) and saturated NaHCO$_3$ solution (30 mL) and stirred for 30 min. The resulting precipitate was collected by filtration and suspended in diethyl ether (150 mL). The resulting suspension was stirred at rt for 30 min and the solids were collected by filtration. The solids were washed with additional diethyl ether and dried under vacuum to give 70 (8.1 g, 98%) as an off-white solid: $^1$H NMR (400 MHz, DMSO-d$_6$) δ 7.66 (br s, 1H), 7.19 (d, J=2.0 Hz, 1H), 2.45 (s, 3H), 2.30 (s, 3H), 2.14 (s, 3H); ESI MS m/z: 306 [M+H]$^+$.

Step 5:

To a degassed solution of 70 (1.0 g, 3.5 mmol), 1,4-dimethyl-5-(4,4,5,5-tetramethyl-1,3,2-dioxaborolan-2-yl)-1H-pyrazole (1.0 g, 4.5 mmol) and K$_2$CO$_3$ (0.958 g, 6.9 mmol) in 1,4-dioxane (30 mL) and water (5 mL) was added Pd(PPh$_3$)$_4$(0.600 g, 0.5 mmol) and the mixture was degassed again. The reaction was heated at 90° C. for 16 h under N$_2$. The reaction was cooled to rt, filtered and concentrated under reduced pressure. The residue was treated with water (50 mL) and extracted with dichloromethane (3×50 mL). The combined organics were dried over Na$_2$SO$_4$ and concentrated. The residue was purified by flash column chromatography (silica gel, 2-4% methanol/dichloromethane) to give Example Compound 178 (0.577 g, 52%) as a white solid: $^1$H NMR (400 MHz, CD$_3$OD) δ 7.51 (br.s, 1H), 7.38 (br.s, 1H), 7.08 (d, J=1.6 Hz, 1H), 3.77 (s, 3H), 2.59 (s, 3H), 2.37 (s, 3H), 2.23 (s, 3H), 2.04 (s, 3H); ESI MS m/z 322 [M+H]$^+$.

Preparation of 4,4'-(3-methyl-1H-indazole-4,6-diyl)bis(3,5-dimethylisoxazole) (Example Compound 179)

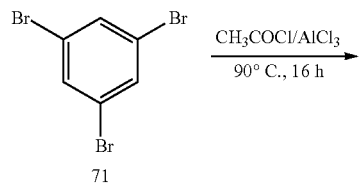

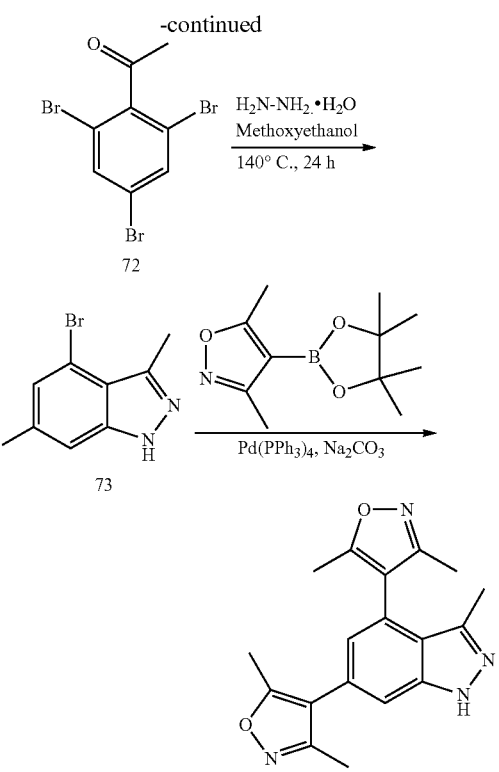

Example 179

Step 1: 71 (5.04 g, 16.0 mmol) and powdered anhydrous aluminum chloride (4.27 g, 32.0 mmol) were mixed thoroughly. Acetyl chloride (3.2 mL, 45 mmol) was added and the mixture was stirred at rt for 1 h. The temperature was increased to 90° C. and stirring was continued for 16 h. The reaction mixture was cooled to rt and quenched with ice-cold water (40 mL). The product was extracted with ethyl acetate (3×40 mL) and the combined organics were washed with brine (40 mL), dried over Na$_2$SO$_4$ and concentrated under reduced pressure. The residue was purified by flash column chromatography (silica gel, 0-10% ethyl acetate/hexanes) to give 72 (2.85 g, 50%) as an off-white solid: $^1$H NMR (400 MHz, CDCl$_3$) δ: 7.71 (s, 2H), 2.57 (s, 3H).

Step 2:

Three drops of acetic acid were added to a solution of 72 (1.0 g, 2.8 mmol) and hydrazine monohydrate (0.5 mL, 10.3 mmol) in methoxyethanol (10 mL). The reaction was heated at 140° C. for 24 h. The reaction was cooled to rt and concentrated under reduced pressure. The residue was treated with ethyl acetate and stirred for 30 min. The resulting precipitate was collected by filtration and dried to give 73 (0.460 g, 57%) as an off-white solid: $^1$H NMR (400 MHz, CDCl$_3$) δ 7.55 (s, 1H), 7.43 (s, 1H), 2.76 (s, 3H); ESI MS m/z 289 [M+H]$^+$.

Step 3:

To a degassed solution of 73 (0.450 g, 1.55 mmol) and 3,5-dimethyl-4-(4,4,5,5-tetramethyl-1,3,2-dioxaborolan-2-yl)isoxazole (0.446 g, 2.0 mmol) in dioxane (30 mL) was added Na$_2$CO$_3$ (0.328 g, 3.1 mmol), Pd(PPh$_3$)$_4$ (0.185 g, 0.16 mmol) and water (3.0 ml). The reaction mixture was degassed again. The reaction was heated at 80° C. for 18 h. The reaction was cooled to rt, filtered and concentrated under reduced pressure. The residue was dissolved in ethyl acetate (30 mL), washed with water (20 mL), brine (20 mL), dried over Na$_2$SO$_4$ and concentrated under reduced pressure.

The residue was purified by flash column chromatography (silica gel, 30-50% ethyl acetate/hexanes) followed by trituration with diethyl ether to afford Example Compound 179 (0.060 g, 12%) as an off-white solid: mp 228-230° C.; $^1$H NMR (400 MHz, CDCl$_3$) δ 10.09 (br.s, 1H), 7.36 (s, 1H), 6.79 (s, 1H), 2.47 (s, 3H), 2.33 (s, 3H), 2.32 (s, 3H), 2.26 (s, 3H), 2.15 (s, 3H); ESI MS m/z 321 [M−H]$^-$.

Preparation of 4-(4-(3,5-dimethyl-1H-pyrazol-4-yl)-3-methyl-1H-indazol-6-yl)-3,5-dimethylisoxazole (Example Compound 180)

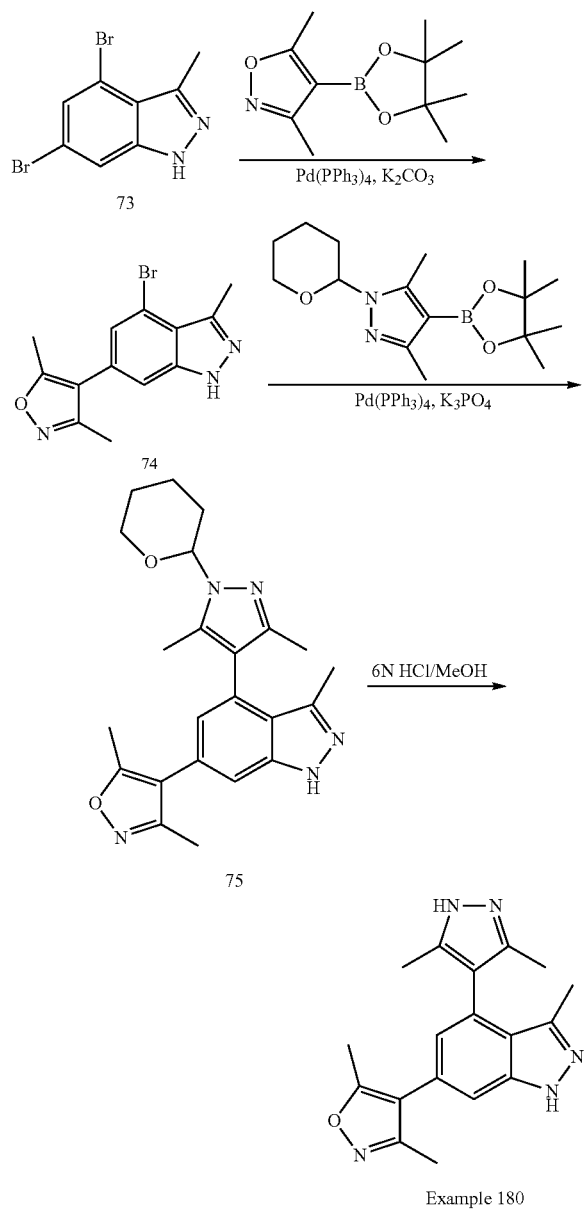

Step 1:
To a degassed solution of 73 (0.400 g, 1.38 mmol) and 3,5-dimethyl-4-(4,4,5,5-tetramethyl-1,3,2-dioxaborolan-2-yl)isoxazole (0.260 g, 1.17 mmol) in dioxane (25 mL) was added K$_2$CO$_3$ (0.386 g, 2.8 mmol), Pd(PPh$_3$)$_4$ (0.080 g, 0.07 mmol) and water (2.5 mL). The reaction mixture was degassed again and then heated at 80° C. for 8 h under N$_2$. The reaction was cooled to rt, filtered and concentrated under reduced pressure. The residue was dissolved in ethyl acetate (40 mL), washed with water (20 mL), brine (20 mL), dried over Na$_2$SO$_4$ and concentrated under reduced pressure. The residue was purified by flash column chromatography (silica gel, 10-50% ethyl acetate/hexanes) followed by trituration with diethyl ether to give 74 (0.100 g, 24%) as an off-white solid: $^1$H NMR (400 MHz, CDCl$_3$) δ 10.05 (br.s, 1H), 7.23 (s, 1H), 7.19 (s, 1H), 2.81 (s, 3H), 2.44 (s, 3H), 2.29 (s, 3H); ESI MS m/z 304 [M−H]$^-$.

Step 2:
To a degassed solution of 74 (0.130 g, 0.43 mmol) and 3,5-dimethyl-1-(tetrahydro-2H-pyran-2-yl)-4-(4,4,5,5-tetramethyl-1,3,2-dioxaborolan-2-yl)-1H-pyrazole (0.170 g, 0.56 mmol) In dioxane (5 mL) was added K$_3$PO$_4$ (0.276 g, 1.3 mmol), Pd(PPh$_3$)$_4$ (0.065 g, 0.06 mmol) and water (0.5 mL). The reaction mixture was degassed again and then heated at 100° C. for 18 h under N$_2$. The reaction was cooled to rt, filtered and concentrated under reduced pressure. The residue was dissolved in dichloromethane (30 mL), washed with water (20 mL), brine (20 mL), dried over Na$_2$SO$_4$ and concentrated under reduced pressure. The residue was purified by flash column chromatography (silica gel, 50-80% ethyl acetate/hexanes) to give 75 (0.060 g, 35%) as a thick gum: ESI MS m/z 404 [M−H]$^-$.

Step 3:
HCl (2.0 mL, 6 N, 12 mmol) was added to a solution of 75 (0.060 g, 0.15 mmol) in methanol. The reaction was heated at 65° C. for 18 h. the reaction was cooled to rt and concentrated under reduced pressure. The residue was purified by preparative HPLC to give Example Compound 180 (0.008 g, 17%) as an off-white solid: $^1$H NMR (400 MHz, CDCl$_3$) δ 7.28 (d, J=1.6 Hz, 1H), 6.78 (d, J=1.6 Hz, 1H), 2.47 (s, 3H), 2.33 (s, 3H), 2.20 (s, 3H), 2.16 (s, 6H); ESI MS m/z 322 [M+H]$^+$.

General Procedure O:

Preparation of 3,5-dimethyl-4-(2-(4-methylpiperazin-1-yl)-4-(1,3,5-trimethyl-1H-pyrazol-4-yl)-1H benzo[d]imidazol-6-yl)isoxazole (Example Compound 181)

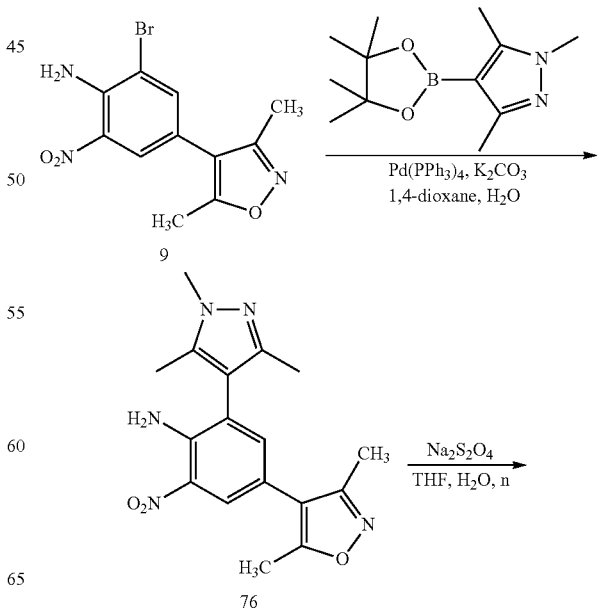

-continued

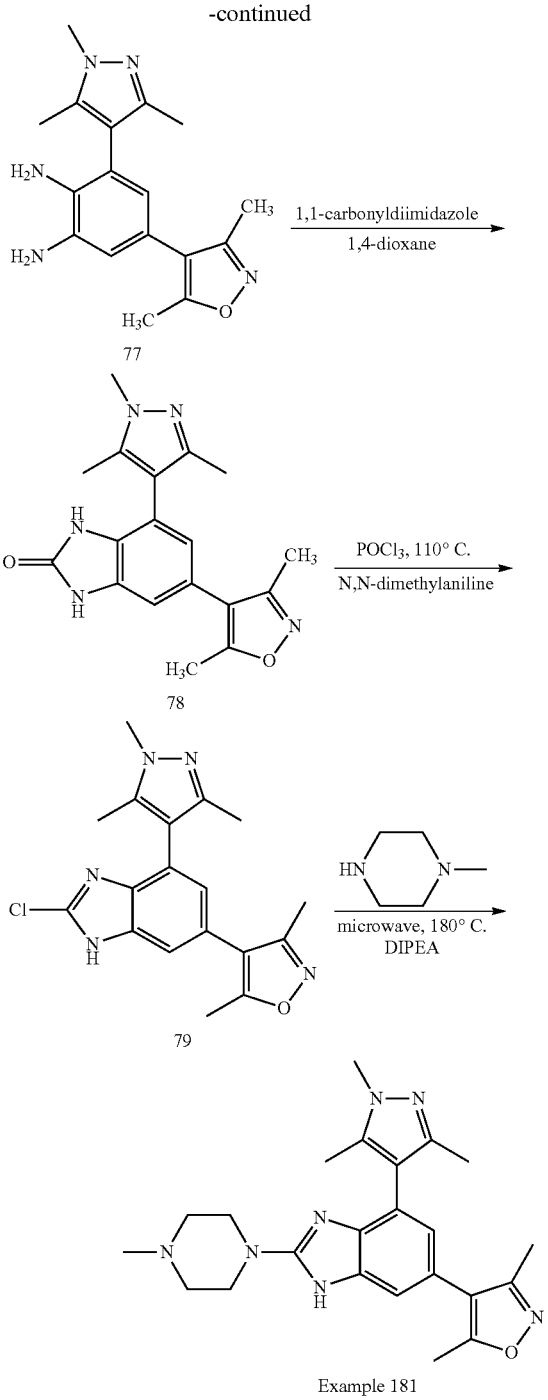

Example 181

Step 1:

To a mixture of 9 (500 mg, 1.6 mmol), 1,3,5-trimethyl-4-(4,4,5,5-tetramethyl-1,3,2-dioxaborolan-2-yl)-1H-pyrazole (454 mg, 1.92 mmol), potassium carbonate (443 mg, 3.20 mmol), water (2 ml) and 1,4-dioxane (9 mL) was added tetrakis(triphenylphosphine)palladium(0) (93 mg, 0.08 mmol). The suspension was heated at 90° C. for 17 h. After cooling to room temperature, methanol (20 ml) and silica gel (10 g) were added. The mixture was concentrated to dryness and the resulting powder was purified by flash chromatography (silica gel, 0-90% ethyl acetate/hexanes) affording 76 as a yellow solid (291 mg, 53%): $^1$H NMR (500 MHz, CDCl$_3$) δ 8.05 (d, J=2.0 Hz, 1H), 7.10 (d, J=2.5 Hz, 1H), 6.26 (br.s, 2H), 3.82 (s, 3H), 2.43 (s, 3H), 2.29 (s, 3H), 2.14 (s, 3H), 2.13 (s, 3H).

Step 2:

To a solution of 76 (290 mg, 0.85 mmol) in THF (20 ml) was added a solution of sodium dithionite (887 mg, 5.10 mmol) in water (20 ml). The solution stirred at room temperature for 17 h. The reaction was concentrated to dryness and methanol (30 mL) was added. The suspension stirred at room temperature for 3 h and was filtered. The filtrate was concentrated to dryness and a solution of 2N aq. HCl (20 mL) was added. The solution was brought to reflux for 5 minutes and then cooled to room temperature. The solvent was removed under reduced pressure and silica gel (10 g) and methanol (20 mL) were added. The methanol was removed and the adsorbed silica mixture was subject to flash chromatography (silica gel, 0-50% CMA (CMA: 80% $CH_2Cl_2$, 18% methanol, 2% $NH_4OH$) in $CH_2Cl_2$) affording 77 as a light brown solid (201 mg, 76%): $^1$H NMR (500 MHz, CDCl$_3$) δ 6.59 (d, J=2.0 Hz, 1H), 6.44 (d, J=2.0 Hz, 1H), 3.80 (s, 3H), 3.48 (br.s, 4H), 2.39 (s, 3H), 2.27 (s, 3H), 2.16 (s, 3H), 2.14 (s, 3H).

Step 3:

To a solution of 77 (200 mg, 0.64 mmol) in anhydrous 1,4-dioxane (10 mL) at room temperature was added 1,1'-carbonyldiimidazole (125 mg, 0.77 mmol). The mixture was heated at 65° C. for 17 h and then cooled to room temperature. After adding silica gel (10 g) and concentrating the mixture to dryness, the material was subject to flash chromatography (silica gel, 0-10% methanol in $CH_2Cl_2$) and the product fractions were concentrated to an off-white solid. The solid was triturated with ethyl acetate (20 mL) and the suspension was filtered. The solid collected was dried in a vacuum oven for 17 h affording 78 (140 mg, 65%) as an off-white solid: $^1$H NMR (500 MHz, DMSO-d$_6$) δ 10.7 (s, 1H), 10.4 (s 1H), 6.82 (d, J=1.5 Hz, 1H), 6.68 (d, J=1.5 Hz, 1H), 3.70 (s, 3H), 2.40 (s, 3H), 2.23 (s, 3H), 2.12 (s, 3H), 2.05 (s, 3H); ESI m/z 338 [M+H]$^+$.

Step 4:

A mixture of phosphorus (V) oxychloride (10 mL), 78 (1.00 g, 2.9 mmol) and N,N-dimethylaniline (4 drops) was heated at reflux for 20 h under $N_2$. The reaction was cooled to rt and concentrated under reduced pressure. The residue was dissolved in dichloromethane and poured onto crushed ice. The pH of the aqueous solution was adjusted to between 8-9 with aqueous saturated $Na_2CO_3$ solution and extracted with dichloromethane (2×100 mL). The combined organics were washed with brine, dried ($Na_2SO_4$) and concentrated under reduced pressure. The residue was purified by flash column chromatography (silica gel, 1-2% methanol/dichloromethane) 79 (0.790 g, 75%) as a light yellow solid: $^1$H NMR (400 MHz, CD$_3$OD) δ 7.44 (br.s, 1H), 7.03 (d, J=1.2 Hz, 1H), 3.80 (s, 3H), 2.44 (s, 3H), 2.28 (s, 3H), 2.19 (s, 3H), 2.14 (s, 3H); ESI MS m/z 356 [M+H]+.

Step 5:

To a solution of 79 (0.100 g, 0.3 mmol) in 1,4-dioxane (2 mL) was added 1-methylpiperazine (3) (0.028 g, 0.3 mmol) followed by N,N-diisopropylethylamine (0.091 g, 0.8 mmol). The reaction was stirred at 180° C. under microwave heating conditions for 4 h. The reaction was cooled to rt and concentrated under reduced pressure. The residue was dissolved in dichloromethane (50 mL), washed with water (50 mL), brine (50 mL), dried (Na$_2$SO$_4$) and concentrated under reduced pressure. Diethyl ether (20 mL) was added, and the resulting suspension was stirred at rt for 30 min. The solids were collected by filtration, washed with additional diethyl ether (20 mL) and dried under vacuum to give Example Compound 181 (0.078 g, 67%) as an off-white solid: m.p. 195-197° C.; $^1$H NMR (400 MHz, CDCl$_3$) δ 9.80 (br.s, 1H), 7.32 (br.s, 1H), 6.64 (br.s, 1H), 3.69-3.74 (m, 4H), 3.68 (s, 3H), 2.51-2.59 (m, 4H), 2.44 (s, 3H), 2.36 (s, 3H), 2.30 (s, 3H), 2.17 (s, 3H), 2.12 (s, 3H); ESI MS m/z 420 [M+H]$^+$.

Preparation of 3,5-dimethyl-4-(2-(4-methylpiperazin-1-yl)-4-(2-methylpyridin-3-yl)-1H-benzo[d]imidazol-6-yl)isoxazole (Example Compound 183)

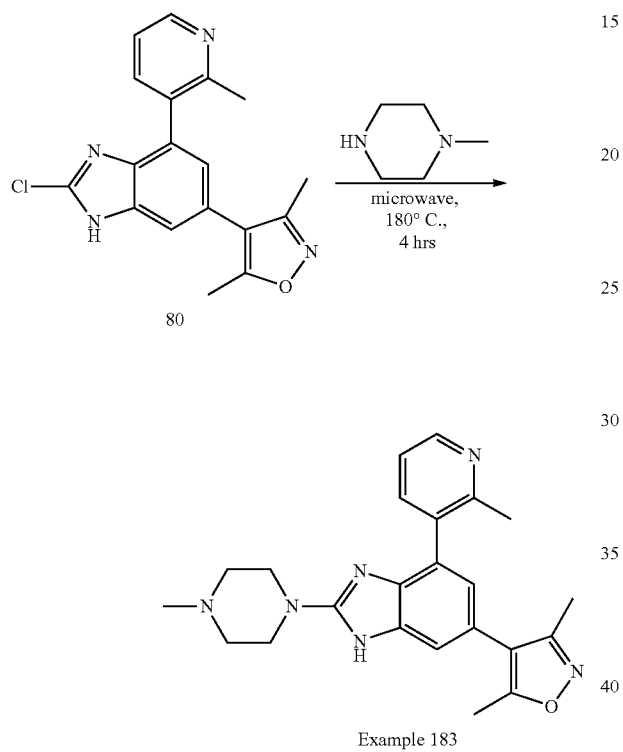

Example 183

Compound 80 was prepared starting with 2-methyl-3-(4,4,5,5-tetramethyl-1,3,2-dioxaborolan-2-yl)pyridine using step 1 through 4 of General Procedure O.

A solution of 80 (0.070 g, 0.207 mmol) and 1-methylpiperazine (0.09 mL, 0.828 mmol) in 1,4-dioxane (2 mL) was heated at 180° C. for 4 h under microwave heating conditions. The reaction was cooled to rt and concentrated under reduced pressure. The residue was dissolved in dichloromethane (50 mL), washed with water (50 mL), brine (50 mL), dried (Na$_2$SO$_4$), and concentrated under reduced pressure. The residue was triturated with diethyl ether (20 mL) and the resulting suspension was stirred at rt for 30 min. The resulting precipitate was collected by filtration, washed with diethyl ether (20 mL) and dried under vacuum to give Example Compound 183 (0.071 g, 85%) as an off-white solid: mp 238-240° C.; $^1$H NMR (400 MHz, CDCl$_3$) δ 11.21 (br.s, 1H), 7.94 (d, J=3.9 Hz, 1H), 7.58 (dd, J=7.6, 1.4 Hz, 1H), 7.40 (s, 1H), 7.04 (dd, J=7.6, 4.9 Hz, 1H), 6.68 (d, J=1.6 Hz, 1H), 3.74 (br.s, 4H), 2.51 (t, J=4.7 Hz, 4H), 2.44 (s, 3H), 2.43 (s, 3H), 2.31 (s, 6H); ESI MS m/z 401 [M−H]$^-$.

General Procedure P:

Preparation of 3-(6-(3,5-dimethylisoxazol-4-yl)-2-(4-methylpiperazin-1-yl)-1H-benzo[d]imidazol-4-yl)-4-methylbenzonitrile (Example Compound 186)

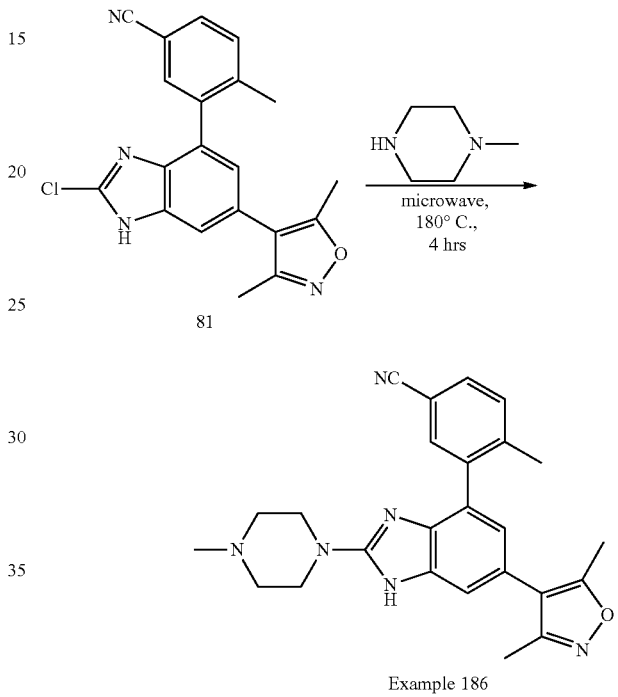

Example 186

Compound 81 was prepared starting with 4-methyl-3-(4,4,5,5-tetramethyl-1,3,2-dioxaborolan-2-yl)benzonitrile using step 1 through 4 of General Procedure 0.

A mixture of 81 (0.110 g, 0.28 mmol) and 1-methylpiperazine (0.112 g, 1.12 mmol) in 1,4-dioxane (2 mL) was stirred at 180° C. under microwave heating conditions for 4 h. The mixture was cooled to rt and concentrated under reduced pressure. The residue was dissolved in ethyl acetate (20 mL), washed with water (10 mL) and brine (10 mL), then dried (Na$_2$SO$_4$) and concentrated under reduced pressure. The crude product was purified by flash column chromatography (silica gel, dichloromethane to 97:3 dichloromethane/methanol) to give Example Compound 186 (0.075 g, 58%) as an off-white solid: mp 133-135° C.; $^1$H NMR (400 MHz, CD$_3$OD) δ: 7.66 (s, 2H), 7.51 (d, J=7.8 Hz, 1H), 7.23 (br.s, 1H), 6.81 (br.s, 1H), 3.58 (t, J=4.9 Hz, 4H), 2.57 (t, J=4.9 Hz, 4H), 2.43 (s, 3H), 2.34 (s, 3H), 2.28 (s, 6H); ESI MS m/z 425 [M−H]$^-$.

General Procedure Q:

Preparation of 3-(6-(3,5-dimethylisoxazol-4-yl)-2-(4-methylpiperazin-1-yl)-1H-benzo[d]imidazol-4-yl)-4-methylbenzamide (Example Compound 189)

General Procedure R:

Preparation of 4-(6-(3,5-dimethylisoxazol-4-yl)-4-(4-methylpyridin-3-yl)-1H-benzo[d]imidazol-2-yl)morpholine (Example Compound 196)

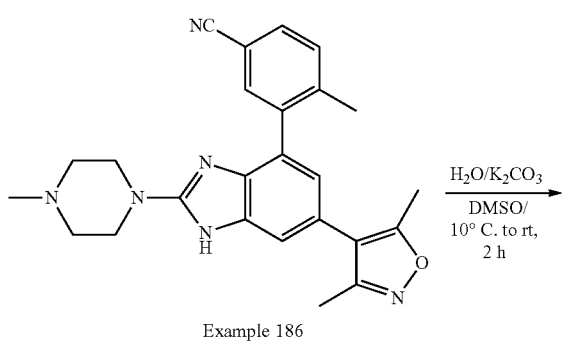

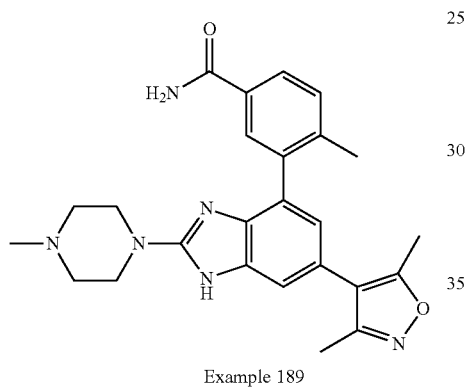

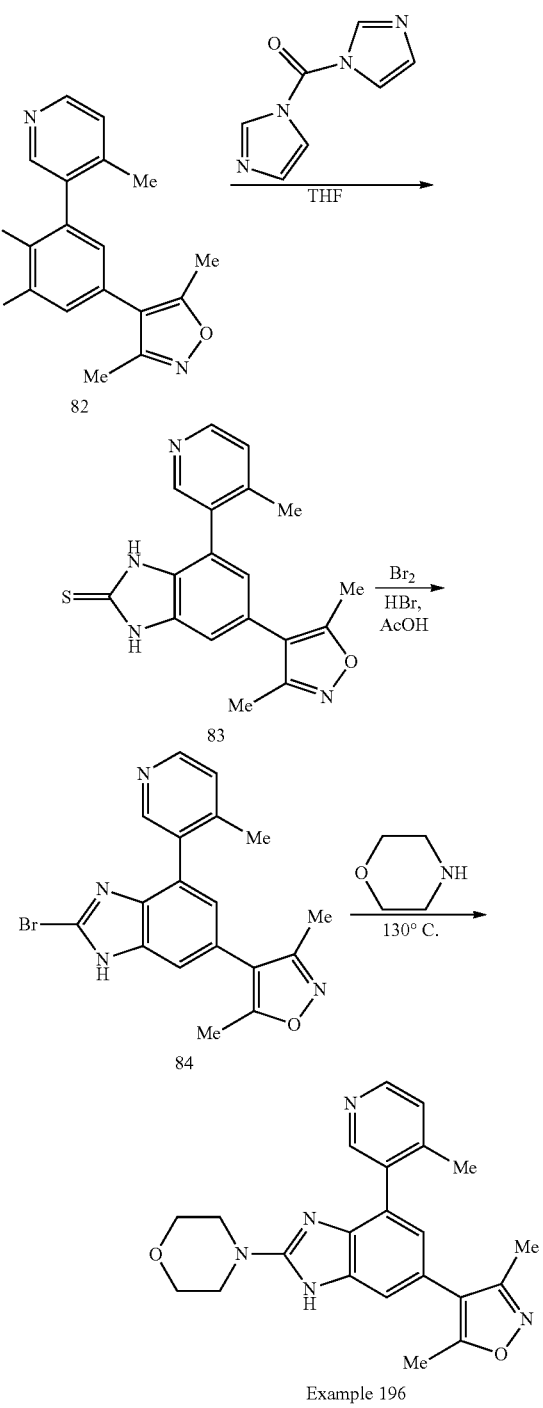

Potassium carbonate (0.042 g, 0.3 mmol) was added to a solution of Example 186 (0.06 g, 0.14 mmol) in DMSO (1.5 mL). The mixture was cooled to 5° C. and 0.3 mL of 30% hydrogen peroxide solution was added dropwise. After the addition was complete the reaction was stirred at 5-10° C. for 1 h. The reaction was allowed to warm to rt and stir an additional 1 h. The reaction was quenched by the addition of crushed ice (10 mL) and the resulting precipitate was collected by filtration. The crude product was dissolved in 1 N HCl (10 mL) and washed with ethyl acetate (10 mL). The aqueous layer was basified with sodium carbonate solution and extracted with CHCl₃ (2×15 mL). The combined organics were filtered and concentrated under reduced pressure. The residue was triturated with hexane to give Example Compound 189 (0.020 g, 32%) as an off-white solid: mp 133-135° C.; ¹H NMR (400 MHz, CD₃OD) δ 7.83 (s, 1H), 7.79 (d, J=7.4 Hz, 1H), 7.44 (br.s, 1H), 7.27 (br.s, 1H), 6.77 (br.s, 1H), 3.60 (br.s, 4H), 2.58 (t, J=4.7 Hz, 4H), 2.44 (s, 3H), 2.36 (s, 3H), 2.30 (s, 6H); ESI MS m/z 445 [M+H]⁺.

Compound 82 was prepared starting with 4-methyl-3-(4,4,5,5-tetramethyl-1,3,2-dioxaborolan-2-yl)pyridine using step 1 and 2 of General Procedure O.

Step 1: 1,1'-Thiocarbonyldiimidazole (0.267 g, 1.5 mmol) was added in one portion to a stirred suspension of 82 (0.294 g, 1.0 mmol) in anhydrous THF (10 ml). The reaction was heated at reflux with stirring for 21 h. The reaction was cooled to rt and concentrated under reduced pressure. The residue was dissolved in chloroform (20 ml), washed with water (3×10 mL), dried over MgSO$_4$, filtered and concentrated under reduced pressure. The residue was purified by flash column chromatography (silica gel, 0-2% methanol/chloroform) to give 83 (0.305 g, 91%) as a yellow solid: $^1$H NMR (400 MHz, CDCl$_3$) δ 12.58 (br.s, 1H), 11.33 (br.s, 1H), 8.45 (s, 1H), 8.23 (d, J=5.4 Hz, 1H), 7.22 (d, J=5.4 Hz, 1H), 7.15 (d, J=1.2 Hz, 1H), 6.91 (d, J=1.2 Hz, 1H), 2.41 (s, 3H), 2.28 (s, 3H), 2.27 (s, 3H); ESI MS m/z 337 [M+H]$^+$.

Step 2:

A solution of bromine (10.91 g, 68.3 mmol) in acetic acid (30 mL) was added drop wise to a stirred solution of 83 (6.38 g, 19 mmol) and HBr (48% aqueous solution, 4.32 g, 25.6 mmol) in acetic acid (100 mL). After the addition was complete the reaction was stirred at rt for 5 h. Then water (130 mL) was added. The reaction was stirred for an additional 1.5 h, cooled to 0° C. and the pH adjusted to 8 by using 28% aqueous NH$_4$OH (250 mL). The mixture was extracted with chloroform (2×50 mL). The combined organics were washed with saturated NaHCO$_3$ (50 mL), dried over MgSO$_4$, filtered and concentrated under reduced pressure. The crude product was purified by flash column chromatography (silica gel, 0-2% methanol/chloroform) to give 84 (4.08 g, 56%) as a yellow solid: $^1$H NMR (400 MHz, CDCl$_3$) δ 8.52 (s, 1H), 8.02 (d, J=4.6 Hz, 1H), 7.65 (s, 1H), 7.20 (d, J=4.6 Hz, 1H), 7.00 (s, 1H), 2.45 (s, 3H), 2.34 (s, 3H), 2.31 (s, 3H).

Step 3:

A mixture of 84 (0.381 g, 0.99 mmol) and morpholine (1.55 g, 17.8 mmol) was heated at 130° C. with stirring for 19 h. The reaction was cooled to rt and diluted with diethyl ether (10 mL) and hexanes (20 mL). The resulting precipitate was collected by filtration, dissolved in chloroform (20 mL), washed with saturated NaHCO$_3$ (10 mL), dried over MgSO$_4$, and concentrated under reduced pressure. The crude product was triturated twice with a mixture of diethyl ether (2 mL) and hexanes (4 mL) followed by flash column chromatography (silica gel, 0-2% methanol/chloroform) to give Example Compound 196 (0.179 g, 46%) as a tan solid: m.p. 137-141° C.; $^1$H NMR (400 MHz, CDCl$_3$) δ 11.65 (br.s, 1H), 8.34 (s, 1H), 7.93 (d, J=4.8 Hz, 1H), 7.39 (s, 1H), 7.11 (d, J=4.8 Hz, 1H), 6.67 (s, 1H), 3.77 (br.s, 4H), 3.62 (br.s, 4H), 2.43 (s, 3H), 2.29 (s, 6H); ESI MS m/z 390 [M+H]+.

General Procedure S:

Preparation of 3-(6-(3,5-dimethylisoxazol-4-yl)-2-(4-methylpiperazin-1-yl)-1H-benzo[d]imidazol-4-yl)-2-methylbenzonitrile (Example Compound 202)

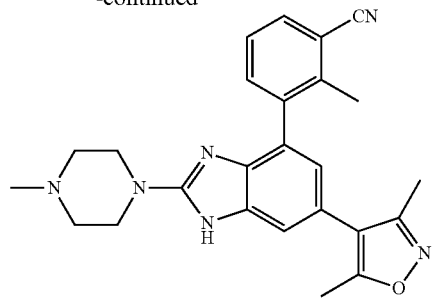

Example 202

Compound 85 was prepared starting with 2-methyl-3-(4,4,5,5-tetramethyl-1,3,2-dioxaborolan-2-yl)benzonitrile using step 1 through 4 of General Procedure O.

A mixture of 85 (0.500 g, 1.37 mmol) and 1-methylpiperazine (0.61 mL, 5.51 mmol) in 1,4-dioxane (2 mL) was stirred at 180° C. under microwave heating conditions for 4 h. The reaction was cooled to rt and concentrated under reduced pressure. The residue was dissolved in chloroform (50 mL), washed with water (50 mL), dried over Na$_2$SO$_4$ and concentrated under reduced pressure. The crude product was purified by flash column chromatography (silica gel, chloroform to 97:3 chloroform/methanol, then 97:3 chloroform/7 N NH$_4$OH in methanol) to give Example Compound 202 (0.156 g 27%) as an off-white solid: m.p. 179-182° C.; $^1$H NMR (400 MHz, CD$_3$OD) δ 7.73 (d, J=7.8 Hz, 1H), 7.61 (d, J=7.4 Hz, 1H), 7.43 (t, J=7.8 Hz, 1H), 7.23 (br.s, 1H), 6.81 (br.s, 1H), 3.57 (t, J=4.8 Hz, 4H), 2.56 (t, J=4.8 Hz, 4H), 2.42 (s, 3H), 2.39 (s, 3H), 2.34 (s, 3H), 2.27 (s, 3H); ESI MS m/z 425 [M−H]$^-$.

Preparation of 3,5-dimethyl-4-(2-(methylthio)-4-(1,3,5-trimethyl-1H-pyrazol-4-yl)-1H-benzo[d]imidazol-6-yl)isoxazole (Example Compound 187), 3,5-dimethyl-4-(1-methyl-2-(methylthio)-4-(1,3,5-trimethyl-1H-pyrazol-4-yl)-1H-benzo[d]imidazol-6-yl)isoxazole (Example Compound 188) and 3,5-dimethyl-4-(1-methyl-2-(methylthio)-7-(1,3,5-trimethyl-1H-pyrazol-4-yl)-1H-benzo[d]imidazol-5-yl)isoxazole (Example Compound 191)

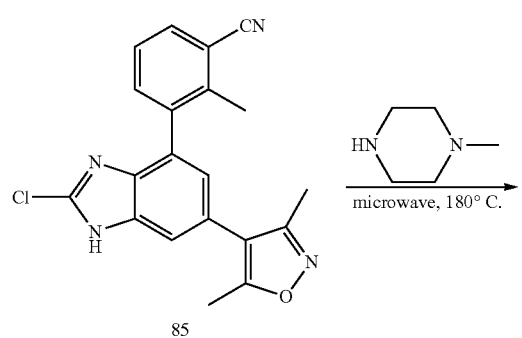

85

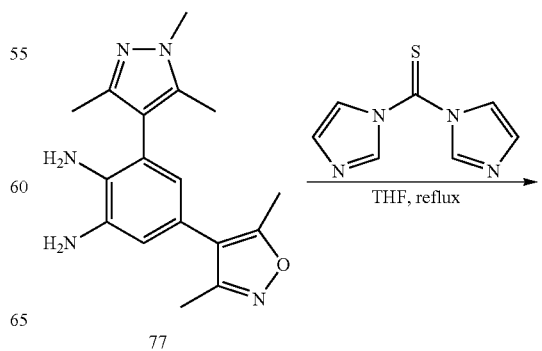

77

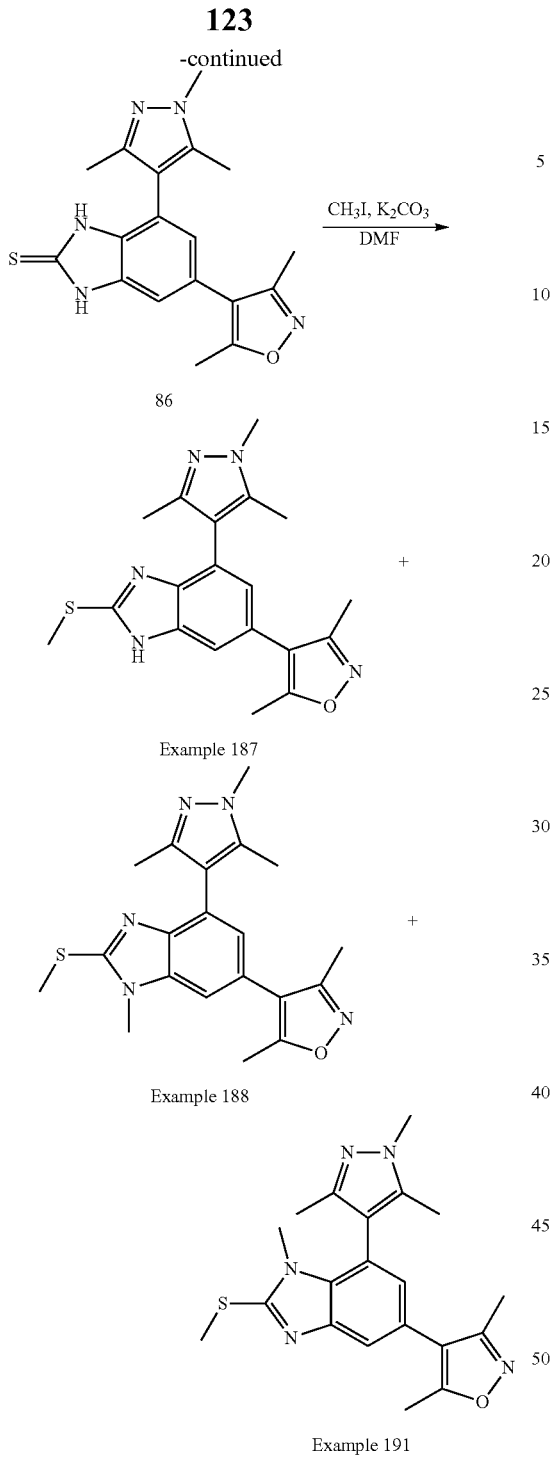

Example 187

Example 188

Example 191

Step 2:

To a suspension of 86 (0.354 g, 1.00 mmol) in anhydrous DMF (10 mL) was added $K_2CO_3$ (0.166 g, 1.20 mmol) followed by methyl iodide (0.075 mL, 1.20 mmol). The reaction was stirred at rt for 16 h. The reaction was concentrated under reduced pressure and the residue was treated with water (50 mL). The resulting precipitate was collected by filtration, washed with water and dried under vacuum. The crude product was purified by flash column chromatography (silica gel, 0-3% methanol/dichloromethane) to give Example Compound 187 (0.110 g, 30%), Example Compound 188 (0.087 g, 23%) and Example Compound 191 (0.067 g, 18%) as white solids. Example Compound 187: $^1$H NMR (400 MHz, $CDCl_3$) δ 11.00 (br.s, 1H), 7.55 (dd, J=1.6, 0.8 Hz, 1H), 6.83 (d, J=1.6 Hz, 1H), 3.71 (s, 3H), 2.83 (s, 3H), 2.45 (s, 3H), 2.32 (s, 3H), 2.17 (s, 3H), 2.07 (s, 3H); ESI MS m/z 368 [M+H]$^+$; Example Compound 188: $^1$H NMR (400 MHz, $CDCl_3$) δ 7.02 (d, J=1.6 Hz, 1H), 6.91 (d, J=1.6 Hz, 1H), 3.82 (s, 3H), 3.72 (s, 3H), 2.78 (s, 3H), 2.45 (s, 3H), 2.32 (s, 3H), 2.31 (s, 3H), 2.30 (s, 3H); ESI MS m/z 382 [M+H]$^+$; Example Compound 191: $^1$H NMR (400 MHz, $CDCl_3$) δ 7.55 (d, J=1.6 Hz, 1H), 6.76 (d, J=1.6 Hz, 1H), 3.84 (s, 3H), 3.36 (s, 3H), 2.82 (s, 3H), 2.44 (s, 3H), 2.31 (s, 3H), 2.12 (s, 3H), 2.10 (s, 3H); ESI MS m/z 382 [M+H]$^+$.

Preparation of 4,4'-(7-bromo-1H-benzo[d]imidazole-4,6-diyl)bis(3,5-dimethylisoxazole) (Example Compound 192)

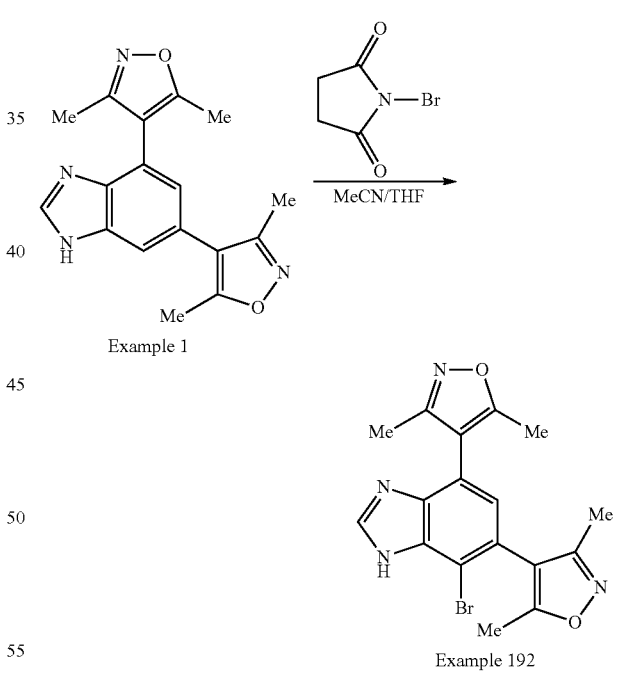

Example 1

Example 192

Step 1:

A solution of 77 (2.10 g, 6.75 mmol) and 1,1'-thiocarbonyldiimidazole (1.80 g, 10.12 mmol) in anhydrous THF (70 mL) was heated at reflux for 16 h under $N_2$. The resulting precipitate was collected by filtration of the hot reaction mixture. The solid material was washed with THF (20 mL) and dried under vacuum to give 86 (1.96 g, 82%) as an off-white solid: $^1$H NMR (400 MHz, DMSO-$d_6$) δ 12.61 (s, 1H), 12.35 (s, 1H), 6.99 (d, J=1.6 Hz, 1H), 6.86 (d, J=1.6 Hz, 1H), 3.68 (s, 3H), 2.40 (s, 3H), 2.22 (s, 3H), 2.08 (s, 3H), 2.03 (s, 3H); ESI MS m/z 354 [M+H]$^+$.

N-bromosuccinimide (0.213 g, 1.2 mmol) was added in one portion to a stirred suspension of Example Compound 1 (0.308 g, 1.0 mmol) in acetonitrile (5 mL) and THF (2 mL). The reaction was stirred at rt for 16 h and the reaction was concentrated under reduced pressure. The residue was dissolved in chloroform (10 mL), washed with saturated $NaHCO_3$ (10 mL), dried over $MgSO_4$, filtered and concentrated under reduced pressure. The crude product was purified by flash column chromatography (silica gel, 0-2% methanol/chloroform) to give Example Compound 192

(0.112 g, 29%) as a white solid: mp 133-135° C.; $^1$H NMR (400 MHz, CDCl$_3$) δ 9.90 (br.s, 1H), 8.19 (br.s, 1H), 6.99 (s, 1H), 2.44 (br.s, 3H), 2.35 (s, 3H), 2.31 (br s, 3H), 2.20 (s, 3H); ESI MS m/z 387 [M+H]$^+$.

Preparation of 3,5-dimethyl-4-(2-(methylsulfinyl)-4-(1,3,5-trimethyl-1H-pyrazol-4-yl)-1H-benzo[d]imidazol-6-yl)isoxazole (Example Compound 194)

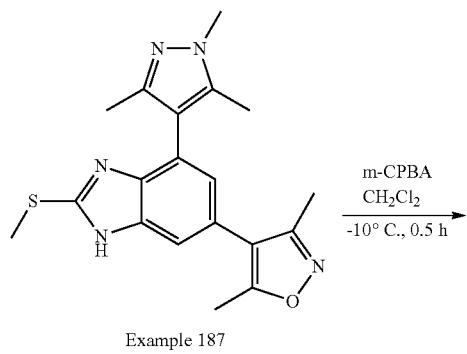

Example 187

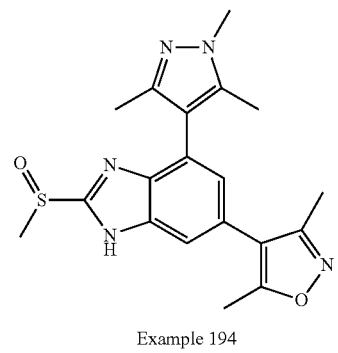

Example 194

To a solution of Example Compound 187 (0.368 g, 1.00 mmol) in anhydrous dichloromethane (50 mL) was added m-chloroperbenzoic acid (0.253 g, 1.10 mmol) at −10° C. in small portions. After the addition was complete the reaction was stirred at −10° C. for 30 min. The reaction was then quenched with saturated NaHCO$_3$ solution (20 mL). The organic phase was separated, washed with water, dried over Na$_2$SO$_4$ and concentrated under reduced pressure. The crude product was purified by flash column chromatography (silica gel, 0-6% methanol/dichloromethane) followed by trituration with diethyl ether to give Example Compound 194 (0.256 g, 67%) as a white solid: m.p. 242-244° C.; $^1$H NMR (400 MHz, CD$_3$OD) δ 7.58 (br.s, 1H), 7.13 (d, J=1.6 Hz, 1H), 3.81 (s, 3H), 3.13 (s, 3H), 2.46 (s, 3H), 2.31 (s, 3H), 2.22 (s, 3H), 2.17 (s, 3H); ESI MS m/z 382 [M−H]$^−$.

Preparation of 3,5-dimethyl-4-(2-(methylsulfonyl)-4-(1,3,5-trimethyl-1H-pyrazol-4-yl)-1H-benzo[d]imidazol-6-yl)isoxazole (Example Compound 195)

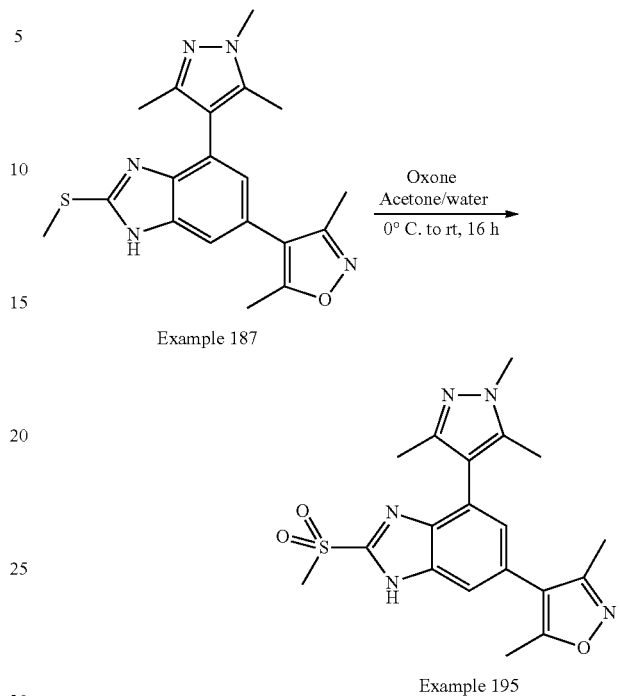

Example 187

Example 195

Oxone (1.35 g, 2.20 mmol) was added at 0° C. to a stirred solution of Example Compound 187 (0.368 g, 1.00 mmol) in acetone (20 mL) and water (20 mL). The reaction was stirred for 30 min. The reaction was allowed to warm to rt and stirred an additional 16 h. The mixture was concentrated under reduced pressure and the residue dissolved in water (20 mL). Solid NaHCO$_3$ was added slowly and a precipitate formed. The mixture was extracted with dichloromethane (100 mL), the organic phase was separated, washed with water, dried over Na$_2$SO$_4$ and concentrated under reduced pressure. The crude product was purified by trituration with diethyl ether to afford Example Compound 195 (0.281 g, 70%) as a white solid: mp 254-256° C.; $^1$H NMR (400 MHz, CD$_3$OD) δ 7.60 (br.s, 1H), 7.18 (d, J 1.1 Hz, 1H), 3.82 (s, 3H), 3.39 (s, 3H), 2.47 (s, 3H), 2.31 (s, 3H), 2.22 (s, 3H), 2.18 (s, 3H); ESI MS m/z 398 [M−H]$^−$.

Preparation of 3-(6-(3,5-dimethylisoxazol-4-yl)-2-(pyrrolidin-1-yl)-1H-benzo[d]imidazol-4-yl)-4-methylbenzonitrile (Example Compound 215) and (3-(6-(3,5-dimethylisoxazol-4-yl)-2-(pyrrolidin-1-yl)-1H-benzo[d]imidazol-4-yl)-4-methylphenyl)(pyrrolidin-1-yl)methanone (Example Compound 218)

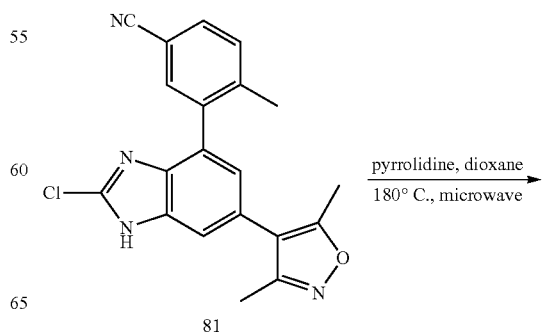

81

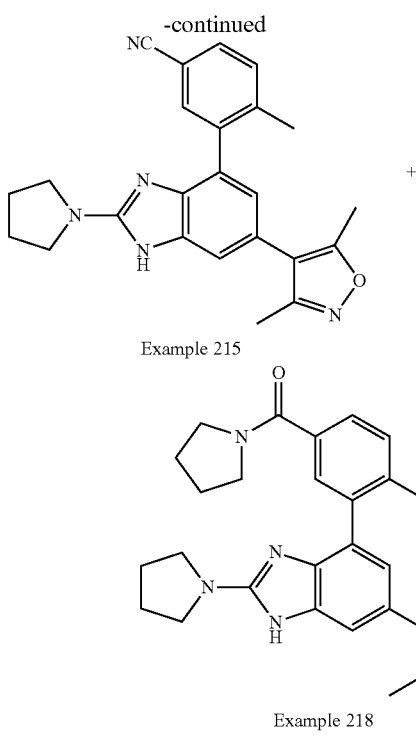

Example 215

Example 218

A mixture of 81 (0.200 g, 0.55 mmol) and pyrrolidine (0.156 g, 2.2 mmol) in 1,4-dioxane (2 mL) was stirred at 180° C. under microwave heating conditions for 4 h. The reaction was cooled to rt and concentrated under reduced pressure. The residue was dissolved in ethyl acetate (20 mL), washed with water (10 mL), brine (10 mL), dried over $Na_2SO_4$ and concentrated under reduced pressure. The crude product was purified by flash column chromatography (silica gel, 0-10% methanol/dichloromethane) to give Example Compound 215 (0.05 g, 22%) and Example Compound 218 (0.02 g, 7.7%) as off-white solids.

Example Compound 215

$^1$H NMR (400 MHz, $CD_3OD$) δ 7.66 (s, 2H), 7.51 (d, J=8.2 Hz, 1H), 7.18 (br.s, 1H), 6.75 (br.s, 1H), 3.53 (t, J=6.4 Hz, 4H), 2.43 (s, 3H), 2.29 (br.s, 3H), 2.28 (s, 3H), 2.04 (t, J=6.4 Hz, 4H); ESI MS m/z 398 [M+H]$^+$; Example Compound 218: $^1$H NMR (400 MHz, $CD_3OD$) δ 7.48 (br.s, 2H), 7.38-7.45 (m, 1H), 7.16 (s, 1H), 6.74 (s, 1H), 3.58 (t, J=6.8 Hz, 4H), 3.53 (t, J=6.4 Hz, 4H), 2.42 (s, 3H), 2.27 (s, 6H), 2.03 (t, J=6.4 Hz, 4H), 1.93-2.00 (m, 2H), 1.85-1.93 (m, 2H); ESI MS m/z 470 [M+H]$^+$.

TABLE 1

Examples prepared using the methods described above

| Example Compound | Chemical Name | Structure | General procedure | Characterization | Purity HPLC (%) |
|---|---|---|---|---|---|
| 1 | 4,4'-(1H-benzo[d]imidazole-4,6-diyl)bis(3,5-dimethyl isoxazole) | $C_{17}H_{16}N_4O_7$ | A | $^1$H NMR (300 MHz, $CD_3OD$) δ 8.26 (s, 1H), 7.57 1H), 7.14 (s, 1H), 2.46 (s, 3H), 2.38 (s, 3H), 2.30 (s, 3H), 2.23 (s, 3H); ESI MS m/z 309 [M + H]+. | 98.7 |
| 2 | 3-(6-(3,5-dimethyl isoxazol-4-yl)-1H-benzo[d]imidazol-4-yl) benzonitrile | $C_{19}H_{14}N_4O$ | D | $^1$H NMR (300 MHz, $CD_3OD$) δ 8.27 (s, 1H), 8.07-8.00 (m, 2H), 7.92 (s, 1H), 7.74-7.63 (m, 2H), 7.48 (d, J = 1.2 Hz, 1H), 2.39 (s, 3H), 2.23 (s, 3H); ESI MS m/z 315 [M + H]+ | 98.0 |

TABLE 1-continued

Examples prepared using the methods described above

| Example Compound | Chemical Name | Structure | General procedure | Characterization | Purity HPLC (%) |
|---|---|---|---|---|---|
| 3 | 4,4'-(quinazoline-2,4-diyl)bis(3,5-dimethylisoxazole) | C₁₈H₁₆N₄O₂ | A | ¹H NMR (500 MHz, CDCl₃) δ 8.09 (d, J = 8.5 Hz, 1H), 7.95-7.91 (m, 1H), 7.75-7.74 (m, 1H), 7.62-7.59 (m, 1H), 2.88 (s, 3H), 2.71 (s, 3H), 2.43 (s, 3H), 2.31 (s, 3H); ESI MS m/z 321 [M + H]+. | 96.5 |
| 4 | N-benzyl-6-(3,5-dimethyl-isoxazol-4-yl)-1H-benzo[d]imidazol-4-amine | C₁₉H₂₈N₄O | G | ¹H NMR (500 MHz, CD₃OD) δ 8.06 (s, 1H), 7.32 (m, 2H), 7.31 (m, 2H), 7.22 (m, 1H), 6.74 (s, 1H), 6.12 (s, 1H), 4.53 (s, 2H), 2.22 (s, 3H), 2.05 (s, 3H); ESI m/z 319 [M + H]+. | 98.5 |
| 5 | N-benzyl-2-(3,5-dimethyl-isoxazol-4-yl)quinazolin-4-amine | C₂₀H₁₈N₄O | B | ¹H NMR (500 MHz, CDCl₃) δ 7.85 (d, J = 7.5 Hz, 1H), 7.75-7.68 (m, 2H), 7.44-7.36 (m, 5H), 7.34-7.31 (m, 1H), 5.93 (s, 1H), 4.91 (d, J = 5.0 Hz, 2H), 2.80 (s, 3H), 2.64 (s, 3H); ESI m/z 331 [M + H]+. | 99.0 |
| 6 | 4,4'-(2-methyl-1H-benzo[d]imidazole-4,6-diyl)bis(3,5-dimethylisoxazole) | C₁₈H₁₈N₄O₂ | A | ¹H NMR (300 MHz, CD₃OD) δ 7.47 (s, 1H), 7.05 (d, J = 1.5 Hz, 1H), 2.58 (s, 3H), 2.44 (s, 3H), 2.37 (s, 3H), 2.29 (s, 3H), 2.22 (s, 3H); ESI MS m/z 323 [M + H]+ | >99 |

TABLE 1-continued

Examples prepared using the methods described above

| Example Compound | Chemical Name | Structure | General procedure | Characterization | Purity HPLC (%) |
|---|---|---|---|---|---|
| 7 | 6-(3,5-dimethyl isoxazol-4-yl)-N-phenyl-1H-benzo[d]imidazol-4-amine | $C_{18}H_{16}N_4O$ | E | $^1$H NMR (300 MHz, CD$_3$OD) δ 8.03 (s, 1H), 7.35 (s, 1H), 7.25-7.20 (m, 2H), 7.12-7.09 (m, 2H), 6.90 (d, J = 1.8 Hz, 1H), 6.86-6.81 (m, 1H), 2.37 (s, 3H), 2.22 (s, 3H); ESI MS m/z 305 [M + H]+ | 97.6 |
| 8 | 4,4'-(imidazo[1,2-a]pyridine-6,8-diyl)bis(3,5-dimethyl isoxazole) | $C_{17}H_{16}N_4O_2$ | A | $^1$H NMR (500 MHz, CDCl$_3$) δ 8.08 (d, J = 1.5 Hz, 1H), 7.73-7.72 (m, 2H), 6.91 (d, J = 2.0 Hz, 1H), 2.47 (s, 3H), 2.46 (s, 3H), 2.32 (s, 3H), 2.31 (s, 3H); ESI m/z 309 [M + H]+. | 95.4 |
| 9 | 3,5-dimethyl-4-(4-(1,3,5-trimethyl-1H-pyrazol-4-yl)-1H-benzo[d]imidazol-6-yl)isoxazole | $C_{18}H_{19}N_5O$ | D | $^1$H NMR (300 MHz, CD$_3$OD) δ 8.23 (s, 1H), 7.56 (s, 1H), 7.06 (d, J = 1.2 Hz, 1H), 3.83 (s, 3H), 2.48 (s, 3H), 2.32 (s, 3H), 2.22 (s, 3H), 2.18 (s, 3H); ESI MS m/z 322 [M + H]+ | >99 |
| 10 | 4,4'-(imidazo[1,2-a]pyrazine-6,8-diyl)bis(3,5-dimethyl isoxazole) | $C_{16}H_{15}N_5O_2$ | A | $^1$H NMR (500 MHz, CDCl$_3$) δ 8.09 (s, 1H), 7.86 (d, J = 1.1 Hz, 1H), 7.80 (d, J = 0.97 Hz, 1H), 2.62 (s, 3H), 2.60 (s, 3H), 2.44 (s, 6H); ESI MS m/z 310 [M + H]+. | >99 |

TABLE 1-continued

Examples prepared using the methods described above

| Example Compound | Chemical Name | Structure | General procedure | Characterization | Purity HPLC (%) |
|---|---|---|---|---|---|
| 11 | 6,8-bis(3,5-dimethyl-isoxazol-4-yl)-2H-benzo[b][1,4]oxazin-3(4H)-one | C$_{18}$H$_{17}$N$_3$O$_4$ | none | $^1$H NMR (300 MHz, DMSO-d$_6$) δ 10.84 (s, 1H), 6.94-6.91 (m, 2H), 4.66 (s, 2H), 2.42 (s, 3H), 2.33 (s, 3H), 2.24 (s, 3H), 2.17 (s, 3H); MM m/z 340 [M + H]+. | >99 |
| 12 | 2-(3,5-dimethyl-isoxazol-4-yl)-6,7-dimethoxy-N-phenyl-quinazolin-4-amine | C$_{21}$H$_{20}$N$_4$O$_3$ | B | $^1$H NMR (500 MHz, CDCl$_3$) δ 10.90 (s, 1H), 7.71 (m, 3H), 7.31 (m, 2H), 7.23 (m, 1H), 7.09 (s, 1H), 3.85 (s, 3H), 3.79 (s, 3H), 2.61 (s, 3H), 2.31 (s, 3H); ESI MS m/z 377 [M + H]+. | >99 |
| 13 | 6,8-bis(3,5-dimethyl-isoxazol-4-yl)-3,4-dihydro-2H-benzo[b][1,4]oxazine | C$_{18}$H$_{29}$N$_3$O$_3$ | none | $^1$H NMR (300 MHz, CDCl$_3$) δ 6.48 (d, J = 2.1 Hz, 1H), 6.35 (d, J = 2.1 Hz, 1H), 4.28 (t, J = 4.4 Hz, 2H), 3.95 (br s, 1H), 3.51-3.47 (m, 2H), 2.40 (s, 3H), 2.35 (s, 3H), 2.27 (s, 3H), 2.23 (s, 3H); MM m/z 326 [M + H]+. | >99 |
| 14 | 3,5-dimethyl-4-(6-(1,3,5-trimethyl-1H-pyrazol-4-yl)-1H-benzo[d]imidazol-4-yl)isoxazole | C$_{18}$H$_{19}$N$_5$O | none | $^1$H NMR (300 MHz, CD$_3$OD) δ 8.23 (s, 1H), 7.54 (s, 1H), 7.07 (d, J = 1.5 Hz, 1H), 3.80 (s, 3H), 2.40 (s, 3H), 2.32 (s, 3H), 2.25 (s, 6H); ESI MS m/z 322 [M + H]+ | 96.3 |

TABLE 1-continued

Examples prepared using the methods described above

| Example Compound | Chemical Name | Structure | General procedure | Characterization | Purity HPLC (%) |
|---|---|---|---|---|---|
| 15 | 6-(3,5-dimethyl isoxazol-4-yl)-N-phenyl-[1,2,4]triazolo[4,3-a]pyridin-8-amine | C₁₇H₁₅N₅O | C | ¹H NMR (500 MHz, CDCl₃) δ 8.32 (s, 1H), 7.99 (d, J = 1.0 Hz, 1H), 7.42-7.39 (m, 2H), 7.31-7.29 (m, 2H), 7.16-7.14 (m, 1H), 7.09 (s, 1H), 6.95 (d, J = 1.5 Hz, 1H), 2.43 (s, 3H), 2.28 (s, 3H); ESI m/z 306 [M + H]+. | 98.6 |
| 16 | 3,5-dimethyl-4-(4-(1-methyl-1H-pyrazol-5-yl)-1H-benzo[d]imidazol-6-yl)isoxazole | C₁₆H₁₅N₅O | D | ¹H NMR (500 MHz, DMSO-d₆) δ 12.90-12.40 (bs, 1H), 8.33 (s, 1H), 7.90-7.50 (m, 2H), 7.22 (s, 1H), 6.54 (d, J = 1.7 Hz, 1H), 3.87 (s, 3H), 2.44 (s, 3H), 2.27 (s, 3H); ESI m/z 294 [M + H]+. | >99 |
| 17 | 4,4'-([1,2,4]triazolo[1,5-a]pyridine-6,8-diyl)bis(3,5-dimethylisoxazole) | C₁₆H₁₅N₅O₂ | A | ¹H NMR (300 MHz, CDCl₃) δ 8.56 (d, J = 1.5 Hz, 1H), 8.43 (s, 1H), 7.27 (s, 1H), 2.50 (s, 3H), 2.49 (s, 3H), 2.35 (s, 3H), 2.34 (s, 3H); ESI m/z 310 [M + H]+. | >99 |
| 18 | 4-(4-(1,3-dimethyl-1H-pyrazol-4-yl)-1H-benzo[d]imidazol-6-yl)-3,5-dimethylisoxazole | C₁₇H₁₇N₅O | D | 1H NMR (300 MHz, CD₃OD) δ 8.31 (s, 1H), 7.92 (s, 1H), 7.50 (d, J = 1.5 Hz, 1H), 7.17 (d, J = 1.5 Hz, 1H), 3.92 (s, 3H), 2.45 (s, 3H), 2.31 (s, 3H), 2.30 (s, 3H); ESI m/z 308 [M + H]+. | >99 |

TABLE 1-continued

Examples prepared using the methods described above

| Example Compound | Chemical Name | Structure | General procedure | Characterization | Purity HPLC (%) |
|---|---|---|---|---|---|
| 19 | 3,5-dimethyl-4-(4-(2-(trifluoromethyl)phenyl)-1H-benzo[d]imidazol-6-yl)isoxazole | $C_{19}H_{14}F_3N_3O$ | D | $^1$H NMR (300 MHz, CD$_3$OD) δ 8.18 (s, 1H), 7.88 (d, J = 7.2 Hz, 1H), 7.73-7.63 (m, 3H), 7.51 (d, J = 7.5 Hz, 1H), 7.08 (s, 1H), 2.43 (s, 3H), 2.28 (s, 3H); ESI m/z 358 [M + H]+. | >99 |
| 20 | 3,5-dimethyl-4-(4-(4-methylpyridin-3-yl)-1H-benzo[d]imidazol-6-yl)isoxazole | $C_{18}H_{16}N_4O$ | D | $^1$H NMR (300 MHz, CD$_3$OD) δ 8.45 (br.s, 2H), 8.25 (s, 1H), 7.67 (br.s, 1H), 7.47 (br.s, 1H), 7.14 (s, 1H), 2.46 (s, 3H), 2.30 (s, 3H), 2.27 (s, 3H); ESI m/z 305 [M + H]+. | >99 |
| 21 | 4,4'-(1H-indazole-5,7-diyl)bis(3,5-dimethylisoxazole) | $C_{17}H_{16}N_4O_2$ | H | $^1$H NMR (300 MHz, DMSO-d$_6$) δ 13.1 (s, 1H), 8.20 (s, 1H), 7.81 (s, 1H), 7.28 (s, 1H), 2.44 (s, 3H), 2.34 (s, 3H), 2.27 (s, 3H), 2.17 (s, 3H). ESI m/z 309 [M + H]+. | >99 |
| 22 | 3,5-dimethyl-4-(4-(pyrimidin-5-yl)-1H-benzo[d]imidazol-6-yl)isoxazole | $C_{16}H_{13}N_5O$ | D | $^1$H NMR (300 MHz, CD$_3$OD) δ 9.38 (s, 2H), 9.19 (s, 1H), 8.34 (s, 1H), 7.63 (s, 1H), 7.46 (s, 1H), 2.46 (s, 3H), 2.31 (s, 3H); ESI MS m/z 297 [M + H]+. | >99 |

TABLE 1-continued

Examples prepared using the methods described above

| Example Compound | Chemical Name | Structure | General procedure | Characterization | Purity HPLC (%) |
|---|---|---|---|---|---|
| 23 | 3,5-dimethyl-4-(4-(1-methyl-1H-indazol-4-yl)-1H-benzo[d]imidazol-6-yl)isoxazole | $C_{20}H_{17}N_5O$ | D | $^1$H NMR (300 MHz, CD$_3$OD) δ 8.24 (s, 1H), 7.87 (s, 1H), 7.67-7.57 (m, 3H), 7.45 (d, J = 6.0 Hz, 1H), 7.39 (s, 1H), 4.13 (s, 3H), 2.48 (s, 3H), 2.33 (s, 3H); ESI MS m/z 344 [M + H]+. | 98.5 |
| 24 | N-benzyl-6-(3,5-dimethyl-isoxazol-4-yl)-[1,2,4]triazolo[4,3-a]pyridin-8-amine | $C_{18}H_{17}N_5O$ | C | $^1$H NMR (500 MHz, CDCl$_3$) δ 8.30 (s, 1H), 7.88 (s, 1H), 7.40-7.34 (m, 4H), 7.31-7.28 (m, 1H), 6.12 (s, 1H), 4.55 (s, 2H), 2.28 (s, 3H), 2.10 (s, 3H); ESI m/z 320 [M + H]+. | >99 |
| 25 | 6-(3,5-dimethyl-isoxazol-4-yl)-N-(4-methoxy-phenyl)-1H-benzo[d]imidazol-4-amine | $C_{19}H_{18}N_4O_2$ | E | $^1$H NMR (500 MHz, CDCl$_3$) δ 8.52 (s, 1H), 7.21 (d, J = 1.0 Hz, 1H), 6.84-6.89 (m, 2H), 6.73 (d, J = 1.0 Hz, 1H), 3.81 (s, 3H), 2.36 (s, 3H), 2.22 (s, 3H); ESI m/z 335 [M + H]+. | 95.0 |
| 26 | 3,5-dimethyl-4-(4-(4-methyl thiazol-5-yl)-1H-benzo[d]imidazol-6-yl)isoxazole | $C_{16}H_{14}N_4OS$ | D | $^1$H NMR (300 MHz, CD$_3$OD) δ 9.03 (s, 1H), 8.28 (s, 1H), 7.56 (s, 1H), 7.25 (d, J = 1.5 Hz, 1H), 2.46 (s, 3H), 2.42 (s, 3H), 2.30 (s, 3H); ESI MS m/z 311 [M + H]+. | 95.5 |

TABLE 1-continued

Examples prepared using the methods described above

| Example Compound | Chemical Name | Structure | General procedure | Characterization | Purity HPLC (%) |
|---|---|---|---|---|---|
| 27 | 3,5-dimethyl-4-(4-(2-methyl pyridin-3-yl)-1H-benzo[d]imidazol-6-yl)isoxazole | $C_{18}H_{16}N_4O$ | D | $^1$H NMR (300 MHz, CD$_3$OD) δ 8.51 (d, J = 6.0 Hz, 1H), 8.24 (s, 1H), 7.83-7.80 (m, 1H), 7.63 (s, 1H), 7.43-7.41 (m, 1H), 7.14 (d, J = 1.5 Hz, 1H), 2.46 (s, 3H), 2.42 (s, 3H), 2.30 (s, 3H); ESI MS m/z 305 [M + H]+. | >99 |
| 28 | 1-(2-(6-(3,5-dimethyl-isoxazol-4-yl)-1H-benzo[d]imidazol-4-yl)phenyl)-N,N-dimethyl methanamine | $C_{21}H_{22}N_4O$ | D | $^1$H NMR (300 MHz, CD$_3$OD) δ 8.20 (s, 1H), 7.63-7.60 (m, 2H), 7.48-7.39 (m, 3H), 7.10 (d, J = 1.8 Hz, 1H), 3.45 (br.s, 2H), 2.45 (s, 3H), 2.29 (s, 3H), 2.07 (s, 6H); ESI m/z 347 [M + H]+. | >99 |
| 29 | 3,5-dimethyl-4-(4-(1-methyl-1H-pyrazol-4-yl)-1H-benzo[d]imidazol-6-yl)isoxazole | $C_{16}H_{15}N_5O$ | D | $^1$H NMR (300 MHz, CD$_3$OD) δ 8.39 (br.s, 1H), 8.25 (s, 1H), 8.16 (br.s, 1H), 7.37 (br.s, 2H), 3.99 (s, 3H), 2.44 (s, 3H), 2.29 (s, 3H); ESI m/z 294 [M + H]+. | >99 |
| 30 | 4,6-bis(3,5-dimethyl-isoxazol-4-yl)-N-methyl-1H-benzo[d]imidazol-2-amine | $C_{18}H_{19}N_5O_2$ | F | $^1$H NMR (300 MHz, CD$_3$OD) δ 7.16 (s, 1H), 6.81 (d, J = 1.5 Hz, 1H), 2.99 (s, 3H), 2.43 (s, 3H), 2.37 (s, 3H), 2.28 (s, 3H), 2.23 (s, 3H); ESI m/z 338 [M + H]+. | >99 |

TABLE 1-continued

Examples prepared using the methods described above

| Example Compound | Chemical Name | Structure | General procedure | Characterization | Purity HPLC (%) |
|---|---|---|---|---|---|
| 31 | N-benzyl-4,6-bis(3,5-dimethyl isoxazol-4-yl)-1H-benzo[d]imidazol-2-amine | C$_{24}$H$_{23}$N$_5$O$_2$ | F | $^1$H NMR (300 MHz, CD$_3$OD) δ 7.40-7.24 (m, 5H), 7.16 (s, 1H), 6.81 (d, J = 1.5 Hz, 1H), 4.59 (s, 2H), 2.42 (s, 3H), 2.31 (s, 3H), 2.27 (s, 3H), 2.18 (s, 3H); ESI m/z 414 [M + H]+. | 98.8 |
| 32 | 6-(3,5-dimethyl-isoxazol-4-yl)-N-(3-fluorophenyl)-1H-benzo[d]imidazol-4-amine | C$_{18}$H$_{25}$FN$_4$O | E | $^1$H NMR (500 MHz, CDCl$_3$) δ 8.06 (s, 1H), 7.15-6.90 (m, 5H), 6.68 (t, J = 2.5 Hz, 1H), 2.42 (s, 3H), 2.28 (s, 3H); ESI m/z 323 [M + H]+. | 95.9 |
| 33 | 6-(3,5-dimethyl-isoxazol-4-yl)-N-(3-methoxy-phenyl)-1H-benzo[d]imidazol-4-amine | C$_{19}$H$_{18}$N$_4$O$_2$ | E | $^1$H NMR (500 MHz, CDCl$_3$) δ 8.09 (s, 1H), 7.24 (d, J = 1.0 Hz, 1H), 7.00 (s, 1H), 6.91 (s, 1H), 6.83 (d, J = 2.5 Hz, 1H), 6.78 (s, 1H), 6.55 (d, J = 2.5 Hz, 1H), 3.81 (s, 3H), 2.36 (s, 3H), 2.22 (s, 3H); ESI m/z 335 [M + H]+. | 96.9 |
| 34 | 4,4'-(2-(trifluoromethyl)-1H-benzo[d]imidazole-4,6-diyl)bis(3,5-dimethyl isoxazole) | C$_{18}$H$_{15}$F$_3$N$_4$O$_2$ | none | $^1$H NMR (500 MHz, CD$_3$OD) δ 7.65 (s, 1H), 7.27 (s, 1H), 2.47 (s, 3H), 2.40 (s, 3H), 2.31 (s, 3H), 2.25 (s, 3H); MM m/z 377 [M + H]+. | >99 |

TABLE 1-continued

Examples prepared using the methods described above

| Example Compound | Chemical Name | Structure | General procedure | Characterization | Purity HPLC (%) |
|---|---|---|---|---|---|
| 35 | 6-(3,5-dimethyl-isoxazol-4-yl)-N-(pyridin-3-ylmethyl)-1H-benzo[d]imidazol-4-amine | C$_{18}$H$_{17}$N$_5$O | G | $^1$H NMR (300 MHz, CD$_3$OD) δ 8.61 (d, J = 1.5 Hz, 1H), 8.42 (dd, J = 8.0, 1.5 Hz, 1H), 8.10 (s, 1H), 7.94-7.90 (m, 1H), 7.43-7.39 (m, 1H), 6.78 (d, J = 1.2 Hz, 1H), 6.13 (d, J = 1.2 Hz, 1H), 4.63 (s, 2H), 2.24 (s, 3H), 2.07 (s, 3H); ESI MS m/z 320 [M + H]+. | >99 |
| 36 | 3-(6-(3,5-dimethyl-isoxazol-4-yl)-1H-benzo[d]imidazol-4-yl)benzamide | C$_{19}$H$_{16}$N$_4$O$_2$ | D | $^1$H NMR (300 MHz, CD$_3$OD) δ 8.30 (d, J = 6.5 Hz, 1H), 8.27 (s, 1H), 7.98-7.96 (m, 1H), 7.91 (d, J = 7.8 Hz, 1H), 7.64 (t, J = 7.8 Hz, 1H), 7.58 (s, 1H), 7.36 (d, J = 1.5 Hz, 1H), 2.46 (s, 3H), 2.31 (s, 3H); ESI MS m/z 333 [M + H]+. | 98.7 |
| 37 | 6-(3,5-dimethyl-isoxazol-4-yl)-N-((1,3,5-trimethyl-1H-pyrazol-4-yl)methyl)-1H-benzo[d]imidazol-4-amine | C$_{19}$H$_{22}$N$_6$O | G | $^1$H NMR (300 MHz, CD$_3$OD) δ 8.04 (s, 1H), 6.79 (d, J = 1.2 Hz, 1H), 6.34 (d, J = 1.5 Hz, 1H), 4.22 (s, 2H), 3.71 (s, 3H), 2.40 (s, 3H), 2.27 (s, 3H), 2.25 (s, 3H), 2.21 (s, 3H), 2.01 (s, 3H); ESI MS m/z 373 [M + Na]+. | 93.0 |

TABLE 1-continued

Examples prepared using the methods described above

| Example Compound | Chemical Name | Structure | General procedure | Characterization | Purity HPLC (%) |
|---|---|---|---|---|---|
| 38 | 6-(3,5-dimethyl-isoxazol-4-yl)-N-(4-fluorobenzyl)-1H-benzo[d]imidazol-4-amine | $C_{19}H_{17}FN_4O$ | G | 1H NMR (300 MHz, CD$_3$OD) δ 8.07 (s, 1H), 7.46-7.42 (m, 2H), 7.08-7.02 (m, 2H), 6.76 (s, 1H), 6.12 (d, J = 0.9 Hz, 1H), 4.51 (s, 2H), 2.25 (s, 3H), 2.08 (s, 3H); ESI m/z 337 [M + H]+. | >99 |
| 39 | 6-(3,5-dimethyl-isoxazol-4-yl)-N-((3,5-dimethyl-isoxazol-4-yl)methyl)-1H-benzo[d]imidazol-4-amine | $C_{18}H_{19}N_5O_2$ | G | $^1$H NMR (300 MHz, CD$_3$OD) δ 8.07 (s, 1H), 6.81 (d, J = 1.2 Hz, 1H), 6.31 (d, J = 1.2 Hz, 1H), 4.28 (s, 2H), 2.39 (s, 3H), 2.38 (s, 3H), 2.27 (s, 3H), 2.23 (s, 3H); ESI MS m/z 338 [M + H]+. | 98.0 |
| 40 | N-(4-chlorophenyl)-6-(3,5-dimethyl-isoxazol-4-yl)-1H-benzo[d]imidazol-4-amine | $C_{18}H_{15}ClN_4O$ | E | $^1$H NMR (500 MHz, CD$_3$OD) δ 9.16 (s, 1H), 7.31-7.29 (m, 3H), 7.16 (s, 1H), 7.09-7.07 (m, 2H), 2.43 (s, 3H), 2.26 (s, 3H); ESI MS m/z 339 [M + H]+. | >99 |
| 41 | 3,5-dimethyl-4-(2-methyl-4-(2-methylpyridin-3-yl)-1H-benzo[d]imidazol-6-yl)isoxazole | $C_{19}H_{18}N_4O$ | D | $^1$H NMR (300 MHz, CD$_3$OD) δ 8.50 (br.s, 1H), 7.80 (dd, J = 7.6, 1.3 Hz, 1H), 7.47-7.38 (m, 2H), 7.04 (d, J = 1.4 Hz, 1H), 2.56 (s, 3H), 2.44 (s, 3H), 2.42 (s, 3H), 2.29 (s, 3H); ESI m/z 319 [M + H]+. | >99 |

TABLE 1-continued

Examples prepared using the methods described above

| Example Compound | Chemical Name | Structure | General procedure | Characterization | Purity HPLC (%) |
|---|---|---|---|---|---|
| 42 | N-(6-(3,5-dimethyl-isoxazol-4-yl)-1H-benzo[d]imidazol-4-yl)-3,5-dimethyl-isoxazol-4-amine | $C_{17}H_{17}N_5O_2$ | E | $^1$H NMR (500 MHz, CDCl$_3$) δ 8.13 (s, 1H), 6.80 (s, 1H), 6.20 (s, 1H), 6.02 (d, J = 1.0 Hz, 1H), 2.38 (s, 6H), 2.21 (s, 3H), 2.18 (s, 3H); ESI m/z 324 [M + H]+. | >99 |
| 43 | 6-(3,5-dimethyl-isoxazol-4-yl)-N-(pyrimidin-2-yl)-1H-benzo[d]imidazol-4-amine | $C_{16}H_{14}N_6O$ | E | $^1$H NMR (500 MHz, CDCl$_3$) δ 8.49 (d, J = 4.5 Hz, 2H), 8.15 (s, 1H), 8.05 (s, 1H), 7.18 (s, 1H), 6.80 (t, J = 4.5 Hz, 1H), 2.47 (s, 3H), 2.34 (s, 3H); ESI m/z 307 [M + H]+. | >99 |
| 44 | N-(6-(3,5-dimethyl-isoxazol-4-yl)-1H-benzo[d]imidazol-4-yl)-4-methyl-isoxazol-3-amine | $C_{16}H_{15}N_5O_2$ | E | $^1$H NMR (500 MHz, CDCl$_3$) δ 8.03 (s, 1H), 7.71 (s, 1H), 7.53 (s, 1H), 6.97 (s, 1H), 5.83 (s, 1H), 2.45 (s, 3H), 2.39 (s, 3H), 2.32 (s, 3H); ESI m/z 310 [M + H]+. | 98.9 |
| 45 | 4,4'-(2-isopropyl-1H-benzo[d]imidazole-4,6-diyl)bis(3,5-dimethylisoxazole) | $C_{20}H_{22}N_4O_2$ | I | $^1$H NMR (500 MHz, CD$_3$OD) δ 7.69 (d, J = 1.4 Hz, 1H), 7.40 (d, J = 1.4 Hz, 1H), 3.55-3.40 (m, 1H), 2.46 (s, 3H), 2.38 (s, 3H), 2.30 (s, 3H) 2.21 (s, 3H), 1.53 (d, J = 7.0 Hz, 6H); ESI m/z 351 [M + H]+. | 99.0 |

TABLE 1-continued

Examples prepared using the methods described above

| Example Compound | Chemical Name | Structure | General procedure | Characterization | Purity HPLC (%) |
|---|---|---|---|---|---|
| 46 | 4,4'-(2-ethoxy-1H-benzo[d]imidazole-4,6-diyl)bis(3,5-dimethylisoxazole) | $C_{19}H_{20}N_4O_3$ | J | $^1$H NMR (500 MHz, CD$_3$OD) δ 7.50-7.10 (m, 1H), 6.94 (d, J = 1.5 Hz, 1H), 4.53 (q, J = 7.1 Hz, 2H), 2.42 (s, 3H), 2.38 (s, 3H), 2.27 (s, 3H), 2.24 (s, 3H), 1.45 (d, J = 7.1 Hz, 3H); ESI m/z 353 [M + H]+. | 98.1 |
| 47 | 6-(3,5-dimethyl-isoxazol-4-yl)-N-(pyridin-2-ylmethyl)-1H-benzo[d]imidazol-4-amine | $C_{18}H_{17}N_5O$ | G | $^1$H NMR (300 MHz, CD$_3$OD) δ 8.53-8.51 (m, 1H), 8.10 (s, 1H), 7.77 (td, J = 7.8, 1.8 Hz, 1H), 7.54 (d, J = 7.8 Hz, 1H), 7.30 (dd, J = 6.3, 1.8 Hz, 1H), 6.77 (s, 1H), 6.06 (s, 1H), 4.65 (s, 2H), 2.23 (s, 3H), 2.06 (s, 3H); ESI MS m/z 320 [M + H]+. | >99 |
| 48 | 4-(4-(2-methoxy-pyridin-3-yl)-1H-benzo[d]imidazol-6-yl)-3,5-dimethyl isoxazole | $C_{18}H_{26}N_4O_2$ | D | $^1$H NMR (300 MHz, CD$_3$OD) δ 8.23 (d, J = 4.5 Hz, 1H), 8.21 (s, 1H), 7.86 (d, J = 6.0 Hz, 1H), 7.60 (s, 1H), 7.24 (s, 1H), 7.12 (dd, J = 7.2, 5.1 Hz, 1H), 3.95 (s, 3H), 2.46 (s, 3H), 2.31 (s, 3H); ESI MS m/z 321 [M + H]+. | 98.4 |
| 49 | 3,5-dimethyl-4-(2-methyl-4-(1,3,5-trimethyl-1H-pyrazol-4-yl)-1H-benzo[d]imidazol-6-yl)isoxazole | $C_{19}H_{21}N_5O$ | D | $^1$H NMR (300 MHz, CD$_3$OD) δ 7.66 (d, J = 1.5 Hz, 1H), 7.34 (d, J = 1.5 Hz, 1H), 3.84 (s, 3H), 2.85 (s, 3H), 7.47 (s, 3H), 2.30 (s, 3H), 2.21 (s, 3H), 2.15 (s, 3H); ESI m/z 336 [M + H]+. | 97.7 |

TABLE 1-continued

Examples prepared using the methods described above

| Example Compound | Chemical Name | Structure | General procedure | Characterization | Purity HPLC (%) |
|---|---|---|---|---|---|
| 50 | 3,5-dimethyl-4-(2-methyl-4-(4-(trifluoromethyl)pyridin-3-yl)-1H-benzo[d]imidazol-6-yl)isoxazole | C₁₉H₁₅F₃N₄O | D | ¹H NMR (500 MHz, CD₃OD) δ 9.00-8.80 (m, 1H), 8.73 (s, 1H), 7.88 (s, 1H), 7.60-7.40 (m, 1H), 7.07 (s, 1H), 2.54 (s, 3H), 2.42 (s, 3H), 2.26 (s, 3H); ESI m/z 373 [M + H]+. | >99 |
| 51 | 4-(4-(2-methoxy-5-methylphenyl)-1H-benzo[d]imidazol-6-yl)-3,5-dimethylisoxazole | C₂₀H₁₉N₃O₂ | D | ¹H NMR (500 MHz, DMSO-d₆) δ 12.5-12.14 (m, 1H), 8.21-8.19 (m, 1H), 7.61 (s, 0.7H), 7.43 (d, J = 1.5 Hz, 0.56H), 7.25-7.03 (m, 3.77H), 3.71 (m, 3H), 2.44 (m, 3H), 2.31-2.26 (m, 6H); ESI m/z 334 [M + H]+. | >99 |
| 52 | 3,5-dimethyl-4-(2-methyl-7-(3-methylisothiazol-4-yl)-1H-benzo[d]imidazol-5-yl)isoxazole | C₁₇H₁₆N₄OS | L | ¹H NMR (300 MHz, CD₃OD-d₄) δ 8.92 (s, 1H), 7.46 (s, 1H), 7.10 (d, J = 1.50 Hz, 1H), 2.57 (s, 3H), 2.44 (br s, 6H), 2.29 (s, 3H); MS m/z 325 [M + H]+. | 97.6 |
| 53 | 3,5-dimethyl-4-(2-methyl-4-(4-methylpyridin-3-yl)-1H-benzo[d]imidazol-6-yl)isoxazole | C₁₉H₁₈N₄O | D | ¹H NMR (300 MHz, CD₃OD) δ 8.45 (s, 2H), 7.60-7.40 (m, 2H), 7.04 (d, J = 1.5 Hz, 1H), 2.56 3H), 2.45 (s, 3H), 2.29 (s, 3H), 2.27 (s, 3H); ESI m/z 319 [M + H]+. | >99 |

TABLE 1-continued

Examples prepared using the methods described above

| Example Compound | Chemical Name | Structure | General procedure | Characterization | Purity HPLC (%) |
|---|---|---|---|---|---|
| 54 | 4,4'-(1-methyl-1H-indazole-5,7-diyl)bis(3,5-dimethyl-isoxazole) | C₁₅H₁₈N₄O₂ | none | ¹H NMR (500 MHz, CDCl₃) δ 8.08 (s, 1H), 7.64 (d, J = 1.5 Hz, 1H), 7.0 (d, J = 1.5 Hz, 1H), 3.80 (s, 3H), 2.44 (s, 3H), 2.34 (s, 3H), 2.30 (s, 3H), 2.16 (s, 3H); ESI m/z 323 [M + H]+. | >99 |
| 55 | 4,4'-(2-methyl-2H-indazole-5,7-diyl)bis(3,5-dimethyl-isoxazole) | C₁₈H₁₈N₄O₂ | none | ¹H NMR (500 MHz, CDCl₃) δ 8.01 (s, 1H), 7.53 (d, J = 1.5 Hz, 1H), 6.98 (d, J = 1.5 Hz, 1H), 4.26 (s, 3H), 2.45 (s, 3H), 2.44 (s, 3H), 2.31 (s, 6H); ESI m/z 323 [M + H]+. | >99 |
| 56 | 3-(6-(3,5-dimethyl-isoxazol-4-yl)-1H-benzo[d]imidazol-4-yl)pyridin-2(1H)-one | C₁₇H₁₄N₄O₂ | D | ¹H NMR (300 MHz, CD₃OD) δ 8.34 (s, 1H), 7.93 (dd, J = 6.6, 2.1 Hz, 1H), 7.61 (d, J = 1.5 Hz, 1H), 7.55 (dd, J = 6.6, 2.1 Hz, 1H), 7.40 (d, J = 1.5 Hz, 1H), 6.59-6.55 (m, 1H), 2.45 (s, 3H), 2.30 (s, 3H); ESI MS m/z 307 [M + H]+. | >99 |
| 57 | 3-(6-(3,5-dimethyl-isoxazol-4-yl)-1H-benzo[d]imidazol-4-yl)-2-methyl-benzonitrile | C₂₀H₁₆N₄O | D | ¹H NMR (300 MHz, CD₃OD) δ 8.24 (s, 1H), 7.78 (d, J = 6.9 Hz, 1H), 7.65 (d, J = 6.9 Hz, 1H), 7.65-7.60 (m, 1H), 7.51-7.46 (m, 1H), 7.11 (s, 1H), 2.45 (s, 3H), 2.38 (s, 3H), 2.30 (s, 3H); ESI MS m/z 329 [M + H]+. | >99 |

TABLE 1-continued

Examples prepared using the methods described above

| Example Compound | Chemical Name | Structure | General procedure | Characterization | Purity HPLC (%) |
|---|---|---|---|---|---|
| 58 | 3-(6-(3,5-dimethyl-isoxazol-4-yl)-2-methyl-1H-benzo[d]imidazol-4-yl)-4-methyl-benzonitrile | C$_{21}$H$_{18}$N$_4$O | D | $^1$H NMR (300 MHz, CD$_3$OD) δ 7.70 (d, J = 7.8 Hz, 1H), 7.69 (s, 1H), 7.55 (d, J = 8.1 Hr, 1H), 7.49 (s, 1H), 7.02 (d, J = 1.5 Hz, 1H), 2.56 (s, 3H), 2.44 (s, 3H), 2.29 (s, 3H), 2.27 (s, 3H); ESI MS m/z 343 [M + H]+. | >99 |
| 59 | 3,5-dimethyl-4-(2-methyl-4-(2-(trifluoromethyl)pyridin-3-yl)-1H-benzo[d]imidazol-6-yl)isoxazole | C$_{19}$H$_{15}$F$_3$N$_4$O | D | $^1$H NMR (300 MHz, CD$_3$OD) δ 8.77 (d, J = 3.9 Hz, 1H), 7.99 (d, J = 7.8 Hz, 1H), 7.77 (dd, J = 7.8, 5.1 Hz, 1H), 7.50 (s, 1H), 7.04 (d, J = 0.9 Hz, 1H), 2.54 (s, 3H), 2.42 (s, 3H), 2.27 (s, 3H); ESI m/z 373 [M + H]+. | >99 |
| 60 | 4-(4-(1,3-dimethyl-1H-pyrazol-4-yl)-2-methyl-1H-benzo[d]imidazol-6-yl)-3,5-dimethyl-isoxazole | C$_{18}$H$_{19}$N$_5$O | D | $^1$H NMR (300 MHz, CD3OD) δ 7.86 (br.s, 1H), 7.35 (br.s, 1H), 7.05 (d, J = 1.2 Hz, 1H), 3.92 (s, 3H), 2.58 (s, 3H), 2.44 (s, 3H), 2.31 (s, 3H), 2.28 (s, 3H); ESI m/z 322 [M + H]+. | >99 |
| 61 | 3-(6-(3,5-dimethyl-isoxazol-4-yl)-2-methyl-1H-benzo[d]imidazol-4-yl)isonicotinonitrile | C$_{19}$H$_{15}$N$_5$O | D | $^1$H NMR (300 MHz, CD3OD) δ 9.67 (s, 1H), 8.79 (d, J = 5.7 Hz, 1H), 8.35 (d, J = 6.0 Hz, 1H), 8.10 (d, J = 1.2 Hz, 1H), 3.12 (s, 3H), 2.47 (s, 3H), 2.32 (s, 3H); ESI m/z 330 [M + H]+. | >99 |

TABLE 1-continued

Examples prepared using the methods described above

| Example Compound | Chemical Name | Structure | General procedure | Characterization | Purity HPLC (%) |
|---|---|---|---|---|---|
| 62 | 6-(3,5 dimethyl-isoxazol-4-yl)-N-(pyrazin-2-yl)-1H-benzo[d]imidazol-4-amine | $C_{16}H_{14}N_6O$ | E | $^1$H NMR (500 MHz, CDCl$_3$) δ 9.29 (s, 1H), 8.32 (s, 1H), 8.19 (s, 1H), 8.05 (s, 1H), 7.62 (d, J = 1.1 Hz, 1H), 7.48 (s, 1H), 2.48 (s, 3H), 2.31 (s, 3H); ESI MS m/z 307 [M + H]+ | >99 |
| 63 | 6-(3,5-dimethyl-isoxazol-4-yl)-2-methyl-N-(3-methyl pyridin-2-yl)-1H-benzo[d]imidazol-4-amine | $C_{19}H_{19}N_5O$ | E | $^1$H NMR (500 MHz, CD$_3$OD) δ 7.81 (s, 1H), 7.72 (s, 1H), 7.60 (d, J = 1.3 Hz, 1H), 7.45 (d, J = 1.3 Hz, 1H), 7.02 (s, 1H), 2.78 (s, 3H), 2.51 (s, 3H), 2.47 (s, 3H), 2.30 (s, 3H); ESI MS m/z 334 [M + H]+ | >99 |
| 64 | N-(2-(6-(3,5-dimethyl-isoxazol-4-yl)-2-methyl-1H-benzo[d]imidazol-4-yl)phenyl)acetamide | $C_{22}H_{20}N_4O_2$ | D | $^1$H NMR (500 MHz, CD3OD) δ 7.70 (d, J = 7.0 Hz, 1H), 7.50 (d, J = 7.2 Hz, 1H), 7.48-7.42 (m, 2H), 7.37 (d, J = 7.2 Hz, 1H), 7.07 (s, 1H), 2.58 (s, 3H), 2.44 (s, 3H), 2.28 (s, 3H), 1.86 (s, 3H); ESI m/z 361 [M + H]+. | >99 |
| 65 | 4,6-bis(3,5-dimethyl-isoxazol-4-yl)-N-(pyridin-3-ylmethyl)-1H-benzo[d]imidazol-2-amine | $C_{23}H_{22}N_6O_2$ | F | $^1$H NMR (300 MHz, CD$_3$OD) δ 8.57 (d, J = 1.8 Hz, 1H), 8.43 (dd, J = 5.1, 1.5 Hz, 1H), 7.89-7.86 (m, 1H), 7.42 (dd, J = 7.8, 5.4 Hz, 1H), 7.17 (s, 1H), 6.82 (s, 1H), 4.66 (s, 2H), 2.42 (s, 3H), 2.31 (s, 3H), 2.27 (s, 3H), 2.18 (s, 3H); ESI m/z 415 [M + H]+. | 98.5 |

TABLE 1-continued

Examples prepared using the methods described above

| Example Compound | Chemical Name | Structure | General procedure | Characterization | Purity HPLC (%) |
|---|---|---|---|---|---|
| 66 | 4-(4-(1,5-dimethyl-3-(trifluoro-methyl)-1H-pyrazol-4-yl)-2-methyl-1H-benzo[d]imidazol-6-yl)-3,5-dimethyl-isoxazole | $C_{19}H_{18}F_3N_5O$ | L | $^1$H NMR (300 MHz, $CD_3OD$-$d_4$) δ 7.46 (br s, 1H), 7.00 (s, 1H), 3.94 (s, 3H), 2.56 (s, 3H), 2.43 (s, 3H), 2.27 (s, 3H), 2.16 (s, 3H); MS m/z 390 [M + H]+. | >99 |
| 67 | 4-(5-(3,5-dimethyl-isoxazol-4-yl)-2-methyl-1H-benzo[d]imidazol-7-yl)-N,3-dimethyl isoxazole-5-carboxamide | $C_{19}H_{19}N_5O_3$ | L | $^1$H NMR (300 MHz, $CD_3OD$-$d_4$) δ 7.49 (br s, 1H), 7.13 (s, 1H), 2.84 (s, 3H), 2.58 (s, 3H), 2.46 (s, 3H), 2.31 (s, 3H), 2.24 (s, 3H); MS m/z 366 [M + H]+. | >99 |
| 68 | 5-(6-(3,5-dimethyl-isoxazol-4-yl)-2-methyl-1H-benzo[d]imidazol-4-yl)-6-methyl-pyridin-2-amine | $C_{19}H_{19}N_5O$ | D | $^1$H NMR (300 MHz, $CD_3OD$) δ 7.45 (d, J = 8.4 Hz, 1H), 7.42 (s, 1H), 6.97 (d, J = 1.5 Hz, 1H), 6.56 (d, J = 8.4 Hz, 1H), 2.55 (s, 3H), 2.43 (s, 3H), 2.28 (s, 3H), 2.23 (s, 3H); ESI m/z 334 [M + H]+. | >99 |
| 69 | 3,5-dimethyl-4-(2-methyl-4-(2-(methyl-sulfonyl)phenyl)-1H-benzo[d]imidazol-6-yl)isoxazole | $C_{20}H_{19}N_3O_3S$ | D | $^1$H NMR (300 MHz, CD3OD) δ 8.24 (d, J = 6.9 Hz, 1H), 7.80-7.72 (m, 2H), 7.53-7.50 (m, 2H), 7.14 (d, 1.5 Hz, 1H), 2.74 (s, 3H), 2.53 (s, 3H), 2.44 (s, 3H), 2.28 (s, 3H); ESI m/z 382 [M + H]+. | >99 |

TABLE 1-continued

Examples prepared using the methods described above

| Example Compound | Chemical Name | Structure | General procedure | Characterization | Purity HPLC (%) |
|---|---|---|---|---|---|
| 70 | 3,5-dimethyl-4-(7-(2-methyl pyridin-3-yl)-1H-indazol-5-yl) isoxazole | C₁₈H₁₆N₄O | H | ¹H NMR (500 MHz, CDCl₃) δ 8.58-8.57 (m, 1H), 8.21 (s, 1H), 7.75-7.74 (m, 1H), 7.69 (d, J = 1.5 Hz, 1H), 7.35-7.33 (m, 1H), 7.15 (d, J = 1.5 Hz, 1H), 2.51 (s, 3H), 2.46 (s, 3H), 2.10 (s, 3H); ESI m/z 305 [M + H]+. | >99 |
| 71 | 2-(6-(3,5-dimethyl-isoxazol-4-yl)-2-methyl-1H-benzo[d]imidazol-4-yl)benzonitrile | C₂₀H₂₆N₄O | D | ¹H NMR (300 MHz, CD₃OD) δ 8.39 (d, J = 8.4 Hz, 2H), 7.93 (d, J = 0.7 Hz, 1H), 7.78 (td, J = 7.8, 1.4 Hz, 1H), 7.65 (t, J = 8.1 Hz, 1H), 7.58 (d, J = 0.9 Hz, 1H), 3.11 (s, 3H), 2.47 (s, 3H), 2.31 (s, 3H); ESI m/z 329 [M + H]+. | 98.9 |
| 72 | 4-(4-(4-methoxy-pyridin-3-yl)-2-methyl-1H-benzo[d]imidazol-6-yl)-3,5-dimethyl isoxazole | C₁₉H₁₈N₄O₂ | D | ¹H NMR (300 MHz, CD₃OD) δ 8.50 (d, J = 5.7 Hz, 1H), 8.45 (s, 1H), 7.49 (br.s, 1H), 7.25 (d, J = 6.0 Hz, 1H), 7.12 (d, J = 0.9 Hz, 1H), 3.92 (s, 1H), 2.57 (s, 3H), 2.45 (s, 3H), 2.29 (s, 3H); ESI m/z 335 [M + H]+. | 98.6 |
| 73 | 3-(6-(3,5-dimethyl-isoxazol-4-yl)-1H-benzo[d]imidazol-4-yl)-2-methyl-benzamide | C₂₀H₁₈N₄O₂ | D | ¹H NMR (300 MHz, CD₃OD) δ 8.23 (s, 1H), 7.62-7.41 (m, 4H), 7.09 (s, 1H), 2.46 (s, 3H), 2.30 (s, 3H), 2.22 (s, 3H); ESI MS m/z 347 [M + H]+. | >99 |

TABLE 1-continued

Examples prepared using the methods described above

| Example Compound | Chemical Name | Structure | General procedure | Characterization | Purity HPLC (%) |
|---|---|---|---|---|---|
| 74 | 3-(6-(3,5-dimethyl-isoxazol-4-yl)-2-methyl-1H-benzo[d]imidazol-4-yl)-4-methyl benzamide | C₂₁H₂₀N₄O₂ | D | ¹H NMR (300 MHz, CD₃OD) δ 7.87-7.85 (m, 2H), 7.49-7.46 (m, 2H), 7.03 (d, J = 1.5 Hz, 1H), 2.55 (s, 3H), 2.44 (s, 3H), 2.29 (s, 3H), 2.26 (s, 3H); ESI MS m/z 361 [M + H]+. | >99 |
| 75 | 3-(6-(3,5-dimethyl-isoxazol-4-yl)-2-methyl-1H-benzo[d]imidazol-4-yl)-4-methyl benzoic acid | C₂₁H₁₉N₃O₃ | D | ¹H NMR (300 MHz, CD₃OD) δ 7.99 (dd, J = 1.8, 8.1 Hz, 1H), 7.95 (d, J = 1.8 Hz, 1H), 7.47 (d, J = 7.8 Hz, 1H), 7.47 (d, J = 1.5 Hz, 1H), 7.01 (d, J = 1.5 Hz, 1H), 2.55 (s, 3H), 2.45 (s, 3H), 2.30 (s, 3H), 2.25 (s, 3H); ESI MS m/z 362 [M + H]+. | >99 |
| 76 | 4,4'-(2-(2,2,2-trifluoro-ethyl)-1H-benzo[d]imidazole-5,7-diyl)bis(3,5-dimethyl isoxazole) | C₁₉H₁₇F₃N₄O₂ | I | ¹H NMR (500 MHz, CD₃OD) δ 7.70-7.45 (m, 1H), 7.14 (s, 3H), 3.89 (q, J = 10.4 Hz, 2H), 2.45 (s, 3H), 2.38 (s, 3H), 2.30 (s, 3H), 2.23 (s, 3H); ESI m/z 391 [M + H]+. | 98.3 |
| 77 | 3,5-dimethyl-4-(2-methyl-4-(2-(trifluoro-methoxy)phenyl)-1H-benzo[d]imidazol-6-yl)isoxazole | C₂₀H₁₆F₃N₃O₂ | D | ¹H NMR (500 MHz, CD₃OD) δ 7.63 (d, J = 7.2 Hz, 1H), 7.55-7.49 (m, 4H), 7.09 (d, J = 1.6 Hz, 1H), 2.56 (s, 3H), 2.43 (s, 3H), 2.27 (s, 3H); ESI m/z 388 [M + H]+. | 98.6 |

TABLE 1-continued

Examples prepared using the methods described above

| Example Compound | Chemical Name | Structure | General procedure | Characterization | Purity HPLC (%) |
|---|---|---|---|---|---|
| 78 | 3,5-dimethyl-4-(2-methyl-4-(2-(trifluoromethyl)phenyl)-1H-benzo[d]imidazol-6-yl)isoxazole | $C_{20}H_{16}F_3N_3O$ | D | $^1$H NMR (500 MHz, CD$_3$OD) δ 7.86 (s, 1H), 7.71 (s, 1H), 7.64 (s, 1H), 7.49 (d, J = 7.4 Hz, 2H), 6.98 (s, 1H), 2.52 (s, 3H), 2.42 (s, 3H), 2.26 (s, 3H); ESI m/z 372 [M + H]+. | 98.6 |
| 79 | 3,5-dimethyl-4-(2-methyl-4-(pyridin-3-yl)-1H-benzo[d]imidazol-6-yl)isoxazole | $C_{18}H_{16}N_4O$ | D | $^1$H NMR (500 MHz, CD$_3$OD) δ 9.03 (br.s, 1H), 8.58 (s, 1H), 8.31 (s, 1H), 7.59 (s, 1H), 7.45 (br.s, 1H), 7.25 (s, 1H), 2.61 (s, 3H), 2.45 (s, 3H), 2.29 (s, 3H); ESI m/z 305 [M + H]+. | 97.3 |
| 80 | 4-(4-(5-fluoro-2-(trifluoromethyl)phenyl)-2-methyl-1H-benzo[d]imidazol-6-yl)-3,5-dimethylisoxazole | $C_{20}H_{15}F_4N_3O$ | D | $^1$H NMR (500 MHz, CD3OD) δ 7.92 (t, J = 6.8 Hz, 1H), 7.48 (s, 1H), 7.38 (t, J = 7.8 Hz, 1H), 7.27 (d, J = 8.3 Hz, 1H), 7.02 (s, 1H), 2.54 (s, 3H), 2.47 (s, 3H), 2.26 (s, 3H); ESI m/z 390 [M + H]+. | >99 |
| 81 | 4-(2-ethoxy-4-(2-methylpyridin-3-yl)-1H-benzo[d]imidazol-6-yl)-3,5-dimethylisoxazole | $C_{20}H_{20}N_4O_2$ | J | $^1$H NMR (500 MHz, CD$_3$OD) δ 8.47 (s, 1H), 7.78 (d, J = 6.6 Hz, 1H), 7.45-7.20 (m, 2H), 6.93 (d, J = 1.6 Hz, 1H), 4.60-4.40 (bs, 2H), 2.43 (s, 6H), 2.28 (s, 3H), 1.55-1.35 (bs, 3H); ESI m/z 349 [M + H]+. | >99 |
| 82 | 3-(6-(3,5-dimethylisoxazol-4-yl)-2-methyl-1H-benzo[d]imidazol-4-yl)pyridin-2-amine | $C_{18}H_{17}N_5O$ | D | $^1$H NMR (500 MHz, CD$_3$OD) δ 8.03 (dd, J = 5.1, 1.8 Hz, 1H), 7.59 (dd, J = 7.5, 1.8 Hz, 1H), 7.48 (s, 1H), 7.12 (d, J = 1.3 Hz, 1H), 6.82 (dd, J = 7.2, 5.1 Hz, 1H), 2.57 (s, 3H), 2.44 (s, 3H), 2.29 (s, 3H); ESI m/z 320 [M + H]+. | 98.4 |

TABLE 1-continued

Examples prepared using the methods described above

| Example Compound | Chemical Name | Structure | General procedure | Characterization | Purity HPLC (%) |
|---|---|---|---|---|---|
| 83 | 2-(6-(3,5-dimethyl-isoxazol-4-yl)-2-methyl-1H-benzo[d]imidazol-4-yl)-6-fluoro-benzonitrile | $C_{20}H_{15}FN_4O$ | D | $^1$H NMR (500 MHz, CD$_3$OD) δ 7.82 (br.s, 1H), 7.58-7.38 (m, 3H), 7.23 (d, J = 1.6 Hz, 1H), 2.60 (s, 3H), 2.46 (s, 3H), 2.30 (s, 3H); ESI m/z 347 [M + H]+. | 97.5 |
| 84 | 3,5-dimethyl-4-(2-methyl-4-(3-methyl-pyridin-2-yl)-1H-benzo[d]imidazol-6 yl)isoxazole | $C_{19}H_{18}N_4O$ | L | $^1$H NMR (300 MHz, CD$_3$OD-d$_4$) δ 8.48 (br s, 1H), 7.85 (d, J = 7.5 Hz, 1H), 7.52 (br s, 1H), 7.42 (dd, J1 = 8.4 Hz, J2 = 4.8 Hz, 1H), 7.13 (br s, 1H), 2.56 (s, 3H), 2.44 (s, 3H), 2.29 (br s, 6H); MS m/z 119 [M + H]+. | >99 |
| 85 | 3,5-dimethyl-4-(2-methyl-4-(pyrazin-2-yl)-1H-benzo[d]imidazol-6-yl)isoxazole | $C_{17}H_{15}N_5O$ | L | $^1$H NMR (300 MHz, CD$_3$OD-d$_4$) δ 9.36 (br s, 1H), 8.82 (br s, 1H), 8.57 (d, J = 2.7 Hz, 1H), 7.87 (s, 1H), 7.60 (br s, 1H), 2.69 (s, 3H), 2.46 (s, 3H), 2.31 (s, 3H); MM m/z 306 [M + H]+. | 98.0 |
| 86 | 3,5-dimethyl-4-(2-methyl-4-(6-methyl-pyridazin-3-yl)-1H-benzo[d]imidazol-6-yl)isoxazole | $C_{18}H_{17}N_5O$ | L | $^1$H NMR (300 MHz, CD$_3$OD-d$_4$) δ 8.34 (br s, 1H), 7.78 (br s, 1H), 7.73 (d, J = 8.7 Hz, 1H), 7.62 (br s, 1H), 2.77 (s, 3H), 2.69 (s, 3H), 2.45 (s, 3H), 2.30 (s, 3H); MM m/z 320 [M + H]+. | >99 |

TABLE 1-continued

Examples prepared using the methods described above

| Example Compound | Chemical Name | Structure | General procedure | Characterization | Purity HPLC (%) |
|---|---|---|---|---|---|
| 87 | 4,4'-(1H-indazole-4,6-diyl)bis(3,5-dimethyl-isoxazole) | C₁₇H₁₆N₄O₂ | none | ¹H NMR (500 MHz, CDCl₃) δ 7.94 (s, 1H), 7.44 (s, 1H), 6.92 (d, J = 1.0 Hz, 1H), 2.48 (s, 3H), 2.41 (s, 3H), 2.33 (s, 3H), 2.27 (s, 3H); ESI m/z 309 [M + H]+. | 97.9 |
| 88 | 3,5-dimethyl-4-(2-methyl-4-phenyl-1H-benzo[d]imidazol 6-yl)isoxazole | C₁₉H₁₇N₃O | D | ¹H NMR (300 MHz, CD₃OD) δ 7.80-7.63 (m, 2H), 7.52 (t, J = 6.6 Hz, 2H), 7.43 (d, J = 6.6 Hz, 2H), 7.17 (d, J = 1.5 Hz, 1H), 2.59 (s, 3H), 2.45 (s, 3H), 2.29 (s, 3H); ESI m/z 304 [M + H]+. | >99 |
| 89 | 3,5-dimethyl-4-(2-methyl-4-(o-tolyl)-1H-benzo[d]imidazol-6-yl)isoxazole | C₂₀H₁₉N₃O | D | ¹H NMR (300 MHz, CD₃OD) δ 7.44 (br.s, 1H), 7.39-7.27 (m, 4H), 6.96 (d, J = 1.2 Hz, 1H), 2.53 (s, 3H), 2.44 (s, 3H), 2.29 (s, 3H), 2.18 (s, 3H); ESI m/z 318 [M + H]+. | >99 |
| 90 | 4-(4-(4-chloro-2-methyl-phenyl)-2-methyl-1H-benzo[d]imidazol-6-yl)-3,5-dimethyl isoxazole | C₂₀H₁₈ClN₃O | D | ¹H NMR (500 MHz, CD₃OD) δ 7.45 (s, 1H), 7.39 (s, 1H), 7.29 (s, 2H), 6.96 (d, J = 1.1 Hz, 1H), 2.54 (s, 3H), 2.43 (s, 3H), 2.28 (s, 3H), 2.18 (s, 3H); ESI m/z 352 [M + H]+. | 98.5 |
| 91 | 4-(4-(2-fluoro-phenyl)-2-methyl-1H-benzo[d]imidazol-6-yl)-3,5-dimethyl isoxazole | C₁₉H₁₆FN₃O | D | ¹H NMR (500 MHz, CD₃OD) δ 7.59, (t, J = 6.7 Hz, 1H), 7.47 (s, 2H), 7.34-7.26 (m, 2H), 7.14 (s, 1H), 2.58 (s, 3H), 2.44 (s, 3H), 2.29 (s, 3H); ESI m/z 322 [M + H]+. | >99 |

TABLE 1-continued

Examples prepared using the methods described above

| Example Compound | Chemical Name | Structure | General procedure | Characterization | Purity HPLC (%) |
|---|---|---|---|---|---|
| 92 | 4-(4-(5-fluoro-2-methyl-phenyl)-2-methyl-1H-benzo[d]imidazol-6-yl)-3,5-dimethyl isoxazole | $C_{20}H_{18}FN_3O$ | D | $^1$H NMR (500 MHz, CD3OD) δ 7.46 (s, 1H), 7.35 (s, 1H), 7.06 (d, J = 9.4 Hz, 2H), 6.98 (s, 1H), 2.55 (s, 3H), 2.44 (s, 3H), 2.28 (s, 3H), 2.15 (s, 3H); ESI m/z 336 [M + H]+. | >99 |
| 93 | 4,4'-(1-methyl-1H-benzo[d]imidazole-5,7-diyl)bis(3,5-dimethyl isoxazole) | $C_{18}H_{18}N_4O_2$ | N | $^1$H NMR (300 MHz, CD$_3$OD) δ 8.18 (s, 1H), 7.69 (d, J = 1.6 Hz, 1H), 7.08 (d, J = 1.6 Hz, 1H), 3.58 (s, 3H), 2.44 (s, 3H), 2.32 (s, 3H), 2.28 (s, 3H), 2.13 (s, 3H); ESI m/z 323 [M + H]+. | 99.0 |
| 94 | 2-(6-(3,5-dimethyl-isoxazol-4-yl)-2-methyl-1H-benzo[d]imidazol-4-yl)-4-fluoro-benzonitrile | $C_{20}H_{15}FN_4O$ | D | $^1$H NMR (300 MHz, CD$_3$OD) δ 8.03-7.93 (m, 1H), 7.64-7.48 (m, 2H), 7.45-7.31 (m, 1H), 7.25 (d, J = 1.5 Hz, 1H), 2.60 (s, 3H), 2.46 (s, 3H), 2.31 (s, 3H); ESI m/z 347 [M + H]+. | >99 |
| 95 | 4,4'-(1H-benzo[d][1,2,3]triazole-4,6-diyl)bis(3,5-dimethyl isoxazole) | $C_{16}H_{15}N_5O_2$ | none | $^1$H NMR (500 MHz, CD$_3$OD) δ 7.83 (s, 1H), 7.34 (s, 1H), 2.48 (s, 3H), 2.43 (s, 3H), 2.32 (s, 3H), 2.27 (s, 3H); ESI m/z 308 [M − H]−. | >99 |

TABLE 1-continued

Examples prepared using the methods described above

| Example Compound | Chemical Name | Structure | General procedure | Characterization | Purity HPLC (%) |
|---|---|---|---|---|---|
| 96 | 3,5-dimethyl-4-(2-methyl-4-(3-(trifluoromethoxy)phenyl)-1H-benzo[d]imidazol-6-yl)isoxazole | C$_{20}$H$_{16}$F$_3$N$_3$O$_2$ | D | $^1$H NMR (500 MHz, CD$_3$OD) δ 7.72 (s, 1H), 7.65 (s, 1H), 7.62-7.58 (m, 1H), 7.44 (s, 1H), 7.34 (s, 1H), 7.19 (s, 1H), 2.60 (s, 3H), 2.44 (s, 3H), 2.29 (s, 3H); ESI m/z 388 [M + H]+. HPLC > 99% | >99 |
| 97 | 4-(4-(3,5-dimethylpyridin-4-yl)-2-methyl-1H-benzo[d]imidazol-6-yl)-3,5-dimethyl isoxazole | C$_{20}$H$_{20}$N$_4$O | L | $^1$H NMR (300 MHz, CD$_3$OD-d$_4$) δ 8.36 (s, 2H), 7.50 (s, 1H), 6.95 (d, J = 1.5 Hz, 1H), 2.54 (s, 3H), 2.44 (s, 3H), 2.29 (s, 3H), 2.06 (s, 6H); MM m/z 333 [M + H]+. | 96.7 |
| 98 | 4-(4-(4,6-dimethylpyrimidin-5-yl)-2-methyl-1H-benzo[d]imidazol-6-yl)-3,5-dimethyl isoxazole | C$_{19}$H$_{19}$N$_5$O | L | $^1$H NMR (300 MHz, CD$_3$OD-d$_4$) δ 8.94 (s, 1H), 7.53 (br s, 1H), 7.07 (d, J = 1.5 Hz, 1H), 2.56 (s, 3H), 2.45 (s, 3H), 2.29 (s, 3H), 2.28 (s, 6H); MM m/z 334 [M + H]+. | 98.1 |
| 99 | 5-(6-(3,5-dimethyl-isoxazol-4-yl)-2-methyl-1H-benzo[d]imidazol-4-yl)-4,6-dimethyl pyrimidin-2-amine | C$_{19}$H$_{20}$N$_6$O | L | $^1$H NMR (300 MHz, CD$_3$OD-d$_4$) δ 7.37 (br s, 1H), 6.88 (d, J = 1.5 Hz, 1H), 2.46 (s, 3H), 2.34 (s, 3H), 2.19 (s, 3H), 1.98 (s, 6H); MM m/z 349 [M + H]+. | 96.5 |

TABLE 1-continued

Examples prepared using the methods described above

| Example Compound | Chemical Name | Structure | General procedure | Characterization | Purity HPLC (%) |
|---|---|---|---|---|---|
| 100 | 6-(3,5-dimethyl-isoxazol-4-yl)-N-ethyl-4-(2-methyl pyridin-3-yl)-1H-benzo[d]imidazol-2-amine | C<sub>20</sub>H<sub>21</sub>N<sub>5</sub>O | none | $^1$H NMR (300 MHz, CD$_3$OD) δ 8.45 (dd, J = 5.1, 1.5 Hz, 1H), 7.78 (dd, J = 7.8, 1.5 Hz, 1H), 7.38 (dd, J = 7.8, 4.8 Hz, 1H), 7.19 (d, J = 1.2 Hz, 1H), 6.79 (d, J = 1.5 Hz, 1H), 3.40 (q, J = 7.2 Hz, 2H), 2.44 (s, 3H), 2.43 (s, 3H), 2.28 (s, 3H), 1.26 (t, J = 7.2 Hz, 3H); ESI m/z 348 [M + H]+. | >99 |
| 101 | 5,7-bis(3,5-dimethyl-isoxazol-4-yl)-2-methyl benzo[d]oxazole | a C$_{18}$H$_{17}$N$_3$O$_3$ | none | $^1$H NMR (500 MHz, CD$_3$OD) δ 7.61 (d, J = 1.5 Hz, 1H), 7.26 (d, J = 1.5 Hz, 1H), 2.67 (s, 3H), 2.45 (s, 3H), 2.44 (s, 3H), 2.29 (s, 3H), 2.28 (s, 3H); ESI m/z 324 [M + H]+. | 97.8 |
| 102 | N-(6-(3,5-dimethyl-isoxazol-4-yl)-1H-benzo[d]imidazol-4-yl)-2-methoxy-benzene-sulfonamide | C$_{19}$H$_{18}$N$_4$O$_4$S | none | $^1$H NMR (300 MHz, CD$_3$OD) δ 8.73 (s, 1H), 7.72 (dd, J = 7.8, 1.5 Hz, 1H), 7.59-7.53 (m, 1H), 7.38 (d, J = 0.9 Hz, 1H), 7.17 (d, J = 7.8 Hz, 1H), 6.98 (td, J = 7.8, 0.9 Hz, 1H), 6.89 (d, J = 1.5 Hz, 1H), 3.93 (s, 3H), 2.22 (s, 3H), 2.05 (s, 3H); ESI MS m/z 399 [M + H]+. | 90.0 |
| 103 | 4-(4-(benzo[d][1,3]dioxol-5-yl)-2-methyl-1H-benzo[d]imidazol-6-yl)-3,5-dimethyl isoxazole | C$_{20}$H$_{17}$N$_3$O$_3$ | D | $^1$H NMR (300 MHz, CD$_3$OD) δ 7.37 (s, 1H), 7.23-7.19 (m, 2H), 7.12 (d, J = 1.5 Hz, 1H), 6.97 (d, J = 7.8 Hz, 1H), 6.02 (s, 2H), 2.59 (s, 3H), 2.44 (s, 3H), 2.29 (s, 3H); ESI MS m/z 348 [M + H]+. | >99 |

TABLE 1-continued

Examples prepared using the methods described above

| Example Compound | Chemical Name | Structure | General procedure | Characterization | Purity HPLC (%) |
|---|---|---|---|---|---|
| 104 | 3,5-dimethyl-4-(2-methyl-4-(4-methyl-thiazol-5-yl)-1H-benzo[d]imidazol-6-yl)isoxazole | $C_{17}H_{16}N_4OS$ | D | $^1$H NMR (300 MHz, CD$_3$OD) δ 9.04 (s, 1H), 7.63-7.36 (m, 1H), 7.15 (d, J = 1.5 Hz, 1H), 2.59 (s, 3H), 2.52-2.36 (m, 6H), 2.29 (s, 3H); ESI m/z 325 [M + H]+. | >99 |
| 105 | 4-(4-(5-chloro-2-methyl-phenyl)-2-methyl-1H-benzo[d]imidazol-6-yl)-3,5-dimethyl isoxazole | $C_{20}H_{18}ClN_3O$ | D | $^1$H NMR (500 MHz, CD$_3$OD) δ 7.47 (br.s, 1H), 7.38-7.30 (m, 3H), 6.97 (s, 1H), 2.55 (s, 3H), 2.44 (s, 3H), 2.28 (s, 3H), 2.15 (s, 3H); ESI m/z 352 [M + H]+. | 97.8 |
| 106 | 4-(4-(2-fluoro-3-methyl-phenyl)-2-methyl-1H-benzo[d]imidazol-6-yl)-3,5-dimethyl isoxazole | $C_{20}H_{18}FN_3O$ | D | $^1$H NMR (500 MHz, CD$_3$OD) δ 7.48 (br.s, 1H), 7.10-7.29 (m, 2H), 7.23-7.16 (m, 1H), 7.12 (s, 1H), 2.58 (s, 3H), 2.44 (s, 3H), 2.38 (s, 3H), 2.29 (s, 3H); ESI m/z 336 [M + H]+. | 98.7 |
| 107 | 4-(4-(5-chloro-2-methoxy-phenyl)-2-methyl-1H-benzo[d]imidazol-6-yl)-3,5-dimethyl isoxazole | $C_{20}H_{18}ClN_3O_2$ | D | $^1$H NMR (300 MHz, CD$_3$OD) δ 7.49-7.35 (m, 3H), 7.14 (d, J = 8.8 Hz, 1H), 7.08 (s, 1H), 3.80 (s, 3H), 2.56 (s, 3H), 2.45 (s, 3H), 2.29 (s, 3H); ESI m/z 368 [M + H]+. | 97.8 |
| 108 | 4-(4-(2-fluoro-5-methoxy-phenyl)-2-methyl-1H-benzo[d]imidazol-6-yl)-3,5-dimethyl isoxazole | $C_{20}H_{18}FN_3O_2$ | D | $^1$H NMR (500 MHz, CD$_3$OD) δ 7.50 (br.s, 1H), 7.19-7.07 (m, 3H), 7.00 (br.s, 1H), 3.83 (s, 3H), 2.58 (s, 3H), 2.44 (s, 3H), 2.29 (s, 3H); ESI m/z 352 [M + H]+. | 96.4 |

TABLE 1-continued

Examples prepared using the methods described above

| Example Compound | Chemical Name | Structure | General procedure | Characterization | Purity HPLC (%) |
|---|---|---|---|---|---|
| 109 | 4-(4-(2-ethoxy-pyridin-3-yl)-2-methyl-1H-benzo[d]imidazol-6-yl)-3,5-dimethyl isoxazole | C$_{20}$H$_{20}$N$_4$O$_2$ | D | $^1$H NMR (300 MHz, CD$_3$OD) δ 8.20 (br.s, 1H), 7.82 (d, J = 5.7 Hz, 1H), 7.48 (br.s, 1H), 7.13-7.07 (m, 2H), 4.42 (q, J = 6.9 Hz, 2H), 2.57 (s, 3H), 2.45 (s, 3H), 2.30 (s, 3H), 1.26 (t, J = 6.9 Hz, 3H); ESI m/z 349 [M + H]+. | >99 |
| 110 | 4-(4-(iso-quinolin-8-yl)-2-methyl-1H-benzo[d]imidazol-6-yl)-3,5-dimethyl isoxazole | C$_{22}$H$_{18}$N$_4$O | D | $^1$H NMR (500 MHz, CD$_3$OD) δ 8.95 (s, 1H), 8.46 (br.s, 1H), 8.06 (br.s, 1H), 7.94-7.93 (m, 2H), 7.78 (d, J = 7.0 Hz, 1H), 7.61-7.55 (m, 1H), 7.22 (s, 1H), 2.51 (s, 3H), 2.47 (s, 3H), 2.32 (s, 3H); ESI m/z 355 [M + H]+. | >99 |
| 111 | 3,5-dimethyl-4-(2-methyl-4-(quinolin-8-yl)-1H-benzo[d]imidazol-6-yl)isoxazole | C$_{22}$H$_{18}$N$_4$O | D | $^1$H NMR (500 MHz, CD$_3$OD) δ 8.76 (d, J = 2.2 Hz, 1H), 8.45 (d, J = 8.5 Hz, 1H), 8.06 (d, J = 8.2 Hz, 1H), 7.89 (dd, J = 7.2 Hz, 1H), 7.74 (t, J = 7.6 Hz, 1H), 7.58-7.53 (m, 2H), 7.23 (d, J = 1.3 Hz, 1H), 2.49 (s, 3H), 2.47 (s, 3H), 2.32 (s, 3H); ESI m/z 355 [M + H]+. | 97.7 |
| 112 | 4-(4-(5-fluoro-2-methoxy-phenyl)-2-methyl-1H-benzo[d]imidazol-6-yl)-3,5-dimethyl-isoxazole | C$_{20}$H$_{18}$FN$_3$O$_2$ | D | $^1$H NMR (500 MHz, CD$_3$OD) δ 7.44 (s, 1H), 7.19-7.10 (m, 4H), 3.78 (s, 3H), 2.56 (s, 3H), 2.45 (s, 3H), 2.29 (s, 3H); ESI m/z 352 [M + H]+. | >99 |

TABLE 1-continued

Examples prepared using the methods described above

| Example Compound | Chemical Name | Structure | General procedure | Characterization | Purity HPLC (%) |
|---|---|---|---|---|---|
| 113 | 3,5-dimethyl-4-(2-methyl-4-(5-methyl-thiazol-4-yl)-1H-benzo[d]imidazol-6-yl)isoxazole | $C_{17}H_{16}N_4OS$ | L | $^1$H NMR (300 MHz, CD$_3$OD-d$_4$) δ 8.97 (s, 1H), 7.50 (br s, 1H), 7.25 (d, J = 1.2 Hz, 1H), 2.60 (s, 3H), 2.57 (br s, 3H), 2.45 (s, 3H), 2.30 (s, 3H); MM m/z 325 [M + H]+. | 95.2 |
| 114 | 4-(4-(2-methoxy-4-methyl-pyridin-3-yl)-2-methyl-1H-benzo[d]imidazol-6-yl)-3,5-dimethyl isoxazole | $C_{20}H_{20}N_4O_2$ | L | $^1$H NMR (300 MHz, CD$_3$OD-d$_4$) δ 8.08 (d, J = 5.4 Hz, 1H), 7.45 (br s, 1H), 7.00 (d, J = 5.4 Hz, 1H), 6.96 (d, J = 1.5 Hz, 1H), 3.82 (s, 3H), 2.53 (s, 3H), 2.44 (s, 3H), 2.29 (s, 3H), 2.12 (s, 3H); MM m/z 349 [M + H]+. | 96.4 |
| 115 | 3,5-dimethyl-4-(2-methyl-4-(1-methyl-3-(trifluoro-methyl)-1H-pyrazol-4-yl)-1H-benzo[d]imidazol-6-yl)isoxazole | $C_{18}H_{16}F_3N_5O$ | L | $^1$H NMR (300 MHz, CD$_3$OD-d$_4$) δ 8.04 (s, 1H), 7.42 (br s, 1H), 7.09 (s, 1H), 4.04 (s, 3H), 2.58 (s, 3H), 2.42 (s, 3H), 2.27 (s, 3H); MM m/z 376 [M + H]+. | >99 |
| 116 | 4,6-bis(3,5-dimethyl-isoxazol-4-yl)-N,N-dimethyl-1H-benzo[d]imidazol-2-amine | $C_{19}H_{21}N_5O_2$ | F | $^1$H NMR (300 MHz, CD$_3$OD) δ 7.34 (d, J = 1.5 Hz, 1H), 7.13 (d, J = 1.5 Hz, 1H), 2.44 (s, 3H), 2.37 (s, 3H), 2.29 (s, 3H), 2.21 (s, 3H); APCI m/z 352 [M + H]+. | 97.9 |

TABLE 1-continued

Examples prepared using the methods described above

| Example Compound | Chemical Name | Structure | General procedure | Characterization | Purity HPLC (%) |
|---|---|---|---|---|---|
| 117 | 4-(4-(2-(methoxymethyl)phenyl)-2-methyl-1H-benzo[d]imidazol-6-yl)-3,5-dimethylisoxazole | C₂₁H₂₁N₃O₂ | D | ¹H NMR (500 MHz, CD₃OD) δ 7.59 (d, J = 7.2 Hz, 1H), 7.47-7.38 (m, 4H), 7.02 (d, J = 6.0 Hz, 1H), 4.31 (s, 2H), 3.17 (s, 3H), 2.53 (s, 3H), 2.44 (s, 3H), 2.29 (s, 3H); ESI m/z 348 [M + H]+. | >99 |
| 118 | 4-(4-(2-methoxypyridin-3-yl)-2-methyl-1H-benzo[d]imidazol-6-yl)-3,5-dimethyl isoxazole | C₁₉H₁₈N₄O₂ | D | ¹H NMR (500 MHz, CD₃OD) δ 8.22 (d, J = 5.0 Hz, 1H), 7.83 (d, J = 6.7 Hz, 1H), 7.45 (s, 1H), 7.13-7.10 (m, 2H), 3.94 (s, 3H), 2.57 (s, 3H), 2.45 (s, 3H), 2.29 (s, 3H); ESI m/z 335 [M + H]+. | >99 |
| 119 | 3,5-dimethyl-4-(7-(4-methylpyridin-3-yl)-1H-indazol-5-yl)isoxazole | C₁₈H₁₆N₄O | H | ¹H NMR (500 MHz, CDCl₃) δ 8.56 (s, 1H), 8.44 (d, J = 4.5 Hz, 1H), 8.20 (s, 1H), 7.68 (d, J = 1.5 Hz, 1H), 7.31 (d, J = 5.0 Hz, 1H), 7.13 (d, J = 1.5 Hz, 1H), 2.45 (s, 3H), 2.32 (s, 3H), 2.29 (s, 3H); ESI m/z 305 [M + H]+. | >99 |
| 120 | 4-(7-(1,3-dimethyl-1H-pyrazol-4-yl)-1H-indazol-5-yl)-3,5-dimethyl isoxazole | C₁₇H₁₇N₅O | H | ¹H NMR (500 MHz, CDCl₃) δ 8.15 (s, 1H), 7.64 (s, 1H), 7.57 (d, J = 1.5 Hz, 1H), 7.17 (d, J = 1.5 Hz, 1H), 3.98 (s, 3H), 2.45 (s, 3H), 2.35 (s, 3H), 2.31 (s, 3H); ESI m/z 308 [M + H]+. | >99 |
| 121 | 1-(6-(3,5-dimethylisoxazol-4-yl)-2-methyl-1H-benzo[d]imidazol-4-yl)-5-methylpyrrolidin-2-one | C₁₈H₂₀N₄O₂ | none | ¹H NMR (300 MHz, CD₃OD) δ 7.63 (s, 1H), 7.39 (s, 1H), 4.62-4.43 (m, 1H), 2.88 (s, 3H), 2.70-2.65 (m, 3H), 2.44 (s, 3H), 2.28 (s, 3H), 2.31-1.84 (m, 1H), 1.23 (d, J = 6.2 Hz, 3H); ESI m/z 325 [M + H]+. HPLC > 99% | >99 |

TABLE 1-continued

Examples prepared using the methods described above

| Example Compound | Chemical Name | Structure | General procedure | Characterization | Purity HPLC (%) |
|---|---|---|---|---|---|
| 122 | 1-(6-(3,5-dimethyl-isoxazol-4-yl)-2-methyl-1H-benzo[d]imidazol-4-yl)piperidin-2-one | $C_{18}H_{20}N_4O_2$ | none | $^1$H NMR (300 MHz, CD$_3$OD) δ 7.62 (s, 1H), 7.48 (s, 1H), 3.90-3.81 (m, 2H), 2.87 (s, 3H), 2.69-G1392.61 (m, 2H), 2.44 (s, 3H), 2.28 (s, 3H), 2.07-2.05 (m, 4H); ESI m/z 325 [M + H]+. HPLC > 99% | >99 |
| 123 | 3-(6-(3,5-dimethyl-isoxazol-4-yl)-2-methyl-1H-benzo[d]imidazol-4-yl)-2-methyl-benzonitrile | $C_{21}H_{18}N_4O$ | D | $^1$H NMR (300 MHz, CD$_3$OD) δ 7.76 (br.s, 1H), 7.63 (d, J = 7.4 Hz, 1H), 7.50-7.47 (m, 2H), 7.02 (s, 1H), 2.55 (s, 3H), 2.44 (s, 3H), 2.38 (s, 3H), 2.29 (s, 3H); ESI m/z 343 [M + H]+. | >99 |
| 124 | 4-(4-(benzo[d]thiazol-5-yl)-2-methyl-1H-benzo[d]imidazol-6-yl)-3,5-dimethyl isoxazole | $C_{20}H_{16}N_4OS$ | D | $^1$H NMR (500 MHz, CD3OD) δ 9.31 (s, 1H), 8.45 (br.s, 1H), 8.21 (d, J = 8.1 Hz, 1H), 7.90 (br.s, 1H), 7.46 (s, 1H), 7.28 (s, 1H), 2.61 (s, 3H), 2.46 (s, 3H), 2.31 (s, 3H); ESI m/z 361 [M + H]+. | >99 |
| 125 | 4-(4-(5-fluoro-4-methyl-pyridin-3-yl)-2-methyl-1H-benzo[d]imidazol-6-yl)-3,5-dimethyl isoxazole | $C_{19}H_{17}FN_4O$ | D | $^1$H NMR (500 MHz, CD$_3$OD) δ 8.43 (s, 1H), 8.34 (s, 1H), 7.52 (br.s, 1H), 7.08 (s, 1H), 2.57 (s, 3H), 2.45 (s, 3H), 2.29 (s, 3H), 2.20 (d, J = 2.0 Hz, 3H); ESI m/z 337 [M + H]+. | >99 |

TABLE 1-continued

Examples prepared using the methods described above

| Example Compound | Chemical Name | Structure | General procedure | Characterization | Purity HPLC (%) |
|---|---|---|---|---|---|
| 126 | 3-(6-(3,5-dimethyl-isoxazol-4-yl)-2-methyl-1H-benzo[d]imidazol-4-yl)-2-methyl-benzamide | C₂₁H₂₀N₄O₂ | none | ¹H NMR (500 MHz, CD₃OD) δ 7.18 (d, J = 7.3 Hz, 2H), 7.40 (d, J = 6.6 Hz, 1H), 7.37 (d, J = 7.6 Hz, 1H), 6.99 (s, 1H), 2.55 (s, 3H), 2.44 (s, 3H), 2.29 (s, 3H), 2.23 (s, 3H); ESI m/z 361 [M + H]+. | >99 |
| 127 | 3,5-dimethyl-4-(7-(1,3,5-trimethyl-1H-pyrazol-4-yl)-1H-indazol-5-yl)isoxazole | C₁₈H₁₉N₅O | H | ¹H NMR (500 MHz, CDCl₃) δ 8.16 (s, 1H), 7.60 (d, J = 1.5 Hz, 1H), 7.05 (d, J = 1.5 Hz, 1H), 3.87 (s, 3H), 2.45 (s, 3H), 2.31 (s, 3H), 2.21 (s, 3H), 2.18 (s, 3H); ESI m/z 322 [M + H]+. | >99 |
| 128 | 3,5-dimethyl-4-(7-(2-(trifluoromethyl)pyridin-3-yl)-1H-indazol-5-yl)isoxazole | C₁₈H₁₃F₃N₄O | H | ¹H NMR (500 MHz, CDCl₃) δ 8.89 (d, J = 4.0 Hz, 1H), 8.23 (s, 1H); 7.93 (d, J = 7.5 Hz, 1H), 7.74 (d, J = 1.5 Hz, 1H), 7.70-7.68 (m, 1H), 7.23 (s, 1H), 2.44 (s, 3H), 2.30 (s, 3H); ESI mz 359 [M + H]+ | >99 |
| 129 | 3,5-dimethyl-4-(7-(4-(trifluoromethyl)pyridin-3-yl)-1H-indazol-5-yl)isoxazole | C₁₈H₁₃F₃N₄O | H | ¹H NMR (500 MHz, CDCl₃) δ 8.85-8.83 (m, 2H), 8.20 (s, 1H), 7.76-7.73 (m, 2H), 7.19 (s, 1H); 2.43 (s, 3H), 2.29 (s, 3H); ESI m/z 359 [M + H]+ | >99 |

TABLE 1-continued

Examples prepared using the methods described above

| Example Compound Chemical Name | Structure | General procedure | Characterization | Purity HPLC (%) |
|---|---|---|---|---|
| 130 4-(4-(3,5-dichloro-pyridin-4-yl)-2-methyl-1H-benzo[d]imidazol-6-yl)-3,5-dimethyl isoxazole | C<sub>18</sub>H<sub>14</sub>Cl<sub>2</sub>N<sub>4</sub>O | L | $^1$H NMR (500 MHz, CD$_3$OD-d$_4$) δ 8.68 (br s, 2H), 7.60-7.53 (m, 1H), 7.07 (br s, 1H), 2.57 (s, 3H), 2.45 (s, 3H), 2.30 (s, 3H); MM m/z 373 [M + H]+. | 96.5 |
| 131 4-(4-(5-fluoro-2-methoxy-pyridin-3-yl)-2-methyl-1H-benzo[d]imidazol-6-yl)-3,5-dimethyl isoxazole | C<sub>19</sub>H<sub>17</sub>FN<sub>4</sub>O<sub>2</sub> | L | $^1$H NMR (300 MHz, CD$_3$OD-d4) δ 8.12 (d, J = 3.0 Hz, 1H), 7.75 (d, J = 6.3 Hz, 1H), 7.48 (s, 1H), 7.21 (s, 1H), 3.94 (s, 3H), 2.60 (s, 3H), 2.47 (s, 3H), 2.31 (s, 3H); MM m/z 353 [M + H]+. | 95.3 |
| 132 4-(4-(3,4-difluoro-2-methyl-phenyl)-2-methyl-1H-benzo[d]imidazol-6-yl)-3,5-dimethyl isoxazole | C<sub>20</sub>H<sub>17</sub>F<sub>2</sub>N<sub>3</sub>O | D | $^1$H NMR (500 MHz, CD$_3$OD) δ 7.48 (s, 1H), 7.26-7.10 (m, 2H), 6.97 (d, J = 1.5 Hz, 1H), 2.54 (s, 3H), 2.43 (s, 3H), 2.28 (s, 3H), 2.12 (s, 3H); ESI m/z 354 [M + H]+. | 98.8 |
| 133 4,6-bis(1,3-dimethyl-1H-pyrazol-4-yl)-2-methyl-1H-benzo[d]imidazole | C<sub>18</sub>H<sub>20</sub>N<sub>5</sub> | A | $^1$H NMR (500 MHz, CD$_3$OD) δ 7.84 (br. s, 1H), 7.69 (s, 1H), 7.42 (br. s, 1H), 7.16 (s, 1H), 3.91 (s, 3H), 3.86 (s, 3H), 2.56 (s, 3H), 2.38 (s, 3H), 2.31 (br s, 3H); ESI m/z 321 [M + H]+. | 98.2 |

TABLE 1-continued

Examples prepared using the methods described above

| Example Compound | Chemical Name | Structure | General procedure | Characterization | Purity HPLC (%) |
|---|---|---|---|---|---|
| 134 | 2-methyl-4,6-bis(1-methyl-1H-pyrazol-5-yl)-1H-benzo[d]imidazole | $C_{16}H_{16}N_6$ | A | $^1$H NMR (500 MHz, CDCl$_3$) δ 7.74 (br.s, 1H), 7.59 (d, J = 1.7 Hz, 1H), 7.54 (d, J = 1.7 Hz, 1H), 7.29 (d, J = 1.5 Hz, 1H), 6.50 (d, J = 1.8 Hz, 1H), 6.36 (d, J = 2.0 Hz, 1H) 3.94 (s, 3H), 3.88 (s, 3H), 2.75 (s, 3H); ESI m/z 293 [M + H]+. | 98.9 |
| 135 | 4-(4-(2-methoxy-6-methyl-pyridin-3-yl)-2-methyl-1H-benzo[d]imidazol-6-yl)-3,5-dimethyl isoxazole | $C_{20}H_{20}N_4O_2$ | L | $^1$H NMR (500 MHz, CD$_3$OD) δ 7.71 (d, J = 7.5 Hz, 1H), 7.45 (br s, 1H), 7.12 (s, 1H), 6.97 (d, J = 7.5 Hz, 1H), 3.95 (s, 3H), 2.58 (s, 3H), 2.53 (s, 3H), 2.47 (s, 3H), 2.32 (s, 3H); MM m/z 349 [M + H]+. | 96.5 |
| 136 | 5-(6-(3,5-dimethyl-isoxazol-4-yl)-2-methyl-1H-benzo[d]imidazol-4-yl)benzo[d]oxazole | $C_{20}H_{16}N_4O_2$ | D | $^1$H NMR (500 MHz, CD$_3$OD) δ 8.52 (s, 1H), 8.11 (br s, 1H), 7.81 (s, 1H), 7.80 (s, 1H), 7.44 (s, 1H), 7.23 (s, 1H), 2.61 (s, 3H), 2.46 (s, 3H), 2.30 (s, 3H); ESI m/z 345 [M + H]+. | 98.8 |
| 137 | 4-(4-(benzo[d]isothiazol-5-yl)-2-methyl-1H-benzo[d]imidazol-6-yl)-3,5-dimethyl isoxazole | $C_{20}H_{16}N_4OS$ | D | $^1$H NMR (500 MHz, CD$_3$OD) δ 9.07 (s, 1H), 8.75-8.40 (m, 1H), 8.21 (s, 1H), 8.15-7.85 (m, 1H), 7.44 (br.s, 1H), 7.30 (s, 1H), 2.62 (s, 3H), 2.46 (s, 3H), 2.31 (s, 3H); ESI m/z 361 [M + H]+. | >99 |

TABLE 1-continued

Examples prepared using the methods described above

| Example Compound | Chemical Name | Structure | General procedure | Characterization | Purity HPLC (%) |
|---|---|---|---|---|---|
| 138 | 3,5-dimethyl-4-(2-methyl-4-(naphthalen-1-yl)-1H-benzo[d]imidazol-6-yl)isoxazole | $C_{23}H_{19}N_3O$ | D | $^1$H NMR (500 MHz, CD$_3$OD) δ 7.97 (d, J = 6.0 Hz, 2H), 7.63-7.48 (m, 5H), 7.40 (br.s, 1H), 7.13 (s, 1H), 2.49 (s, 3H), 2.46 (s, 3H), 2.31 (s, 3H); ESI m/z 354 [M + H]+. | 97.2 |
| 139 | 4,4'-(2-methyl-1H-benzo[d]imidazole-4,6-diyl)bis(3-methyl isothiazole) | $C_{16}H_{14}N_4S_2$ | none | $^1$H NMR (500 MHz, CD$_3$OD) δ 8.91 (s, 1H), 8.80 (s, 1H), 7.58 (s, 1H), 7.22 (d, J = 1.5 Hz, 1H), 2.57 (s, 3H), 2.54 (s, 3H), 2.44 (s, 3H); ESI m/z 327 [M + H]+. | 95.5 |
| 140 | 4,4'-(3-methyl-1H-indole-4,6-diyl)bis(3,5-dimethyl isoxazole) | $C_{19}H_{19}N_3O_2$ | none | $^1$H NMR (500 MHz, CD$_3$OD) δ 7.33 (d, J = 1.4 Hz, 1H), 7.09 (d, J = 0.9 Hz, 1H), 6.72 (d, J = 1.5 Hz, 1H), 2.43 (s, 3H), 2.28 (s, 3H), 2.27 (s, 3H), 2.08 (s, 3H), 1.93 (d, J = 0.9 Hz, 3H); ESI m/z 322 [M + H]+. | >99 |
| 141 | 2-methyl-4,6-bis(4-methyl thiophen-3-yl)-1H-benzo[d]imidazole | $C_{18}H_{16}N_2S_2$ | A | $^1$H NMR (500 MHz, CD$_3$OD) δ 7.47 (s, 1H), 7.39 (d, J = 3.5 Hz, 1H), 7.25 (d, J = 4.0 Hz, 1H), 7.16 (s, 1H), 7.10 (d, J = 1.5 Hz, 1H), 7.09 (d, J = 1.5 Hz, 1H), 2.54 (s, 3H), 2.28 (s, 3H), 2.18 (s, 3H); ESI m/z 325 [M + H]+. | >99 |

TABLE 1-continued

Examples prepared using the methods described above

| Example Compound | Chemical Name | Structure | General procedure | Characterization | Purity HPLC (%) |
|---|---|---|---|---|---|
| 142 | 6-(3,5-dimethyl-isoxazol-4-yl)-N-phenethyl-1H-benzo[d]imidazol-4-amine | C$_{20}$H$_{20}$N$_4$O | G | $^1$H NMR (300 MHz, CD$_3$OD) δ 8.04 (s, 1H), 7.28-7.17 (m, 6H), 6.77 (s, 1H), 6.31 (s, 1H), 3.56 (t, J = 7.2 Hz, 2H), 3.01 (t, J = 7.2 Hz, 2H), 2.43 (s, 3H), 2.27 (s, 3H); ESI MS m/z 333 [M + H]+. | 95.0 |
| 143 | 6-(3,5-dimethyl-isoxazol-4-yl)-2-methyl-N-(2-methylpyridin-3-yl)-1H-benzo[d]imidazol-4-amine | C$_{19}$H$_{19}$N$_5$O | K | $^1$H NMR (500 MHz, CD$_3$OD) δ 7.99 (s, 1H), 7.30-7.80 (bs, 1H), 7.05 (s, 1H), 7.90-7.30 (bs, 1H), 6.60-6.90 (bs, 1H), 2.58 (s, 3H), 2.57 (s, 3H), 2.39 (s, 3H), 2.24 (s, 3H); ESI m/z 334 [M + H]+. | >99 |
| 144 | 4-(4-(2-chlorophenyl)-2-methyl-1H-benzo[d]imidazol-6-yl)-3,5-dimethyl isoxazole | C$_{19}$H$_{16}$ClN$_3$O | D | $^1$H NMR (500 MHz, CD$_3$OD) δ 7.58 (br.s, 1H), 7.51-7.39 (m, 4H), 7.05 (d, J = 1.5 Hz, 1H), 2.55 (s, 3H), 2.45 (s, 3H), 2.29 (s, 3H); ESI m/z 338 [M + H]+. | 96.9 |
| 145 | 4-(4-(benzo[b]thiophen-2-yl)-2-methyl-1H-benzo[d]imidazol-6-yl)-3,5-dimethyl isoxazole | C$_{21}$H$_{17}$N$_3$OS | D | $^1$H NMR (500 MHz, DMSO-d6) δ 12.57 and 12.44 (s, 1H), 8.56 (s, 1H), 8.04 and 7.99 (d, J = 8.0 Hz, 1H), 7.94 and 7.91 (d, J = 8.0 Hz, 1H), 7.57 and 7.49 (d, J = 1.0 Hz, 1H), 7.40 (s, 1H), 7.39-7.30 (m, 2H), 2.62 and 2.59 (s, 3H), 2.46 and 2.45 (s, 3H), 2.29 and 2.28 (s, 3H); ESI m/z 360 [M + H]+. | >99 |

TABLE 1-continued

Examples prepared using the methods described above

| Example Compound | Chemical Name | Structure | General procedure | Characterization | Purity HPLC (%) |
|---|---|---|---|---|---|
| 146 | 6-(3,5-dimethyl-isoxazol-4-yl)-2-methyl-N-(1,3,5-trimethyl-1H-pyrazol-4-yl)-1H-benzo[d]imidazol-4-amine | C₁₉H₂₂N₆O | K | ¹H NMR (500 MHz, CD₃OD) δ 6.67 (s, 1H), 5.81 (s, 1H), 3.74 (s, 3H), 2.60 (s, 3H), 2.30 (s, 3H), 2.15 (s, 3H), 2.13 (s, 3H), 2.06 (s, 3H); ESI m/z 351 [M + H]+; | 98.8 |
| 147 | 1-(6-(3,5-dimethyl-isoxazol-4-yl)-2-methyl-1H-benzo[d]imidazol-4-yl)azetidin-2-one | C₁₆H₁₆N₄O₂ | K | ¹H NMR (500 MHz, CD₃OD) δ 6.60-7.80 (bm, 2H), 3.70-4.30 (bm, 2H), 3.20 (t, J = 4.4 Hz, 2H), 2.61 (s, 3H), 2.41 (s, 3H), 2.25 (s, 3H); ESI m/z 297 [M + H]+; | 98.8 |
| 148 | 3,5-dimethyl-4-(2-methyl-4-phenoxy-1H-benzo[d]imidazol-6-yl)isoxazole | C₁₉H₁₇N₃O₂ | M | ¹H NMR (300 MHz, CD₃OD) δ 7.40-7.34 (m, 2H), 7.21 (s, 1H), 7.15-7.05 (m, 3H), 6.58 (d, J = 1.2 Hz, 1H), 2.58 (s, 3H), 2.36 (s, 3H), 2.19 (s, 3H); ESI m/z 320 [M + H]+. | 95.6 |
| 149 | 6,8-bis(3,5-dimethyl-isoxazol-4-yl)-[1,2,4]triazolo[4,3-a]pyridin-3(2H)-one | C₁₆H₁₅N₅O₃ | A | ¹H NMR (300 MHz, DMSO-d₆) δ 12.68 (s, 1H), 7.91 (d, J = 1.58 Hz, 1H), 7.26 (d, J = 1.5 Hz, 1H), 2.45 (s, 3H), 2.42 (s, 3H), 2.27 (s, 3H), 2.25 (s, 3H); ESI m/z 326 [M + H]+. | >99 |

TABLE 1-continued

Examples prepared using the methods described above

| Example Compound | Chemical Name | Structure | General procedure | Characterization | Purity HPLC (%) |
|---|---|---|---|---|---|
| 150 | 2-((4,6-bis(3,5-dimethyl-isoxazol-4-yl)-1H-benzo[d]imidazol-2-yl)amino)ethanol | 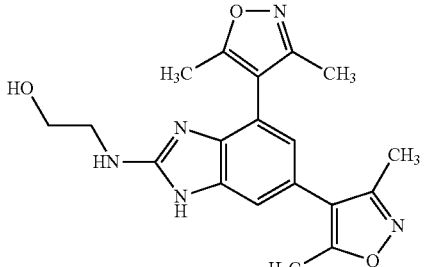 C₁₉H₂₁N₅O₃ | F | ¹H NMR (300 MHz, CD₃OD) δ 7.17 (s, 1H), 6.82 (s, 1H), 3.75 (t, J = 5.4 Hz, 2H), 3.50 (t, J = 5.4 Hz, 2H), 2.43 (s, 3H), 2.37 (s, 3H), 2.28 (s, 3H), 2.24 (s, 3H); ESI MS m/z 368 [M + H]+. | >99 |
| 151 | 6-(3,5-dimethyl-isoxazol-4-yl)-N,N-diphenethyl-1H-benzo[d]imidazol-4-amine | 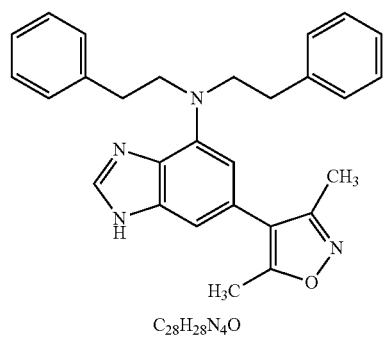 C₂₈H₂₈N₄O | G | ¹H NMR (300 MHz, DMSO-d6) δ 12.35 (s, 1H), 8.13 (s, 1H), 7.30-7.16 (m, 10H), 6.79 (d, J = 1.5 Hz, 1H), 6.30 (s, 1H), 3.97-3.92 (m, 4H), 2.92-2.87 (m, 4H), 2.44 (s, 3H), 2.26 (s, 3H); ESI MS m/z 437 [M + H]+. | >99 |
| 152 | 4-(4-(2-fluoro-3-methoxy-phenyl)-2-methyl-1H-benzo[d]imidazol-6-yl)-3,5-dimethyl isoxazole | 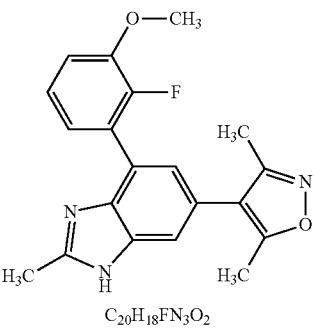 C₂₀H₁₈FN₃O₂ | D | ¹H NMR (500 MHz, CD₃OD) δ 7.47 (br.s, 1H), 7.23 (dd, J = 7.8, 7.5 Hz, 1H), 7.18 (dd, J = 7.8, 7.5 Hz, 1H), 7.13-7.08 (m, 2H), 3.94 (s, 3H), 2.57 (s, 3H), 2.44 (s, 3H), 2.29 (s, 3H); ESI m/z 352 [M + H]+. | >99 |
| 153 | 3,5-dimethyl-4-(2-methyl-4-(quinoxalin-6-yl)-1H-benzo[d]imidazol-6-yl)isoxazole | 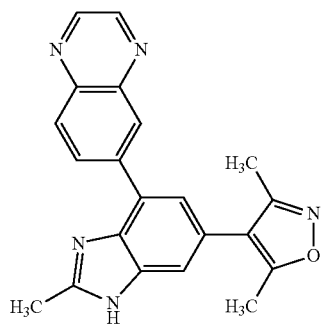 C₂₁H₁₇N₅O | D | ¹H NMR (500 MHz, CD₃OD) δ 8.92 (d, J = 11.0 Hz, 2H), 8.65-8.15 (m, 3H), 7.49 (br.s, 1H), 7.37 (s, 1H), 2.64 (s, 3H), 2.47 (s, 3H), 2.32 (s, 3H); ESI m/z 356 [M + H]+. | >99 |

TABLE 1-continued

Examples prepared using the methods described above

| Example Compound | Chemical Name | Structure | General procedure | Characterization | Purity HPLC (%) |
|---|---|---|---|---|---|
| 154 | 3,5-dimethyl-4-(2-methyl-4-(3-(methylsulfonyl)phenyl)-1H-benzo[d]imidazol-6-yl)isoxazole | $C_{20}H_{19}N_3O_3S$ | D | $^1$H NMR (500 MHz, CD$_3$OD) δ 8.43 (br.s, 1H), 8.17 (br.s, 1H), 8.00 (br.s, 1H), 7.78 (br.s, 1H), 7.44 (br.s, 1H), 7.26 (s, 1H), 3.23 (s, 3H), 2.62 (s, 3H), 2.45 (s, 3H), 2.29 (s, 3H); ESI m/z 382 [M + H]+. | >99 |
| 155 | 3,5-dimethyl-4-(2-methyl-4-((2-methylpyridin-3-yl)oxy)-1H-benzo[d]imidazol-6-yl)isoxazole | $C_{19}H_{18}N_4O_2$ | M | $^1$H NMR (300 MHz, CD$_3$OD) δ 8.50 (d, J = 5.7 Hz, 1H), 8.45 (s, 1H), 7.49 (br.s, 1H), 7.25 (d, J = 6.0 Hz, 1H), 7.12 (d, J = 0.9 Hz, 1H), 3.92 (s, 1H), 2.57 (s, 3H), 7.45 (s, 3H), 2.29 (s, 3H); ESI m/z 335 [M + H]+. | 99.0 |
| 156 | 4-(4-([1,2,4]triazolo[4,3-a]pyridin-6-yl)-2-methyl-1H-benzo[d]imidazol-6-yl)-3,5-dimethyl isoxazole | $C_{19}H_{16}N_6O$ | L | $^1$H NMR (300 MHz, CD$_3$OD) δ 9.55 (s, 1H), 9.23 (s, 1H), 8.29-8.19 (m, 2H), 7.84 (d, J = 1.5 Hz, 1H), 7.71 (d, J = 1.5 Hz, 1H), 2.93 (s, 3H), 2.49 (s, 3H), 2.32 (s, 3H); ESI m/z 345 [M + H]+. | 93.5 |
| 157 | 4-(4-(2-fluoro-5-(trifluoromethyl)phenyl)-2-methyl-1H-benzo[d]imidazol-6-yl)-3,5-dimethyl isoxazole | $C_{20}H_{15}F_4N_3O$ | D | $^1$H NMR (300 MHz, CD$_3$OD) δ 7.91 (br.s, 1H), 7.80 (br.s, 1H), 7.48 (br.s, 2H), 7.19 (s, 1H), 2.59 (s, 3H), 2.45 (s, 3H), 2.29 (s, 3H); ESI m/z 390 [M + H]+. | >99 |

TABLE 1-continued

Examples prepared using the methods described above

| Example Compound | Chemical Name | Structure | General procedure | Characterization | Purity HPLC (%) |
|---|---|---|---|---|---|
| 158 | (E)-3,5-dimethyl-4-(2-methyl-4-styryl-1H-benzo[d]imidazol-6-yl)isoxazole | $C_{21}H_{19}N_3O$ | D | $^1$H NMR (300 MHz, CD$_3$OD) δ 7.72-7.65 (m, 3H), 7.49-7.24 (m, 6H), 2.65 (s, 3H), 2.44 (s, 3H), 2.29 (s, 3H); ESI MS m/z 330 [M + H]+. | >99 |
| 159 | 4,4'-(quinoxaline-5,7-diyl)bis(3,5-dimethyl isoxazole) | $C_{18}H_{16}N_4O_2$ | none | $^1$H NMR (500 MHz, CD$_3$OD) δ 8.95 (d, J = 2.0 Hz, 1H), 8.92 (d, J = 1.5 Hz, 1H), 8.13 (d, J = 2.0 Hz, 1H), 7.81 (d, J = 2.0 Hz, 1H), 2.54 (s, 3H), 2.39 (s, 3H), 2.35 (s, 3H), 2.17 (s, 3H); ESI m/z 321 [M + H]+ >99%. | >99 |
| 160 | 4,6-di(furan-3-yl)-2-methyl-1H-benzo[d]midazole | $C_{16}H_{12}N_2O_2$ | A | $^1$H NMR (500 MHz, CD$_3$OD) δ 8.27 (br s, 1H), 7.91 (d, J = 1.0 Hz, 1H), 7.68-7.60 (m, 2H), 7.55 (t, J = 2.0 Hz, 1H), 7.52 (d, J = 1.0 Hz, 1H), 7.01 (br s, 1H), 6.85 (d, J = 2.0 Hz, 1H), 2.59 (s, 3H); ESI m/z 265 [M + H]+ | >99 |
| 161 | 3,5-dimethyl-4-(2-methyl-4-phenethyl-1H-benzo[d]imidazol-6-yl)isoxazole | $C_{21}H_{23}N_3O$ | none | $^1$H NMR (300 MHz, CD$_3$OD) δ 7.24-7.13 (m, 6H), 6.74 (s, 1H), 3.33-3.31 (m, 2H), 3.08-3.03 (m, 2H), 2.62 (s, 3H), 2.29 (s, 3H), 2.13 (s, 3H); ESI MS m/z 332 [M + H]+. | 96.2 |

TABLE 1-continued

Examples prepared using the methods described above

| Example Compound | Chemical Name | Structure | General procedure | Characterization | Purity HPLC (%) |
|---|---|---|---|---|---|
| 162 | 4-(4-(2-chloro-5-(trifluoromethyl)phenyl)-2-methyl-1H-benzo[d]imidazol-6-yl)-3,5-dimethyl isoxazole | 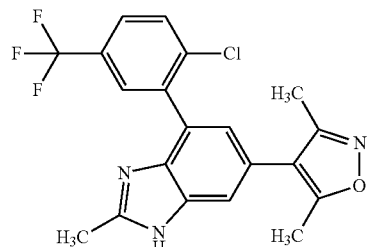<br>$C_{20}H_{15}ClF_3N_3O$ | D | $^1$H NMR (300 MHz, CD$_3$OD) δ 7.78 (br.s, 3H), 7.51 (br.s, 1H), 7.09 (d, J = 0.9 Hz, 1H), 2.57 (s, 3H), 2.45 (s, 3H), 2.29 (s, 3H); ESI m/z 406 [M + H]+. | >99 |
| 163 | 3,5-dimethyl-4-(2-methyl-4-(quinolin-3-yl)-1H-benzo[d]imidazol-6-yl)isoxazole | 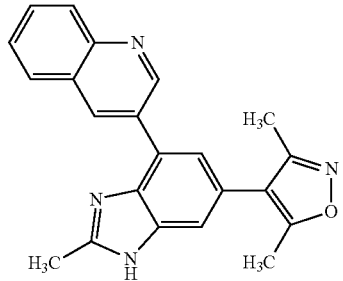<br>$C_{22}H_{18}N_4O$ | D | $^1$H NMR (300 MHz, CD$_3$OD) δ 9.31 (br.s, 1H), 8.77 (br.s, 1H), 8.09 (t, J = 8.4 Hz, 2H), 7.82 (dd, J = 6.9, 6.6 Hz, 1H), 7.68 (dd, J = 7.5, 7.2 Hz, 1H), 7.50 (s, 1H), 7.39 (s, 1H), 2.64 (s, 3H), 2.47 (s, 3H), 2.32 (s, 3H); ESI m/z 355 [M + H]+. | >99 |
| 164 | 2-methyl-4,6-di(1H-pyrrol-3-yl)-1H-benzo[d]imidazole | 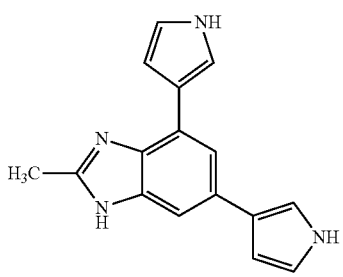<br>$C_{16}H_{14}N_4$ | none | $^1$H NMR (500 MHz, CD$_3$OD) δ 7.50 (d, J = 1.0 Hz, 1H), 7.52-7.20 (m, 2H), 7.09 (t, J = 2.0 Hz, 1H), 6.83 (s, 1H), 6.77 (dd, J = 2.5, 2.0 Hz, 1H), 6.60 (br s, 1H), 6.47 (dd, J = 2.5, 1.5 Hz, 1H), 2.56 (s, 3H); ESI m/z 263 [M + H]+ | >99 |
| 165 | N-(6-(3,5-dimethyl-isoxazol-4-yl)-2-methyl-1H-benzo[d]imidazol-4-yl)benzamide | 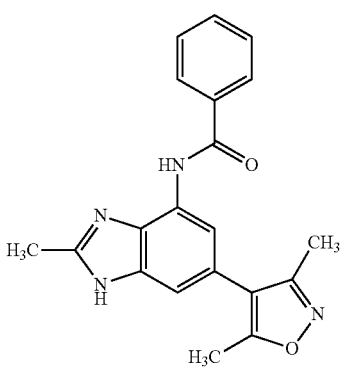<br>$C_{20}H_{18}N_4O_2$ | K | $^1$H NMR (500 MHz, CD$_3$OD) δ 8.09 (d, J = 7.5 Hz, 2H), 7.61 (t, J = 7.5 Hz, 1H), 7.55 (t, J = 7.5 Hz, 2H), 7.00-7.50 (br, 2H), 2.62 (s, 3H), 2.45 (s, 3H), 2.30 (s, 3H); ESI m/z 347 [M + H]+ | 98.2 |

TABLE 1-continued

Examples prepared using the methods described above

| Example Compound | Chemical Name | Structure | General procedure | Characterization | Purity HPLC (%) |
|---|---|---|---|---|---|
| 166 | 3,5-dimethyl-4-(2-methyl-4-(4-methyl-thiophen-3-yl)-1H-benzo[d]imidazol-6-yl)isoxazole | $C_{18}H_{17}N_3OS$ | D | $^1$H NMR (300 MHz, CD$_3$OD) δ 7.43 (s, 1H), 7.42 (s, 1H), 7.20 (br.s, 2H), 7.02 (d, J = 1.5 Hz, 1H); ESI m/z 324 [M + H]+. | >99 |
| 167 | 4,6-bis(1,4-dimethyl-1H-pyrazol-5-yl)-2-methyl-1H-benzo[d]imidazole | $C_{18}H_{20}N_6$ | A | $^1$H NMR (500 MHz, CD$_3$OD) δ 7.64-7.53 (m, 1H), 7.48-7.41 (m, 1H), 7.38 (s, 1H), 7.12 (br.s, 1H), 3.78 (s, 3H), 3.72 (s, 3H), 2.60 (s, 3H), 2.05 (s, 3H), 2.00 (s, 3H); ESI m/z 321 [M + H]+. | >99 |
| 168 | 5,5'-(2-methyl-1H-benzo[d]imidazole-4,6-diyl)bis(2,4-dimethylthiazole) | $C_{18}H_{18}N_4S_2$ | A | $^1$H NMR (300 MHz, CD$_3$OD) δ 7.63-7.51 (m, 1H), 7.22 (s, 1H), 2.73 (s, 3H), 2.68 (s, 3H), 2.58 (s, 3H), 2.44 (s, 3H), 2.36-2.29 (m, 3H); ESI m/z 355 [M + H]+. | >99 |
| 169 | 4-(4-(1,4-dimethyl-1H-pyrazol-5-yl)-2-methyl-1H-benzo[d]imidazol-6-yl)-3,5-dimethylisoxazole | $C_{18}H_{19}N_5O$ | D | $^1$H NMR (500 MHz, CD$_3$OD) δ 7.60-7.49 (m, 1H), 7.47-7.42 (m, 1H), 7.12-7.06 (m, 1H), 3.71 (s, 3H), 2.58 (s, 3H), 2.45 (s, 3H), 2.29 (s, 3H), 2.00 (br.s, 3H); ESI m/z 322 [M + H]+. | >99 |
| 170 | 4-(4-(2,4-dimethylthiazol-5-yl)-2-methyl-1H-benzo[d]imidazol-6-yl)-3,5-dimethylisoxazole | $C_{18}H_{18}N_4OS$ | D | $^1$H NMR (500 MHz, CD$_3$OD) δ 7.53-7.41 (m, 1H), 7.11 (d, J = 1.5 Hz, 1H), 2.72 (s, 3H), 2.59 (s, 3H), 2.43 (s, 3H), 2.37-2.30 (m, 3H), 2.28 (s, 3H); ESI m/z 339 [M + H]+. | >99 |

TABLE 1-continued

Examples prepared using the methods described above

| Example Compound | Chemical Name | Structure | General procedure | Characterization | Purity HPLC (%) |
|---|---|---|---|---|---|
| 171 | 4-(4-((4-methoxy-pyridin-3-yl)oxy)-2-methyl-1H-benzo[d]imidazol-6-yl)-3,5-dimethyl isoxazole | $C_{19}H_{18}N_4O_3$ | M | $^1$H NMR (300 MHz, CD$_3$OD) δ 8.32 (d, J = 5.7 Hz, 1H), 8.17 (s, 1H), 7.25 (d, J = 5.7 Hz, 1H), 7.17 (s, 1H), 6.35 (d, J = 1.2 Hz, 1H), 3.91 (s, 3H), 2.60 (s, 3H), 2.33 (s, 3H), 2.16 (s, 3H); ESI m/z 351 [M + H]+. | >99 |
| 172 | 3-((6-(3,5-dimethyl-isoxazol-4-yl)-2-methyl-1H-benzo[d]imidazol-4-yl)oxy)-4-methyl benzonitrile | $C_{21}H_{18}N_4O_2$ | M | $^1$H NMR (300 MHz, CD$_3$OD) δ 7.49 (d, J = 4.8 Hz, 1H), 7.40 (d, J = 4.5 Hz, 1H), 7.27 (s, 1H), 7.05 (br.s, 1H), 6.59 (d, J = 0.6 Hz, 1H), 2.59 (s, 3H), 2.45 (s, 3H), 2.38 (s, 3H), 2.21(s, 3H); ESI m/z 359 [M + H]+. | >99 |
| 173 | 4-(6-(3,5-dimethyl-isoxazol-4-yl)-2-methyl-1H-benzo[d]imidazol-4-yl) morpholine | $C_{17}H_{20}N_4O_2$ | K | $^1$H NMR (500 MHz, CD$_3$OD) δ 6.99 (brs, 1H), 6.53 (brs, 1H), 3.93 (t, J = 4.5 Hz, 4H), 3.20-3.40 (m, 4H), 2.58 (s, 3H), 2.40 (s, 3H), 2.25 (s, 3H); ESI m/z 313 [M + H]+; | 97.6 |
| 174 | 3-((6-(3,5-dimethyl-isoxazol-4-yl)-2-methyl-1H-benzo[d]imidazol-4-yl)oxy)-4-methyl benzamide | $C_{21}H_{20}N_4O_3$ | none | $^1$H NMR (300 MHz, CD$_3$OD) δ 7.61 (dd, J = 7.5, 1.2 Hz, 1H), 7.46 (d, J = 1.2 Hz, 1H), 7.41 (d, J = 7.8 Hz, 1H), 7.19 (br.s, 1H), 6.42 (s, 1H), 2.60 (s, 3H), 2.38 (s, 3H), 2.34 (s, 3H), 2.17 (s, 3H); APCI m/z 377 [M + H]+ | >99 |

TABLE 1-continued

Examples prepared using the methods described above

| Example Compound | Chemical Name | Structure | General procedure | Characterization | Purity HPLC (%) |
|---|---|---|---|---|---|
| 175 | 3-((6-(3,5-dimethyl-isoxazol-4-yl)-2-methyl-1H-benzo[d]imidazol-4-yl)oxy)-4-methyl benzoic acid | C$_{21}$H$_{19}$N$_{3}$O$_{4}$ | none | $^1$H NMR (300 MHz, CD$_3$OD) δ 7.73 (dd, J = 7.8, 1.2 Hz, 1H), 7.48 (d, J = 1.2 Hz, 1H), 7.42 (d, J = 7.8 Hz, 1H), 7.23 (s, 1H), 6.49 (d, J = 1.2 Hz, 1H), 2.60 (s, 3H), 2.41 (s, 3H), 2.35 (s, 3H), 2.18 (s, 3H); APCI m/z 378 [M + H]+. | >99 |
| 176 | 4,4'-(2-methyl-3H-imidazo[4,5-b]pyridine-5,7-diyl)bis(3,5-dimethyl-isoxazole) | C$_{17}$H$_{17}$N$_{5}$O$_{2}$ | No general procedure | $^1$H NMR (300 MHz, CD$_3$OD) δ 8.18 (s, 1H), 7.69 (d, J = 1.6 Hz, 1H), 7.08 (d, J = 1.6 Hz, 1H), 3.58 (s, 3H), 2.44 (s, 3H), 2.32 (s, 3H), 2.28 (s, 3H), 2.13 (s, 3H); ESI m/z 321 [M + H]+. | >99 |
| 177 | 4-(6-(3,5-dimethyl-isoxazol-4-yl)-2-methyl-1H-benzo[d]imidazol-4-yl)-3-methyl morpholine | C$_{18}$H$_{22}$N$_{4}$O$_{2}$ | K | $^1$H NMR (500 MHz, CD$_3$OD) δ 7.40-6.40 (m, 2H), 4.20-3.70 (m, 4H), 3.20-3.40 (m, 3H), 2.58 (s, 3H), 2.41 (s, 3H), 2.25 (s, 3H), 0.95 (s, 3H); ESI m/z 327 [M + H]+. | 96.7 |
| 178 | 4-(6-(1,4-dimethyl-1H-pyrazol-5-yl)-2-methyl-1H-benzo[d]imidazol-4-yl)-3,5-dimethyl isoxazole | C$_{18}$H$_{19}$N$_{5}$O | No general procedure | $^1$H NMR (400 MHz, CD$_3$OD) δ 7.51 (br s, 1H), 7.38 (br s, 1H), 7.08 (d, J = 3.6 Hz, 1H), 3.77 (s, 3H), 2.59 (s, 3H), 2.37 (s, 3H), 2.23 (s, 3H), 2.04 (s, 3H); ESI MS m/z 322 [M + H]+. | |

TABLE 1-continued

Examples prepared using the methods described above

| Example Compound | Chemical Name | Structure | General procedure | Characterization | Purity HPLC (%) |
|---|---|---|---|---|---|
| 179 | 4,4'-(3-methyl-1H-indazole-4,6-diyl)bis(3,5-dimethyl isoxazole) | $C_{18}H_{18}N_4O_2$ | No general procedure | $^1$H NMR (400 MHz, CDCl$_3$) δ 10.09 (br s, 1H), 7.36 (s, 1H), 6.79 (s, 1H), 2.47 (s, 3H), 2.33 (s, 3H), 2.32 (s, 3H), 2.26 (s, 3H), 2.15 (s, 3H); ESI MS m/z 321 [M − H]−. | |
| 180 | 4-(4-(3,5-dimethyl-1H-pyrazol-4-yl)-3-methyl-1H-indazol-6-yl)-3,5-dimethyl isoxazole | $C_{18}H_{19}N_5O$ | No general procedure | $^1$H NMR (400 MHz, CDCl$_3$) δ 7.28 (d, J = 1.6 Hz, 1H), 6.78 (d, J = 1.6 Hz, 1H), 2.47 (s, 3H), 2.33 (s, 3H), 2.20 (s, 3H), 2.16 (s, 6H); ESI MS m/z 322 [M + H]+. | |
| 181 | 3,5-dimethyl-4-(2-(4-methyl-piperazin-1-yl)-4-(1,3,5-trimethyl-1H-pyrazol-4-yl)-1H-benzo[d]imidazol-6-yl)isoxazole | $C_{23}H_{29}N_7O$ | O | $^1$H NMR (400 MHz, CDCl$_3$) δ 9.80 (br s, 1H), 7.32 (br s, 1H), 6.64 (br s, 1H), 3.69-3.74 (m, 4H), 3.68 (s, 3H), 2.51-2.59 (m, 4H), 2.44 (s, 3H), 2.36 (s, 3H), 2.30 (s, 3H), 2.17 (s, 3H), 2.12 (s, 3H); ESI MS m/z 420 [M + H]+. | |
| 182 | 3,5-dimethyl-4-(1-methyl-7-(1,3,5-trimethyl-1H-pyrazol-4-yl)-1H-benzo[d]imidazol-5-yl)isoxazole | $C_{19}H_{21}N_5O$ | N | $^1$H NMR (400 MHz, CDCl$_3$) δ 7.84 (br s, 1H), 7.67 (d, J = 1.6 Hz, 1H), 7.89 (d, J = 1.6 Hz, 1H), 3.85 (s, 3H), 3.49 (s, 3H), 2.45 (s, 3H), 2.32 (s, 3H), 2.13 (s, 3H), 2.09 (s, 3H); ESI MS m/z 336 [M + H]+. | |

TABLE 1-continued

Examples prepared using the methods described above

| Example Compound | Chemical Name | Structure | General procedure | Characterization | Purity HPLC (%) |
|---|---|---|---|---|---|
| 183 | 3,5-dimethyl-4-(2-(4-methyl-piperazin-1-yl)-4-(2-methyl-pyridin-3-yl)-1H-benzo[d]imidazol-6-yl)isoxazole | C₂₃H₂₆N₆O | No general procedure | $^1$H NMR (400 MHz, CDCl$_3$) δ 11.21 (br s, 1H), 7.94 (d, J = 3.9 Hz, 1H), 7.58 (dd, J = 7.6, 1.4 Hz, 1H), 7.40 (s, 1H), 7.04 (dd, J = 7.6, 4.9 Hz, 1H), 6.68 (d, J = 1.6 Hz, 1H), 3.74 (br s, 4H), 2.51 (t, J = 4.7 Hz, 4H), 2.44 (s, 3H), 2.43 (s, 3H), 2.31 (s, 6H); ESI MS m/z 401 [M − H]−. | |
| 184 | 4-(6-(3,5-dimethyl-isoxazol-4-yl)-4-(1,3,5-trimethyl-1H-pyrazol-4-yl)-1H-benzo[d]imidazol-2-yl)morpholine | C₂₂H₂₆N₆O₂ | O | $^1$H NMR (400 MHz, CD$_3$OD) δ 7.17 (br s, 1H), 6.77 (br s, 1H), 3.78-3.82 (m, 4H), 3.79 (s, 3H), 3.51-3.53 (m, 4H), 2.43 (s, 3H), 2.28 (s, 3H), 2.19 (s, 3H), 2.16 (s, 3H); ESI MS m/z 407 [M + H]+. | |
| 185 | 6-(3,5-dimethyl-isoxazol-4-yl)-N-(1-methyl-piperidin-4-yl)-4-(1,3,5-trimethyl-1H-pyrazol-4-yl)-1H-benzo[d]imidazol-2-amine | C₂₄H₃₁N₇O | O | $^1$H NMR (400 MHz, CD$_3$OD) δ 7.12 (br s, 1H), 6.71 (br s, 1H), 3.79 (s, 3H), 5.70 (br s, 1H), 2.88-2.90 (m, 2H), 2.43 (s, 3H), 2.31 (s, 3H), 2.28 (s, 3H), 2.23-2.27 (m, 2H), 2.19 (s, 3H), 2.15 (s, 3H), 2.10-2.19 (m, 2H), 2.07-2.10 (m, 2H), 1.59-1.64 (m, 2H); ESI MS m/z 434 [M + H]+. | |

TABLE 1-continued

Examples prepared using the methods described above

| Example Compound | Chemical Name | Structure | General procedure | Characterization | Purity HPLC (%) |
|---|---|---|---|---|---|
| 186 | 3-(6-(3,5-dimethyl-isoxazol-4-yl)-2-(4-methyl-piperazin-1-yl)-1H-benzo[d]imidazol-4-yl)-4-methyl benzonitrile | C$_{25}$H$_{26}$N$_6$O | P | $^1$H NMR (400 MHz, CD$_3$OD) δ 7.66 (s, 2H), 7.51 (d, J = 7.8 Hz, 1H), 7.23 (br s, 1H), 6.81 (br s, 1H), 3.58 (t, J = 4.9 Hz, 4H), 2.57 (t, J = 4.9 Hz, 4H), 2.43 (s, 3H), 2.34 (s, 3H), 2.28 (s, 6H); ESI MS m/z 425 [M − H]−. | |
| 187 | 3,5-dimethyl-4-(2-(methylthio)-4-(1,3,5-tri methyl-1H-pyrazol-4-yl)-1H-benzo[d]imidazol-6-yl)isoxazole | C$_{19}$H$_{21}$N$_5$OS | No general procedure | $^1$H NMR (400 MHz, CDCl$_3$) δ 11.00 (br s, 1H), 7.55 (dd, J = 1.6, 0.8 Hz, 1H), 6.83 (d, J = 1.6 Hz, 1H), 3.71 (s, 3H), 2.83 (s, 3H), 2.45 (s, 3H), 2.32 (s, 3H), 2.17 (s, 3H), 2.07 (s, 3H); ESI MS m/z 368 [M + H]+. | |
| 188 | 3,5-dimethyl-4-(1-methyl-2-(methylthio)-4-(1,3,5 trimethyl-1H-pyrazol-4-yl)-1H-benzo[d]imidazol-6-yl)isoxazole | C$_{20}$H$_{23}$N$_5$OS | No general procedure | $^1$H NMR (400 MHz, CDCl$_3$) δ 7.02 (d, J = 1.6 Hz, 1H), 6.91 (d, J = 1.6 Hz, 1H), 3.82 (s, 3H), 3.72 (s, 3H), 2.78 (s, 3H), 2.45 (s, 3H), 2.32 (s, 3H), 2.31 (s, 3H), 2.30 (s, 3H); ESI MS m/z 382 [M + H]+. | |
| 189 | 3-(6-(3,5-dimethyl-isoxazol-4-yl)-2-(4-methyl-piperazin-1-yl)-1H-benzo[d]imidazol-4-yl)-4-methyl benzamide | C$_{25}$H$_{28}$N$_6$O$_2$ | Q | $^1$H NMR (400 MHz, CD$_3$OD) δ 7.83 (s, 1H), 7.79 (d, J = 7.4 Hz, 1H), 7.44 (br s, 1H), 7.27 (br s, 1H), 6.77 (br s, 1H), 3.60 (br s, 4H), 2.58 (t, J = 4.7 Hz, 4H), 2.44 (s, 3H), 2.36 (s, 3H), 2.30 (s, 6H); ESI MS m/z 445 [M + H]+. | |

TABLE 1-continued

Examples prepared using the methods described above

| Example Compound | Chemical Name | Structure | General procedure | Characterization | Purity HPLC (%) |
|---|---|---|---|---|---|
| 190 | 6-(3,5-dimethyl-isoxazol-4-yl)-N-(tetrahydro-2H-pyran-4-yl)-4-(1,3,5-trimethyl-1H-pyrazol-4-yl)-1H-benzo[d]imidazol-2-amine | 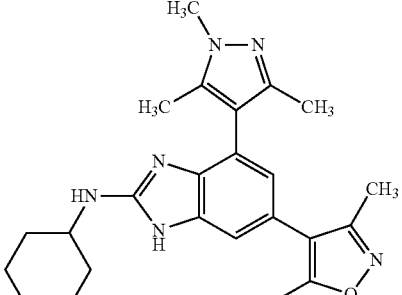 C₂₃H₂₈N₆O₂ | O | ¹H NMR (400 MHz, CD₃OD) δ 7.12 (br s, 1H), 6.71 (br s, 1H), 3.96-3.40 (m, 2H), 3.86-3.91 (m, 1H), 3.79 (s, 3H), 3.52-3.58 (m, 2H), 2.42 (s, 3H), 2.21 (s, 3H), 2.19 (s, 3H), 2.15 (s, 3H), 2.02-2.05 (m, 2H), 1.53-1.63 (m, 2H); ESI MS m/z 421 [M + H]+. | |
| 191 | 3,5-dimethyl-4-(1-methyl-2-(methylthio)-7-(1,3,5-trimethyl-1H-pyrazol-4-yl)-1H-benzo[d]imidazol-5-yl) isoxazole | 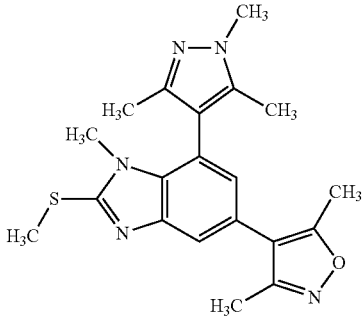 C₂₀H₂₃N₅OS | No general procedure | ¹H NMR (400 MHz, CDCl₃) δ 7.55 (d, J = 1.6 Hz, 1H), 6.76 (d, J = 1.6 Hz, 1H), 3.84 (s, 3H), 3.36 (s, 3H), 2.82 (s, 3H), 2.44 (s, 3H), 2.31 (s, 3H), 2.12 (s, 3H), 2.10 (s, 3H); ESI MS m/z 382 [M + H]+. | |
| 192 | 4,4'-(7-bromo-1H-benzo[d]imidazole-4,6-diyl)bis(3,5-dimethyl isoxazole) | 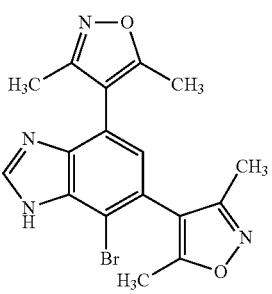 C₁₇H₁₅BrN₄O₂ | No general procedure | ¹H NMR (400 MHz, CDCl₃) δ 9.90 (br s, 1H), 8.19 (br s, 1H), 6.99 (s, 1H), 2.44 (br s, 3H), 2.35 (s, 3H), 2.31 (br s, 3H), 2.20 (s, 3H); ESI MS m/z 387 [M + H]+. | |
| 192 | 3-(6-(3,5-dimethyl-isoxazol-4-yl)-2-morpholino-1H-benzo[d]imidazol-4-yl)-4-methyl benzonitrile | 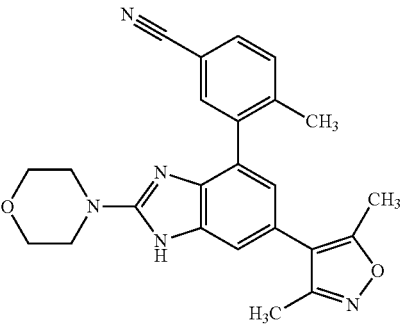 C₂₄H₂₃N₅O₂ | P | ¹H NMR (400 MHz, CD₃OD) δ 7.63-7.69 (m, 2H), 7.51 (d, J = 8.2 Hz, 1H), 7.24 (br s, 1H), 6.82 (s, 1H), 3.76-3.82 (m, 4H), 3.49-3.55 (m, 4H), 2.43 (s, 3H), 2.28 (s, 6H); ESI MS m/z 414 [M + H]+. | |

TABLE 1-continued

Examples prepared using the methods described above

| Example Compound | Chemical Name | Structure | General procedure | Characterization | Purity HPLC (%) |
|---|---|---|---|---|---|
| 194 | 3,5-dimethyl-4-(2-(methylsulfinyl)-7-(1,3,5-trimethyl-1H-pyrazol-4-yl)-1H-benzo[d]imidazol-5-yl)isoxazole | $C_{19}H_{21}N_5O_2S$ | No general procedure | $^1$H NMR (400 MHz, CD$_3$OD) δ 7.58 (br s, 1H), 7.13 (d, J = 1.6 Hz, 1H), 3.81 (s, 3H), 3.13 (s, 3H), 2.46 (s, 3H), 2.31 (s, 3H), 2.22 (s, 3H), 2.17 (s, 3H); ESI MS m/z 382 [M − H]−. | |
| 195 | 3,5-dimethyl-4-(2-(methylsulfonyl)-7-(1,3,5-trimethyl-1H-pyrazol-4-yl)-1H-benzo[d]imidazol-5-yl)isoxazole | $C_{19}H_{21}N_5O_3S$ | No general procedure | $^1$H NMR (400 MHz, CD$_3$OD) δ 7.60 (br s, 1H), 7.18 (d, J = 1.1 Hz, 1H), 3.82 (s, 3H), 3.39 (s, 3H), 2.47 (s, 3H), 2.31 (s, 3H), 2.22 (s, 3H), 2.18 (s, 3H); ESI MS m/z 398 [M − H]−. | |
| 196 | 4-(6-(3,5-dimethylisoxazol-4-yl)-4-(4-methylpyridin-3-yl)-1H-benzo[d]imidazol-2-yl)morpholine | $C_{22}H_{23}N_5O_2$ | R | $^1$H NMR (400 MHz, CDCl$_3$) δ 11.65 (br s, 1H), 8.34 (s, 1H), 7.93 (d, J = 4.8 Hz, 1H), 7.39 (s, 1H), 7.11 (d, J = 4.8 Hz, 1H), 6.67 (s, 1H), 3.77 (br s, 4H), 3.62 (br s, 4H), 2.43 (s, 3H), 2.29 (s, 6H); ESI MS m/z 390 [M + H]+. | |
| 197 | 3-(6-(3,5-dimethylisoxazol-4-yl)-2-morpholino-1H-benzo[d]imidazol-4-yl)-4-methyl benzamide | $C_{24}H_{25}N_5O_3$ | Q | $^1$H NMR (400 MHz, CD$_3$OD) δ 7.80-7.86 (m, 2H), 7.43 (d, J = 7.8 Hz, 1H), 7.23 (br s, 1H), 6.83 (br s, 1H), 3.76-3.82 (m, 4H), 3.49-3.55 (m, 4H), 2.43 (s, 3H), 2.28 (s, 3H), 2.26 (s, 3H); ESI MS m/z 432 [M + H]+. | |

TABLE 1-continued

Examples prepared using the methods described above

| Example Compound | Chemical Name | Structure | General procedure | Characterization | Purity HPLC (%) |
|---|---|---|---|---|---|
| 198 | 3-(6-(3,5-dimethyl-isoxazol-4-yl)-2-((tetrahydro-2H-pyran-4-yl)amino)-1H-benzo[d]imidazol-4-yl)-4-methyl benzonitrile | C₂₅H₂₅N₅O₂ | P | ¹H NMR (400 MHz, CD₃OD) δ 7.66 (s, 2H), 7.52 (d, J = 7.8 Hz, 1H), 7.19 (br s, 1H), 6.77 (s, 1H), 3.97 (d, J = 11.3 Hz, 2H), 3.86 (br s, 1H), 3.53 (t, J = 11.3 Hz, 2H), 2.43 (s, 3H), 2.29 (s, 3H), 2.27 (s, 3H), 2.01 (d, J = 12.1 Hz, 2H), 1.58 (m, 2H); ESI MS m/z 428 [M + H]+. | |
| 199 | 3,5-dimethyl-4-(2-(4-methyl piperazin-1-yl)-4-(4-methyl pyridin-3-yl)-1H-benzo[d]imidazol-6-yl)isoxazole | C₂₃H₂₆N₆O | R | ¹H NMR (400 MHz, CDCl₃) δ 11.51 (br s, 1H), 8.34 (s, 1H), 7.94 (d, J = 5.0 Hz, 1H), 7.37 (d, J = 1.0 Hz, 1H), 7.10 (d, J = 5.0 Hz, 1H), 6.65 (d, J = 1.0 Hz, 1H), 3.67 (br t, J = 5.0 Hz, 4H), 2.47 (br t, J = 5.0 Hz, 4H), 2.43 (s, 3H), 2.29 (s, 9H); ESI MS m/z 403 [M + 1]+. | |
| 200 | 3-(6-(3,5-dimethyl-isoxazol-4-yl)-2-((tetrahydro-2H-pyran-4-yl)amino)-1H-benzo[d]imidazol-4-yl)-4-methyl benzamide | C₂₅H₂₇N₅O₃ | Q | ¹H NMR (400 MHz, CD₃OD) δ 7.80-7.87 (m, 2H), 7.45 (d, J = 7.4 Hz, 1H), 7.18 (br s, 1H), 6.79 (s, 1H), 3.97 (d, J = 11.3 Hz, 2H), 3.87 (br s, 1H), 3.53 (t, J = 11.3 Hz, 2H), 2.43 (s, 3H), 2.28 (s, 6H), 2.02 (d, J = 12.1 Hz, 2H), 1.48-1.64 (m, 2H); ESI MS m/z 446 [M + H]+. | |

TABLE 1-continued

Examples prepared using the methods described above

| Example Compound | Chemical Name | Structure | General procedure | Characterization | Purity HPLC (%) |
|---|---|---|---|---|---|
| 201 | 6-(3,5-dimethyl-isoxazol-4-yl)-4-(4-methyl-pyridin-3-yl)-N-(tetrahydro-2H-pyran-4-yl)-1H-benzo[d]imidazol-2-amine | 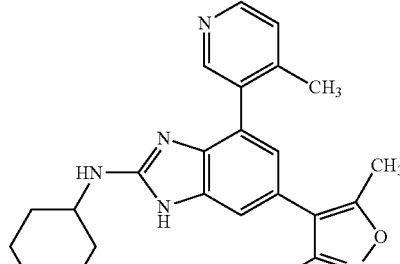 C<sub>23</sub>H<sub>25</sub>N<sub>5</sub>O<sub>2</sub> | R | $^1$H NMR (400 MHz, CDCl$_3$) δ ppm 11.40 (br s, 1H), 8.46 (s, 1H), 8.10 (br s, 1H), 7.34 (br s, 1H), 7.18 (d, J = 4.8 Hz, 1H), 6.71 (s, 1H), 4.71 (br s, 1H), 4.04 (br s, 1H), 3.95-3.92 (m, 2H), 3.44 (t, J = 10.8 Hz, 2H), 2.42 (s, 3H), 2.33 (s, 3H), 2.29 (s, 3H), 2.10-2.04 (m, 2H), 1.55-1.45 (m, 2H). ESI MS m/z 404 [M + H]+. | |
| 202 | 3-(6-(3,5-dimethyl-isoxazol-4-yl)-2-(4-methyl-piperazin-1-yl)-1H-benzo[d]imidazol-4-yl)-2-methyl benzonitrile | 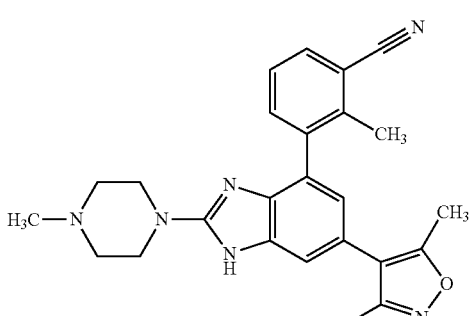 C<sub>25</sub>H<sub>26</sub>N<sub>6</sub>O | S | $^1$H NMR (400 MHz, CD$_3$OD) δ 7.73 (d, J = 7.8 Hz, 1H), 7.61 (d, J = 7.4 Hz, 1H), 7.43 (t, J = 7.8 Hz, 1H), 7.23 (br s, 1H), 6.81 (br s, 1H), 3.57 (t, J = 4.8 Hz, 4H), 2.56 (t, J = 4.8 Hz, 4H), 2.42 (s, 3H), 2.39 (s, 3H), 2.34 (s, 3H), 2.27 (s, 3H); ESI MS m/z 425 [M − H]−. | |
| 203 | 3-(6-(3,5-dimethyl-isoxazol-4-yl)-2-morpholino-1H-benzo[d]imidazol-4-yl)-2-methyl benzonitrile | 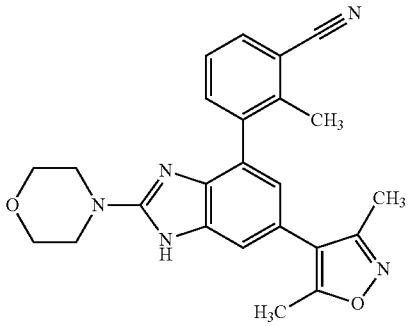 C<sub>24</sub>H<sub>23</sub>N<sub>5</sub>O<sub>2</sub> | S | $^1$H NMR (400 MHz, CD$_3$OD) δ 7.72 (d, J = 8.0 Hz, 1H), 7.61 (d, J = 7.2 Hz, 1H), 7.44 (t, J = 8.0 Hz, 1H), 7.24 (br s, 1H), 6.81 (br s, 1H), 3.79 (m, 4H), 3.51 (m, 4H), 2.42 (s, 3H), 2.39 (s, 3H), 2.27 (s, 3H); ESI MS m/z 414 [M + H]+. | |

TABLE 1-continued

Examples prepared using the methods described above

| Example Compound | Chemical Name | Structure | General procedure | Characterization | Purity HPLC (%) |
|---|---|---|---|---|---|
| 204 | 3-(6-(3,5-dimethyl-isoxazol-4-yl)-2-((tetrahydro-2H-pyran-4-yl)amino)-1H-benzo[d]imidazol-4-yl)-2-methyl benzonitrile | C₂₅H₂₅N₅O₂ | S | ¹H NMR (400 MHz, CD₃OD) δ 7.73 (d, J = 8.0 Hz, 1H), 7.60 (d, J = 7.6 Hz, 1H), 7.44 (t, J = 8.0 Hz, 1H), 7.19 (br s, 1H), 6.76 (d, J = 1.2 Hz, 1H), 3.96 (m, 2H), 3.86 (m, 1H), 3.52 (m, 2H), 2.42 (s, 3H), 2.40 (s, 3H), 2.27 (s, 3H), 2.01 (m, 2H), 1.57 (m, 2H); ESI MS m/z: 428 [M + H]+. | |
| 205 | 3-(6-(3,5-dimethyl-isoxazol-4-yl)-2-((1-methyl-piperidin-4-yl)amino)-1H-benzo[d]imidazol-4-yl)-4-methyl benzonitrile | C₂₆H₂₈N₆O | P | ¹H NMR (400 MHz, CD₃OD) 7.66 (br s, 2H), 7.52 (d, J = 8.2 Hz, 1H), 7.18 (s, 1H), 6.77 (s, 1H), 3.67 (br s, 1H), 2.84-2.92 (m, 2H), 2.43 (s, 3H), 2.30 (br s, 3H), 2.29 (s, 3H), 2.27 (s, 3H), 2.21 (t, J = 11.5 Hz, 2H), 2.02-2.12 (m, 2H), 1.52-1.67 (m, 2H); ESI MS m/z 441 [M + H]⁺. | |
| 206 | 3-(6-(3,5-dimethyl-isoxazol-4-yl)-2-(4-methyl-piperazin-1-yl)-1H-benzo[d]imidazol-4-yl)-2-methyl benzamide | C₂₅H₂₈N₆O₂ | Q | ¹H NMR (400 MHz, CD₃OD) 7.42-7.50 (m, 1H), 7.37-7.42 (m, 1H), 7.29-7.37 (m, 1H), 7.23 (br s, 1H), 6.78 (br s, 1H), 3.59 (br s, 4H), 2.56 (br s, 4H), 2.43 (s, 3H), 2.34 (s, 3H), 2.28 (s, 3H), 2.23 (s, 3H); ESI MS m/z 445 [M + H]⁺. | |

TABLE 1-continued

Examples prepared using the methods described above

| Example Compound | Chemical Name | Structure | General procedure | Characterization | Purity HPLC (%) |
|---|---|---|---|---|---|
| 207 | 3-(6-(3,5-dimethyl-isoxazol-4-yl)-2-((tetrahydro-2H-pyran-4-yl)amino)-1H-benzo[d]imidazol-4-yl)-2-methyl benzamide | 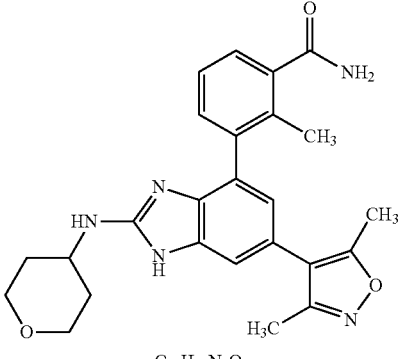 C25H27N5O3 | Q | $^1$H NMR (400 MHz, CD$_3$OD) 7.45 (d, J = 6.8 Hz, 1H), 7.37-7.42 (m, 1H), 7.32-7.35 (m, 1H), 7.17 (br s, 1H), 6.75 (br s, 1H), 3.95-3.98 (m, 2H), 3.88 (m, 1H), 3.46-3.56 (m, 2H), 2.42 (s, 3H), 2.27 (s, 3H), 2.25 (s, 3H), 2.01-2.04 (m, 2H), 1.52-1.62 (m, 2H); ESI MS m/z 446 [M + H]$^+$. | |
| 208 | 3-(6-(3,5-dimethyl-isoxazol-4-yl)-2-morpholino-1H-benzo[d]imidazol-4-yl)-2-methyl benzamide | 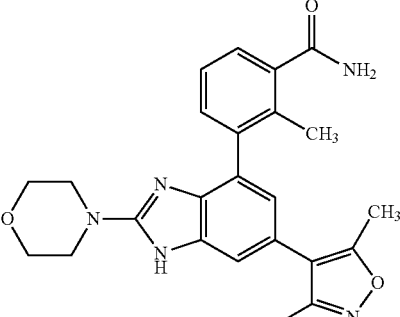 C24H25N5O3 | Q | $^1$H NMR (400 MHz, CD$_3$OD) δ 7.45 (d, J = 7.6 Hz, 1H), 7.40 (d, J = 6.4 Hz, 1H), 7.32-7.35 (m, 1H), 7.23 (br s, 1H), 6.79 (br s, 1H), 3.78-3.81 (m, 4H), 3.52-3.54 (m, 4H), 2.43 (s, 3H), 2.28 (s, 3H), 2.24 (s, 3H); ESI MS m/z 432 [M + H]+. | |
| 209 | 3-(2-(4-amino-piperidin-1-yl)-6-(3,5-dimethyl-isoxazol-4-yl)-1H-benzo[d]imidazol-4-yl)-2-methyl benzonitrile | 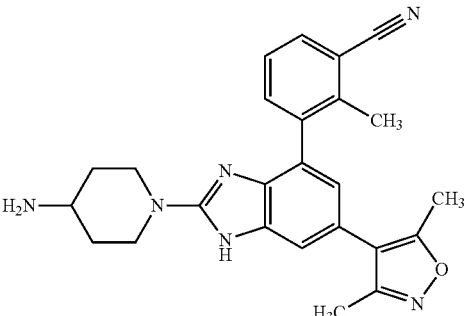 C25H26N6O | S | $^1$H NMR (400 MHz, CD$_3$OD) δ 7.73 (d, J = 7.4 Hz, 1H), 7.61 (d, J = 7.8 Hz, 1H), 7.43 (t, J = 7.8 Hz, 1H), 7.20 (s, 1H), 6.78 (s, 1H), 4.09 (d, J = 13.3 Hz, 2H), 3.02-3.14 (m, 2H), 2.81-2.95 (m, 1H), 2.42 (s, 3H), 2.40 (s, 3H), 2.27 (s, 3H), 1.37-1.96 (m, 2H), 1.34-1.49 (m, 2H); ESI MS m/z 425 [M − H]−. | |

TABLE 1-continued

Examples prepared using the methods described above

| Example Compound | Chemical Name | Structure | General procedure | Characterization | Purity HPLC (%) |
|---|---|---|---|---|---|
| 210 | 3-(2-(benzyl amino)-6-(3,5-dimethyl-isoxazol-4-yl)-1H-benzo[d]imidazol-4-yl)-4-methyl benzonitrile | $C_{27}H_{23}N_5O$ | P | $^1$H NMR (400 MHz, CD$_3$OD) δ 7.66 (s, 1H), 7.64 (br s, 1H), 7.51 (d, J = 7.4 Hz, 1H), 7.37 (d, J = 7.4 Hz, 2H), 7.32 (t, J = 7.6 Hz, 2H), 7.21-7.27 (m, 1H), 7.18 (br s, 1H), 6.78 (s, 1H), 4.57 (s, 2H), 2.42 (s, 3H), 2.27 (s, 6H); ESI MS m/z 434 [M + H]+. | |
| 211 | 3-(6-(3,5-dimethyl-isoxazol-4-yl)-2-((pyridin-3-ylmethyl)amino)-1H-benzo[d]imidazol-4-yl)-4-methyl-benzonitrile | $C_{26}H_{22}N_6O$ | P | $^1$H NMR (400 MHz, CD$_3$OD) δ 8.56 (s, 1H), 8.43 (d, J = 4.7 Hz, 1H), 7.87 (d, J = 7.8 Hz, 1H), 7.65 (br s, 2H), 7.47-7.54 (m, 1H), 7.41 (dd, J = 7.6, 4.9 Hz, 1H), 7.19 (br s, 1H), 6.78 (s, 1H), 4.64 (s, 2H), 2.41 (s, 3H), 2.26 (s, 3H), 2.25 (s, 3H); ESI MS m/z 435 [M + H]+. | |
| 212 | N-benzyl-6-(3,5-dimethyl-isoxazol-4-yl)-4-(1,3,5-trimethyl-1H-pyrazol-4-yl)-1H-benzo[d]imidazol-2-amine | $C_{25}H_{26}N_6O$ | O | $^1$H NMR (400 MHz, CD$_3$OD) δ 7.28-7.49 (m, 6H), 6.69 (s, 1H), 4.65 (d, J = 5.1 Hz, 2H), 3.73 (s, 3H), 2.43 (s, 3H), 2.30 (s, 3H), 2.11 (s, 3H), 2.07 (s, 3H); ESI MS m/z 427 [M + H]+. | |
| 213 | 3,5-dimethyl-4-(2-(pyrrolidin-1-yl)-4-(1,3,5-trimethyl-1H-pyrazol-4-yl)-1H-benzo[d]imidazol-6-yl)isoxazole | $C_{22}H_{26}N_6O$ | O | $^1$H NMR (400 MHz, CD$_3$OD) δ 7.27 (s, 1H), 6.65 (s, 1H), 3.79 (s, 3H), 3.54-3.62 (m, 4H), 2.44 (s, 3H), 2.31 (s, 3H), 2.20 (s, 6H), 2.03-2.11 (m, 4H); ESI MS m/z 389 [M − H]−. | |

| Example Compound | Chemical Name | Structure | General procedure | Characterization | Purity HPLC (%) |
|---|---|---|---|---|---|
| 214 | 6-(3,5-dimethyl-isoxazol-4-yl)-N-methyl-4-(4-methyl pyridin-3-yl)-1H-benzo[d]imidazol-2-amine | C₁₉H₁₉N₅O | R | ¹H NMR (400 MHz, CD₃OD) δ 8.49 (s, 1H), 8.24 (br s, 1H), 7.28-7.39 (m, 1H), 7.20 (d, J = 4.7 Hz, 1H), 6.73 (br s, 1H), 3.08 (d, J = 3.9 Hz, 3H), 2.43 (s, 3H), 2.31 (s, 3H), 2.30 (s, 3H); ESI MS m/z 334 [M + H]+. | |
| 215 | 3-(6-(3,5-dimethyl-isoxazol-4-yl)-2-(pyrrolidin-1-yl)-1H-benzo[d]imidazol-4-yl)-4-methyl-benzonitrile | C₂₄H₂₃N₅O | P | ¹H NMR (400 MHz, CD₃OD) δ 7.66 (s, 2H), 7.51 (d, J = 8.2 Hz, 1H), 7.18 (br. s., 1H), 6.75 (br. s., 1H), 3.53 (t, J = 6.4 Hz, 4H), 2.43 (s, 3H), 2.29 (br.s., 3H), 2.28 (s, 3H), 2.04 (t, J = 6.4 Hz, 4H); ESI MS m/z 398 [M + H]+. | |
| 216 | 3-(6-(3,5-dimethyl-isoxazol-4-yl)-2-((1-methyl-piperidin-4-yl)amino)-1H-benzo[d]imidazol-4-yl)-2-methyl benzonitrile | C₂₆H₂₈N₆O | S | ¹H NMR (400 MHz, CD₃OD) δ 7.73 (d, J = 7.4 Hz, 1H), 7.61 (d, J = 7.8 Hz, 1H), 7.45 (t, J = 7.4 Hz, 1H), 7.19 (s., 1H), 6.76 (s, 1H), 3.60-3.74 (m, 1H), 2.82-2.94 (m, 2H), 2.42 (s, 3H), 2.40 (s, 3H), 2.30 (s, 3H), 2.27 (s, 3H), 2.17-2.26 (m, 2H), 1.99-2.10 (m, 2H), 1.51-1.68 (m, 2H); ESI MS m/z 439 [M − H]−. | |
| 217 | 4-(2-(azetidin-1-yl)-4-(1,3,5-trimethyl-1H-pyrazol-4-yl)-1H-benzo[d]imidazol-6-yl)-(3,5-dimethyl isoxazole | C₂₁H₂₄N₆O | O | ¹H NMR (400 MHz, CD₃OD) δ 7.32 (s, 1H), 6.66 (s, 1H), 4.22 (t, J = 7.4 Hz, 4H), 3.74 (s, 3H), 2.45-2.55 (m, 2H), 2.43 (s, 3H), 2.31 (s, 3H), 2.17 (s, 3H), 2.14 (s, 3H); ESI MS m/z 375 [M − H]−. | |

TABLE 1-continued

Examples prepared using the methods described above

| Example Compound | Chemical Name | Structure | General procedure | Characterization | Purity HPLC (%) |
|---|---|---|---|---|---|
| 218 | (3-(6-(3,5-dimethyl-isoxazol-4-yl)-2-(pyrrolidin-1-yl)-1H-benzo[d]imidazol-4-yl)-4-methyl-phenyl)(pyrrolidin-1-yl)methanone | 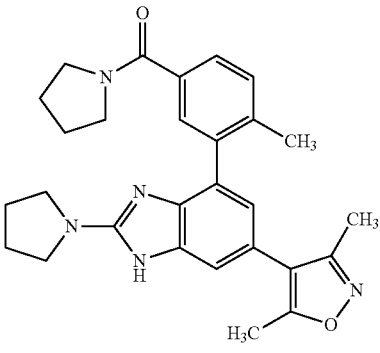 C₂₈H₃₁N₅O₂ | No general procedure | $^1$H NMR (400 MHz, CD$_3$OD) δ 7.48 (br. s., 2H), 7.38-7.45 (m, 1H), 7.16 (s, 1H), 6.74 (s, 1H), 3.58 (t, J = 6.8 Hz, 4H), 3.53 (t, J = 6.4 Hz, 4H), 2.42 (s, 3H), 2.27 (s, 6H), 2.03 (t, J = 6.4 Hz, 4H), 1.93-2.00 (m, 2H), 1.85-1.93 (m, 2H); ESI MS m/z 470 [M + H]+. | |
| 219 | 3-(6-(3,5-dimethyl-isoxazol-4-yl)-2-((pyridin-3-ylmethyl)amino)-1H-benzo[d]imidazol-4-yl)-4-methyl-benzamide | 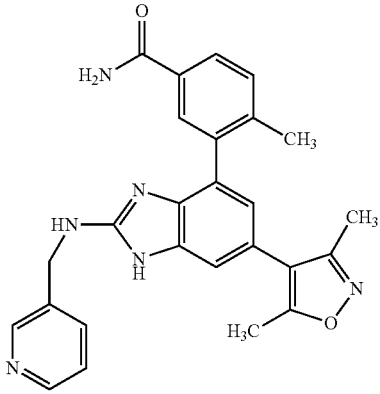 C₂₆H₂₆N₆O₂ | Q | $^1$H NMR (400 MHz, CD$_3$OD) δ 8.57 (s, 1H), 8.43 (d, J = 4.7 Hz, 1H), 7.79-7.91 (m, 3H), 7.36-7.48 (m, 2H), 7.18 (br s, 1H), 6.81 (s, 1H), 4.65 (s, 2H), 2.42 (s, 3H), 2.27 (s, 3H), 2.24 (br s, 3H); ESI MS m/z 453 [M + H]+. | |
| 220 | 3-(2-(benzyl-amino)-6-(3,5-dimethyl isoxazol-4-yl)-1H-benzo[d]imidazol-4-yl)-4-methyl-benzamide | 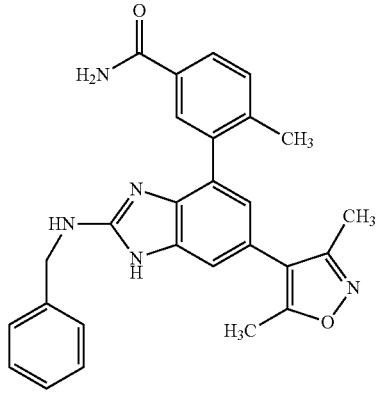 C₂₇H₂₅N₅O₂ | Q | $^1$H NMR (400 MHz, CD$_3$OD) δ 7.79-7.90 (m, 2H), 7.21-7.49 (m, 6H), 7.18 (br s, 1H), 6.80 (s, 1H), 4.58 (s, 2H), 2.43 (s, 3H), 2.28 (s, 3H), 2.26 (s, 3H); ESI MS m/z 452 [M + H]+. | |

TABLE 1-continued

Examples prepared using the methods described above

| Example Compound | Chemical Name | Structure | General procedure | Characterization | Purity HPLC (%) |
|---|---|---|---|---|---|
| 221 | 6-(3,5-dimethyl-isoxazol-4-yl)-N-(pyridin-3-ylmethyl)-4-(1,3,5-trimethyl-1H-pyrazol-4-yl)-1H-benzo[d]imidazol-2-amine | $C_{24}H_{25}N_7O$ | O | $^1$H NMR (400 MHz, CDCl$_3$) δ 8.65 (br s, 1H), 8.55 (d, J = 5.1 Hz, 1H), 8.09 (s, 1H), 7.78 (d, J = 7.4 Hz, 1H), 7.27-7.34 (m, 2H), 6.71 (br s, 1H), 4.98 (br s, 1H), 4.64-4.80 (m, 2H), 3.74 (s, 3H), 2.44 (s, 3H), 2.31 (s, 3H), 2.06-2.20 (m, 6H); ESI MS m/z 426 [M − H]−. | |
| 222 | N-benzyl-6-(3,5-dimethyl-isoxazol-4-yl)-4-(4-methyl-pyridin-3-yl)-1H-benzo[d]imidazol-2-amine | $C_{25}H_{23}N_5O$ | R | $^1$H NMR (400 MHz, CDCl$_3$) δ 8.34 (s, 1H), 8.02 (br s, 1H), 7.32-7.21 (m, 6H), 7.09 (d, J = 4.8 Hz, 1H), 6.67 (br s, 1H), 5.24 (br. s, 1H), 4.62 (s, 2H), 2.40 (s, 3H), 2.27 (s, 3H), 2.26 (s, 3H); ESI MS m/z 410 [M + H]+. | |
| 223 | 6-(3,5-dimethyl-isoxazol-4-yl)-4-(4-methyl-pyridin-3-yl)-N-(pyridin-3-ylmethyl)-1H-benzo[d]imidazol-2-amine | $C_{24}H_{22}N_6O$ | R | $^1$H NMR (400 MHz, CDCl$_3$) δ 8.51 (s, 1H), 8.42-8.39 (m, 2H), 8.07 (br s, 1H), 7.70 (d, J = 8.0 Hz, 1H), 7.28 (br s, 1H), 7.26-7.19 (m, 1H), 7.10 (d, J = 5.6 Hz, 1H), 6.71 (br s, 1H), 5.45 (br s, 1H), 4.67 (s, 2H), 2.40 (s, 3H), 2.27 (s, 3H), 2.26 (s, 3H). | |
| 224 | 3,5-dimethyl-4-(4-(4-methyl pyridin-3-yl)-2-(pyrrolidin-1-yl)-1H-benzo[d]imidazol-6-yl)isoxazole | $C_{22}H_{23}N_5O$ | R | $^1$H NMR (400 MHz, CDCl$_3$) δ 11.21 (br. s, 1H), 8.41 (s, 1H), 7.98 (br s, 1H), 7.35 (br. s, 1H), 7.10 (d, J = 4.8 Hz, 1H), 6.62 (s, 1H), 3.60-3.56 (m, 4H), 2.43 (s, 3H), 2.30 (s, 6H), 2.01-1.97 (m, 4H); ESI MS m/z 374 [M + H]+. | |

TABLE 1-continued

Examples prepared using the methods described above

| Example Compound | Chemical Name | Structure | General procedure | Characterization | Purity HPLC (%) |
|---|---|---|---|---|---|
| 225 | 3-amino-5-(6-(3,5-dimethylisoxazol-4-yl)-1H-benzo[d]imidazol-4-yl)-1-methylpyridin-2(1H)-one | $C_{18}H_{17}N_5O_2$ | D | $^1$H NMR (300 MHz, CD$_3$OD) δ 8.27 (s, 1H), 7.68 (s, 1H), 7.49 (s, 1H), 7.23 (s, 1H), 7.22 (s, 1H), 3.70 (s, 3H), 2.45 (s, 3H), 2.29 (s, 3H); ESI MS m/z 336 [M + H]+. | 94.8 |
| 226 | 4-(4,6-bis(3,5-dimethyl-isoxazol-4-yl)-1H-benzo[d]imidazol-2-yl)morpholine | $C_{21}H_{23}N_5O_3$ | F | $^1$H NMR (300 MHz, CD$_3$OD) δ 7.21 (s, 1H), 6.88 (s, 1H), 3.82 (t, J = 5.1 Hz, 4H), 3.54 (t, J = 5.1 Hz, 4H), 2.43 (s, 3H), 2.38 (s, 3H), 2.28 (s, 3H), 2.24 (s, 3H); ESI m/z 394 [M + H]+. | 98.6 |
| 227 | 4,4'-(5-methoxy-2-methyl-1H-benzo[d]imidazole-4,6-diyl)bis(3,5-dimethylisoxazole) | $C_{19}H_{20}N_4O_3$ | No general procedure | $^1$H NMR (300 MHz, CD$_3$OD) δ 7.40 (s, 1H), 3.17 (s, 3H), 2.55 (s, 3H), 2.39 (s, 3H), 2.34 (s, 3H), 2.22 (s, 3H), 2.20 (s, 3H); ESI m/z 353 [M + H]+. | 98.6 |
| 228 | 4,4'-(2-(tetrahydro-2H-pyran-4-yl)-1H-benzo[d]imidazole-4,6-diyl)bis(3,5-dimethyl isoxazole) | $C_{22}H_{24}N_4O_3$ | No general procedure | $^1$H NMR (300 MHz, DMSO-d$_6$) δ 12.49 (s, 0.7H), 12.18 (s, 0.3H), 7.60 (s, 0.3H), 7.41 (s, 0.7H), 7.06 (s, 1H), 3.96-3.93 (m, 2H), 3.51-3.45 (m, 2H), 3.21-3.01 (m, 1H), 2.44-2.33 (m, 6H), 2.28-2.17 (m, 6H), 1.93-1.82 (m, 4H); ESI m/z 393 [M + H]+. | 94.8 |

TABLE 1-continued

Examples prepared using the methods described above

| Example Compound | Chemical Name | Structure | General procedure | Characterization | Purity HPLC (%) |
|---|---|---|---|---|---|
| 229 | 4,6-bis(3,5-dimethyl-isoxazol-4-yl)-N-(tetrahydro-2H-pyran-4-yl)-1H-benzo[d]imidazol-2-amine | 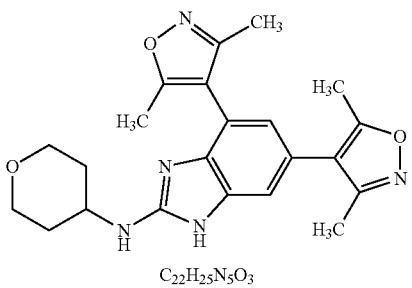 C22H25N5O3 | F | 1H NMR (300 MHz, CD3OD) δ 7.17 (s, 1H), 6.81 (s, 1H), 4.00-3.84 (m, 3H), 3.59-3.50 (m, 2H), 2.43 (s, 3H), 2.37 (s, 3H), 2.28 (s, 3H), 2.23 (s, 3H), 2.05-2.00 (m, 2H), 1.66-1.53 (m, 2H); ESI m/z 408 [M + H]+. | >99 |
| 230 | 3,5-dimethyl-4-(5-(1-methyl-1H-pyrazol-5-yl)-1H-benzo[d]imidazol-7-yl)isoxazole | 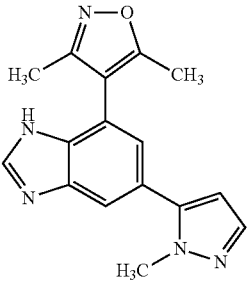 C16H15N5O | No general procedure | 1H NMR (500 MHz, CD3OD) δ 8.29 (s, 1H), 7.75 (br.s, 1H), 7.52 (d, J = 2.0 Hz, 1H), 7.29 (s, 1H), 6.43 (d, J = 2.0 Hz, 1H), 3.92 (s, 3H), 2.38 (s, 3H), 2.23 (s, 3H); ESI m/z 294 [M + H]+. | >99 |
| 231 | 4,4'-(2-(4-methyl-piperazin-1-yl)-1H-benzo[d]imidazole-4,6-diyl)bis(3,5-dimethyl isoxazole) | 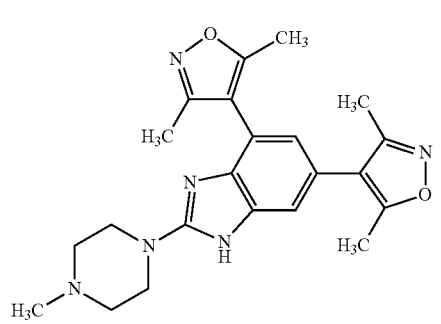 C22H26N6O2 | F | 1H NMR (300 MHz, CD3OD) δ 7.18 (s, 1H), 6.87 (s, 1H), 3.60 (t, J = 5.1 Hz, 4H), 2.59 (t, J = 5.1 Hz, 4H), 2.43 (s, 3H), 2.38 (s, 3H), 2.36 (s, 3H), 2.28 (s, 3H), 2.25 (s, 3H); ESI m/z 407 [M + H]+. | >99 |
| 232 | 4,6-bis(3,5-dimethyl-isoxazol-4-yl)-N-(1-methyl-piperidin-4-yl)-1H-benzo[d]imidazol-2-amine | 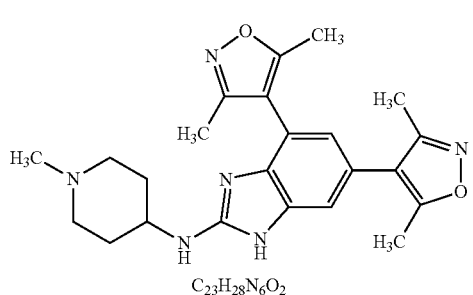 C23H28N6O2 | F | 1H NMR (300 MHz, CD3OD) δ 7.17 (s, 1H), 6.81 (s, 1H), 3.72-3.67 (m, 1H), 3.07-2.96 (m, 2H), 2.42-2.27 (m, 11H), 2.23 (s, 3H), 2.18 (s, 3H), 2.13-2.09 (m, 2H), 1.70-1.59 (m, 2H); ESI m/z 421 [M + H]+. | >99 |

TABLE 1-continued

Examples prepared using the methods described above

| Example Compound | Chemical Name | Structure | General procedure | Characterization | Purity HPLC (%) |
|---|---|---|---|---|---|
| 233 | 4,6-bis(3,5-dimethyl-isoxazol-4-yl)-N-(piperidin-4-yl)-1H-benzo[d]imidazol-2-amine | $C_{22}H_{26}N_6O_2$ | F | $^1$H NMR (300 MHz, CD$_3$OD) δ 7.18 (s, 1H), 6.84 (s, 1H), 4.14-4.12 (m, 2H), 3.16-3.09 (m, 2H), 3.00-2.94 (m, 1H), 2.43 (s, 3H), 2.38 (s, 3H), 2.28 (s, 3H), 2.24 (s, 3H), 1.97-1.95 (m, 2H), 1.51-1.43 (m, 2H); ESI m/z 407 [M + H]+. | >99 |

Example 1: Inhibition of Tetra-Acetylated Histone H4 Binding Individual BET Bromodomains Proteins were cloned and overexpressed with a N-terminal 6×His tag, then purified by nickel affinity followed by size exclusion chromatography. Briefly, E. coli BL21(DE3) cells were transformed with a recombinant expression vector encoding N-terminally Nickel affinity tagged bromodomains from Brd2, Brd3, Brd4. Cell cultures were incubated at 37° C. with shaking to the appropriate density and induced overnight with IPTG. The supernatant of lysed cells was loaded onto Ni-IDA column for purification. Eluted protein was pooled, concentrated and further purified by size exclusion chromatography. Fractions representing monomeric protein were pooled, concentrated, aliquoted, and frozen at −80° C. for use in subsequent experiments.

Binding of tetra-acetylated histone H4 and BET bromodomains was confirmed by a Homogenous Time Resolved Fluorescence Resonance Energy Transfer (HTRF®) method. N-terminally His-tagged bromodomains (200 nM) and biotinylated tetra-acetylated histone H4 peptide (25-50 nM, Millipore) were incubated in the presence of Europium Cryptate-labeled streptavidin (Cisbio Cat. #610SAKLB) and XL665-labeled monoclonal anti-His antibody (Cisbio Cat. #61HISXLB) in a white 96 well microtiter plate (Greiner). For inhibition assays, serially diluted test compound was added to these reactions in a 0.2% final concentration of DMSO. Duplicate wells were used for each concentration tested. Final buffer concentrations were 30 mM HEPES pH 7.4, 30 mM NaCl, 0.3 mM CHAPS, 20 mM phosphate pH 7.0, 320 mM KF, 0.08% BSA. After a 2 h incubation at room temperature, fluorescence was measured at 665 and 620 nm with a SynergyH4 plate reader (Biotek). The binding inhibitory activity was shown by a decrease in 665 nm relative to 620 nm fluorescence. IC$_{50}$ values were determined from a dose response curve.

Compounds with an IC$_{50}$ value less than or equal to 0.3 µM were deemed to be highly active (+++); compounds with an IC$_{50}$ value between 0.3 and 3 µM were deemed to be very active (++); compounds with an IC$_{50}$ value between 3 and 30 µM were deemed to be active (+).

TABLE 2

Inhibition of Tetra-acetylated Histone H4 Binding to Brd4 bromodomain 1 (BRD4(1)) as Measured by FRET

| Example Compound | FRET activity BRD4(1) | Example Compound | FRET activity BRD4(1) | Example Compound | FRET activity BRD4(1) | Example Compound | FRET activity BRD4(1) |
|---|---|---|---|---|---|---|---|
| 1 | +++ | 2 | +++ | 3 | + | 4 | +++ |
| 5 | + | 6 | +++ | 7 | +++ | 8 | ++ |
| 9 | +++ | 10 | + | 11 | +++ | 12 | Not Active |
| 13 | +++ | 14 | + | 15 | +++ | 16 | +++ |
| 17 | + | 18 | +++ | 19 | ++ | 20 | +++ |
| 21 | +++ | 22 | ++ | 23 | +++ | 24 | +++ |
| 25 | ++ | 26 | +++ | 27 | +++ | 28 | ++ |
| 29 | +++ | 30 | +++ | 31 | +++ | 32 | +++ |
| 33 | +++ | 34 | +++ | 35 | +++ | 36 | +++ |
| 37 | +++ | 38 | +++ | 39 | +++ | 40 | +++ |
| 41 | +++ | 42 | +++ | 43 | +++ | 44 | ++ |
| 45 | +++ | 46 | +++ | 47 | +++ | 48 | +++ |
| 49 | +++ | 50 | +++ | 51 | +++ | 52 | +++ |
| 53 | +++ | 54 | +++ | 55 | +++ | 56 | ++ |
| 57 | +++ | 58 | +++ | 59 | +++ | 60 | +++ |
| 61 | Not active | 62 | ++ | 63 | ++ | 64 | +++ |

TABLE 2-continued

Inhibition of Tetra-acetylated Histone H4 Binding to Brd4 bromodomain 1 (BRD4(1)) as Measured by FRET

| Example Compound | FRET activity BRD4(1) | Example Compound | FRET activity BRD4(1) | Example Compound | FRET activity BRD4(1) | Example Compound | FRET activity BRD4(1) |
|---|---|---|---|---|---|---|---|
| 65 | +++ | 66 | +++ | 67 | +++ | 68 | +++ |
| 69 | +++ | 70 | +++ | 71 | + | 72 | +++ |
| 73 | +++ | 74 | +++ | 75 | ++ | 76 | +++ |
| 77 | +++ | 78 | ++ | 79 | +++ | 80 | +++ |
| 81 | +++ | 82 | ++ | 83 | ++ | 84 | ++ |
| 85 | +++ | 86 | ++ | 87 | +++ | 88 | +++ |
| 89 | +++ | 90 | ++ | 91 | +++ | 92 | +++ |
| 93 | +++ | 94 | +++ | 95 | ++ | 96 | +++ |
| 97 | +++ | 98 | +++ | 99 | +++ | 100 | +++ |
| 101 | +++ | 102 | ++ | 103 | +++ | 104 | +++ |
| 105 | +++ | 106 | +++ | 107 | +++ | 108 | +++ |
| 109 | +++ | 110 | +++ | 111 | ++ | 112 | +++ |
| 113 | ++ | 114 | ++ | 115 | ++ | 116 | ++ |
| 117 | +++ | 118 | +++ | 119 | +++ | 120 | +++ |
| 121 | ++ | 122 | ++ | 123 | +++ | 124 | +++ |
| 125 | +++ | 126 | +++ | 127 | +++ | 128 | ++ |
| 129 | ++ | 130 | +++ | 131 | ++ | 132 | ++ |
| 133 | + | 134 | ++ | 135 | +++ | 136 | +++ |
| 137 | +++ | 138 | +++ | 139 | ++ | 140 | +++ |
| 141 | Not Active | 142 | ++ | 143 | +++ | 144 | +++ |
| 145 | ++ | 146 | +++ | 147 | ++ | 148 | +++ |
| 149 | + | 150 | +++ | 151 | ++ | 152 | +++ |
| 153 | +++ | 154 | +++ | 155 | +++ | 156 | +++ |
| 157 | +++ | 158 | +++ | 159 | ++ | 160 | Not active |
| 161 | +++ | 162 | ++ | 163 | +++ | 164 | Not active |
| 165 | ++ | 166 | +++ | 167 | ++ | 168 | + |
| 169 | +++ | 170 | +++ | 171 | +++ | 172 | +++ |
| 173 | +++ | 174 | +++ | 175 | +++ | 176 | ++ |
| 177 | +++ | 178 | ++ | 179 | +++ | 180 | +++ |
| 181 | +++ | 182 | +++ | 183 | +++ | 184 | +++ |
| 185 | +++ | 186 | +++ | 187 | +++ | 188 | ++ |
| 189 | +++ | 190 | +++ | 191 | +++ | 192 | +++ |
| 193 | +++ | 194 | +++ | 195 | +++ | 196 | ++ |
| 197 | +++ | 198 | +++ | 199 | ++ | 200 | +++ |
| 201 | +++ | 202 | ++ | 203 | +++ | 204 | +++ |
| 205 | +++ | 206 | +++ | 207 | +++ | 208 | +++ |
| 209 | +++ | 210 | +++ | 211 | +++ | 212 | +++ |
| 213 | +++ | 214 | +++ | 215 | +++ | 216 | +++ |
| 217 | +++ | 218 | +++ | 219 | +++ | 220 | +++ |
| 221 | +++ | 222 | | 223 | | 224 | |
| 225 | ++ | 226 | +++ | 227 | ++ | 228 | +++ |
| 229 | +++ | 230 | ++ | 231 | +++ | 232 | +++ |
| 233 | +++ | — | | — | | — | |

Example 2: Inhibition of cMYC Expression in Cancer Cell Lines

MV4-11 cells (CRL-9591) were plated at a density of 2.5×10$^4$ cells per well in 96 well U-bottom plates and treated with increasing concentrations of test compound or DMSO (0.1%) in IMDM media containing 10% FBS and penicillin/streptomycin, and incubated for 3 h at 37'C. Triplicate wells were used for each concentration. Cells were pelleted by centrifugation and harvested using the mRNA Catcher PLUS kit according to manufacturer's instructions. The eluted mRNA isolated was then used in a one-step quantitative real-time PCR reaction, using components of the RNA UltraSense™ One-Step Kit (Life Technologies) together with Applied Biosystems TaqMan® primer-probes for cMYC and Cyclophilin. Real-time PCR plates were run on a ViiA™7 real time PCR machine (Applied Biosystems), data was analyzed, normalizing the Ct values for cMYC to an internal control, prior to determining the fold expression of each sample, relative to the control.

Compounds with an IC$_{50}$ value less than or equal to 0.3 µM were deemed to be highly active (+++); compounds with an IC$_{50}$ value between 0.3 and 3 µM were deemed to be very active (++); compounds with an IC$_{50}$ value between 3 and 30 µM were deemed to be active (+).

TABLE 3

Inhibition of c-myc Activity in Human AML MV4-11 cells

| Example Compound | c-myc activity | Example Compound | c-myc activity | Example Compound | c-myc activity | Example Compound | c-myc activity |
|---|---|---|---|---|---|---|---|
| 1 | ++ | 2 | ++ | 4 | ++ | 6 | ++ |
| 7 | ++ | 8 | Not active | 9 | ++ | 11 | ++ |
| 13 | ++ | 15 | + | 16 | ++ | 18 | ++ |
| 19 | ++ | 20 | ++ | 21 | ++ | 22 | Not active |
| 23 | ++ | 24 | ++ | 25 | ++ | 26 | ++ |
| 27 | ++ | 28 | ++ | 29 | ++ | 32 | ++ |
| 33 | ++ | 34 | ++ | 35 | ++ | 36 | ++ |
| 37 | ++ | 38 | ++ | 39 | ++ | 40 | Not active |
| 41 | ++ | 42 | +++ | 43 | Not active | 44 | ++ |
| 45 | ++ | 46 | ++ | 47 | ++ | 48 | ++ |
| 49 | +++ | 50 | ++ | 51 | ++ | 52 | ++ |
| 53 | ++ | 54 | ++ | 55 | ++ | 56 | Not Active |
| 57 | +++ | 60 | +++ | 64 | ++ | 66 | ++ |
| 67 | ++ | 68 | +++ | 69 | ++ | 70 | ++ |
| 72 | ++ | 73 | +++ | 74 | ++ | 76 | ++ |
| 77 | +++ | 79 | +++ | 80 | +++ | 81 | +++ |
| 84 | ++ | 85 | + | 87 | ++ | 88 | ++ |
| 89 | +++ | 91 | +++ | 92 | ++ | 93 | +++ |
| 94 | ++ | 95 | Not active | 97 | ++ | 98 | ++ |
| 99 | +++ | 100 | +++ | 103 | ++ | 104 | ++ |
| 105 | +++ | 106 | ++ | 107 | ++ | 108 | ++ |
| 109 | ++ | 110 | ++ | 112 | +++ | 117 | +++ |
| 118 | ++ | 119 | ++ | 120 | +++ | 121 | Not active |
| 123 | +++ | 124 | ++ | 125 | ++ | 126 | +++ |
| 127 | +++ | 128 | ++ | 129 | ++ | 130 | ++ |
| 131 | ++ | 132 | ++ | 135 | +++ | 136 | +++ |
| 137 | ++ | 138 | ++ | 139 | + | 140 | +++ |
| 142 | ++ | 143 | ++ | 144 | +++ | 145 | ++ |
| 146 | +++ | 147 | ++ | 148 | +++ | 150 | ++ |
| 151 | ++ | 152 | ++ | 153 | ++ | 154 | Not active |
| 155 | ++ | 156 | ++ | 157 | ++ | 158 | Not active |
| 161 | ++ | 162 | ++ | 163 | ++ | 165 | Not active |
| 166 | ++ | 169 | ++ | 170 | ++ | 171 | ++ |
| 172 | ++ | 173 | ++ | 174 | ++ | 175 | Not active |
| 177 | +++ | 178 | ++ | 179 | ++ | 180 | +++ |
| 181 | +++ | 182 | +++ | 183 | +++ | 184 | +++ |
| 185 | ++ | 186 | +++ | 187 | +++ | 188 | ++ |
| 189 | ++ | 190 | ++ | 192 | ++ | 195 | ++ |
| 196 | ++ | 197 | ++ | 198 | +++ | 200 | +++ |
| 201 | +++ | 202 | +++ | 203 | +++ | 204 | +++ |
| 205 | +++ | 206 | ++ | 207 | ++ | 209 | ++ |
| 210 | ++ | 214 | +++ | 215 | +++ | 216 | ++ |
| 225 | ++ | 226 | +++ | 227 | ++ | 228 | ++ |
| 229 | +++ | 230 | ++ | 231 | +++ | 233 | ++ |

Example 3: Inhibition of Cell Proliferation in Cancer Cell Lines

MV4-11 cells (CRL-9591) were plated at a density of $5 \times 10^4$ cells per well in 96 well flat bottom plates and treated with increasing concentrations of test compound or DMSO (0.1%) in IMDM media containing 10% FBS and penicillin/streptomycin. Triplicate wells were used for each concentration and a well containing only media was used as a control. Plates were incubated at 37° C., 5% $CO_2$ for 72 h before adding 20 L of the CellTiter Aqueous One Solution (Promega) to each well and incubated at 37° C., 5% $CO_2$ for an additional 3-4 h. The absorbance was read at 490 nm in a spectrophotometer and the percentage of cell titer relative to DMSO-treated cells was calculated after correcting for background by subtracting the blank well's signal. $IC_{50}$ values were calculated using the GraphPad Prism software.

Compounds with an $IC_{50}$ value less than or equal to 0.3 μM were deemed to be highly active (+++); compounds with an $IC_{50}$ value between 0.3 and 3 μM were deemed to be very active (++); compounds with an $IC_{50}$ value between 3 and 30 μM were deemed to be active (+).

TABLE 4

Inhibition of Cell Proliferation in Human AML MV-4-11 cells

| Example Compound | Cell Proliferation activity | Example Compound | Cell Proliferation activity | Example Compound | Cell Proliferation activity | Example Compound | Cell Proliferation activity |
|---|---|---|---|---|---|---|---|
| 1 | ++ | 2 | ++ | 4 | ++ | 6 | ++ |
| 7 | ++ | 8 | Not active | 9 | ++ | 11 | ++ |
| 13 | ++ | 15 | Not active | 16 | ++ | 18 | ++ |
| 19 | ++ | 20 | ++ | 21 | ++ | 22 | Not active |
| 23 | ++ | 24 | + | 25 | ++ | 26 | ++ |
| 27 | ++ | 28 | ++ | 29 | + | 32 | ++ |
| 33 | ++ | 34 | ++ | 35 | ++ | 36 | ++ |
| 37 | ++ | 38 | ++ | 39 | ++ | 40 | + |
| 41 | ++ | 42 | +++ | 43 | + | 44 | ++ |
| 45 | ++ | 46 | ++ | 47 | ++ | 48 | ++ |
| 49 | ++ | 50 | +++ | 51 | ++ | 52 | ++ |
| 53 | ++ | 54 | +++ | 55 | ++ | 56 | Not active |
| 57 | +++ | 58 | +++ | 59 | +++ | 60 | ++ |
| 64 | ++ | 66 | +++ | 67 | + | 68 | +++ |
| 69 | ++ | 70 | ++ | 72 | ++ | 73 | +++ |
| 74 | ++ | 76 | ++ | 77 | ++ | 79 | ++ |
| 80 | ++ | 81 | +++ | 84 | + | 85 | + |
| 87 | ++ | 88 | ++ | 89 | ++ | 91 | ++ |
| 92 | ++ | 93 | ++ | 94 | ++ | 95 | Not active |
| 97 | ++ | 98 | ++ | 99 | +++ | 100 | ++ |
| 103 | ++ | 104 | ++ | 105 | ++ | 106 | ++ |
| 107 | ++ | 108 | ++ | 109 | ++ | 110 | ++ |
| 112 | ++ | 117 | +++ | 118 | ++ | 119 | ++ |
| 120 | ++ | 121 | Not active | 123 | ++ | 124 | ++ |
| 125 | ++ | 126 | ++ | 127 | +++ | 128 | ++ |
| 129 | ++ | 130 | ++ | 131 | ++ | 132 | ++ |
| 135 | ++ | 136 | ++ | 137 | ++ | 138 | ++ |
| 139 | Not active | 140 | +++ | 142 | ++ | 143 | ++ |
| 144 | +++ | 145 | +++ | 146 | +++ | 147 | Not active |
| 148 | ++ | 150 | ++ | 151 | ++ | 152 | ++ |
| 153 | ++ | 154 | ++ | 155 | ++ | 156 | + |
| 157 | ++ | 158 | ++ | 161 | + | 162 | ++ |
| 163 | ++ | 165 | + | 166 | ++ | 169 | ++ |
| 170 | ++ | 171 | ++ | 172 | ++ | 173 | ++ |
| 174 | ++ | 175 | Not active | 177 | ++ | 178 | + |
| 179 | ++ | 180 | +++ | 181 | +++ | 182 | ++ |
| 183 | +++ | 184 | +++ | 185 | ++ | 186 | +++ |
| 187 | +++ | 188 | ++ | 189 | ++ | 190 | +++ |
| 192 | + | 194 | ++ | 195 | ++ | 196 | ++ |
| 197 | ++ | 198 | +++ | 200 | +++ | 201 | +++ |
| 202 | +++ | 203 | ++ | 204 | +++ | 205 | ++ |
| 206 | ++ | 207 | ++ | 209 | +++ | 210 | +++ |
| 214 | +++ | 225 | + | 226 | +++ | 227 | + |
| 228 | ++ | 229 | ++ | 230 | Not active | 231 | +++ |
| 232 | ++ | 233 | ++ | — | — | — | — |

Example 4: Inhibition of hIL-6 mRNA Transcription

Human leukemic monocyte lymphoma U937 cells (CRL-1593.2) were plated at a density of 3.2×104 cells per well in a 96-well plate in 100 μL RPMI-1640 containing 10% FBS and penicillin/streptomycin, and differentiated into macrophages for 3 days in 60 ng/mL PMA (phorbol-13-myristate-12-acetate) at 37° C. in 5% CO2 prior to the addition of compound. The cells were pretreated for 1 h with increasing concentrations of test compound in 0.1% DMSO prior to stimulation with 1 ug/mL lipopolysaccharide from *Escherichia coli*. Triplicate wells were used for each concentration. The cells were incubated at 37° C., 5% CO2 for 3 h before the cells were harvested. At time of harvest, media was removed and cells were rinsed in 200 μL PBS. Cells were harvested using the mRNA Catcher PLUS kit according to manufacturer's instructions. The eluted mRNA was then used in a one-step quantitative real-time PCR reaction using components of the RNA UltraSense™ One-Step Kit (Life Technologies) together with Applied Biosystems TaqMan® primer-probes for hIL-6 and Cyclophilin. Real-time PCR plates were run on a ViiA™7 real time PCR machine (Applied Biosystems), data was analyzed, normalizing the Ct values for hIL-6 to an internal control, prior to determining the fold expression of each sample, relative to the control.

Compounds with an $IC_{50}$ value less than or equal to 0.3 μM were deemed to be highly active (+++); compounds with an $IC_{50}$ value between 0.3 and 3 μM were deemed to be very active (++); compounds with an $IC_{50}$ value between 3 and 30 μM were deemed to be active (+).

TABLE 5

Inhibition of hIL-6 mRNA Transcription

| Example Compound | IL-6 activity | Example Compound | IL-6 activity | Example Compound | IL-6 activity | Example Compound | IL-6 activity |
|---|---|---|---|---|---|---|---|
| 1 | +++ | 2 | ++ | 4 | ++ | 6 | ++ |
| 7 | +++ | 8 | Not active | 9 | +++ | 11 | ++ |
| 13 | ++ | 15 | + | 16 | +++ | 18 | +++ |
| 19 | ++ | 20 | +++ | 21 | ++ | 22 | ++ |
| 23 | +++ | 24 | ++ | 25 | ++ | 26 | +++ |
| 27 | +++ | 28 | ++ | 32 | ++ | 33 | ++ |
| 34 | ++ | 35 | ++ | 36 | ++ | 37 | ++ |
| 38 | ++ | 41 | +++ | 42 | +++ | 43 | ++ |
| 44 | ++ | 49 | +++ | 50 | +++ | 51 | ++ |
| 52 | ++ | 53 | +++ | 54 | ++ | 55 | ++ |
| 57 | +++ | 58 | +++ | 59 | +++ | 60 | +++ |
| 64 | +++ | 66 | +++ | 67 | Not active | 68 | +++ |
| 69 | ++ | 70 | ++ | 72 | ++ | 73 | +++ |
| 74 | ++ | 76 | ++ | 77 | ++ | 79 | ++ |
| 80 | ++ | 81 | ++ | 84 | ++ | 85 | ++ |
| 87 | ++ | 88 | ++ | 89 | ++ | 91 | +++ |
| 92 | +++ | 93 | +++ | 94 | ++ | 95 | Not active |
| 97 | +++ | 98 | ++ | 99 | +++ | 104 | +++ |
| 105 | +++ | 106 | ++ | 107 | ++ | 108 | ++ |
| 109 | +++ | 110 | ++ | 112 | +++ | 114 | +++ |
| 117 | +++ | 118 | ++ | 119 | +++ | 120 | +++ |
| 121 | ++ | 123 | +++ | 124 | ++ | 127 | +++ |
| 128 | +++ | 129 | ++ | 130 | +++ | 131 | ++ |
| 132 | ++ | 135 | ++ | 136 | ++ | 137 | ++ |
| 138 | +++ | 139 | ++ | 140 | +++ | 142 | ++ |
| 143 | ++ | 144 | +++ | 145 | ++ | 146 | +++ |
| 147 | ++ | 148 | +++ | 150 | ++ | 151 | ++ |
| 152 | +++ | 153 | ++ | 154 | +++ | 155 | ++ |
| 156 | + | 157 | ++ | 158 | ++ | 161 | ++ |
| 162 | ++ | 163 | ++ | 165 | ++ | 166 | ++ |
| 169 | ++ | 170 | ++ | 171 | ++ | 172 | ++ |
| 173 | ++ | 174 | ++ | 175 | Not active | 177 | ++ |
| 178 | ++ | 180 | +++ | 181 | +++ | 182 | +++ |
| 201 | +++ | 203 | +++ | 204 | +++ | 205 | ++ |
| 206 | ++ | 207 | ++ | 208 | +++ | 209 | ++ |
| 210 | ++ | 211 | ++ | 212 | +++ | 213 | +++ |
| 214 | ++ | 215 | ++ | 216 | +++ | 225 | + |
| 226 | +++ | 227 | ++ | 228 | ++ | 229 | +++ |
| 230 | + | 231 | +++ | — | — | — | — |

Example 5: Inhibition of hIL-17 mRNA Transcription

Human peripheral blood mononuclear cells were plated (2.0×10⁵ cells per well) in a 96-well plate in 45 μL OpTimizer T Cell expansion media (Life Technologies) containing 20 ng/ml IL-2 and penicillin/streptomycin. The cells were treated with increasing concentrations of the test compound or DMSO (0.1%), and incubated at 37° C., 5% CO2 for 1 h before addition of 10× stock OKT3 antibody at 10 ug/ml in media. Triplicate wells were used for each concentration. Cells were incubated at 37° C., 5% CO2 for 6 h before the cells were harvested. At time of harvest, cells were pelleted by centrifugation at 800 rpm for 5 min. Cells were harvested using the mRNA Catcher PLUS kit according to manufacturer's instructions. The eluted mRNA was then used in a one-step quantitative real-time PCR reaction, using components of the RNA UltraSense™ One-Step Kit (Life Technologies) together with Applied Biosystems Taq-Man® primer-probes for hIL-17 and Cyclophilin. Real-time PCR plates were run on a ViiA™7 real time PCR machine (Applied Biosystems), data was analyzed, normalizing the Ct values for hIL-17 to an internal control, prior to determining the fold induction of each unknown sample, relative to the control.

Compounds with an $IC_{50}$ value less than or equal to 0.3 μM were deemed to be highly active (+++); compounds with an $IC_{50}$ value between 0.3 and 3 μM were deemed to be very active (++); compounds with an $IC_{50}$ value between 3 and 30 μM were deemed to be active (+).

TABLE 6

Inhibition of hIL-17 mRNA Transcription

| Example Compound | IL-17 Activity | Example compound | IL-17 Activity |
|---|---|---|---|
| 1 | ++ | 4 | ++ |
| 6 | +++ | 7 | ++ |
| 9 | +++ | 11 | ++ |
| 13 | ++ | 19 | +++ |
| 20 | ++ | 21 | ++ |
| 27 | +++ | 37 | ++ |
| 41 | ++ | 42 | ++ |
| 45 | ++ | 48 | ++ |
| 49 | +++ | 50 | ++ |
| 57 | ++ | 58 | ++ |
| 59 | ++ | 60 | ++ |
| 66 | +++ | 68 | +++ |
| 73 | ++ | 81 | +++ |
| 92 | ++ | 97 | ++ |
| 137 | ++ | 140 | ++ |
| 146 | +++ | 178 | +++ |

Example 6: Inhibition of hVCAM mRNA Transcription

Human umbilical vein endothelial cells (HUVECs) are plated in a 96-well plate ($4.0 \times 10^3$ cells per well) in 100 µL EGM media and incubated for 24 h prior to the addition of increasing concentrations of the compound of interest or DMSO (0.1%). Triplicate wells were used for each concentration. The cells are pretreated for 1 h with the test compound prior to stimulation with tumor necrosis factor-α when they are incubated for an additional 24 h before the cells are harvested. At time of harvest, the spent media is removed and HUVECs are rinsed in 200 µL PBS. Cells were harvested using the mRNA Catcher PLUS kit according to manufacturer's instructions. The eluted mRNA was then used in a one-step quantitative real-time PCR reaction, using components of the RNA UltraSense™ One-Step Kit (Life Technologies) together with Applied Biosystems TaqMan® primer-probes for hVCAM and Cyclophilin. Real-time PCR plates were run on a ViiA™7 real time PCR machine (Applied Biosystems), data was analyzed, normalizing the Ct values for hVCAM to an internal control, prior to determining the fold induction of each unknown sample, relative to the control.

Example 7: Inhibition of hMCP-1 mRNA Transcription

Human Peripheral Blood Mononuclear Cells are plated at a density of $1.0 \times 10^5$ cells per well in a 96-well plate in RPMI-1640 containing 10% FBS and penicillin/streptomycin. The cells are treated with increasing concentrations of the compound or DMSO (0.1%), and incubated at 37° C., 5% CO2 for 3 h before the cells are harvested. At time of harvest, cells are transferred to V-bottom plates and pelleted by centrifugation at 800 rpm for 5 min. Cells were harvested using the mRNA Catcher PLUS kit according to manufacturer's instructions. The eluted mRNA was then used in a one-step quantitative real-time PCR reaction, using components of the RNA UltraSense™ One-Step Kit (Life Technologies) together with Applied Biosystems TaqMan® primer-probes for hMCP-1 and Cyclophilin. Real-time PCR plates were run on a ViiA™7 real time PCR machine (Applied Biosystems), data was analyzed, normalizing the Ct values for hMCP-1 to an internal control, prior to determining the fold induction of each unknown sample, relative to the control.

Example 8: Up-Regulation of hApoA-1 mRNA Transcription

Huh7 cells ($2.5 \times 10^5$ per well) were plated in a 96-well plate using 100 µL DMEM per well, (Gibco DMEM supplemented with penicillin/streptomycin and 10% FBS), 72 h before the addition of the compound. The cells are treated with increasing concentrations of the compound or DMSO (0.1%), and incubated at 37° C., 5% CO2 for 48 h. Spent media was removed from the Huh-7 cells and placed on ice for immediate use with the "LDH cytotoxicity assay Kit II" from Abcam. The cells remaining in the plate were rinsed with 100 µL PBS. Cells were harvested using the mRNA Catcher PLUS kit according to manufacturer's instructions. The eluted mRNA was then used in a one-step quantitative real-time PCR reaction, using components of the RNA UltraSense™ One-Step Kit (Life Technologies) together with Applied Biosystems TaqMan® primer-probes for hApoA-1 and Cyclophilin. Real-time PCR plates were run on a ViiA™7 real time PCR machine (Applied Biosystems), data was analyzed, normalizing the Ct values for hApoA-1 to an internal control, prior to determining the fold induction of each unknown sample, relative to the control.

Compounds with an $EC_{170}$ value less than or equal to 0.3 µM were deemed to be highly active (+++); compounds with an $EC_{170}$ value between 0.3 and 3 µM were deemed to be very active (++); compounds with an $EC_{170}$ value between 3 and 30 µM were deemed to be active (+).

TABLE 7

Up-regulation of hApoA-1 mRNA Transcription.

| Example Compound | ApoA-1 activity | Example Compound | ApoA-1 activity | Example Compound | ApoA-1 activity | Example Compound | ApoA-1 activity |
|---|---|---|---|---|---|---|---|
| 1 | ++ | 4 | + | 5 | +++ | 37 | +++ |
| 41 | +++ | 49 | +++ | 57 | +++ | 60 | +++ |
| 97 | +++ | — | — | — | — | — | — |

Examples 9: In Vivo Efficacy in Athymic Nude Mouse Strain of an Acute Myeloid Leukemia Xenograft Model Using MV4-11° Cells MV4-11 cells (ATCC) were grown under standard cell culture conditions and (NCr) nu/nu fisol strain of female mice age 6-7 weeks were injected with $5 \times 10^6$ cells/animal in 100 µL PBS+100 µL Matrigel in the lower left abdominal flank. By approximately day 18-21 after MV4-11 cells injection, mice were randomized based on tumor volume (L×W×H)/2) of average ~100-300 mm³. Mice were dosed orally with compound at 5 to 120 mg/kg b.i.d and/or q.d. on a continuous dosing schedule and at 2.5 to 85 mg/kg q.d. on a 5 day on 2 day off, 100 mg/kg q.d. on a 4 day on and 3 day off, 135 mg/kg q.d. on a 3 day on and 4 day off, 180 mg/kg on a 2 day on and 5 day off and 240 mg/kg on a 1 day on and 6 days off dosing schedules in EA006 formulation at 10 mL/kg body weight dose volume. Tumor measurements were taken with electronic micro calipers and body weights measured on alternate days beginning from dosing period. The average tumor volumes, percent Tumor Growth Inhibition (TGI) and % change in body weights were compared relative to Vehicle control animals. The means, statistical analysis and the comparison between groups were calculated using Student's t-test in Excel.

TABLE 8

In vivo efficacy in athymic nude mouse strain of an acute myeloid leukemia xenograft model

| Example | In vivo activity |
|---|---|
| Example Compound 1 | Active |
| Example Compound 6 | Active |
| Example Compound 9 | Active |

TABLE 8-continued

In vivo efficacy in athymic nude mouse strain of an acute myeloid leukemia xenograft model

| Example | In vivo activity |
|---|---|
| Example Compound 27 | Active |
| Example Compound 41 | Active |
| Example Compound 49 | Active |

Example 10: In Vivo Efficacy in Athymic Nude Mouse Strain of an Acute Myeloid Leukemia Xenograft Model Using OCI-3 AML Cells OCI-3 AML cells (DMSZ) are grown under standard cell culture conditions and (NCr) nu/nu fisol strain of female mice age 6-7 weeks are injected with $10 \times 10^6$ cells/animal in 100 µL PBS+100 µL Matrigel in the lower left abdominal flank. By approximately day 18-21 after OCI-3 AML cells injection, mice are randomized based on tumor volume $(L \times W \times H)/2$ of average 100-300 mm$^3$. Mice are dosed orally with compound at 30 mg/kg b.i.d on a continuous dosing schedule and at 2.5 to 45 mg/kg q.d. on a 5 day on and 2 day off dosing schedule in EA006 formulation at 10 mL/kg body weight dose volume. Tumor measurements are taken with electronic micro calipers and body weights measured on alternate days beginning from dosing period. The average tumor volumes, percent Tumor Growth Inhibition (TGI) and % change in body weights are compared relative to Vehicle control animals. The means, statistical analysis and the comparison between groups are calculated using Student's t-test in Excel.

Example 11: Evaluation of Target Engagement

MV4-11 and MM1.s cells (ATCC) are grown under standard cell culture conditions and (NCr) nu/nu fisol strain of female mice age 6-7 weeks are injected with $5 \times 10^6$ cells/animal in 100 µL PBS+100 µL Matrigel in the lower left abdominal flank. By approximately day 28 after MV4-11 and MM1.s cells injection, mice are randomized based on tumor volume $(L \times W \times H)/2$ of average ~500 mm$^3$. Mice are dosed orally with compound in EA006 formulation at 10 mL/kg body weight dose volume and tumors harvested 3, 6, 12, 24 hrs post dose for Bcl2 and c-myc gene expression analysis as PD biomarkers.

TABLE 9

Evaluation of Target Engagement.

| Example Compound | In vivo activity |
|---|---|
| Example Compound 1 | Active |

Example 12: In Vivo Efficacy in Mouse Endotoxemia Model Assay

Sub lethal doses of Endotoxin (*E. Coli* bacterial lipopolysaccharide) are administered to animals to produce a generalized inflammatory response which is monitored by increases in secreted cytokines. Compounds are administered to C57/Bl6 mice at T=4 hours orally at 75 mg/kg dose to evaluate inhibition in IL-6 and IL-17 and MCP-1 cytokines post 3-h challenge with lipopolysaccharide (LPS) at T=0 hours at 0.5 mg/kg dose intraperitoneally.

TABLE 10

In vivo Efficacy in Mouse Endotoxemia Model

| Example Compound | In vivo activity |
|---|---|
| Example Compound 1 | Active |

Example 13: In Vivo Efficacy in Rat Collagen-Induced Arthritis

Rat collagen-induced arthritis is an experimental model of polyarthritis that has been widely used for preclinical testing of numerous anti-arthritic agents. Following administration of collagen, this model establishes a measurable polyarticular inflammation, marked cartilage destruction in association with pannus formation and mild to moderate bone resorption and periosteal bone proliferation. In this model, collagen was administered to female Lewis strain of rats on Day 1 and 7 of study and dosed with compounds from Day 11 to Day 17. Test compounds were administered at 25 mg/kg to 120 mg/kg b.i.d and 7.5 mg/kg to 30 mg/kg q.d dose to assess the potential to inhibit the inflammation (including paw swelling), cartilage destruction and bone resorption in arthritic rats, using a model in which the treatment is administered after the disease has been established.

TABLE 11

In Vivo Efficacy in Rat Collagen-induced Arthritis.

| Example Compound | In vivo activity |
|---|---|
| Example Compound 1 | Active |
| Example Compound 41 | Active |

Example 14: In Vivo Efficacy in Experimental Autoimmune Encephalomyelitis (EAE) Model of MS Experimental autoimmune encephalomyelitis (EAE) is a T-cell-mediated autoimmune disease of the CNS which shares many clinical and histopathological features with human multiple sclerosis (MS). EAE is the most commonly used animal model of MS. T cells of both Th1 and Th17 lineage have been shown to induce EAE. Cytokines IL-23, IL-6 and IL-17, which are either critical for Th1 and Th17 differentiation or produced by these T cells, play a critical and non-redundant role in EAE development. Therefore, drugs targeting production of these cytokines are likely to have therapeutic potential in treatment of MS.

Compounds of Formula I were administered at 50 to 125 mg/kg b.i.d. from time of immunization to EAE mice to assess anti-inflammatory activity. In this model, EAE is induced by $MOG_{35-55}$/CFA immunization and pertussis toxin injection in female C57Bl/6 mice.

TABLE 12

In Vivo Efficacy in Experimental autoimmune encephalomyelitis (EAE) Model of MS

| Example Compound | In vivo activity |
|---|---|
| Example Compound 1 | Active |
| Example Compound 6 | Active |

Example 15: Ex Vivo Effects on T Cell Function from Splenocyte and Lymphocyte Cultures Stimulated with External MOG Stimulation Mice were immunized with MOG/CFA and simultaneously treated with the compound for 11 days on a b.i.d regimen. Inguinal Lymph node and spleen were harvested, cultures were set up for lymphocytes and splenocytes and stimulated with external antigen (MOG) for 72 hours. Supernatants from these cultures were analyzed for TH1, Th2 and Th17 cytokines using a Cytometric Bead Array assay.

TABLE 13

Ex Vivo effects on T cell function from Splenocyte and Lymphocyte cultures

| Example Compound | In vivo activity |
|---|---|
| Example Compound 1 | Active |
| Example Compound 6 | Active |

Example 16: In Vivo Efficacy in Athymic Nude Mouse Strain of Multiple Myeloma Xenograft Model Using MM1.s Cells MM1.s cells (ATCC) were grown under standard cell culture conditions and SCID-Beige strain of female mice age 6-7 weeks were injected with $10\times10^6$ cells/animal in 100 µL PBS+100 µL Matrigel in the lower left abdominal flank. By approximately day 21 after MM1.s cells injection, mice were randomized based on tumor volume (L×W×H)/2) of average 120 mm³. Mice were dosed orally with compound at 25 to 90 mg/kg b.i.d and or q.d in EA006 formulation at 10 mL/kg body weight dose volume. Tumor measurements were taken with electronic micro calipers and body weights measured on alternate days beginning from dosing period. The average tumor volumes, percent Tumor Growth Inhibition (TGI) and % change in body weights were compared relative to Vehicle control animals. The means, statistical analysis and the comparison between groups were calculated using Student's t-test in Excel.

TABLE 14

In vivo efficacy in athymic nude mouse strain of multiple myeloma xenograft model using MM1.s cells

| Example Compound | In vivo activity |
|---|---|
| Example Compound 1 | Active |
| Example Compound 6 | Active |
| Example Compound 41 | Active |

Other embodiments of the present disclosure will be apparent to those skilled in the art from consideration of the specification and practice of the present disclosure disclosed herein. It is intended that the specification and examples be considered as exemplary only, with a true scope and spirit of the present disclosure being indicated by the following claims.

What is claimed is:

1. A method for inhibiting BET proteins in a mammal, comprising administering a therapeutically effective amount of a compound of formula:

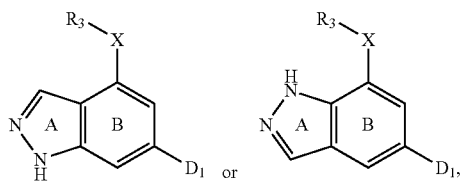

or a stereoisomer, tautomer, pharmaceutically acceptable salt, or hydrate thereof, wherein:
  the A-B bicyclic ring is optionally substituted with one or more groups independently selected from deuterium, —$NH_2$, —OH, alkyl($C_1$-$C_6$), thioalkyl($C_1$-$C_6$), and alkoxy($C_1$-$C_9$);
  $D_1$ is selected from isoxazole and pyrazole optionally substituted with one or more groups independently selected from deuterium, alkyl($C_1$-$C_4$), —OH, alkoxy ($C_1$-$C_4$), amino, halogen, amide, —$CF_3$, CN, —$OCF_3$, —$N_3$, ketone ($C_1$-$C_4$), —S(O)Alkyl($C_1$-$C_4$), —$SO_2$alkyl($C_1$-$C_4$), -thioalkyl($C_1$-$C_4$), carboxyl, and/or ester,
    wherein said alkyl($C_1$-$C_4$), alkoxy($C_1$-$C_4$), amino, amide, ketone ($C_1$-$C_4$), —S(O)Alkyl($C_1$-$C_4$), —$SO_2$alkyl($C_1$-$C_4$), -thioalkyl($C_1$-$C_4$), and ester may be optionally substituted with F, Cl, Br, —OH, —$NH_2$, —NHMe, —$NMe_2$, —OMe, —SMe, oxo, and/or thio-oxo;
  X is optionally present, and if present, is selected from —(NH)—, —O—, —NHCR$_x$R$_y$—, —$NHSO_2$—, —CR$_x$R$_y$NH—, or —$NH_2$ and $R_3$ is absent; and
  $R_3$ is selected from isoxazolyl, oxazolyl, pyrazolyl, pyridyl, pyridonyl, thiazolyl, isothiazolyl, pyrimidinyl, thiozolyl, pyrazinyl, pyridazinyl, azetidinyl, pyrrolidyl, piperidinyl, morpholinyl, cyclopropyl, cyclobutyl, cyclopentyl, cyclohexyl, and phenyl, optionally substituted with one or more groups independently selected from deuterium, alkyl($C_1$-$C_4$), —OH, alkoxy($C_1$-$C_4$), amino, halogen, amide, —$CF_3$, CN, —$OCF_3$, —$N_3$, ketone ($C_1$-$C_4$), —S(O)Alkyl($C_1$-$C_4$), —$SO_2$alkyl($C_1$-$C_4$), -thioalkyl($C_1$-$C_4$), carboxyl, and/or ester,
    wherein said alkyl($C_1$-$C_4$), alkoxy($C_1$-$C_4$), amino, amide, ketone ($C_1$-$C_4$), —S(O)Alkyl($C_1$-$C_4$), —$SO_2$alkyl($C_i$-$C_4$), -thioalkyl($C_1$-$C_4$), and ester may be optionally substituted with F, Cl, Br, —OH, —$NH_2$, —NHMe, —$NMe_2$, —OMe, SMe, oxo, and/or thio-oxo.

2. The method of claim 1, wherein $D_1$ is

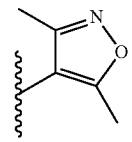

and X is absent.

3. A method for inhibiting BET proteins in a mammal, comprising administering a therapeutically effective amount of a compound selected from:
  4,4'-(1H-benzo[d]imidazole-4,6-diyl)bis(3,5-dimethylisoxazole);
  3-(6-(3,5-dimethylisoxazol-4-yl)-1H-benzo[d]imidazol-4-yl)benzonitrile;
  4,4'-(quinazoline-2,4-diyl)bis(3,5-dimethylisoxazole);

N-benzyl-6-(3,5-dimethylisoxazol-4-yl)-1H-benzo[d]imidazol-4-amine;
N-benzyl-2-(3,5-dimethylisoxazol-4-yl)quinazolin-4-amine;
4,4'-(2-methyl-1H-benzo[d]imidazole-4,6-diyl)bis(3,5-dimethylisoxazole);
6-(3,5-dimethylisoxazol-4-yl)-N-phenyl-1H-benzo[d]imidazol-4-amine;
4,4'-(imidazo[1,2-a]pyridine-6,8-diyl)bis(3,5-dimethylisoxazole);
3,5-dimethyl-4-(4-(1,3,5-trimethyl-1H-pyrazol-4-yl)-1H-benzo[d]imidazol-6-yl)isoxazole;
4,4'-(imidazo[1,2-a]pyrazine-6,8-diyl)bis(3,5-dimethylisoxazole);
6,8-bis(3,5-dimethylisoxazol-4-yl)-2H-benzo[b][1,4]oxazin-3(4H)-one;
2-(3,5-dimethylisoxazol-4-yl)-6,7-dimethoxy-N-phenylquinazolin-4-amine;
6,8-bis(3,5-dimethylisoxazol-4-yl)-3,4-dihydro-2H-benzo[b][1,4]oxazine;
3,5-dimethyl-4-(6-(1,3,5-trimethyl-1H-pyrazol-4-yl)-1H-benzo[d]imidazol-4-yl)isoxazole;
6-(3,5-dimethylisoxazol-4-yl)-N-phenyl-[1,2,4]triazolo[4,3-a]pyridin-8-amine;
3,5-dimethyl-4-(4-(1-methyl-1H-pyrazol-5-O-1H-benzo[d]imidazol-6-yl)isoxazole;
4,4'-([1,2,4]triazolo[1,5-a]pyridine-6,8-diyl)bis(3,5-dimethylisoxazole);
4-(4-(1,3-dimethyl-1H-pyrazol-4-yl)-1H-benzo[d]imidazol-6-yl)-3,5-dimethylisoxazole;
3,5-dimethyl-4-(4-(2-(trifluoromethyl)phenyl)-1H-benzo[d]imidazol-6-yl)isoxazole;
3,5-dimethyl-4-(4-(4-methylpyridin-3-yl)-1H-benzo[d]imidazol-6-yl)isoxazole;
4,4'-(1H-indazole-5,7-diyl)bis(3,5-dimethylisoxazole);
3,5-dimethyl-4-(4-(pyrimidin-5-yl)-1H-benzo[d]imidazol-6-yl)isoxazole;
3,5-dimethyl-4-(4-(1-methyl-1H-indazol-4-yl)-1H-benzo[d]imidazol-6-yl)isoxazole;
N-benzyl-6-(3,5-dimethylisoxazol-4-yl)-[1,2,4]triazolo[4,3-a]pyridin-8-amine;
6-(3,5-dimethylisoxazol-4-yl)-N-(4-methoxyphenyl)-1H-benzo[d]imidazol-4-amine;
3,5-dimethyl-4-(4-(4-methylthiazol-5-yl)-1H-benzo[d]imidazol-6-yl)isoxazole;
3,5-dimethyl-4-(4-(2-methylpyridin-3-yl)-1H-benzo[d]imidazol-6-yl)isoxazole;
1-(2-(6-(3,5-dimethylisoxazol-4-yl)-1H-benzo[d]imidazol-4-yl)phenyl)-N,N-dimethylmethanamine;
3,5-dimethyl-4-(4-(1-methyl-1H-pyrazol-4-yl)-1H-benzo[d]imidazol-6-yl)isoxazole;
4,6-bis(3,5-dimethylisoxazol-4-yl)-N-methyl-1H-benzo[d]imidazol-2-amine;
N-benzyl-4,6-bis(3,5-dimethylisoxazol-4-yl)-1H-benzo[d]imidazol-2-amine;
6-(3,5-dimethylisoxazol-4-yl)-N-(3-fluorophenyl)-1H-benzo[d]imidazol-4-amine;
6-(3,5-dimethylisoxazol-4-yl)-N-(3-methoxyphenyl)-1H-benzo[d]imidazol-4-amine;
4,4'-(2-(trifluoromethyl)-1H-benzo[d]imidazole-4,6-diyl)bis(3,5-dimethylisoxazole);
6-(3,5-dimethylisoxazol-4-yl)-N-(pyridin-3-ylmethyl)-1H-benzo[d]imidazol-4-amine;
3-(6-(3,5-dimethylisoxazol-4-yl)-1H-benzo[d]imidazol-4-yl)benzamide;
6-(3,5-dimethylisoxazol-4-yl)-N-((1,3,5-trimethyl-1H-pyrazol-4-yl)methyl)-1H-benzo[d]imidazol-4-amine;
6-(3,5-dimethylisoxazol-4-yl)-N-(4-fluorobenzyl)-1H-benzo[d]imidazol-4-amine;
6-(3,5-dimethylisoxazol-4-yl)-N-((3,5-dimethylisoxazol-4-yl)methyl)-1H-benzo[d]imidazol-4-amine;
N-(4-chlorophenyl)-6-(3,5-dimethylisoxazol-4-yl)-1H-benzo[d]imidazol-4-amine;
3,5-dimethyl-4-(2-methyl-4-(2-methylpyridin-3-yl)-1H-benzo[d]imidazol-6-yl)isoxazole;
N-(6-(3,5-dimethylisoxazol-4-yl)-1H-benzo[d]imidazol-4-yl)-3,5-dimethylisoxazol-4-amine;
6-(3,5-dimethylisoxazol-4-yl)-N-(pyrimidin-2-yl)-1H-benzo[d]imidazol-4-amine;
N-(6-(3,5-dimethylisoxazol-4-yl)-1H-benzo[d]imidazol-4-yl)-4-methylisoxazol-3-amine;
4,4'-(2-isopropyl-1H-benzo[d]imidazole-4,6-diyl)bis(3,5-dimethylisoxazole);
4,4)-(2-ethoxy-1H-benzo[d]imidazole-4,6-diyl)bis(3,5-dimethylisoxazole);
6-(3,5-dimethylisoxazol-4-yl)-N-(pyridin-2-ylmethyl)-1H-benzo[d]imidazol-4-amine;
4-(4-(2-methoxypyridin-3-yl)-1H-benzo[d]imidazol-6-yl)-3,5-dimethylisoxazole;
3,5-dimethyl-4-(2-methyl-4-(1,3,5-trimethyl-1H-pyrazol-4-yl)-1H-benzo[d]imidazol-6-yl)isoxazole;
3,5-dimethyl-4-(2-methyl-4-(4-(trifluoromethyl)pyridin-3-yl)-1H-benzo[d]imidazol-6-yl)isoxazole;
4-(4-(2-methoxy-5-methylphenyl)-1H-benzo[d]imidazol-6-yl)-3,5-dimethylisoxazole;
3,5-dimethyl-4-(2-methyl-7-(3-methylisothiazol-4-yl)-1H-benzo[d]imidazol-5-yl)isoxazole;
3,5-dimethyl-4-(2-methyl-4-(4-methylpyridin-3-yl)-1H-benzo[d]imidazol-6-yl)isoxazole;
4,4'-(1-methyl-1H-indazole-5,7-diyl)bis(3,5-dimethylisoxazole);
4,4°-(2-methyl-2H-indazole-5,7-diyl)bis(3,5-dimethylisoxazole);
3-(6-(3,5-dimethylisoxazol-4-yl)-1H-benzo[d]imidazol-4-yl)pyridin-2(1H)-one;
3-(6-(3,5-dimethylisoxazol-4-yl)-1H-benzo[d]imidazol-4-yl)-2-methylbenzonitrile;
3-(6-(3,5-dimethylisoxazol-4-yl)-2-methyl-1H-benzo[d]imidazol-4-yl)-4-methylbenzonitrile;
3,5-dimethyl-4-(2-methyl-4-(2-trifluoromethyl)pyridin-3-yl)-1H-benzo[d]imidazol-6-yl)isoxazole;
4-(4-(1,3-dimethyl-1H-pyrazol-4-yl)-2-methyl-1H-benzo[d]imidazol-6-yl)-3,5-dimethylisoxazole;
3-(6-(3,5-dimethylisoxazol-4-yl)-2-methyl-1H-benzo[d]imidazol-4-yl)isonicotinonitrile;
6-(3,5-dimethylisoxazol-4-yl)-N-(pyrazin-2-yl)-1H-benzo[d]imidazol-4-amine;
6-(3,5-dimethylisoxazol-4-yl)-2-methyl-N-(3-methylpyridin-2-yl)-1H-benzo[d]imidazol-4-amine;
N-(2-(6-(3,5-dimethylisoxazol-4-yl)-2-methyl-1H-benzo[d]imidazol-4-yl)phenyl)acetamide;
4,6-bis(3,5-dimethylisoxazol-4-yl)-N-(pyridin-3-ylmethyl)-1H-benzo[d]imidazol-2-amine;
4-(4-(1,5-dimethyl-3-(trifluoromethyl)-1H-pyrazol-4-yl)-2-methyl-1H-benzo[d]imidazol-6-yl)-3,5-dimethylisoxazole;
4-(5-(3,5-dimethylisoxazol-4-yl)-2-methyl-1H-benzo[d]imidazol-7-yl)-N,3-dimethylisoxazole-5-carboxamide;
5-(6-(3,5-dimethylisoxazol-4-yl)-2-ethyl-1H-benzo[d]imidazol-4-yl)-6-methylpyridin-2-amine;
3,5-dimethyl-4-(2-methyl-4-(2-(methylsulfonyl)phenyl)-1H-benzo[d]imidazol-6-yl)isoxazole;
3,5-dimethyl-4-(7-(2-methylpyridin-3-yl)-1H-indazol-5-yl)isoxazole;

2-(6-(3,5-dimethylisoxazol-4-yl)-2-methyl-1H-benzo[d]imidazol-4-yl)benzonitrile;
4-(4-(4-methoxypyridin-3-yl)-2-methyl-1H-benzo[d]imidazol-6-yl)-3,5-dimethylisoxazole;
3-(6-(3,5-dimethylisoxazol-4-yl)-1H-benzo[d]imidazol-4-yl)-2-methylbenzamide;
3-(6-(3,5-dimethylisoxazol-4-yl)-2-methyl-1H-benzo[d]imidazole-4-yl)-4-methylbenzamide;
3-(6-(3,5-dimethylisoxazol-4-yl)-2-methyl-1H-benzo[d]imidazol-4-yl)-4-methylbenzoic acid;
4,4'-(2-(2,2,2-trifluoroethyl)-1H-benzo[d]imidazole-5,7-diyl)bis(3,5-dimethylisoxazole);
3,5-diethyl-4-(2-methyl-4-(2-(trifluoromethoxy)phenyl)-1H-benzo[d]imidazol-6-yl)isoxazole;
3,5-dimethyl-4-(2-methyl-4-(2-(trifluoromethyl)phenyl)-1H-benzo[d]imidazol-6-yl)isoxazole;
3,5-dimethyl-4-(2-methyl-4-(pyridin-3-yl)-1H-benzo[d]imidazol-6-yl)isoxazole;
4-(4-(5-fluoro-2-(trifluoromethyl)phenyl)-2-methyl-1H-benzo[d]imidazol-6-yl)-3,5-dimethylisoxazole;
4-2-ethoxy-4-(2-methylpyridin-3-yl)-1H-benzo[d]imidazol-6-yl)-3,5-dimethylisoxazole;
3-(6-(3,5-dimethylisoxazol-4-yl)-2-methyl-1H-benzo[d]imidazol-4-yl)pyridin-2-amine;
2-(6-(3,5-dimethylisoxazol-4-yl)-2-methyl-1H-benzo[d]imidazol-4-yl)-6-fluorobenzonitrile;
3,5-dimethyl-4-(2-methyl-4-(3-methylpyridin-2-yl)-1H-benzo[d]imidazol-6-yl)isoxazole;
3,5-dimethyl-4-(2-methyl-4-(pyrazin-2-yl)-1H-benzo[d]imidazol-6-yl)isoxazole;
3,5-dimethyl-4-(2-methyl-4-(6-methylpyridazin-3-yl)-1H-benzo[d]imidazol-6-yl)isoxazole;
4,4'-(1H-indazole-4,6-diyl)bis(3,5-dimethylisoxazole);
3,5-dimethyl-4-(2-methyl-4-phenyl-1H-benzo[d]imidazol-6-yl)isoxazole;
3,5-dimethyl-4-(2-methyl-4-O-tolyl)-1H-benzo[d]imidazol-6-yl)isoxazole;
4-(4-(4-chloro-2-methylphenyl)-2-methyl-1H-benzo[d]imidazol-6-yl)-3,5-dimethylisoxazole;
4-(4-(2-fluorophenyl)-2-methyl-1H-benzo[d]imidazol-6-yl)-3,5-dimethylisoxazole;
4-(4-(5-fluoro-2-methylphenyl)-2-methyl-1H-benzo[d]imidazol-6-yl)-3,5-dimethylisoxazole;
4,4'-(1-methyl-1H-benzo[d]imidazole-5,7-diyl)bis(3,5-dimethylisoxazole);
2-(6-(3,5-dimethylisoxazol-4-yl)-2-methyl-1H-benzo[d]imidazol-4-yl)-4-fluorobenzonitrile;
4,4'-(1H-benzo[d][1,2,3]triazole-4,6-diyl)bis(3,5-dimethylisoxazole);
3,5-dimethyl-4-(2-methyl-4-(3-(trifluoromethoxy)phenyl)-1H-benzo[d]imidazol-6-yl)isoxazole;
4-(4-(3,5-dimethylpyridin-4-yl)-2-methyl-1H-benzo[d]imidazol-6-yl)-3,5-dimethylisoxazole;
4-(4-(4,6-dimethylpyrimidin-5-yl)-2-methyl-1H-benzo[d]imidazol-6-yl)-3,5-dimethylisoxazole;
5-(6-(3,5-dimethylisoxazol-4-yl)-2-methyl-1H-benzo[d]imidazol-4-yl)-4,6-dimethylpyrimidin-2-amine;
6-(3,5-dimethylisoxazol-4-yl)-N-ethyl-4-(2-methylpyridin-3-yl)-1H-benzo[d]imidazol-2-amine;
5,7-bis(3,5-dimethylisoxazol-4-yl)-2-methylbenzo[d]oxazole;
N-(6-(3,5-dimethylisoxazol-4-yl)-1H-benzo[d]imidazol-4-yl)-2-methoxybenzenesulfonamide;
4-(4-(benzo[d][1,3]dioxol-5-yl)-2-methyl-1H-benzo[d]imidazol-6-yl)-3,5-dimethylisoxazole;
3,5-dimethyl-4-(2-methyl-4-(4-methylthiazol-5-yl)-1H-benzo[d]imidazol-6-yl)isoxazole;
4-(4-(5-chloro-2-methylphenyl)-2-methyl-1H-benzo[d]imidazol-6-yl)-3,5-dimethylisoxazole;
4-(4-(2-fluoro-3-methylphenyl)-2-methyl-1H-benzo[d]imidazol-6-yl)-3,5-dimethylisoxazole;
4-(4-(5-chloro-2-methoxyphenyl)-2-methyl-1H-benzo[d]imidazol-6-yl)-3,5-dimethylisoxazole;
4-(4-(2-fluoro-5-methoxyphenyl)-2-methyl-1H-benzo[d]imidazol-6-yl)-3,5-dimethylisoxazole;
4-(4-(2-ethoxypyridin-3-yl)-2-methyl-1H-benzo[d]imidazol-6-yl)-3,5-dimethylisoxazole;
4-(4-(isoquinolin-8-yl)-2-methyl-1H-benzo[d]imidazol-6-yl)-3,5-dimethylisoxazole;
3,5-dimethyl-4-(2-methyl-4-(quinolin-8-yl)-1H-benzo[d]imidazol-6-yl)isoxazole;
4-(4-(5-fluoro-2-methoxyphenyl)-2-methyl-1H-benzo[d]imidazol-6-yl)-3,5-dimethylisoxazole;
3,5-dimethyl-4-(2-methyl-4-(5-methylthiazol-4-yl)-1H-benzo[d]imidazol-6-yl)isoxazole;
4-(4-(2-methoxy-4-methylpyridin-3-yl)-2-methyl-1H-benzo[d]imidazol-6-yl)-3,5-dimethylisoxazole;
3,5-dimethyl-4-(2-methyl-4-(1-methyl-3-(trifluoromethyl)-1H-pyrazol-4-yl)-1H-benzo[d]imidazol-6-yl)isoxazole;
4,6-bis(3,5-dimethylisoxazol-4-yl)-N,N-dimethyl-1H-benzo[d]imidazol-2-amine;
4-(4-(2-(methoxymethyl)phenyl)-2-methyl-1H-benzo[d]imidazol-6-yl)-3,5-dimethylisoxazole;
4-(4-(2-methoxypyridin-3-yl)-2-methyl-1H-benzo[d]imidazol-6-yl)-3,5-dimethylisoxazole;
3,5-dimethyl-4-(7-(4-methylpyridin-3-yl)-1H-indazol-5-yl)isoxazole;
4-(7-(1,3-dimethyl-1H-pyrazol-4-yl)-1H-indazol-5-yl)-3,5-dimethylisoxazole;
1-(6-(3,5-dimethylisoxazol-4-yl)-2-methyl-1H-benzo[d]imidazol-4-yl)-5-methylpyrrolidin-2-one;
1-(6-(3,5-dimethylisoxazol-4-yl)-2-methyl-1H-benzo[d]imidazol-4-yl)piperidin-2-one;
3-(6-(3,5-dimethylisoxazol-4-yl)-2-methyl-1H-benzo[d]imidazol-4-yl)-2-methylbenzonitrile;
4-(4-(benzo[d]thiazol-5-yl)-2-methyl-1H-benzo[d]imidazol-6-yl)-3,5-dimethylisoxazole;
4-(4-(5-fluoro-4-methylpyridin-3-yl)-2-methyl-1H-benzo[d]imidazol-6-yl)-3,5-dimethylisoxazole;
3-(6(3,5-dimethylisoxazol-4-yl)-2-methyl-1H-benzo[d]imidazol-4-yl)-2-methylbenzamide;
3,5-dimethyl-4-(7-(1,3,5-trimethyl-1H-pyrazol-4-yl)-1H-indazol-5-yl)isoxazole;
3,5-dimethyl-4-(7-(2-(trifluoromethyl)pyridin-3-yl)-1H-indazol-5-yl)isoxazole;
3,5-dimethyl-4-(7-(4-(trifluoromethyl)pyridin-3-yl)-1H-indazol-5-ylisoxazole;
4-(4-(3,5-dichloropyridin-4-yl)-2-methyl-1H-benzo[d]imidazol-6-yl)-3,5-dimethylisoxazole;
4-(4-(5-fluoro-2-methoxypyridin-3-yl)-2-methyl-1H-benzo[d]imidazol-6-yl)-3,5-dimethylisoxazole;
4-(4-(3,4-difluoro-2-methylphenyl)-2-methyl-1H-benzo[d]imidazol-6-yl)-3,5-dimethylisoxazole;
4,6-bis(1,3-dimethyl-1H-pyrazol-4-yl)-2-methyl-1H-benzo[d]imidazole;
2-methyl-4,6-bis(1-methyl-1H-pyrazol-5-yl)-1H-benzo[d]imidazole;
4-(4-(2-methoxy-6-methylpyridin-3-yl)-2-methyl-1H-benzo[d]imidazol-6-yl)-3,5-dimethylisoxazole;
5-(6-(3,5-dimethylisoxazol-4-yl)-2-methyl-1H-benzo[d]imidazol-4-yl)benzo[d]oxazole;
4-(4-(benzo[d]isothiazol-5-yl)-2-methyl-1H-benzo[d]imidazol-6-yl)-3,5-dimethylisoxazole;

3,5-dimethyl-4-(2-methyl-4-(naphthalen-1-yl)-1H-benzo[d]imidazol-6-yl)isoxazole;
4,4'-(2-methyl-1H-benzo[d]imidazole-4,6-diyl)bis(3-methylisothiazole);
4,4'-(3-methyl-1H-indole-4,6-diyl)bis(3,5-dimethylisoxazole);
2-methyl-4,6-bis(4-methylthiophen-3-yl)-1H-benzo[d]imidazole;
6-(3,5-dimethylisoxazol-4-yl)-N-phenethyl-1H-benzo[d]imidazol-4-amine;
6-(3,5-dimethylisoxazol-4-yl)-2-methyl-N-(2-methylpyridin-3-yl)-1H-benzo[d]imidazol-4-amine;
4-(4-(2-chlorophenyl)-2-methyl-1H-benzo[d]imidazol-6-yl)-3,5-dimethylisoxazole;
4-(4-(benzo[b]thiophen-2-yl)-2-methyl-1H-benzo[d]imidazol-6-yl)-3,5-dimethylisoxazole;
6-(3,5-dimethylisoxazol-4-yl)-2-methyl-N-(1,3,5-trimethyl-1H-pyrazol-4-yl)-1H-benzo[d]imidazol-4-amine;
1-(6-(3,5-dimethylisoxazol-4-yl)-2-methyl-1H-benzo[d]imidazol-4-yl)azetidin-2-one;
3,5-dimethyl-4-(2-methyl-4-phenoxy-1H-benzo[d]imidazol-6-yl)isoxazole;
6,8-bis(3,5-dimethylisoxazol-4-yl)-[1,2,4]triazolo[4,3-a]pyridin-3(2H)-one;
2-((4,6-bis(3,5-dimethylisoxazol-4-yl)-1H-benzo[d]imidazol-2-yl)amino)ethanol;
6-(3,5-dimethylisoxazol-4-yl)-N,N-diphenethyl-1H-benzo[d]imidazol-4-amine;
4-(4-(2-fluoro-3-methoxyphenyl)-2-methyl-1H-benzo[d]imidazol-6-yl)-3,5-dimethylisoxazole;
3,5-dimethyl-4-(2-methyl-4-(quinoxalin-6-yl)-1H-benzo[d]imidazol-6-yl)isoxazole;
3,5-dimethyl-4-(2-methyl-4-(3-(methylsulfonyl)phenyl)-1H-benzo[d]imidazol-6-yl)isoxazole;
3,5-dimethyl-4-(2-methyl-4-((2-methylpyridin-3-yl)oxy)-1H-benzo[d]imidazol-6-yl)isoxazole;
4-(4-([1,2,4]triazolo[4,3-a]pyridin-6-yl)-2-methyl-1H-benzo[d]imidazol-6-yl)-3,5-dimethylisoxazole;
4-(4-(2-fluoro-5-(trifluoromethyl)phenyl)-2-methyl-1H-benzo[d]imidazol-6-yl)-3,5-dimethylisoxazole;
(E)-3,5-dimethyl-4-(2-methyl-4-styryl-1H-benzo[d]imidazol-6-yl)isoxazole;
4,4'-(quinoxaline-5,7-diyl)bis(3,5-dimethylisoxazole);
4,6-di(furan-3-yl)-2-methyl-1H-benzo[d]imidazole;
3,5-dimethyl-4-(2-methyl-4-phenethyl-1H-benzo[d]imidazol-6-yl)isoxazole;
4-(4-(2-chloro-5-(trifluoromethyl)phenyl)-2-methyl-1H-benzo[d]imidazol-6-yl)-3,5-dimethylisoxazole;
3,5-dimethyl-4-(2-methyl-4-(quinolin-3-yl)-1H-benzo[d]imidazol-6-yl)isoxazole;
2-methyl-4,6-di(1H-pyrrol-3-yl)-1H-benzo[d]imidazole;
N-(6-(3,5-dimethylisoxazol-4-yl)-2-methyl-1H-benzo[d]imidazol-4-yl)benzamide;
3,5-dimethyl-4-(2-methyl-4-(4-methylthiophen-3-yl)-1H-benzo[d]imidazol-6-yl)isoxazole;
4,6-bis(1,4-dimethyl-1H-pyrazol-5-yl)-2-methyl-1H-benzo[d]imidazole;
5,5'-(2-methyl-1H-benzo[d]imidazole-4,6-diyl)bis(2,4-dimethylthiazole);
4-(4-(1,4-dimethyl-1H-pyrazol-5-yl)-2-methyl-1H-benzo[d]imidazol-6-yl)-3,5-dimethylisoxazole;
4-(4-(2,4-dimethylthiazol-5-yl)-2-methyl-1H-benzo[d]imidazol-6-yl)-3,5-dimethylisoxazole;
4-(4-((4-methoxypyridin-3-yl)oxy)-2-methyl-1H-benzo[d]imidazol-6-yl)-3,5-dimethylisoxazole;
3-((6-(3,5-dimethylisoxazol-4-yl)-2-methyl-1H-benzo[d]imidazol-4-yl)oxy)-4-methylbenzonitrile;
4-(6-(3,5-dimethylisoxazol-4-yl)-2-methyl-1H-benzo[d]imidazol-4-yl)morpholine;
3-((6-(3,5-dimethylisoxazol-4-yl)-2-methyl-1H-benzo[d]imidazol-4-yl)oxy)-4-methylbenzamide;
3-((6-(3,5-dimethylisoxazol-4-yl)-2-methyl-1H-benzo[d]imidazol-4-yl)oxy)-4-methylbenzoic acid;
4,4'-(2-methyl-3H-imidazo[4,5-b]pyridine-5,7-diyl)bis(3,5-dimethylisoxazole);
4-(6-(3,5-dimethylisoxazol-4-yl)-2-methyl-1H-benzo[d]imidazol-4-yl)-3-methylmorpholine;
4-(6-(1,4-dimethyl-1H-pyrazol-5-yl)-2-methyl-1H-benzo[d]imidazol-4-yl)-3,5-dimethylisoxazole;
4,4'-(3-methyl-1H-indazole-4,6-diyl)bis(3,5-dimethylisoxazole);
4-(4-(3,5-dimethyl-1H-pyrazol-4-yl)-3-methyl-1H-indazol-6-yl)-3, dimethylisoxazole;
3,5-dimethyl-4-(2-(4-methylpiperazin-1-yl)-4-(1,3,5-trimethyl-1H-pyrazol-4-yl)-1H-benzo[d]imidazol-6-yl)isoxazole;
3,5-dimethyl-4-(1-methyl-7-(1,3,5-trimethyl-1H-pyrazol-4-yl)-1H-benzo[d]imidazol-5-yl)isoxazole;
3-dimethyl-4-(2-(4-methylpiperazin-1-yl)-4-(2-methylpyridin-3-yl)-1H-benzo[d]imidazol-6-yl)isoxazole;
4-(6-(3,5-dimethylisoxazol-4-yl)-4-(1,3,5-trimethyl-1H-pyrazol-4-yl)-1H-benzo[d]imidazol-2-yl)morpholine;
6-(3,5-dimethylisoxazol-4-yl)-N-(1-methylpiperidin-4-yl)-4-(1,3,5-trimethyl-1H-pyrazol-4-yl)-1H-benzo[d]imidazol-2-amine;
3-(6-(3,5-dimethylisoxazol-4-yl)-2-(4-methylpiperazin-1H-yl)-1H-benzo[d]imidazol-4-yl)-4-methylbenzonitrile;
3,5-dimethyl-4-(2-(methylthio)-4-(1,3,5-trimethyl-1H-pyrazol-4-yl)-1H-benzo[d]imidazol-6-yl)isoxazole;
3,5-dimethyl-4-(1-methyl-2-(methylthio)-4-(1,3,5-trimethyl-1H-pyrazol-4-yl)-1H-benzo[d]imidazol-6-yl)isoxazole;
3-(6-(3,5-dimethylisoxazol-4-yl)-2-(4-methylpiperazin-1H-yl)-1H-benzo[d]imidazol-4-yl)-4-methylbenzamide;
6-(3,5-dimethylisoxazol-4-yl)-N-(tetrahydro-2H-pyran-4-yl)-4-(1,3,5-trimethyl-1H-pyrazol-4-yl)-1H-benzo[d]imidazol-2-amine;
3,5-dimethyl-4-(1-methyl-2-(methylthio)-7-(1,3,5-trimethyl-1H-pyrazol-4-yl)-1H-benzo[d]imidazol-5-yl)isoxazole;
4,4'-(7-bromo-1H-benzo[d]imidazole-4,6-diyl)bis(3,5-dimethylisoxazole);
3-(6-(3,5-dimethylisoxazol-4-yl)-2-morpholino-1H-benzo[d]imidazol-4-yl)-4-methylbenzonitrile;
3,5-dimethyl-4-(2-(methylsulfinyl)-7-(1,3,5-trimethyl-1H-pyrazol-4-yl)-1H-benzo[d]imidazol-5-yl)isoxazole;
3,5-dimethyl-4-(2-(methylsulfonyl)-7-(1,3,5-trimethyl-1H-pyrazol-4-yl)-1H-benzo[d]imidazol-5-yl)isoxazole;
4-(6-(3,5-dimethylisoxazol-4-yl)-4-(4-methylpyridin-3-yl)-1H-benzo[d]imidazol-2-yl)morpholine;
3-(6-(3,5-dimethylisoxazol-4-yl)-2-morpholino-1H-benzo[d]imidazol-4-yl)-4-methylbenzamide;
3-(6-(3,5-dimethylisoxazol-4-yl)-2-((tetrahydro-2H-pyran-4-yl)amino)-1H-benzo[d]imidazol-4-yl)-4-methylbenzonitrile;
3,5-dimethyl-4-(2-(4-methylpiperazin-1-yl)-4-(4-methylpyridin-3-yl)-1H-benzo[d]imidazol-6-yl)isoxazole;
3-(6-(3,5-dimethylisoxazol-4-yl)-2-((tetrahydro-2H-pyran-4-yl)amino)-1H-benzo[d]imidazol-4-yl)-4-methylbenzamide;

6-(3,5-dimethylisoxazol-4-yl)-4-(4-methylpyridin-3-yl)-N-(tetrahydro-2H-pyran-4-yl)-1H-benzo[d]imidazol-2-amine;
3-(6-(3,5-dimethylisoxazol-4-yl)-2-(4-methylpiperazin-1-yl)-1H-benzo[d]imidazol-4-yl)-2-methylbenzonitrile;
3-(6-(3,5-dimethylisoxazol-4-yl)-2-morpholino-1H-benzo[d]imidazol-4-yl)-2-methylbenzonitrile;
3-(6-(3,5-dimethylisoxazol-4-yl)-2-((tetrahydro-2H-pyran-4-yl)amino)-1H-benzo[d]imidazol-4-yl)-2-methylbenzonitrile;
3-(6-(3,5-dimethylisoxazol-4-yl)-2-(1-methylpiperidin-4-yl)amino)-1H-benzo[d]imidazol-4-yl)-4-methylbenzonitrile;
3-(6-(3,5-dimethylisoxazol-4-yl)-2-(4-methylpiperazin-1-yl)-1H-benzo[d]imidazol-4-yl)-2-methylbenzamide;
3-(6-(3,5-dimethylisoxazol-4-yl)-2-((tetrahydro-2H-pyran-4-yl)amino)-1H-benzo[d]imidazol-4-yl)-2-methylbenzamide;
3-(6-(3,5-dimethylisoxazol-4-yl)-2-morpholino-1H-benzo[d]imidazol-4-yl)-2-methylbenzamide;
3-(2-(4-aminopiperidin-1-yl)-6-(3,5-dimethylisoxazol-4-yl)-1H-benzo[d]imidazol-4-yl)-2-methylbenzonitrile;
3-(2-(benzylamino)-6-(3,5-dimethylisoxazol-4-yl)-1H-benzo[d]imidazol-4-yl)-4-methylbenzonitrile;
3-(6-(3,5-dimethylisoxazol-4-yl)-2-((pyridin-3-ylmethyl)amino)-1H-benzo[d]imidazol-4-yl)-4-methylbenzonitrile;
N-benzyl-6-(3,5-dimethylisoxazol-4-yl)-4-(1,3,5-trimethyl-1H-pyrazol-4-yl)-1H-benzo[d]imidazol-2-amine;
3,5-dimethyl-4-(2-(pyrrolidin-1-yl)-4-(1,3,5-trimethyl-1H-pyrazol-4-yl)-1H-benzo[d]imidazol-6-yl)isoxazole;
6-(3,5-dimethylisoxazol-4-yl)-N-methyl-4-(4-methylpyridin-3-yl)-1H-benzo[d]imidazol-2-amine;
3-(6-(3,5-dimethylisoxazol-4-yl)-2-(pyrrolidin-1H-benzo[d]imidazol-4-yl)-4-methylbenzonitrile;
3-(6-(3,5-dimethylisoxazol-4-yl)-2-((1-methylpiperidin-4-yl)amino)-1H-benzo[d]imidazol-4-yl)-2-methylbenzonitrile;
4-(2-(azetidin-1-yl)-4-(1,3,5-trimethyl-1H-pyrazol-4-yl)-1H-benzo[d]imidazol-6-yl)3,5-dimethylisoxazole;
(3-(6-(3,5-dimethylisoxazol-4-yl)-2-(pyrrolidin-1-yl)-1H-benzo[d]imidazol-4-yl)-4-methylphenyl)(pyrrolidin-1-yl)methanone;
3-(6-(3,5-dimethylisoxazol-4-yl)-2-((pyridin-3-ylmethyl)amino)-1H-benzo[d]imidazol-4-yl)-4-methylbenzamide;
3-(2-(benzylamino)-6-(3,5-dimethylisoxazol-4-yl)-1H-benzo[d]imidazol-4-yl)-4-methylbenzamide;
6-(3,5-dimethylisoxazol-4-yl)-N-(pyridin-3-ylmethyl)-4-(1,3,5-trimethyl-1H-pyrazol-4-yl)-1H-benzo[d]imidazol-2-amine;
N-benzyl-6-(3,5-dimethylisoxazol-4-yl)-4-(4-methylpyridin-3-yl)-1H-benzo[d]imidazol-2-amine;
6-(3,5-dimethylisoxazol-4-yl)-4-(4-methylpyridin-3-yl)-N-(pyridin-3-ylmethyl)-1H-benzo[d]imidazol-2-amine;
3,5-dimethyl-4-(4-(4-methylpyridin-3-yl)-2-(pyrrolidin-1-yl)-1H-benzo[d]imidazol-6-yl)isoxazole;
3-amino-5-(6-(3,5-dimethylisoxazol-4-yl)-1H-benzo[d]imidazol-4-yl)-1-methylpyridin-2(1H)-one;
4-(4,6-bis(3,5-dimethylisoxazol-4-yl)-1H-benzo[d]imidazol-2-yl)morpholine;
4,4'-(5-methoxy-2-methyl-1H-benzo[d]imidazole-4,6-diyl)bis(3,5-dimethylisoxazole);
4,4'-(2-(tetrahydro-2H-pyran-4-yl)-1H-benzo[d]imidazole-4,6-diyl)bis(3,5-dimethylisoxazole);
4,6-bis(3,5-dimethylisoxazol-4-yl)-N-(tetrahydro-2H-pyran-4-yl)-1H-benzo[d]imidazol-2-amine;
3,5-dimethyl-4-(5-(1-methyl-1H-pyrazol-5-yl)-1H-benzo[d]imidazol-7-yl)isoxazole;
4,4'-(2-(4-methylpiperazin-1-yl)-1H-benzo[d]imidazole-4,6-diyl)bis(3,5-dimethylisoxazole);
4,6-bis(3,5-dimethylisoxazol-4-yl)-N-(1-methylpiperidin-4-yl)-1H-benzo[d]imidazol-2-amine;
4,6-bis(3,5-dimethylisoxazol-4-yl)-N-(piperidin-4-yl)-1H-benzo[d]imidazol-2-amine; and
stereoisomers, tautomers, pharmaceutically acceptable salts, and hydrates thereof.

4. The method of claim 3, wherein the method further comprises treating insulin resistance diabetes.

5. The method according to claim 3, wherein the method further comprises treating a disease or disorder selected from Acute Disseminated Encephalomyelitis, Agammaglobulinemia, Allergic Disease, Ankylosing spondylitis, Anti-GBM/Anti-TBM nephritis, Anti-phospholipid syndrome, Autoimmune aplastic anemia, Autoimmune hepatitis, Autoimmune inner ear disease, Autoimmune myocarditis, Autoimmune pancreatitis, Autoimmune retinopathy, Autoimmune thrombocytopenic purpura, Behcet's Disease, Bullous pemphigoid, Castleman's Disease, Celiac Disease, Churg-Strauss syndrome, Crohn's Disease, Cogan's syndrome, Dry eye syndrome, Essential mixed cryoglobulinemia, Dermatomyositis, Devic's Disease, Encephalitis, Eosinophilic esophagitis, Eosinophilic fasciitis, Erythema nodosum, Giant cell arteritis, Glomerulonephritis, Goodpasture's syndrome, Granulomatosis with Polyangiitis (Wegener's), Graves' Disease, Guillain-Barre syndrome, Hashimoto's thyroiditis, Hemolytic anemia, Henoch-Schonlein purpura, IgA nephropathy, Inclusion body myositis, Type I diabetes, Interstitial cystitis, Kawasaki's Disease, Leukocytoclastic vasculitis, Lichen planus, Lupus (SLE), Microscopic polyangitis, Multiple sclerosis, Myasthenia gravis, myositis, Optic neuritis, Pemphigus, POEMS syndrome, Polyarteritis nodosa, Primary biliary cirrhosis, Psoriasis, Psoriatic arthritis, Pyoderma gangrenosum, Relapsing polychondritis, Rheumatoid arthritis, Sarcoidosis, Scleroderma, Sjogren's syndrome, Takayasu's arteritis, Transverse myelitis, Ulcerative colitis, Uveitis, and Vitiligo.

6. The method of claim 3, wherein the method further comprises treating a disease or disorder selected from sinusitis, pneumonitis, osteomyelitis, gastritis, enteritis, gingivitis, appendicitis, irritable bowel syndrome, tissue graft rejection, chronic obstructive pulmonary disease (COPD), septic shock, toxic shock syndrome, SIRS, bacterial sepsis, osteoarthritis, acute gout, acute lung injury, acute renal failure, burns, Herxheimer reaction, and SIRS associated with viral infections.

7. The method of claim 3, wherein the method further comprises treating a disease or disorder selected from dyslipidemia, atherosclerosis, hypercholesterolemia, and metabolic syndrome.

8. The method of claim 3, wherein the method further comprises treating a disease or disorder selected from Alzheimer's disease, Parkinson's disease, Huntington disease, bipolar disorder, schizophrenia, Rubinstein-Taybi syndrome, and epilepsy.

9. The method of claim 3, further comprising a method of male contraception.

10. The method of claim 3, wherein the method further comprises treating a cancer selected from B-acute lymphocytic leukemia, Burkitt's lymphoma, diffuse large cell lymphoma, multiple myeloma, primary plasma cell leukemia, atypical carcinoid lung cancer, bladder cancer, breast cancer, cervix cancer, colon cancer, gastric cancer, glioblastoma, hepatocellular carcinoma, large cell neuroendocrine carcinoma, medulloblastoma, melanoma, nodular melanoma, neuroblastoma, esophageal squamous cell carcinoma, osteosarcoma, ovarian cancer, prostate cancer, renal clear cell carcinoma, retinoblastoma, rhabdomyosarcoma, small cell lung carcinoma, NUT midline carcinoma, B-cell lymphoma, non-small cell lung cancer, head and neck squamous cell carcinoma, chronic lymphocytic leukemia, follicular lymphoma, diffuse large B cell lymphoma with germinal center phenotype, Hodgkin's lymphoma, activated anaplastic large cell lymphoma, primary neuroectodermal tumor, pancreatic cancer, adenoid cystic carcinoma, T-cell prolymphocytic leukemia, malignant glioma, thyroid cancer, Barret's adenocarcinoma, hepatoma, pro-myelocytic leukemia, and mantle cell lymphoma.

11. The method of claim 3, wherein the method further comprises treating a cancer that:
   (a) exhibits overexpression, translocation, amplification, or rearrangement of a myc family oncoprotein;
   (b) results from aberrant regulation of BET proteins;
   (c) relies on pTEFb (Cdk9/cyclin T) and BET proteins to regulate oncogenes;
   (d) associated with upregulation of BET responsive genes CDK6, Bcl2, TYRO3, MYB and/or hTERT; and/or
   (e) is associated with a viral infection.

12. The method of claim 11, wherein:
   (a) the cancer exhibiting overexpression, translocation, amplification, or rearrangement of a myc family oncoprotein is selected from B-acute lymphocytic leukemia, Burkitt's lymphoma, Diffuse large cell lymphoma, Multiple myeloma, Primary plasma cell leukemia, Atypical carcinoid lung cancer, Bladder cancer, Breast cancer, Cervix cancer, Colon cancer, Gastric cancer, Glioblastoma, Hepatocellular carcinoma, Large cell neuroendocrine carcinoma, Medulloblastoma, Melanoma, nodular, Melanoma, superficial spreading, Neuroblastoma, esophageal squamous cell carcinoma, Osteosarcoma, Ovarian cancer, Prostate cancer, Renal clear cell carcinoma, Retinoblastoma, Rhabdomyosarcoma, and Small cell lung carcinoma;
   (b) the cancer resulting from aberrant regulation of BET proteins is selected from NUT midline carcinoma, B-cell lymphoma, non-small cell lung cancer, esophageal cancer, head and neck squamous cell carcinoma, and colon cancer;
   (c) the cancer relying on pTEFb (Cdk9/cyclin 7) and BET proteins to regulate oncogenes is selected from chronic lymphocytic leukemia and multiple myeloma, follicular lymphoma, diffuse large B cell lymphoma with germinal center phenotype, Burkitt's lymphoma, Hodgkin's lymphoma, anaplastic large cell lymphoma, neuroblastoma and primary neuroectodermal tumor, rhabdomyosarcoma, prostate cancer, and breast cancer;
   (d) the cancer associated with upregulation of BET responsive genes CDK6, Bcl2, TYRO3, MYB, and hTERT is selected from pancreatic cancer, breast cancer, colon cancer, glioblastoma, adenoid cystic carcinoma, T-cell prolymphocytic leukemia, malignant glioma, bladder cancer, medulloblastoma, thyroid cancer, melanoma, multiple myeloma, Barret's adenocarcinoma, hepatoma, prostate cancer, pro-myelocytic leukemia, chronic lymphocytic leukemia, mantle cell lymphoma, diffuse large B-cell lymphoma, small cell lung cancer, and renal carcinoma; and/or
   (e) the viral infection is selected from Epstein-Barr Virus, hepatitis B virus, hepatitis C virus, Kaposi's sarcoma associated virus, human papilloma virus, Merkel cell polyomavirus, and human cytomegalovirus.

13. The method of claim 10, wherein the compound of Formula II is administered in combination with another anticancer agent.

14. The method of claim 13, wherein the anticancer agent is selected from ABT-737, Azacitidine (Vidaza), AZD1152 (Barasertib), AZD2281 (Olaparib), AZD6244 (Selumetinib), BEZ235, Bleomycin Sulfate, Bortezomib (Velcade), Busulfan (Myleran), Camptothecin, Cisplatin, Cyclophosphamide (Clafen), CYT387, Cytarabine (Ara-C), Dacarbazine, DAPT (GSI-IX), Decitabine, Dexamethasone, Doxorubicin (Adriamycin), Etoposide, Everolimus (RAD001), Flavopiridol (Alvocidib), Ganetespib (STA-9090), Gefitinib (Iressa), Idarubicin, Ifosfamide (Mitoxana), IFNa2a (Roferon A), Melphalan (Alkeran), Methazolastone (temozolomide), Metformin, Mitoxantrone (Novantrone), Paclitaxel, Phenformin, PKC412 (Midostaurin), PLX4032 (Vemurafenib), Pomalidomide (CC-4047), Prednisone (Deltasone), Rapamycin, Revlimid (Lenalidomide), Ruxolitinib (INCB018424), Sorafenib (Nexavar), SU11248 (Sunitnib), SU11274, Vinblastine, Vincristine (Oncovin), Vinorelbine (Navelbine), Vorinostat (SAHA), and WP1130 (Degrasyn).

* * * * *

UNITED STATES PATENT AND TRADEMARK OFFICE
CERTIFICATE OF CORRECTION

PATENT NO. : 10,166,215 B2
APPLICATION NO. : 15/492838
DATED : January 1, 2019
INVENTOR(S) : Shuang Liu et al.

It is certified that error appears in the above-identified patent and that said Letters Patent is hereby corrected as shown below:

In the Claims

Claim 1, Column 260, Line 15, "alkoxy($C_1$-$C_9$);" should read -- alkoxy($C_1$-$C_6$); --.

Claim 1, Column 260, Line 45, "-$SO_2$alkyl($C_i$-$C_4$)," should read -- -$SO_2$alkyl($C_1$-$C_4$), --.

Claim 3, Column 261, Line 25, "5-O-1H-benzo" should read -- 5-yl)-1H-benzo --.

Claim 3, Column 262, Line 17, "4,4)-(2-ethoxy" should read -- 4,4'-(2-ethoxy --.

Claim 3, Column 262, Line 35, "4,4°-(2-methyl" should read -- 4,4'-(2-methyl --.

Claim 3, Column 262, Line 62, "2-ethyl" should read -- 2-methyl --.

Claim 3, Column 263, Line 8, "imidazole" should read -- imidazol --.

Claim 3, Column 263, Line 13, "diethyl" should read -- dimethyl --.

Claim 3, Column 263, Line 36, "(2-methyl-4-O-tolyl)" should read -- -(2-methyl-4-(o-tolyl) --.

Claim 3, Column 264, Line 51, "indazol-5-ylisoxazole;" should read -- indazol-5-yl)isoxazole; --.

Claim 3, Column 266, Line 15, "4-(4(3,5-dimethyl" should read -- 4-(4-(3,5-dimethyl --.

Claim 3, Column 266, Line 16, "yl)-3, dimethylisoxazole" should read -- yl-3,5-dimethylisoxazole --.

Claim 3, Column 266, Line 22, "3-dimethyl" should read -- 3,5-dimethyl --.

Claim 3, Column 266, Line 30, "1H-yl)" should read -- 1-yl) --.

Signed and Sealed this
Ninth Day of April, 2019

Andrei Iancu
*Director of the United States Patent and Trademark Office*

CERTIFICATE OF CORRECTION (continued)
U.S. Pat. No. 10,166,215 B2

Claim 3, Column 266, Line 38, "1H-yl)" should read -- 1-yl) --.

Claim 12, Column 270, Line 1, "(Cdk9/cyclin 7)" should read -- (Cdk9/cyclin T) --.